United States Patent
Mueller et al.

(10) Patent No.: US 9,346,816 B2
(45) Date of Patent: May 24, 2016

(54) 6,7,8,9-TETRAHYDRO-5H-1,4,7,10A-TETRAAZA-CYCLOHEPT[F]INDENE DERIVATIVES, PHARMACEUTICAL COMPOSITIONS CONTAINING THESE COMPOUNDS, THEIR USE AND PROCESSES FOR PREPARING THEM

(71) Applicants: Stephan-Georg Mueller, Warthausen (DE); Christopher John Brown, Marcham (GB); Alexander Heifetz, Didcot (GB); Bernd Nosse, Biberach an der Riss (DE); Juergen Prestle, Biberach an der Riss (DE); Natacha Prevost, Sutton Courtenay (GB); Klaus Rudolf, Warthausen (DE); Stefan Scheuerer, Warthausen (DE); Marcus Schindler, Nuneham Courtenay (GB); Dirk Stenkamp, Biberach an der Riss (DE); Leo Thomas, Biberach an der Riss (DE); Heather Tye, East Hagbourne (GB)

(72) Inventors: Stephan-Georg Mueller, Warthausen (DE); Christopher John Brown, Marcham (GB); Alexander Heifetz, Didcot (GB); Bernd Nosse, Biberach an der Riss (DE); Juergen Prestle, Biberach an der Riss (DE); Natacha Prevost, Sutton Courtenay (GB); Klaus Rudolf, Warthausen (DE); Stefan Scheuerer, Warthausen (DE); Marcus Schindler, Nuneham Courtenay (GB); Dirk Stenkamp, Biberach an der Riss (DE); Leo Thomas, Biberach an der Riss (DE); Heather Tye, East Hagbourne (GB)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 116 days.

(21) Appl. No.: 14/072,324

(22) Filed: Nov. 5, 2013

(65) Prior Publication Data
US 2014/0066428 A1    Mar. 6, 2014

Related U.S. Application Data

(63) Continuation of application No. 13/130,663, filed as application No. PCT/EP2009/065883 on Nov. 26, 2009, now abandoned.

(30) Foreign Application Priority Data

Nov. 27, 2008 (EP) .................... 08170154

(51) Int. Cl.
 *A61K 31/55* (2006.01)
 *C07D 487/14* (2006.01)
(52) U.S. Cl.
 CPC .................... *C07D 487/14* (2013.01)
(58) Field of Classification Search
 CPC ............... A61K 31/55; C07D 487/14
 USPC .......................... 514/215; 540/578
 See application file for complete search history.

(56) References Cited

U.S. PATENT DOCUMENTS

| | | |
|---|---|---|
| 6,194,410 B1 | 2/2001 | Bos et al. |
| 2003/0091505 A1 | 5/2003 | Fu |
| 2012/0165304 A1 | 6/2012 | Mueller et al. |

FOREIGN PATENT DOCUMENTS

| | | |
|---|---|---|
| JP | 2000186090 A | 7/2000 |
| JP | 2008505102 A | 2/2008 |
| JP | 2008540368 A | 11/2008 |
| WO | 2006004937 A2 | 1/2006 |
| WO | 2006117304 A1 | 11/2006 |
| WO | 2008117169 A1 | 10/2008 |
| WO | 2010060952 A1 | 6/2010 |

OTHER PUBLICATIONS

International Search Report and Written Opinion for PCT/EP2009/065883 mailed Apr. 21, 2010.
Sofan, M.A-M, et al., "Acylation reactions of 5-amino-3-phenylpyrazole: Routes to pyrazolo-pyrimidines, pyrazolodiazepine, pyrazoloquinazoline and pyrazolopyrrolo-pyrimidine derivatives." Indian Journal of Chemistry, vol. 33B, 1994, pp. 738-741.

*Primary Examiner* — Brenda Coleman
(74) *Attorney, Agent, or Firm* — Michael P. Morris; Usha R. Patel

(57) ABSTRACT

The present invention relates to compounds defined by formula I

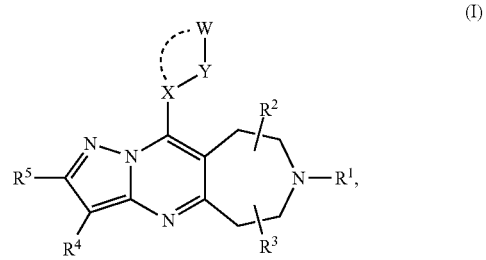

wherein the groups X, Y, W and $R^1$ to $R^4$ are defined as in claim 1, possessing valuable pharmacological activity. Particularly the compounds are agonists of the 5-HT2C receptor, and thus are suitable for treatment and prevention of diseases which can be influenced by inhibition of this receptor, such as metabolic and CNS-related disorders.

9 Claims, No Drawings

6,7,8,9-TETRAHYDRO-5H-1,4,7,10A-TETRAAZA-CYCLOHEPT[F]INDENE DERIVATIVES, PHARMACEUTICAL COMPOSITIONS CONTAINING THESE COMPOUNDS, THEIR USE AND PROCESSES FOR PREPARING THEM

FIELD OF THE INVENTION

The present invention relates to novel 6,7,8,9-Tetrahydro-5H-1,4,7,10a-tetraaza-cyclohept[f]indene derivatives that are modulators of the 5-HT2C receptor, to processes for their preparation, to pharmaceutical compositions containing them and to their medicinal use. The active compounds of the present invention are useful for treatment of 5-HT2C receptor-associated diseases, conditions or disorders, such as, obesity and related CNS-related disorders.

BACKGROUND OF THE INVENTION

Serotonin (5-hydroxytryptamine, 5-HT) is a biogenic monoamine which plays a prominent role in a variety of physiological functions in both the central nervous system (CNS) and the periphery of the body. These pleiotropic effects are mediated by at least 14 different receptors which are grouped into seven families ($5-HT_{1-7}$) according to their primary structure and their intracellular signal transduction coupling systems (Hoyer, D., et al., Pharmacol Biochem Behav, 2002. 71(4): p. 533-54). With the exception of the $5-HT_3$ receptor, which is an ion channel, all serotonin receptors are G-protein coupled receptors (GPCRs).

The $5-HT_2$ receptor family consists of $5-HT_{2A}$, $5-HT_{2B}$, and $5-HT_{2C}$ receptors. A number of studies suggest that the $5-HT_{2C}$ receptor system is specifically involved in diseases or conditions such as the metabolic syndrome including obesity, type II diabetes, and dyslipidemia, as well as CNS-related disorders including depression, schizophrenia, obsessive-compulsive disorder, drug abuse, sleep disorders, anxiety and epilepsy.

Obesity is a life-threatening disorder in which there is an increased risk of morbidity and mortality arising from concomitant diseases such as, but not limited to, type II diabetes, hypertension, stroke, certain forms of cancers and gallbladder disease. Obesity has become a major healthcare issue in the Western World and increasingly in some third world countries. The increase in the number of obese people is due largely to the increasing preference for high fat content foods but also, and this can be a more important factor, the decrease in activity in most people's lives. In the last 10 years there has been a 30% increase in the incidence of obesity in the USA and that about 30% of the population of the USA is now considered obese. In spite of the growing awareness of the health concerns linked to obesity the percentage of individuals that are overweight or obese continue to increase. In fact, the percentage of children and adolescents who are defined as overweight has more than doubled since the early 1970s and about 13 percent of children and adolescents are now seriously overweight. The most significant concern, from a public health perspective, is that children who are overweight grow up to be overweight or obese adults, and accordingly are at greater risk for major health problems. Therefore, it appears that the number of individuals that are overweight or obese will continue to increase. Whether someone is classified as overweight or obese is generally determined on the basis of his or her body mass index (BMI) which is more highly correlated with body fat than any other indicator of height and weight. A person is considered overweight when they have a BMI in the range of 25-30 $kg/m^2$, whereas a person with a BMI over 30 $kg/m^2$ is classified as obese. Obesity is further divided into three classes, Class I (BMI of about 30 to about 34.9 $kg/m^2$), Class II (BMI of about 35 to 39.9 $kg/m^2$) and Class III (about 40 $kg/m^2$ or greater). There are problems with this definition in that it does not take into account the proportion of body mass that is muscle in relation to fat (adipose tissue). To account for this, obesity can also be defined on the basis of body fat content: greater than 25% and 30% in males and females, respectively.

It has been recognized that obesity is a disease process influenced by environmental factors in which the traditional weight loss methods of dieting and exercise need to be supplemented by therapeutic products (S. Parker, "Obesity: Trends and Treatments", Scrip Reports, PJB Publications Ltd, 1996). As the BMI increases there is an increased risk of death from a variety of causes that is independent of other risk factors. The most common diseases with obesity are cardiovascular disease (hypertension, coronary insufficiency, coronary heart disease, angina pectoris, congestive heart failure, atheromatous disease, cardiac insufficiency), high blood cholesterol, dyslipidemia, type II (non-insulin dependent) diabetes, insulin resistance, glucose intolerance, hyperinsulinemia, stroke, gall bladder disease (particularly gallstones and cancer), cholescystitis and cholelithiasis, gout, osteoarthritis, obstructive sleep apnea and respiratory problems, some types of cancer (such as endometrial, breast, prostate, and colon), complications of pregnancy, poor female reproductive health (such as menstrual irregularities, infertility, irregular ovulation), diseases of reproduction (such as sexual dysfunction, both male and female, including male erectile dysfunction), bladder control problems (such as stress incontinence), uric acid nephrolithiasis, psychological disorders (such as depression, eating disorders, distorted body image, and low self esteem). Research has shown that even a modest reduction in body weight can correspond to a significant reduction in the risk of developing coronary heart disease.

As the 5HT2C receptor is expressed in high density in the brain (notably in the limbic structures, extrapyramidal pathways, thalamus and hypothalamus i.e. PVN and DMH, and predominantly in the choroid plexus) and is expressed in low density or is absent in peripheral tissues, a selective 5HT2C receptor agonist can be an effective and safe pharmaceutical agent. Also, 5HT2C knockout mice are overweight with cognitive impairment and susceptibility to seizure thus establishing the clear use for a 5HT2C receptor agonist in 5HT2C receptor associated diseases or disorders. The 5HT2C receptor plays a role in obsessive compulsive disorder, some forms of depression, and epilepsy. Accordingly, 5HT2C receptor agonists can have anti-panic properties, and properties useful for the treatment of sexual dysfunction. In addition, 5HT2C receptor agonists are useful for the treatment of psychiatric symptoms and behaviors in individuals with eating disorders such as, but not limited to, anorexia nervosa and bulimia nervosa. Individuals with anorexia nervosa often demonstrate social isolation. Anorexic individuals often present symptoms of being depressed, anxious, obsession, perfectionistic traits, and rigid cognitive styles as well as sexual disinterest. Other eating disorders include, anorexia nervosa, bulimia nervosa, binge eating disorder (compulsive eating) and ED-NOS (i.e., eating disorders not otherwise specified-an official diagnosis). An individual diagnosed with ED-NOS possess atypical eating disorders including situations in which the individual meets all but a few of the criteria for a particular diagnosis. What the individual is doing with regard to food and weight is neither normal nor healthy.

The first line of treatment for individuals that are overweight or obese is to offer diet and life style advice, such as, reducing the fat content of their diet and increasing their physical activity. However many patients find these difficult to maintain and need additional help from drug therapy to sustain results from these efforts.

Compounds marketed as anti-obesity agents include Orlistat and Sibutramine. Orlistat (a lipase inhibitor) inhibits fat absorption directly and tends to produce a high incidence of unpleasant (though relatively harmless) side-effects such as diarrhea. Sibutramine (a mixed 5-HT/noradrenalin reuptake inhibitor) can increase blood pressure and heart rate in some patients. The serotonin releaser/reuptake inhibitors fenfluramine and dexfenfluramine have been reported to decrease food intake and body weight over a prolonged period (greater than 6 months). However, both products were withdrawn after reports of preliminary evidence of heart valve abnormalities associated with their use. There is therefore a need for the development of a safer anti-obesity agent.

The compounds of formula (I) are useful in the treatment and/or prevention of disorders involving elevated plasma blood glucose, particularly diabetes mellitus (including Type II or non-insulin dependent diabetes mellitus (NIDDM); Type I or insulin dependent diabetes mellitus (IDDM); and Type III or malnutrition-related diabetes). The diabetes maybe diabetes secondary to pancreatic disease; or diabetes related to steroid use. The compounds of formula (I) are also useful in the treatment and/or prevention of the sequelae of hyperglycemia; in the treatment and/or prevention of diabetic complications; and in the treatment of insulin dependence. The invention is of particular use in the treatment or prevention of diabetes mellitus (including Type II or non-insulin dependent diabetes mellitus (NIDDM); Type I or insulin dependent diabetes mellitus (IDDM); and Type III or malnutrition-related diabetes), and particularly in the treatment or prevention of Type II diabetes.

Diabetes has also been implicated in the development of severe sequelae such as kidney disease, eye diseases and nervous-system problems. Kidney disease, also called nephropathy, occurs when the kidney's "filter mechanism" is damaged and protein leaks into urine in excessive amounts and eventually the kidney fails. Diabetes is also a leading cause of damage to the retina and increases the risk of cataracts and glaucoma Finally, diabetes is associated with nerve damage, especially in the legs and feet, which interferes with the ability to sense pain and contributes to serious infections. Taken together, diabetes complications are one of the leading causes of death.

OBJECT OF THE INVENTION

It is an object of this invention to provide selective, directly acting 5-HT2 receptor ligands, hereinafter described as compounds of formula (I), for use in prevention and/or treatment of metabolic and CNS-related disorders, particularly diabetes, obesity, dyslipidemia, depression, schizophrenia, obsessive-compulsive disorder, drug abuse, sleep disorders, anxiety and epilepsy. It is a further object of this invention to provide selective, directly acting 5-HT2C receptor ligands, preferably 5-HT2C receptor agonists, for use in therapy and particularly for use as anti-obesity agents and diseases/disorders mentioned above.

SUMMARY OF THE INVENTION

In one aspect the invention provides a compound of formula I:

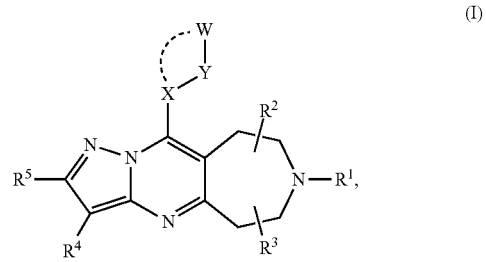

as defined hereinafter, the isoforms, tautomers, stereoisomers, solvates, hydrates, and the salts thereof, particularly the physiologically acceptable salts thereof with inorganic or organic acids or bases, or the combinations thereof.

The present invention further provides a composition comprising a compound of formula (I) and a pharmaceutically acceptable carrier.

The present invention further provides a method of modulating a 5HT2C receptor comprising contacting the receptor with a compound of formula (I).

The present invention further provides a method of treating disorders of the central nervous system, damage to the central nervous system, cardiovascular disorders, gastrointestinal disorders, diabetes insipidus, sleep apnea or HDL-related condition comprising administering to a patient in need of the treating a therapeutically effective amount of a compound of formula (I).

The present invention further provides a method of decreasing food intake of a mammal comprising administering to the mammal a therapeutically effective amount of a compound of formula (I).

The present invention further provides a method of inducing satiety in a mammal comprising administering to the mammal a therapeutically effective amount of a compound of formula (I).

The present invention further provides a method of controlling weight gain of a mammal comprising administering to the mammal a therapeutically effective amount of a compound of formula (I).

The present invention further provides a method of treating obesity comprising administering to a patient in need of such treating a therapeutically effective amount of a compound of formula (I).

The present invention further provides a compound of formula (I), as described herein, for use in a method of treatment of the human or animal body by therapy.

The present invention further provides compounds of formula (I) for treatment or prevention of diseases or conditions which can be influenced by modulating the 5-HT2C receptor, such as metabolic and CNS-related disorders, particularly Type II diabetes, obesity, dyslipidemia, depression, schizophrenia, obsessive-compulsive disorder, drug abuse, sleep disorders, anxiety and epilepsy.

The present invention further provides the use of a compound of formula (I) for preparing a pharmaceutical composition which is suitable for the treatment or prevention or diseases or conditions which can be influenced by modulating 5-HT2C receptor activity, such as metabolic and CNS-related disorders, particularly diabetes, obesity, dyslipidemia, depression, schizophrenia, obsessive-compulsive disorder, drug abuse, sleep disorders, anxiety and epilepsy.

In some embodiments, disorders of the central nervous system include, for example, depression, atypical depression, bipolar disorders, anxiety disorders, obsessive-compulsive disorders, social phobias or panic states, sleep disorders, sexual dysfunction, psychoses, schizophrenia, migraine and other conditions associated with cephalic pain or other pain, raised intracranial pressure, epilepsy, personality disorders, age-related behavioral disorders, behavioral disorders associated with dementia, organic mental disorders, mental disorders in childhood, aggressivity, age-related memory disorders, chronic fatigue syndrome, drug and alcohol addiction, obesity, bulimia, anorexia nervosa and premenstrual tension. In some embodiments, sexual dysfunction is male erectile dysfunction.

DETAILED DESCRIPTION OF THE INVENTION

The present invention provides in its broadest/first embodiment E-0 a compound of formula (I):

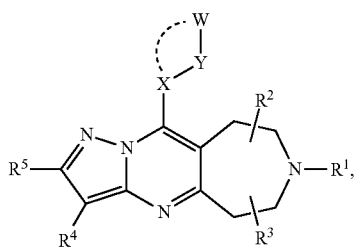

wherein:

X denotes a divalent 4- to 10-membered monocylic, 7- to 12-membered spirocyclic or 6- to 12-membered bicyclic saturated, partially or fully unsaturated group selected from a carbocycle, a monoaza-heterocycle and a diaza-heterocycle, which is linked to the adjacent groups via carbon atoms or, if present, via nitrogen atoms, e.g. via one carbon and one nitrogen atom or via two nitrogen atoms,
wherein 1 or 2 —$CH_2$— groups optionally are replaced independently of each other by O, S, carbonyl, or sulfonyl, with the proviso that two heteroatoms are not directly linked together, and/or
1 —$CH_2$— group optionally is replaced by the divalent group >C=C($R^x$)$_2$, wherein $R^x$ independently denotes H or $C_{1-3}$-alkyl, and/or
wherein in an unsaturated group 1 double bond optionally is condensed with an aryl or a 5- or 6-membered hetaryl group, and/or
wherein in any of the resulting groups one or two carbon atoms optionally and independently are substituted by halogen atoms, $C_{1-6}$-alkyl, $C_{2-6}$-alkenyl, $C_{2-6}$-alkynyl, cyclo-$C_{3-7}$-alkyl, cyclo-$C_{3-7}$-alkenyl, phenyl, cyano, hydroxy, hydroxy-$C_{1-6}$-alkyl, hydroxy-$C_{3-6}$-alkenyl, hydroxy-$C_{3-6}$-alkynyl, $C_{1-6}$-alkoxy, $C_{1-6}$-alkoxy-$C_{1-6}$-alkyl, $C_{1-6}$-alkoxy-$C_{3-6}$-alkenyl, $C_{1-6}$-alkoxy-$C_{3-6}$-alkynyl, $C_{3-6}$-alkenoxy-$C_{1-6}$-alkyl, thiohydroxy, $C_{1-6}$-alkylthio, $C_{3-6}$-alkenylthio, $C_{3-6}$-alkynylthio, amino, $C_{1-6}$-alkyl-amino, $C_{3-6}$-alkenyl-amino, $C_{3-6}$-alkynyl-amino, di-($C_{1-6}$-alkyl)-amino, di-($C_{3-6}$-alkenyl)-amino, di-($C_{3-6}$-alkynyl)-amino, amino-$C_{1-6}$-alkyl, $C_{1-3}$-alkyl-amino-$C_{1-6}$-alkyl, di-($C_{1-3}$-alkyl)-amino-$C_{1-6}$-alkyl, amino-$C_{3-6}$-alkenyl, $C_{1-3}$-alkyl-amino-$C_{3-6}$-alkenyl, di-($C_{1-3}$-alkyl)-amino-$C_{3-6}$-alkenyl, amino-$C_{3-6}$-alkynyl, $C_{1-3}$-alkyl-amino-$C_{3-6}$-alkynyl, di-($C_{1-3}$-alkyl)-amino-$C_{3-6}$-alkynyl, hydroxycarbonyl, $C_{1-6}$-alkyl-carbonyl, $C_{2-6}$-alkenyl-carbonyl, $C_{2-6}$-alkynyl-carbonyl, formyl, $C_{1-6}$-alkoxy-carbonyl, $C_{3-6}$-alkenoxy-carbonyl, $C_{3-6}$-alkynoxy-carbonyl, aminocarbonyl, $C_{1-6}$-alkyl-aminocarbonyl, $C_{3-6}$-alkenyl-aminocarbonyl, $C_{3-6}$-alkynyl-aminocarbonyl, di-($C_{1-6}$-alkyl)-aminocarbonyl, di-($C_{3-6}$-alkenyl)-aminocarbonyl, di-($C_{3-6}$-alkynyl)-aminocarbonyl, formylamino, $C_{1-6}$-alkyl-carbonylamino, $C_{1-6}$-alkyl-carbonyl-($C_{1-3}$-alkyl)-amino, $C_{2-6}$-alkenyl-carbonylamino, $C_{2-6}$-alkynyl-carbonylamino, $C_{1-6}$-alkyl-sulphonyl, $C_{2-6}$-alkenyl-sulphonyl, $C_{2-6}$-alkynyl-sulphonyl, $C_{1-6}$-alkyl-sulphinyl, $C_{2-6}$-alkenyl-sulphinyl, $C_{2-6}$-alkynyl-sulphinyl, $C_{1-6}$-alkyl-sulphonylamino, $C_{2-6}$-alkenyl-sulphonylamino, $C_{2-6}$-alkynyl-sulphonylamino, aminosulphonyl, $C_{1-6}$-alkylaminosulphonyl, di-($C_{1-6}$-alkyl)-aminosulphonyl, $C_{3-6}$-alkenylaminosulphonyl, di-($C_{3-6}$-alkenyl)-aminosulphonyl, $C_{3-6}$-alkynylaminosulphonyl, or di-($C_{3-6}$-alkynyl)-amino sulphonyl groups, while the substituents may be identical or different, and/or
wherein one ring member nitrogen atom optionally is substituted by a $C_{1-6}$-alkyl, $C_{3-6}$-alkenyl, $C_{3-6}$-alkynyl, cyclo-$C_{3-7}$-alkyl, cyclo-$C_{3-7}$-alkenyl, hydroxy, hydroxy-$C_{1-6}$-alkyl, hydroxy-$C_{3-6}$-alkenyl, hydroxy-$C_{3-6}$-alkynyl, $C_{1-6}$-alkoxy, $C_{1-6}$-alkoxy-$C_{1-6}$-alkyl, $C_{1-6}$-alkoxy-$C_{3-6}$-alkenyl, $C_{1-6}$-alkoxy-$C_{3-6}$-alkynyl, $C_{3-6}$-alkenoxy-$C_{1-6}$-alkyl, $C_{1-6}$-alkyl-carbonyl, $C_{2-6}$-alkenyl-carbonyl, $C_{2-6}$-alkynyl-carbonyl, formyl, $C_{1-6}$-alkoxy-carbonyl, $C_{3-6}$-alkenoxy-carbonyl, $C_{3-6}$-alkynoxy-carbonyl, $C_{1-6}$-alkyl-sulphonyl, $C_{2-6}$-alkenyl-sulphonyl, $C_{2-6}$-alkynyl-sulphonyl, $C_{1-6}$-alkyl-sulphinyl, $C_{2-6}$-alkenyl-sulphinyl, $C_{2-6}$-alkynyl-sulphinyl, aminosulphonyl, phenyl or phenyl-$C_{1-3}$-alkyl group, Y is absent or denotes a —$(CH_2)_n$— group, wherein n is 1, 2, 3, 4, 5 or 6 and wherein 1 or 2 —$CH_2$— groups optionally are replaced independently by O, S, carbonyl, sulfonyl, or —NH—, with the proviso that two heteroatoms are not directly linked together, or
wherein 1 —$CH_2$— group is replaced by O, S, carbonyl, sulfonyl, or —NH—, and additionally a —$CH_2$—$CH_2$— subgroup is replaced by —C(O)—O—, —O—C(O)—, —C(O)—NH—, or —NH—C(O)—, with the proviso that two heteroatoms are not directly linked together, and
wherein any hydrogen atom of the —NH— groups mentioned hereinbefore optionally and independently is replaced by a $C_{3-6}$-cycloalkyl or phenyl group, or by a straight-chained or branched $C_{1-6}$-alkyl, $C_{3-6}$-alkenyl, $C_{3-6}$-alkynyl, phenyl-$C_{1-6}$-alkyl, $C_{1-6}$-alkyl-carbonyl, or $C_{1-6}$-alkyl-sulphonyl group, and/or
wherein 1 or 2 hydrogen atoms attached to carbon atoms optionally are replaced by halogen atoms, trifluoromethyl, $C_{1-6}$-alkyl, $C_{2-6}$-alkenyl, $C_{2-6}$-alkynyl, $C_{3-6}$-cycloalkyl, phenyl, phenyl-$C_{1-6}$-alkyl, cyano, hydroxy, hydroxy-$C_{1-6}$-alkyl, $C_{1-6}$-alkoxy, $C_{1-6}$-alkoxy-$C_{1-6}$-alkyl, $C_{1-6}$-alkyl-carbonyl, $C_{1-6}$-alkoxy-carbonyl, $C_{1-6}$-alkyl-carbonylamino, $C_{1-6}$-alkyl-carbonyl-($C_{1-3}$-alkyl)-amino, $C_{1-3}$-alkyl-aminocarbonyl, di-($C_{1-3}$-alkyl)-aminocarbonyl or $C_{1-6}$-alkyl-sulphonyl groups, while the substituents may be identical or different, or 2 geminal hydrogen atoms are replaced by a —$(CH_2)_m$— bridge, wherein m is 2, 3, 4, or 5, W denotes H or an optionally substituted straight-chained or branched $C_{1-6}$-alkyl, $C_{2-6}$-alkenyl or $C_{2-6}$-alkynyl group, wherein 1 or 2 methyl groups optionally are replaced by optionally substituted phenyl groups or an optionally substituted cyclo-$C_{3-9}$-alkyl group, wherein independently in a cyclo-$C_{4-9}$-alkyl group 2 hydrogen atoms attached to adjacent carbon atoms optionally are replaced to form a double bond within the ring, which optionally is condensed with an optionally substituted aryl or an optionally substituted 5- or 6-membered hetaryl group, and the resulting group is bound via a saturated or unsaturated carbon atom, or in a cyclo-$C_{4-9}$-alkyl group 2 hydrogen atoms attached to the same carbon atom (relative 1,1-position) optionally are replaced by a $C_{2-5}$-alkylenyl bridge or 2 hydrogen atoms attached to carbon atoms in relative 1,2-, 1,3- or 1,4-position optionally are replaced by a $C_{1-5}$-alkylenyl bridge, wherein any of the resulting polycyclic groups one or two —CH$_2$— groups optionally are replaced by —NH— (or N-atoms for replacement of —CH< members), >N—($C_{1-6}$-alkyl), O, S, carbonyl, or sulfonyl, and/or two —CH$_2$— groups in relative 1,3-position within a $C_{4-5}$-alkylenyl bridge optionally are replaced by O atoms, and/or 2 hydrogen atoms attached to adjacent carbon atoms within a $C_{4-5}$-alkylenyl bridge optionally are replaced to form a double bond, which optionally is condensed with an optionally substituted aryl or an optionally substituted 5- or 6-membered hetaryl group, and/or in a cyclo-$C_{4-8}$-alkyl group one, two or three ring members optionally are replaced independently of each other by —NH—, >N—($C_{1-6}$-alkyl) (or N-atoms for replacement of —CH< members), O, S, carbonyl, or sulfonyl, with the proviso that two heteroatoms are not directly linked together, and additionally but optionally 2 or 4 hydrogen atoms attached to adjacent ring carbon atoms are replaced to form a double bond or two conjugated double bonds within the ring, either of the double bonds optionally being condensed with an optionally substituted aryl or an optionally substituted 5- or 6-membered hetaryl group, and any of the resulting groups is bound via a saturated or unsaturated carbon atom or a nitrogen atom, and wherein any of the resulting open-chained or cyclic groups independently 1 to 4 hydrogen atoms optionally are replaced by $C_{1-6}$-alkyl or $C_{1-6}$-alkoxy groups, and/or any 1 to 6 hydrogen atoms attached to carbon atoms optionally are replaced by fluorine atoms, or W denotes an optionally substituted aryl or hetaryl group, an optionally substituted cyclo-$C_{3-8}$-alkyl-aryl or cyclo-$C_{3-8}$-alkyl-hetaryl group, wherein the cyclo-$C_{5-8}$-alkyl-submoieties one or two ring members optionally are replaced independently of each other by —NH— (or N-atoms for replacement of —CH< members), >N($C_{1-3}$-alkyl), O, S, carbonyl, or sulfonyl, with the proviso that two heteroatoms are not directly linked together, or if Y is absent W additionally denotes a divalent —(CH$_2$)$_p$— group, wherein p is 2, 3, 4, 5, 6 or 7, attached in relative 1,1-position (geminal) to a carbon atom of group X, including the options:

if p is 3, 4, 5, 6 or 7 it follows that 1 —CH$_2$— group optionally is replaced by O, S, carbonyl, sulfonyl, —NH— or —N($C_{1-6}$-alkyl)-, or if p is 4, 5 or 7 it follows that a —CH$_2$—CH$_2$— group optionally is replaced by —C(O)—O—, —O—C(O)—, —C(O)—NH—, —NH—C(O)—, —C(O)—N($C_{1-6}$-alkyl)-, —N($C_{1-6}$-alkyl)-C(O)—, or —CH=CH—, wherein the double bond optionally is condensed with an aryl or a 5- or 6-membered hetaryl group, a divalent —(CH$_2$)$_q$— group, wherein q is 3, 4, or 5, attached in relative 1,2-position (vicinal) to carbon atoms of group X, including the options:

that 1 —CH$_2$— group optionally is replaced by O, S, carbonyl, sulfonyl, —NH— or —N($C_{1-6}$-alkyl)-, or a —CH$_2$—CH$_2$— group optionally is replaced by —C(O)—O—, —O—C(O)—, —C(O)—NH—, —NH—C(O)—, —C(O)—N($C_{1-6}$-alkyl)-, —N($C_{1-6}$-alkyl)-C(O)—, or that in the resulting 5-, 6- and 7-membered carbocyclic ring 2, 4 or 6 hydrogen atoms optionally are replaced by 1, 2 or 3 bonds to form a partially or fully unsaturated ring with isolated or conjugated double bonds, wherein 1 —CH$_2$— group optionally is replaced by O, S, carbonyl, sulfonyl, —NH— or —N($C_{1-6}$-alkyl)-, and/or one —CH= unit is replaced by —N=, a divalent —(CH$_2$)$_r$— group, wherein r is 5, 6 or 7, attached in relative 1,3-position to carbon atoms as binding sites of group X, including the options:

that in the resulting 8-, 9- or 10-membered carbocyclic ring 2, 4, 6, 8 or 10 hydrogen atoms optionally are replaced by 1, 2, 3, 4 or 5 bonds to form a partially or fully unsaturated ring with isolated or conjugated double bonds, and/or that in the resulting 8-, 9- or 10-membered carbocyclic ring 1 hydrogen atom attached to the carbon atom in position 2 relative to the binding sites of group X and 1 hydrogen atom attached to a carbon atom of the —(CH$_2$)$_r$— group in position 6 or 7 relative to the binding sites of group X optionally are replaced by a bond ($C_0$-bridge) to form a bicyclic ring system condensed with the group X, $R^1$ denotes H, $C_{1-6}$-alkyl, $C_{3-6}$-alkenyl or $C_{3-6}$-alkynyl, any of those groups being optionally substituted by 1 to 3 fluorine, chlorine or bromine atoms, or by a cyano, hydroxy, $C_{1-3}$-alkoxy or cyclo-$C_{3-7}$-alkyl-group, $R^2$ and $R^3$ independently denote H, halogen, $C_{1-6}$-alkyl, $C_{2-6}$-alkenyl, $C_{2-6}$-alkynyl, hydroxy or $C_{1-6}$-alkoxy, any of those $C_{1-6}$-alkyl, $C_{2-6}$-alkenyl or $C_{3-6}$-alkynyl groups being optionally substituted by 1 to 3 fluorine, chlorine or bromine atoms, or by a cyano or cyclo-$C_{3-7}$-alkyl-group, $R^4$ and $R^5$ independently denote H, halogen, $C_{1-6}$-alkyl, $C_{2-6}$-alkenyl, $C_{2-6}$-alkynyl, cyclo-$C_{3-7}$-alkyl, hydroxy or $C_{1-3}$-alkoxy, any of those $C_{1-6}$-alkyl, $C_{2-6}$-alkenyl or $C_{3-6}$-alkynyl groups being optionally substituted by 1 to 3 fluorine, chlorine or bromine atoms, by a cyano, hydroxy, $C_{1-3}$-alkoxy, or cyclo-$C_{3-5}$-alkyl-group, or by a phenyl or pyridyl group both optionally substituted independently by 1, 2 or 3 substituents selected from halogen atoms, $C_{1-6}$-alkyl, cyclo-$C_{3-7}$-alkyl, cyano, hydroxy, $C_{1-6}$-alkoxy, amino, $C_{1-6}$-alkyl-amino, or di-($C_{1-6}$-alkyl)-amino groups, wherein, if not specified otherwise, any alkyl groups or subgroups mentioned hereinbefore are straight-chained or branched, and the isoforms, tautomers, stereoisomers, solvates, hydrates, and the salts thereof, particularly the physiologically acceptable salts thereof with inorganic or organic acids or bases, or the combinations thereof.

TERMS AND DEFINITIONS

The term "aryl" as used herein, either alone or in combination (e.g. as a sub-moiety) with another substituent, if not otherwise specified means either an aromatic monocyclic system or aromatic multicyclic systems containing carbon atoms, for example a phenyl or a naphthyl group. Any of the aryl groups mentioned hereinbefore is optionally substituted, if not otherwise specified.

The term "hetaryl" as used herein, either alone or in combination (e.g. as a sub-moiety) with another substituent, if not otherwise specified denotes five- or six-membered heterocyclic aromatic groups or 5-10 membered, bicyclic hetaryl rings which may contain one, two or three heteroatoms, selected from among oxygen, sulphur and nitrogen, which contain sufficient conjugated double bonds that an aromatic system is formed. The ring may be linked to the molecule through a carbon atom or, if present, through a nitrogen atom. Any of the hetaryl groups mentioned hereinbefore is optionally substituted, if not otherwise specified, including substitution at carbon atoms and/or a nitrogen atom. The following are examples of five- or six-membered heterocyclic aromatic groups:

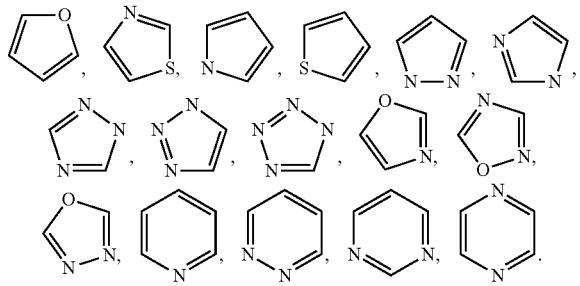

Examples of 5-10-membered bicyclic hetaryl rings include pyrrolizine, indole, indolizine, isoindole, indazole, purine, quinoline, isoquinoline, benzimidazole, benzofuran, benzopyrane, benzothiazole, benzoisothiazole, pyridopyrimidine, pteridine, pyrimidopyrimidine.

The expression "substituted" or "optionally substituted" as used herein, if not otherwise specified, means that any one or more hydrogen atoms attached to the designated carbon or nitrogen atom is or optionally is replaced by a lower-molecular group, provided that the designated atom's normal valence is not exceeded and that the substitution results in a stable compound. In connection with aryl or hetaryl groups this expressions includes at least mono- di- and trisubstitution. Examples of lower-molecular groups regarded as chemically meaningful are groups consisting of 1-200 atoms. Preferably such groups have no negative effect on the pharmacological efficacy of the compounds. For example the groups may comprise:
  straight-chain or branched carbon chains, optionally interrupted by heteroatoms, optionally substituted by rings, heteroatoms or other common functional groups;
  aromatic or non-aromatic ring systems consisting of carbon atoms and optionally heteroatoms, which may in turn be substituted by functional groups;
  a number of aromatic or non-aromatic ring systems consisting of carbon atoms and optionally heteroatoms which may be linked by one or more carbon chains, optionally interrupted by heteroatoms, optionally substituted by heteroatoms or other common functional groups.

More specifically, the expression "substituted" or "optionally substituted" as used herein means substitution with a group selected from the indicated substituents or, if not otherwise specified, with one, two, three, four or more substituents attached to carbon atoms selected from the group consisting of
halogen atoms (fluorine, chlorine, bromine or iodine atoms), $C_{1-6}$-alkyl, $C_{2-6}$-alkenyl, $C_{2-6}$-alkynyl, cyclo-$C_{3-8}$-alkyl, cyclo-$C_{3-7}$-alkenyl, cyano, hydroxy, hydroxy-$C_{1-6}$-alkyl, hydroxy-$C_{3-6}$-alkenyl, hydroxy-$C_{3-6}$-alkynyl, $C_{1-6}$-alkoxy, $C_{1-6}$-alkoxy-$C_{1-6}$-alkyl, $C_{1-6}$-alkoxy-$C_{3-6}$-alkenyl, $C_{1-6}$-alkoxy-$C_{3-6}$-alkynyl, $C_{3-6}$-alkenoxy-$C_{1-6}$-alkyl, $C_{3-6}$-alkenoxy-$C_{3-6}$-alkenyl, $C_{3-6}$-alkenoxy-$C_{3-6}$-alkynyl, $C_{3-6}$-alkynoxy-$C_{1-6}$-alkyl, $C_{3-6}$-alkynoxy-$C_{3-6}$-alkenyl, $C_{3-6}$-alkynoxy-$C_{3-6}$-alkynyl, oxetanyl, tetrahydrofuranyl, tetrahydropyranyl, pyrrolidino, piperidino, thiohydroxy, $C_{1-6}$-alkylthio, $C_{3-6}$-alkenylthio, $C_{3-6}$-alkynylthio, amino, $C_{1-6}$-alkyl-amino, $C_{3-6}$-alkenyl-amino, $C_{3-6}$-alkynyl-amino, di-($C_{1-6}$-alkyl)-amino, di-($C_{3-6}$-alkenyl)-amino, di-($C_{3-6}$-alkynyl)-amino, amino-$C_{1-6}$-alkyl, $C_{1-3}$-alkyl-amino-$C_{1-6}$-alkyl, di-($C_{1-3}$-alkyl)-amino-$C_{1-6}$-alkyl, amino-$C_{3-6}$-alkenyl, $C_{1-3}$-alkyl-amino-$C_{3-6}$-alkenyl, di-($C_{1-3}$-alkyl)-amino-$C_{3-6}$-alkenyl, amino-$C_{3-6}$-alkynyl, $C_{1-3}$-alkyl-amino-$C_{3-6}$-alkynyl, di-($C_{1-3}$-alkyl)-amino-$C_{3-6}$-alkynyl, hydroxycarbonyl, phenyl, phenyl-$C_{1-3}$-alkyl, phenyloxy, phenyl-$C_{1-3}$-alkoxy, phenyloxy-$C_{1-3}$-alkyl, phenylcarbonyl, pyridyl, thiazolyl; pyridylcarbonyl, $C_{1-6}$-alkyl-carbonyl, $C_{2-6}$-alkenyl-carbonyl, $C_{2-6}$-alkynyl-carbonyl, formyl, $C_{1-6}$-alkoxy-carbonyl, $C_{3-6}$-alkenoxy-carbonyl, $C_{3-6}$-alkynoxy-carbonyl, aminocarbonyl, $C_{1-6}$-alkyl-aminocarbonyl, $C_{3-6}$-alkenyl-aminocarbonyl, $C_{3-6}$-alkynyl-aminocarbonyl, di-($C_{1-6}$-alkyl)-aminocarbonyl, di-($C_{3-6}$-alkenyl)-aminocarbonyl, di-($C_{3-6}$-alkynyl)-aminocarbonyl, formylamino, $C_{1-6}$-alkyl-carbonylamino, $C_{2-6}$-alkenyl-carbonylamino, $C_{2-6}$-alkynyl-carbonylamino, formyl-$C_{1-6}$-alkyl-amino, formyl-$C_{3-6}$-alkenyl-amino, formyl-$C_{3-6}$-alkynyl-amino, $C_{1-6}$-alkyl-carbonyl-$C_{1-6}$-alkyl-amino, $C_{2-6}$-alkenyl-carbonyl-$C_{1-6}$-alkyl-amino, $C_{2-6}$-alkynyl-carbonyl-$C_{1-6}$-alkyl-amino, $C_{1-6}$-alkyl-carbonyl-$C_{3-6}$-alkenyl-amino, $C_{2-6}$-alkenyl-carbonyl-$C_{3-6}$-alkenyl-amino, $C_{2-6}$-alkynyl-carbonyl-$C_{3-6}$-alkenyl-amino, $C_{1-6}$-alkyl-carbonyl-$C_{3-6}$-alkynyl-amino, $C_{2-6}$-alkenyl-carbonyl-$C_{3-6}$-alkynyl-amino, $C_{2-6}$-alkynyl-carbonyl-$C_{3-6}$-alkynyl-amino, $C_{1-6}$-alkyl-sulphonyl, $C_{2-6}$-alkenyl-sulphonyl, $C_{2-6}$-alkynyl-sulphonyl, $C_{1-6}$-alkyl-sulphinyl, $C_{2-6}$-alkenyl-sulphinyl, $C_{2-6}$-alkynyl-sulphinyl, $C_{1-6}$-alkyl-sulphonylamino, $C_{2-6}$-alkenyl-sulphonylamino, $C_{2-6}$-alkynyl-sulphonylamino, $C_{1-6}$-alkyl-sulphonyl-$C_{1-6}$-alkylamino, $C_{1-6}$-alkyl-sulphonyl-$C_{3-6}$-alkenylamino, $C_{1-6}$-alkyl-sulphonyl-$C_{3-6}$-alkynylamino, $C_{2-6}$-alkenyl-sulphonyl-$C_{1-6}$-alkylamino, $C_{2-6}$-alkenyl-sulphonyl-$C_{3-6}$-alkenyl amino, $C_{2-6}$-alkenyl-sulphonyl-$C_{3-6}$-alkynylamino, $C_{2-6}$-alkynyl-sulphonyl-$C_{1-6}$-alkylamino, $C_{2-6}$-alkynyl-sulphonyl-$C_{3-6}$-alkenylamino, $C_{2-6}$-alkynyl-sulphonyl-$C_{3-6}$-alkynylamino, aminosulphonyl, $C_{1-6}$-alkylaminosulphonyl, di-($C_{1-6}$-alkyl)-aminosulphonyl, $C_{3-6}$-alkenylaminosulphonyl, di-($C_{3-6}$-alkenyl)-aminosulphonyl, $C_{3-6}$-alkynylaminosulphonyl and di-($C_{3-6}$-alkynyl)-aminosulphonyl groups, while the substituents may be identical or different and wherein any alkyl groups or alkyl sub-moieties optionally are partially or fully fluorinated, e.g. a $CH_3$-substituent or methyl sub-moiety within the substituents mentioned herein is meant to include the corresponding fluoro-analogs such as the $CFH_2$—, $CF_2H$— and $CF_3$— group,
and wherein any phenyl, pyridyl and thiazolyl groups or phenyl-, pyridyl and thiazolyl-submoieties optionally are substituted with 1 or 2 substituents independently of each other selected from fluorine, chlorine, bromine, iodine, $C_{1-3}$-alkyl, $C_{1-3}$-alkoxy, amino, $C_{1-3}$-alkyl-amino, di-($C_{1-3}$-alkyl)-amino $C_{1-3}$-alkylcarbonyl-amino, $C_{1-3}$-alkylcarbonyl-$C_{1-3}$-alkyl-amino, cyano or hydroxy, and with substituents attached to a nitrogen atom selected from the group consisting of
$C_{1-6}$-alkyl, $C_{3-6}$-alkenyl, $C_{3-6}$-alkynyl, cyclo-$C_{3-7}$-alkyl, cyclo-$C_{3-7}$-alkenyl, cyclo-$C_{3-7}$-alkyl-$C_{1-6}$-alkyl, pyrrolidino, piperidino, morpholino, oxetanyl, tetrahydrofuranyl, tetrahydropyranyl, cyano, hydroxy, hydroxy-$C_{1-6}$-alkyl, hydroxy-$C_{3-6}$-alkenyl, hydroxy-$C_{3-6}$-alkynyl, $C_{1-6}$-alkoxy, $C_{1-6}$-alkoxy-$C_{1-6}$-alkyl, $C_{1-6}$-alkoxy-$C_{3-6}$-alkenyl, $C_{1-6}$-alkoxy-$C_{3-6}$-alkynyl, $C_{3-6}$-alkenoxy-$C_{1-6}$-alkyl, $C_{3-6}$-alkenoxy-$C_{3-6}$-alkenyl, $C_{3-6}$-alkenoxy-$C_{3-6}$-alkynyl, $C_{3-6}$-alkynoxy-$C_{1-6}$-alkyl, $C_{3-6}$-alkynoxy-$C_{3-6}$-alkenyl, $C_{3-6}$-alkynoxy-$C_{3-6}$-alkynyl, amino-$C_{1-6}$-alkyl, $C_{1-3}$-alkyl-amino-$C_{1-6}$-alkyl, di-($C_{1-3}$-alkyl)-amino-$C_{1-6}$-alkyl, amino-$C_{3-6}$-alkenyl, $C_{1-3}$-alkyl-amino-$C_{3-6}$-alkenyl, di-($C_{1-3}$-alkyl)-amino-$C_{3-6}$-alkenyl, amino-$C_{3-6}$-alkynyl, $C_{1-3}$-alkyl-amino-$C_{3-6}$-alkynyl, di-($C_{1-3}$-alkyl)-amino-$C_{3-6}$-alkynyl, hydroxycarbonyl, phenyl, phenyl-$C_{1-6}$-alkyl, phenylcarbonyl, pyridyl, pyridylcarbonyl, $C_{1-6}$-alkyl-carbonyl, $C_{2-6}$-alkenyl-carbonyl, $C_{2-6}$-alkynyl-carbonyl, $C_{1-6}$-alkoxy-carbonyl, $C_{3-6}$-alkenoxy-carbonyl, $C_{3-6}$-alkynoxy-carbonyl, aminocarbonyl, $C_{1-6}$-alkyl-aminocarbonyl, $C_{3-6}$-alkenyl-aminocarbonyl, $C_{3-6}$-alkynyl-aminocarbonyl, di-($C_{1-6}$-alkyl)-aminocarbonyl, di-($C_{3-6}$-alkenyl)-aminocarbonyl, di-($C_{3-6}$-alkynyl)-aminocarbonyl, $C_{1-6}$-alkyl-sulphonyl, $C_{2-6}$-alkenyl-sulphonyl, $C_{2-6}$-alkynyl-sulphonyl, $C_{1-6}$-alkyl-sulphinyl, $C_{2-6}$-alkenyl-sulphinyl, $C_{2-6}$-alkynyl-sulphinyl, aminosulphonyl, $C_{1-6}$-alkylaminosulphonyl, di-($C_{1-6}$-alkyl)-aminosulphonyl, $C_{3-6}$-alkenylaminosulphonyl, di-($C_{3-6}$-alkenyl)-aminosulphonyl, $C_{3-6}$-alkynylaminosulphonyl and di-($C_{3-6}$-alkynyl)-aminosulphonyl groups, while the substituents may be identical or different and wherein any alkyl groups or alkyl sub-moieties optionally are partially or fully fluorinated, e.g. a $CH_3$— substituent or methyl sub-moiety within the substituents mentioned herein is meant to include the corresponding fluoro-analogs such as the $CFH_2$—, $CF_2H$— and $CF_3$— group,
and wherein any of the di-($C_{1-3}$-alkyl)-amino or di-($C_{1-6}$-alkyl)-amino moieties may form optionally with the nitrogen atom a 4 to 8 membered ring system,
and wherein any phenyl and pyridyl groups or phenyl- and pyridyl-submoieties optionally are substituted with 1 or 2 substituents independently of each other selected from fluorine, chlorine, bromine, iodine, $C_{1-3}$-alkyl, $C_{1-3}$-alkoxy, amino, $C_{1-3}$-alkyl-amino, $C_{1-3}$-alkylcarbonyl-amino, cyano or hydroxy.

The expressions "prevention", "prophylaxis", "prophylactic treatment" or "preventive treatment" used herein should be understood synonymous and in the sense that the risk to develop a condition mentioned hereinbefore is reduced, especially in a patient having elevated risk for said conditions or a corresponding anamnesis, e.g. elevated risk of developing metabolic disorder such as diabetes or obesity or a CNS-related disorder mentioned herein. Thus the expression "prevention of a disease" as used herein means the management and care of an individual at risk of developing the disease prior to the clinical onset of the disease. The purpose of prevention is to combat the development of the disease, condition or disorder, and includes the administration of the active compounds to prevent or delay the onset of the symptoms or complications and to prevent or delay the development of related diseases, conditions or disorders. Success of said preventive treatment is reflected statistically by reduced incidence of said condition within a patient population at risk for this condition in comparison to an equivalent patient population without preventive treatment.

The expression "treatment" or "therapy" means therapeutic treatment of patients having already developed one or more of said conditions in manifest, acute or chronic form, including symptomatic treatment in order to relieve symptoms of the specific indication or causal treatment in order to reverse or partially reverse the condition or to delay the progression of the indication as far as this may be possible, depending on the condition and the severity thereof. Thus the expression "treatment of a disease" as used herein means the management and care of a patient having developed the disease, condition or disorder. The purpose of treatment is to combat the disease, condition or disorder. Treatment includes the administration of the active compounds to eliminate or control the disease, condition or disorder as well as to alleviate the symptoms or complications associated with the disease, condition or disorder.

PREFERRED EMBODIMENTS OF THE INVENTION

Further preferred embodiments of the invention are characterized by the following definitions:

a) Definitions ($a^i$) for X in the order of preference, ascending from preferably ($a^1$) to more preferably ($a^2$) up to most preferably ($a^6$):

($a^1$): According to a first preferred embodiment, X is defined as mentioned hereinbefore under the broadest/first embodiment of the invention E-0.

($a^2$): According to a second preferred embodiment,

X denotes a divalent 4- to 8-membered monocylic, 7- to 10-membered spirocyclic or 6- to 12-membered bicyclic saturated, partially or fully unsaturated group selected from a carbocycle, a monoaza-heterocycle and a diaza-heterocycle, which is linked to the adjacent groups via carbon atoms or, if present, via nitrogen atoms, e.g. via one carbon and one nitrogen atom or via both nitrogen atoms, wherein 1 to 2 —$CH_2$— groups optionally are replaced independently of each other by O, S, carbonyl, or sulfonyl, with the proviso that two heteroatoms are not directly linked together, and/or wherein 1 double bond optionally is condensed with an aryl or a 5- or 6-membered hetaryl group, and/or wherein in all groups falling under the above definition of X one or two carbon atoms optionally and independently are substituted by halogen atoms, $C_{1-6}$-alkyl, $C_{2-6}$-alkenyl, $C_{2-6}$-alkynyl, cyclo-$C_{3-7}$-alkenyl, phenyl, cyano, hydroxy, hydroxy-$C_{1-6}$-alkyl, $C_{1-6}$-alkoxy, $C_{1-6}$-alkoxy-$C_{1-6}$-alkyl, $C_{1-6}$-alkoxy-$C_{1-6}$-alkyl-carbonyl, formyl, aminocarbonyl, $C_{1-6}$-alkyl-aminocarbonyl, $C_{3-6}$-alkenyl-aminocarbonyl, $C_{3-6}$-alkynyl-aminocarbonyl, di-($C_{1-6}$-alkyl)-aminocarbonyl, di-($C_{3-6}$-alkenyl)-aminocarbonyl, di-($C_{3-6}$-alkynyl)-aminocarbonyl, formylamino, $C_{1-6}$-alkyl-carbonylamino, $C_{1-6}$-alkyl-carbonyl-($C_{1-3}$-alkyl)-amino $C_{2-6}$-alkenyl-carbonylamino or $C_{2-6}$-alkynyl-carbonylamino groups, while the substituents may be identical or different, and/or, wherein one ring member nitrogen atom optionally is substituted by a $C_{1-3}$-alkyl, $C_{1-3}$-alkoxy, $C_{1-3}$-alkoxy-$C_{1-3}$-alkyl, $C_{1-3}$-alkyl-carbonyl, $C_{1-3}$-alkoxy-carbonyl or $C_{1-3}$-alkyl-sulphonyl group.

(a³): According to a third preferred embodiment,

X denotes a divalent phenyl group or a group selected from formulas (II) to (XIII),

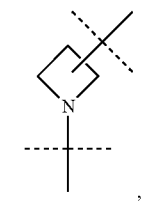
(II)

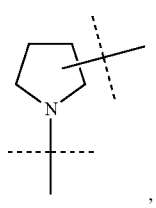
(III)

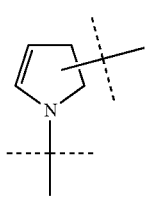
(IV)

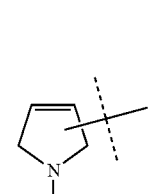
(V)

(VI)

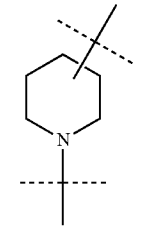
(VII)

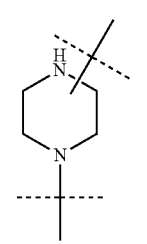

-continued

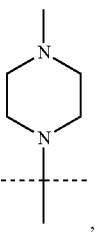
(VIII)

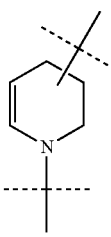
(IX)

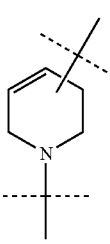
(X)

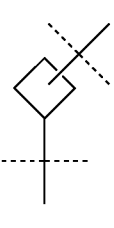
(XI)

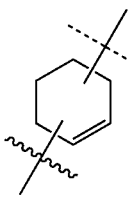
(XII)

(XIII)

wherein 1 —CH$_2$— group optionally is replaced by O, S, carbonyl, or sulfonyl, with the proviso that two heteroatoms are not directly linked together, and/or wherein a double bond, if present, optionally is condensed with an aryl or a 5- or 6-membered hetaryl group, and/or wherein in all groups falling under the above definition of X one or two carbon atoms optionally and independently are substituted by halogen atoms, C$_{1-6}$-alkyl, C$_{2-6}$-alkenyl, C$_{2-6}$-alkynyl, cyclo-C$_{3-7}$-alkyl, cyclo-C$_{3-7}$-alkenyl, phenyl, cyano, hydroxy, hydroxy-$C_{1-6}$-alkyl, $C_{1-6}$-alkoxy, $C_{1-6}$-alkoxy-$C_{1-6}$-alkyl, $C_{1-6}$-alkoxy-$C_{1-6}$-alkyl-carbonyl, formyl, aminocarbonyl, $C_{1-6}$-alkyl-aminocarbonyl, $C_{3-6}$-alkenyl-aminocarbonyl, $C_{3-6}$-alkynyl-aminocarbonyl, di-($C_{1-6}$-alkyl)-aminocarbonyl, di-($C_{3-6}$-alkenyl)-aminocarbonyl, di-($C_{3-6}$-alkynyl)-aminocarbonyl, formylamino, $C_{1-6}$-alkyl-carbonylamino, $C_{1-6}$-alkyl-carbonyl-($C_{1-3}$-alkyl)-amino $C_{2-6}$-alkenyl-carbonylamino or $C_{2-6}$-alkynyl-carbonylamino groups, while the substituents may be identical or different, and/or, wherein one ring member nitrogen atom, if present, optionally is substituted by a $C_{1-3}$-alkyl, cyclo-$C_{3-6}$-alkyl, $C_{1-3}$-alkoxy, $C_{1-3}$-alkoxy-$C_{1-3}$-alkyl, $C_{1-3}$-alkyl-carbonyl, $C_{1-3}$-alkoxy-carbonyl or $C_{1-3}$-alkyl-sulphonyl group.

($a^4$): According to a fourth preferred embodiment,
X denotes a divalent phenyl group or a group selected from formulas (II-XIII) mentioned under embodiment ($a^3$),
which is linked to the adjacent groups of formula (I) via carbon atoms or, if present, via nitrogen atoms, e.g. via one carbon and one nitrogen atom or via both nitrogen atoms, wherein 1 —$CH_2$— group optionally is replaced by O, S, carbonyl, or sulfonyl, with the proviso that two heteroatoms are not directly linked together, and/or wherein a double bond, if present, optionally is condensed with a phenyl, naphthyl, pyridyl, pyrimidinyl, pyrazinyl, pyridazinyl, pyrazolyl, imidazolyl, triazolyl, furyl, thienyl, oxazolyl, thiazolyl group, and/or wherein in all groups falling under the above definition of X one or two carbon atoms optionally and independently are substituted by halogen atoms, $C_{1-6}$-alkyl, $C_{2-6}$-alkenyl, $C_{2-6}$-alkynyl, cyclo-$C_{3-7}$-alkenyl, cyano, hydroxy, hydroxy-$C_{1-6}$-alkyl, $C_{1-6}$-alkoxy, $C_{1-6}$-alkoxy-$C_{1-6}$-alkyl, $C_{1-6}$-alkoxy-$C_{1-6}$-alkyl-carbonyl, formyl, aminocarbonyl, $C_{1-6}$-alkyl-aminocarbonyl, $C_{3-6}$-alkenyl-aminocarbonyl, $C_{3-6}$-alkynyl-aminocarbonyl, di-($C_{1-6}$-alkyl)-aminocarbonyl, di-($C_{3-6}$-alkenyl)-aminocarbonyl, di-($C_{3-6}$-alkynyl)-aminocarbonyl, formylamino, $C_{1-6}$-alkyl-carbonylamino, $C_{1-6}$-alkyl-carbonyl-($C_{1-3}$-alkyl)-amino $C_{2-6}$-alkenyl-carbonylamino or $C_{2-6}$-alkynyl-carbonylamino groups, while the substituents may be identical or different, and/or, wherein one ring member nitrogen atom, if present, optionally is substituted by a $C_{1-3}$ alkyl, cyclo $C_{3-6}$ alkyl, $C_{1-3}$-alkoxy, $C_{1-3}$-alkoxy-$C_{1-3}$-alkyl, $C_{1-3}$-alkyl-carbonyl, $C_{1-3}$-alkoxy-carbonyl or $C_{1-3}$-alkyl-sulphonyl group.

($a^5$): According to a fifth preferred embodiment,
X denotes a group selected from formulas (II), (Ill), (VI) or (XIII) mentioned under embodiment ($a^3$),
wherein 1 —$CH_2$— group optionally is replaced independently of each other by O or carbonyl,
wherein one or two carbon atoms optionally and independently are substituted by halogen atoms, $C_{1-6}$-alkyl, $C_{2-6}$-alkenyl, $C_{2-6}$-alkynyl, cyclo-$C_{3-7}$-alkenyl, phenyl, cyano, hydroxy, hydroxy-$C_{1-6}$-alkyl, $C_{1-6}$-alkoxy, $C_{1-6}$-alkoxy-$C_{1-6}$-alkyl, $C_{1-6}$-alkoxy-$C_{1-6}$-alkyl-carbonyl, formyl, aminocarbonyl, $C_{1-6}$-alkyl-aminocarbonyl, $C_{3-6}$-alkenyl-amino-carbonyl, $C_{3-6}$-alkynyl-aminocarbonyl, di-($C_{1-6}$-alkyl)-aminocarbonyl, di-($C_{3-6}$-alkenyl)-aminocarbonyl, di-($C_{3-6}$-alkynyl)-aminocarbonyl, formylamino, $C_{1-6}$-alkyl-carbonylamino, $C_{1-6}$-alkyl-carbonyl-($C_{1-3}$-alkyl)-amino $C_{2-6}$-alkenyl-carbonylamino or $C_{2-6}$-alkynyl-carbonylamino groups, while the substituents may be identical or different.

($a^6$): According to a sixth preferred embodiment,
X denotes a group selected from formulas (II), (III), (VI), (VII) or (XIII) mentioned under embodiment ($a^3$),
wherein 1 —$CH_2$— group optionally is replaced independently of each other by O, S, carbonyl, or sulfonyl, with the proviso that two heteroatoms are not directly linked together,
wherein one or two carbon atoms optionally and independently are substituted by halogen atoms, $C_{1-6}$-alkyl, $C_{2-6}$-alkenyl, $C_{2-6}$-alkynyl, cyclo-$C_{3-7}$-alkenyl, phenyl, cyano, hydroxy, hydroxy-$C_{1-6}$-alkyl, $C_{1-6}$-alkoxy, $C_{1-6}$-alkoxy-$C_{1-6}$-alkyl, $C_{1-6}$-alkoxy-$C_{1-6}$-alkyl-carbonyl, formyl, aminocarbonyl, $C_{1-6}$-alkyl-aminocarbonyl, $C_{3-6}$-alkenyl-amino-carbonyl, $C_{3-6}$-alkynyl-aminocarbonyl, di-($C_{1-6}$-alkyl)-aminocarbonyl, di-($C_{3-6}$-alkenyl)-aminocarbonyl, di-($C_{3-6}$-alkynyl)-aminocarbonyl, formylamino, $C_{1-6}$-alkyl-carbonylamino, $C_{1-6}$-alkyl-carbonyl-($C_{1-3}$-alkyl)-amino $C_{2-6}$-alkenyl-carbonylamino or $C_{2-6}$-alkynyl-carbonylamino groups, while the substituents may be identical or different,
and/or one ring member nitrogen atom is substituted by $C_{1-6}$-alkyl, $C_{3-6}$-alkenyl, $C_{3-6}$-alkynyl, cyclo-$C_{3-7}$-alkyl or cyclo-$C_{3-7}$-alkenyl.

b) Definitions ($b^i$) for Y in the order of preference, ascending from preferably ($b^1$) to more preferably ($b^2$) up to most preferably ($b^7$):

($b^1$): According to a first preferred embodiment Y is defined as mentioned hereinbefore under the broadest/first embodiment of the invention E-0.

($b^2$): According to a second preferred embodiment,
Y is absent or denotes a —$(CH_2)_n$— group, wherein n is 1, 2, 3, 4, 5 or 6 and wherein 1 —$CH_2$— group optionally is replaced by O, S, carbonyl or —NH—, or
wherein 1 —$CH_2$— group is replaced by O, S or —NH—, and additionally a second —$CH_2$— group is replaced by carbonyl, or
wherein 1 —$CH_2$— group is replaced by O, S or —NH—, and additionally a —$CH_2$—$CH_2$— subgroup is replaced by —C(O)—O—, —O—C(O)—, —C(O)—NH—, or —NH—C(O)—, and
wherein any hydrogen atom of the —NH— groups mentioned hereinbefore optionally and independently is replaced by a $C_{3-6}$-cycloalkyl or phenyl group, or by a straight-chained or branched $C_{1-6}$-alkyl, phenyl-$C_{1-6}$-alkyl, $C_{1-6}$-alkyl-carbonyl, or $C_{1-6}$-alkyl-sulphonyl group, and/or
wherein 1 or 2 hydrogen atoms attached to carbon atoms optionally are replaced by halogen atoms, trifluoromethyl, $C_{1-6}$-alkyl, $C_{2-6}$-alkenyl, $C_{2-6}$-alkynyl, $C_{3-6}$-cycloalkyl, phenyl, phenyl-$C_{1-3}$-alkyl, hydroxy, hydroxy-$C_{1-6}$-alkyl, $C_{1-6}$-alkoxy, $C_{1-3}$-alkoxy-$C_{1-3}$-alkyl, $C_{1-6}$-alkyl-carbonyl, $C_{1-6}$-alkoxy-carbonyl, $C_{1-6}$-alkyl-carbonylamino, $C_{1-6}$-alkyl-carbonyl-($C_{1-3}$-alkyl)-amino, $C_{1-3}$-alkyl-aminocarbonyl, di-($C_{1-3}$-alkyl)-aminocarbonyl or $C_{1-6}$-alkyl-sulphonyl groups, while the substituents may be identical or different, or 2 geminal hydrogen atoms are replaced by a —$(CH_2)_m$— bridge, wherein m is 2, 3, 4, or 5.

($b^3$): According to a third preferred embodiment,
Y is absent or denotes a —$(CH_2)_n$— group, wherein n is 1, 2, 3, 4, 5 or 6 and wherein 1 —$CH_2$— group optionally is replaced by O, carbonyl or —NH—, or
wherein 1 —$CH_2$— group is replaced by O or —NH—, and additionally a second —$CH_2$— group is replaced by carbonyl, or
wherein 1 —$CH_2$— group is replaced by O and additionally a —$CH_2$—$CH_2$— subgroup is replaced by —C(O)—NH—, or —NH—C(O)—, and wherein any hydrogen atom of the —NH— groups mentioned hereinbefore optionally and independently is replaced by a $C_{3-6}$-cycloalkyl or phenyl group, or by a straight-chained or branched $C_{1-4}$-alkyl, phenyl-$C_{1-3}$-alkyl, $C_{1-4}$-alkyl-carbonyl, or $C_{1-4}$-alkyl-sulphonyl group, and/or wherein 1 or 2 hydrogen atoms attached to carbon atoms optionally are replaced by halogen atoms, trifluoromethyl, $C_{1-4}$-alkyl, $C_{2-4}$-alkenyl, $C_{3-6}$-cycloalkyl, phenyl, phenyl-$C_{1-3}$ alkyl, hydroxy, hydroxy-$C_{1-3}$-alkyl, $C_{1-3}$-alkoxy, $C_{1-3}$-alkoxy-$C_{1-3}$-alkyl, $C_{1-4}$-alkyl-carbonyl, $C_{1-4}$-alkoxy-carbonyl, $C_{1-4}$-alkyl-carbonylamino, $C_{1-4}$-alkyl-carbonyl-($C_{1-3}$-alkyl)-amino, $C_{1-3}$-alkyl-aminocarbonyl, or di-($C_{1-3}$-alkyl)-aminocarbonyl groups, while the substituents may be identical or different, or 2 geminal hydrogen atoms are replaced by a —$(CH_2)_m$— bridge, wherein m is 2, 3, 4, or 5.

($b^4$): According to a fourth preferred embodiment,
Y is absent.

($b^5$): According to a fifth preferred embodiment,
Y denotes a —$(CH_2)_n$— group, wherein n is 1, 2, 3, 4, 5 or 6 and wherein 1 —$CH_2$— group optionally is replaced by O, carbonyl or —NH—, or wherein 1 —$CH_2$— group is replaced by O or —NH—, and additionally a second —$CH_2$— group is replaced by carbonyl, or wherein 1 —$CH_2$— group is replaced by O and additionally a —$CH_2$—$CH_2$— subgroup is replaced by —C(O)—NH—, or —NH—C(O)—, and wherein any hydrogen atom of the —NH— groups mentioned hereinbefore optionally and independently is replaced by a $C_{3-6}$-cycloalkyl or phenyl group, or by a straight-chained or branched $C_{1-4}$-alkyl, phenyl-$C_{1-3}$-alkyl, or $C_{1-3}$-alkyl-carbonyl, and/or wherein 1 or 2 hydrogen atoms attached to carbon atoms optionally are independently replaced by F, Cl, $C_{1-4}$-alkyl or trifluoromethyl, or 1 hydrogen atom attached to a carbon atom optionally is replaced by $C_{3-6}$-cycloalkyl, phenyl, phenyl-$C_{1-3}$-alkyl, hydroxy, or $C_{1-3}$-alkoxy groups, while the substituents may be identical or different, or 2 geminal hydrogen atoms are replaced by a —$(CH_2)_m$— bridge, wherein m is 2, 3, or 4.

($b^6$): According to a sixth preferred embodiment,
Y denotes a $C_{1-2}$-alkyl-linker wherein 1 —$CH_2$— group optionally is replaced by O.

($b^7$): According to a seventh preferred embodiment,
Y denotes a carbonyl group.

c) Definitions ($c^i$) for W in the order of preference, ascending from preferably ($c^1$) to more preferably ($c^2$) up to most preferably ($c^4$):

($c^1$): According to a first preferred embodiment W is defined as mentioned hereinbefore under the broadest/first embodiment of the invention E-0.

($c^2$): According to a second preferred embodiment,
W denotes H or an optionally substituted straight-chained or branched $C_{1-6}$-alkyl, $C_{2-6}$-alkenyl or $C_{2-6}$-alkynyl group, wherein 1 or 2 methyl groups optionally are replaced by optionally substituted phenyl groups or an optionally substituted cyclo-$C_{3-9}$-alkyl group, wherein independently in a cyclo-$C_{4-7}$-alkyl group 2 hydrogen atoms attached to adjacent carbon atoms optionally are replaced to form a double bond within the ring, which optionally is condensed with an optionally substituted aryl or an optionally substituted 5- or 6-membered hetaryl group, and the resulting group is bound via a saturated or unsaturated carbon atom, or in a cyclo-$C_{4-9}$-alkyl group 2 hydrogen atoms attached to the same carbon atom (relative 1,1-position) optionally are replaced by a $C_{2-5}$-alkylenyl bridge, or 2 hydrogen atoms attached to carbon atoms in relative 1,2-, 1,3- or 1,4-position optionally are replaced by a $C_{1-5}$-alkylenyl bridge, wherein any of the resulting polycyclic groups one or two —$CH_2$— groups optionally are replaced by —NH—, >N—($C_{1-6}$-alkyl), (or N-atoms for replacement of —CH< members), O, or carbonyl, and/or two —$CH_2$— groups in relative 1,3-position of a $C_{4-5}$-alkylenyl bridge optionally are replaced by O atoms, and/or 2 hydrogen atoms attached to adjacent carbon atoms within a $C_{4-5}$-alkylenyl bridge optionally are replaced to form a double bond, which optionally is condensed with an optionally substituted aryl or an optionally substituted 5- or 6-membered hetaryl group, and/or in a cyclo-$C_{4-8}$-alkyl group one, two or three ring members optionally are replaced independently of each other by —NH—, >N—($C_{1-6}$-alkyl), (or N-atoms for replacement of —CH< members), O, or carbonyl, with the proviso that two heteroatoms are not directly linked together, and additionally but optionally 2 or 4 hydrogen atoms attached to adjacent ring carbon atoms are replaced to form a double bond or two conjugated double bonds within the ring, either of the double bonds optionally being condensed with an optionally substituted aryl or an optionally substituted 5- or 6-membered hetaryl group, and any of the resulting groups is bound via a saturated or unsaturated carbon atom or a nitrogen atom, and wherein any of the resulting open-chained or cyclic groups independently 1 to 3 hydrogen atoms optionally are replaced by $C_{1-4}$-alkyl or $C_{1-4}$-alkoxy groups, and/or any 1 to 6 hydrogen atoms attached to carbon atoms optionally are replaced by fluorine atoms, or W denotes an optionally substituted aryl or hetaryl group, an optionally substituted cyclo-$C_{3-8}$-alkyl-aryl or cyclo-$C_{3-8}$-alkyl-hetaryl group, wherein the cyclo-$C_{5-8}$-alkyl-submoieties one or two ring members optionally are replaced independently of each other by —NH— (or N-atoms for replacement of —CH< members), O, or carbonyl, with the proviso that two heteroatoms are not directly linked together, or if Y is absent W additionally denotes a divalent —$(CH_2)_p$— group, wherein p is 2, 3, 4, or 5, attached in relative 1,1-position (geminal) to a carbon atom of group X, including the options:

if p is 3, 4, or 5 it follows that 1 —$CH_2$— group optionally is replaced by O, carbonyl, —NH— or —N($C_{1-6}$-alkyl)-, or if p is 4 or 5 it follows that a —$CH_2$—$CH_2$— group optionally is replaced by —C(O)—NH—, —NH—C(O)—, —C(O)—N($C_{1-6}$-alkyl)-, —N($C_{1-6}$-alkyl)-C(O)—, or —CH═CH—, wherein the double bond optionally is condensed with an aryl or a 5- or 6-membered hetaryl group, a divalent —$(CH_2)_q$— group, wherein q is 3, or 4 attached in relative 1,2-position (vicinal) to carbon atoms of group X, including the options:

that 1 —$CH_2$— group optionally is replaced by O, carbonyl, —NH— or —N($C_{1-6}$-alkyl)-, or a —$CH_2$—$CH_2$— group optionally is replaced by —C(O)—NH—, —NH—C(O)—, —C(O)—N($C_{1-6}$-alkyl)-, —N($C_{1-6}$-alkyl)-C(O)—, or that in the resulting 5- or 6-membered carbocyclic ring 2, 4 or, in case of the 6-membered ring, also 6 hydrogen atoms optionally are replaced by 1, 2 or 3 bonds to form a partially or fully unsaturated ring with isolated or conjugated double bonds, wherein 1 —CH$_2$— group optionally is replaced by O, S, carbonyl, —NH— or —N(C$_{1-6}$-alkyl)-, and/or one —CH= unit is replaced by —N=, a divalent —(CH$_2$)$_7$— group, attached in relative 1,3-position to carbon atoms as binding sites of group X, including the options:
that in the resulting 10-membered carbocyclic ring 2, 4, 6, 8 or 10 hydrogen atoms optionally are replaced by 1, 2, 3, 4 or 5 bonds to form a partially or fully unsaturated ring with isolated or conjugated double bonds, and/or
that in the resulting 10-membered carbocyclic ring 1 hydrogen atom attached to the carbon atom in position 2 relative to the binding sites of group X and 1 hydrogen atom attached to a carbon atom of the —(CH$_2$)$_r$— group in position 7 relative to the binding sites of group X optionally are replaced by a bond (C$_0$-bridge) to form a bicyclic ring system condensed with the group X,
e.g. X and W together denote the group

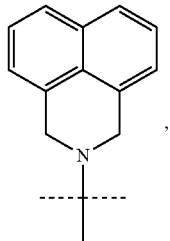

wherein any aryl groups or subgroups mentioned above in the definition of W are selected from optionally substituted phenyl, naphthyl, and tetrahydronaphthyl groups, and wherein any hetaryl groups or subgroups mentioned above in the definition of W are selected from optionally substituted pyridyl, pyrimidinyl, pyrazinyl, pyridazinyl, pyrazolyl, imidazolyl, triazolyl, furyl, thienyl, oxazolyl, benzoxazolyl, thiazolyl, benzthiazolyl, indolyl, indolinyl, benzimidazolyl, tetrahydrobenzimidazolyl, tetrahydrocyclopentaimidazolyl, indazolyl, tetrahydroindazolyl, tetrahydrocyclopentapyrazolyl, hexahydrocycloheptapyrazolyl, benztriazolyl, quinolyl, tetrandyroquinolinly, isoquinolyl, tetrandyroisoquinolinly, cinnolyl, quinoxazolyl and benzpyrimidinyl groups, wherein the expression "substituted" or "optionally substituted" as used herein has the same meaning as within embodiment (c$^1$).

(c$^3$): According to a third preferred embodiment,

W denotes H or an optionally substituted straight-chained or branched C$_{1-6}$-alkyl, C$_{2-6}$-alkenyl or C$_{2-6}$-alkynyl group, wherein 1 or 2 methyl groups optionally are replaced by optionally substituted phenyl groups or an optionally substituted cyclo-C$_{3-9}$-alkyl group, wherein independently
in a cyclo-C$_{4-7}$-alkyl group 2 hydrogen atoms attached to adjacent carbon atoms optionally are replaced to form a double bond within the ring, which optionally is condensed with an optionally substituted aryl or an optionally substituted 5- or 6-membered hetaryl group, and the resulting group is bound via a saturated or unsaturated carbon atom, or in a cyclo-C$_{4-9}$-alkyl group 2 hydrogen atoms attached to the same carbon atom (relative 1,1-position) optionally are replaced by a C$_{2-5}$-alkylenyl bridge, or 2 hydrogen atoms attached to carbon atoms in relative 1,2-, 1,3- or 1,4-position optionally are replaced by a C$_{1-5}$-alkylenyl bridge, wherein any of the resulting polycyclic groups one or two —CH$_2$— groups optionally are replaced by —NH—, >N—(C$_{1-6}$-alkyl), (or N-atoms for replacement of —CH< members), O, or carbonyl, and/or two —CH$_2$— groups in relative 1,3-position of a C$_{4-5}$-alkylenyl bridge optionally are replaced by O atoms, and/or 2 hydrogen atoms attached to adjacent carbon atoms within a C$_{4-5}$-alkylenyl bridge optionally are replaced to form a double bond, which optionally is condensed with an optionally substituted aryl or an optionally substituted 5- or 6-membered hetaryl group, and/or in a cyclo-C$_{4-8}$-alkyl group, two or three ring members optionally are replaced independently of each other by —NH—, >N—(C$_{1-6}$-alkyl), (or N-atoms for replacement of a —CH< members), O, or carbonyl, with the proviso that two heteroatoms are not directly linked together, and additionally but optionally 2 or 4 hydrogen atoms attached to adjacent ring carbon atoms are replaced to form a double bond or two conjugated double bonds within the ring, either of the double bonds optionally being condensed with an optionally substituted aryl or an optionally substituted 5- or 6-membered hetaryl group, and any of the resulting groups is bound via a saturated or unsaturated carbon atom or a nitrogen atom, and wherein any of the resulting open-chained or cyclic groups independently 1 to 3 hydrogen atoms optionally are replaced by C$_{1-4}$-alkyl or C$_{1-4}$-alkoxy groups, and/or any 1 to 6 hydrogen atoms attached to carbon atoms optionally are replaced by fluorine atoms, or W denotes an optionally substituted aryl or hetaryl group, an optionally substituted cyclo-C$_{3-6}$-alkyl-aryl or cyclo-C$_{3-6}$-alkyl-hetaryl group, wherein the cyclo-C$_{5-6}$-alkyl-submoieties one or two ring members optionally are replaced independently of each other by —NH— (or a N-atom for replacement of a —CH< member), O, or carbonyl, with the proviso that two heteroatoms are not directly linked together, or if Y is absent W additionally denotes
a divalent —(CH$_2$)$_p$— group, wherein p is 2, 3, 4, or 5, attached in relative 1,1-position (geminal) to a carbon atom of group X, including the options:
if p is 3, 4, or 5 it follows that 1 —CH$_2$— group optionally is replaced by O, —NH— or —N(C$_{1-4}$-alkyl)-, or
if p is 4 or 5 it follows that a —CH$_2$—CH$_2$— group optionally is replaced by —C(O)—NH—, —NH—C(O)—, —C(O)—N(C$_{1-4}$-alkyl)-, —N(C$_{1-4}$-alkyl)-C(O)—, or —CH=CH—, wherein the double bond optionally is condensed with an aryl or a 5- or 6-membered hetaryl group, a divalent —(CH$_2$)$_q$— group, wherein q is 3 or 4 attached in relative 1,2-position (vicinal) to carbon atoms of group X, including the options:
a —CH$_2$—CH$_2$— group optionally is replaced by —C(O)—NH—, —NH—C(O)—, —C(O)—N(C$_{1-6}$-alkyl)-, —N(C$_{1-6}$-alkyl)-C(O)—, or
that in the resulting 5- or 6-membered carbocyclic ring 2, 4 or, in case of the 6-membered ring, also 6 hydrogen atoms optionally are replaced by 1, 2 or 3 bonds to form a partially or fully unsaturated ring with isolated or conjugated double bonds, wherein 1 —CH$_2$— group optionally is replaced by O, —NH— or —N($C_{1-6}$-alkyl)-, and/or one —CH= unit is replaced by —N=,
the trivalent group

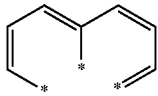

attached in relative 1,2,3-position to carbon atoms * as binding sites of group X,
wherein any aryl groups or aryl-subgroups mentioned above in the definition of W are selected from optionally substituted phenyl, naphthyl, and tetrahydronaphthyl groups, and
wherein any hetaryl groups or hetaryl-subgroups mentioned above in the definition of W are selected from optionally substituted pyridyl, pyrimidinyl, pyrazinyl, pyridazinyl, pyrazolyl, imidazolyl, triazolyl, furyl, thienyl, oxazolyl, benzoxazolyl, thiazolyl, benzthiazolyl, indolyl, indolinyl, benzimidazolyl, tetrahydrobenzimidazolyl, tetrahydrocyclopentaimidazolyl, indazolyl, tetrahydroindazolyl, tetrahydrocyclopentapyrazolyl, hexahydrocycloheptapyrazolyl, benztriazolyl, quinolyl, tetrandyroquinolinly, isoquinolyl, tetrandyroisoquinolinly, cinnolyl, quinoxazolyl and benzpyrimidinyl groups,
wherein the expression "optionally substituted" means that 1, 2, 3 or 4 hydrogen atoms of the respective group independently are optionally replaced by substituents selected from fluorine, chlorine, bromine and iodine atoms, by $C_{1-6}$-alkyl, trifluoromethyl, $C_{2-6}$-alkenyl, $C_{2-6}$-alkynyl, cyclo-$C_{3-7}$-alkyl, cyclo-$C_{3-7}$-alkenyl, cyano, hydroxy, hydroxy-$C_{1-6}$-alkyl, $C_{1-6}$-alkoxy, $C_{1-6}$-alkoxy-$C_{1-6}$-alkyl, $C_{1-6}$-alkoxy-$C_{1-6}$-alkyl-carbonyl, formyl, amino, $C_{1-6}$-alkyl-amino, ($C_{1-6}$-alkyl)$_2$-amino, phenylamino, N-phenyl-N—($C_{1-6}$-alkyl)-amino, pyrrolidino, piperidino, aminocarbonyl, $C_{1-6}$-alkyl-aminocarbonyl, $C_{3-6}$-alkenyl-aminocarbonyl, $C_{3-6}$-alkynyl-aminocarbonyl, di-($C_{1-6}$-alkyl)-aminocarbonyl, di-($C_{3-6}$-alkenyl)-aminocarbonyl, di-($C_{3-6}$-alkynyl)-aminocarbonyl, formylamino, $C_{1-6}$-alkyl-carbonylamino, $C_{1-6}$-alkyl-carbonyl-($C_{1-3}$-alkyl)-amino $C_{2-6}$-alkenyl-carbonylamino or $C_{2-6}$-alkynyl-carbonylamino groups, and/or
wherein a hydrogen atom attached to a nitrogen atom, if present in the respective group, optionally is replaced by a $C_{1-4}$-alkyl, $C_{2-4}$-alkenyl, $C_{2-4}$-alkynyl, cyclo-$C_{3-6}$-alkyl, cyclo-$C_{3-7}$-alkyl-$C_{1-3}$-alkyl, cyclo-$C_{3-7}$-alkyl-carbonyl, pyrrolidino, piperidino, morpholino, $C_{1-3}$-alkoxy, $C_{1-3}$-alkoxy-$C_{1-3}$-alkyl, phenyl, phenyl-$C_{1-3}$-alkyl, $C_{1-4}$-alkyl-carbonyl, $C_{1-3}$-alkoxy-carbonyl or $C_{1-3}$-alkyl-sulphonyl group,
and wherein any phenyl and pyridyl groups or phenyl- and pyridyl-submoieties optionally are substituted with 1 or 2 substituents independently of each other selected from fluorine, chlorine, bromine, iodine, $C_{1-3}$-alkyl, $C_{1-3}$-alkoxy, amino, $C_{1-3}$-alkyl-amino, $C_{1-3}$-alkylcarbonyl-amino, cyano or hydroxy.

($c^4$): According to a fourth preferred embodiment,
W denotes H or an optionally substituted straight-chained or branched $C_{1-6}$-alkyl, $C_{2-6}$-alkenyl or $C_{2-6}$-alkynyl group,
wherein 1 or 2 methyl groups optionally are replaced by optionally substituted phenyl groups or
an optionally substituted cyclo-$C_{3-8}$-alkyl group, wherein independently
in a cyclo-$C_{4-8}$-alkyl group one or two ring members optionally are replaced independently of each other by —NH—, >N—($C_{1-6}$-alkyl) (or N-atoms for replacement of —CH< members), O, or carbonyl, with the proviso that two heteroatoms are not directly linked together, and additionally but optionally 2 or 4 hydrogen atoms attached to adjacent ring carbon atoms are replaced to form a double bond or two conjugated double bonds within the ring, either of the double bonds optionally being condensed with an optionally substituted aryl or an optionally substituted 5- or 6-membered hetaryl group, and/or
in a cyclo-$C_{4-5}$-alkyl group 2 hydrogen atoms attached to the same carbon atom (relative 1,1-position) optionally are replaced by a $C_{2-5}$-alkylenyl bridge, wherein one —CH$_2$— group optionally is replaced by —NH—, >N—($C_{1-6}$-alkyl), O, or carbonyl or wherein two —CH$_2$— groups in relative 1,3-position of a $C_{4-5}$-alkylenyl bridge optionally are replaced O atoms, or wherein a —CH$_2$—CH$_2$— group optionally is replaced by —C(O)—NH—, —NH—C(O)—, —C(O)—N($C_{1-6}$-alkyl)- or —N($C_{1-6}$-alkyl)-C(O)— and/or 2 hydrogen atoms attached to adjacent carbon atoms within a $C_{4-5}$-alkylenyl bridge optionally are replaced to form a double bond, which optionally is condensed with an optionally substituted aryl or an optionally substituted 5- or 6-membered hetaryl group, or
an optionally substituted cyclo-$C_{5-9}$-alkyl group, wherein independently 22 hydrogen atoms attached to carbon atoms in relative 1,2-, 1,3-, 1, 4 or 1,5-position optionally are replaced by a $C_{1-3}$-alkylenyl bridge, wherein any of the resulting polycyclic groups one —CH$_2$— group optionally is replaced by —NH—, >N—($C_{1-6}$-alkyl), O, or carbonyl,
wherein any of the resulting groups is bound via a saturated or unsaturated carbon atom or a nitrogen atom,
and wherein any of the resulting open-chained or cyclic groups independently 1 to 3 hydrogen atoms optionally are replaced by $C_{1-4}$-alkyl or $C_{1-4}$-alkoxy groups, and/or any 1 to 6 hydrogen atoms attached to carbon atoms optionally are replaced by fluorine atoms, or W denotes an optionally substituted aryl or hetaryl group,
an optionally substituted cyclo-$C_{3-6}$-alkyl-aryl or cyclo-$C_{3-6}$-alkyl-hetaryl group, wherein the cyclo-$C_{5-6}$-alkyl-submoieties one or two ring members optionally are replaced independently of each other by —NH— (or a N-atom for replacement of a —CH< member), O, or carbonyl, with the proviso that two heteroatoms are not directly linked together, or if Y is absent W additionally denotes
a divalent —(CH$_2$)$_p$— group, wherein p is 2, 3, 4, or 5, attached in relative 1,1-position (geminal) to a carbon atom of group X, including the options:
if p is 4 or 5 it follows that 1 —CH$_2$— group optionally is replaced by O, —NH— or —N($C_{1-4}$-alkyl)-, or that a —CH$_2$—CH$_2$— group optionally is replaced by —C(O)—NH—, —NH—C(O)—, —C(O)—N($C_{1-4}$-alkyl)-, —N($C_{1-4}$-alkyl)-C(O)—, or —CH=CH—, wherein the double bond optionally is condensed with an aryl or a 5- or 6-membered hetaryl group,
a divalent —(CH$_2$)$_q$— group, wherein q is 3 or 4 attached in relative 1,2-position (vicinal) to carbon atoms of group X, including the options:
a —CH$_2$—CH$_2$— group optionally is replaced by —C(O)—NH—, —NH—C(O)—, —C(O)—N($C_{1-6}$-alkyl)-, —N($C_{1-6}$-alkyl)-C(O)—, or
that in the resulting 5- or 6-membered carbocyclic ring 2, 4 or, in case of the 6-membered ring, also 6 hydrogen atoms optionally are replaced by 1, 2 or 3 bonds to form a partially or fully unsaturated ring with isolated or conjugated double bonds, wherein 1 —CH$_2$— group optionally is replaced by O, —NH— or —N(C$_{1-6}$-alkyl)-, and/or one —CH═ unit is replaced by —N═, the trivalent group

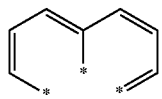

attached in relative 1,2,3-position to carbon atoms * as binding sites of group X, wherein any aryl groups or aryl-subgroups mentioned above in the definition of W are selected from optionally substituted phenyl, naphthyl, and tetrahydronaphthyl groups, and wherein any hetaryl groups or hetaryl-subgroups mentioned above in the definition of W are selected from optionally substituted pyridyl, pyrimidinyl, pyrazinyl, pyridazinyl, pyrazolyl, imidazolyl, triazolyl, furyl, thienyl, oxazolyl, benzoxazolyl, thiazolyl, benzthiazolyl, indolyl, indolinyl, benzimidazolyl, tetrahydrobenzimidazolyl, tetrahydrocyclopentaimidazolyl, indazolyl, tetrahydroindazolyl, tetrahydrocyclopentapyrazolyl, hexahydrocycloheptapyrazolyl, benztriazolyl, quinolyl, tetrandyroquinolinly, isoquinolyl, tetrandyroisoquinolinly, cinnolyl, quinoxazolyl and benzpyrimidinyl groups, wherein the expression "optionally substituted" means that 1, 2 or 3 hydrogen atoms of the respective group independently are optionally replaced by substituents selected from fluorine, chlorine and bromine atoms, atoms, by C$_{1-6}$-alkyl, trifluoromethyl, C$_{2-6}$-alkenyl, C$_{2-6}$-alkynyl, cyclo-C$_{3-7}$-alkyl, cyclo-C$_{3-7}$-alkenyl, cyano, hydroxy, hydroxy-C$_{1-6}$-alkyl, C$_{1-6}$-alkoxy, C$_{1-6}$-alkoxy-C$_{1-6}$-alkyl, C$_{1-6}$-alkoxy-C$_{1-6}$-alkyl-carbonyl, formyl, amino, C$_{1-4}$-alkyl-amino, (C$_{1-4}$-alkyl)$_2$-amino, phenylamino, N-phenyl-N—(C$_{1-4}$-alkyl)-amino, pyrrolidino, piperidino, aminocarbonyl, C$_{1-6}$-alkyl-aminocarbonyl, C$_{3-6}$-alkenyl-aminocarbonyl, C$_{3-6}$-alkynyl-aminocarbonyl, di-(C$_{1-6}$-alkyl)-aminocarbonyl, di-(C$_{3-6}$-alkenyl)-aminocarbonyl, di-(C$_{3-6}$-alkynyl)-aminocarbonyl, formylamino, C$_{1-6}$-alkyl-carbonylamino, C$_{1-6}$-alkyl-carbonyl-(C$_{1-3}$-alkyl)-amino C$_{2-6}$-alkenyl-carbonylamino or C$_{2-6}$-alkynyl-carbonylamino groups, or the expression "optionally substituted" means that 4 hydrogen atoms of the respective group independently are optionally replaced by substituents selected from fluorine atoms and C$_{1-6}$-alkyl groups, and/or wherein a hydrogen atom attached to a nitrogen atom, if present in the respective group, optionally is replaced by a C$_{1-4}$-alkyl, C$_{2-4}$-alkenyl, C$_{2-4}$-alkynyl, cyclo-C$_{3-6}$-alkyl, cyclo-C$_{3-7}$-alkyl-carbonyl, pyrrolidino, piperidino, morpholino, C$_{1-3}$-alkoxy, C$_{1-3}$-alkoxy-C$_{1-3}$-alkyl, phenyl, phenyl-C$_{1-3}$-alkyl, C$_{1-4}$-alkyl-carbonyl, C$_{1-3}$-alkoxy-carbonyl or C$_{1-3}$-alkyl-sulphonyl group and wherein any phenyl and pyridyl groups or phenyl- and pyridyl-submoieties optionally are substituted with 1 or 2 substituents independently of each other selected from fluorine, chlorine, bromine, C$_{1-3}$-alkyl, C$_{1-3}$-alkoxy, amino, C$_{1-3}$-alkyl-amino, C$_{1-3}$-alkylcarbonyl-amino or hydroxy.

d) Definitions (d$^i$) for R$^1$, R$^2$, R$^3$, R$^4$ and R$^5$ in the order of preference, ascending from preferably (d$^1$) to more preferably (d$^2$) up to most preferably (d$^4$):

(d$^1$): According to a first preferred embodiment R$^1$, R$^2$, R$^3$, R$^4$ and R$^5$ are defined as mentioned hereinbefore under the broadest/first embodiment of the invention E-0.

(d$^2$): According to a second preferred embodiment, R$^1$ denotes H, C$_{1-4}$-alkyl, C$_{3-4}$-alkenyl or C$_{3-4}$-alkynyl, any of those groups being optionally substituted by 1 to 3 fluorine, chlorine or bromine atoms, or by a cyano, hydroxy, C$_{1-3}$-alkoxy or cyclo-C$_{3-6}$-alkyl-group, R$^2$ and R$^3$ independently denote H, halogen, C$_{1-3}$-alkyl, hydroxy or C$_{1-3}$-alkoxy, any of those C$_{1-3}$-alkyl groups being optionally substituted by 1 to 3 fluorine atoms, R$^4$ and R$^5$ independently denote H, halogen, C$_{1-3}$-alkyl, C$_{2-4}$-alkenyl, C$_{2-3}$-alkynyl, cyclo-C$_{3-6}$-alkyl, hydroxy or C$_{1-3}$-alkoxy, any of those C$_{1-3}$-alkyl, C$_{2-4}$-alkenyl or C$_{2-3}$-alkynyl groups being optionally substituted by 1 to 3 fluorine atoms, by a methyl, hydroxy, C$_{1-3}$-alkoxy, or cyclo-C$_{3-5}$-alkyl-group, or by a phenyl or pyridyl group both optionally substituted independently by 1, 2 or 3 substituents selected from halogen atoms, C$_{1-3}$-alkyl, cyclo-C$_{3-6}$-alkyl, cyano, hydroxy, C$_{1-3}$-alkoxy, amino, C$_{1-3}$-alkyl-amino, and di-(C$_{1-3}$-alkyl)-amino groups, (d$^3$): According to a third preferred embodiment, R$^1$ denote H, C$_{1-4}$-alkyl, C$_{3-4}$-alkenyl or C$_{3-4}$-alkynyl, any of those groups being optionally substituted by 1 to 3 fluorine or chlorine atoms, or by a or cyclo-C$_{3-6}$-alkyl-group, R$^2$ and R$^3$ independently denote H, halogen, C$_{1-3}$-alkyl, any of those C$_{1-3}$-alkyl groups being optionally substituted by 1 to 3 fluorine atoms, R$^4$ and R$^5$ independently denote H, halogen, C$_{1-3}$-alkyl, cyclo-C$_{3-6}$-alkyl, any of those C$_{1-3}$-alkyl, groups being optionally substituted by 1 to 3 fluorine atoms, by a methyl, or cyclo-C$_{3-5}$-alkyl group, or by aphenyl or pyridyl group, both optionally substituted independently by 1, 2 or 3 substituents selected from halogen atoms, C$_{1-3}$-alkyl, hydroxy, C$_{1-3}$-alkoxy, amino, and C$_{1-3}$-alkyl-amino groups.

(d$^4$): According to a fourth preferred embodiment, R$^1$ denote H, C$_{1-4}$-alkyl, C$_{3-4}$-alkenyl or C$_{3-4}$-alkynyl, any of those groups being optionally substituted by 1 to 3 fluorine or chlorine atoms, or by a cyclo-C$_{3-7}$-alkyl-group, R$^2$ and R$^3$ independently denote H, halogen, or C$_{1-3}$-alkyl, any of those C$_{1-3}$-alkyl groups being optionally substituted by 1 to 3 fluorine atoms, R$^4$ and R$^5$ independently denote H, halogen, C$_{1-3}$-alkyl, cyclo-C$_{3-5}$-alkyl, any of those C$_{1-3}$-alkyl groups being optionally substituted by 1 to 3 fluorine atoms, by a methyl or cyclo-C$_{3-5}$-alkyl-group, or by a phenyl or pyridyl group, both optionally substituted independently by 1, 2 or 3 substituents selected from halogen atoms, C$_{1-3}$-alkyl, hydroxy, C$_{1-3}$-alkoxy, amino, and C$_{1-3}$-alkyl-amino groups.

Each a$^i$, b$^i$, c$^i$, d$^i$ represents a characterised, individual embodiment for the corresponding substituent as described above. So given the above definitions, preferred individual embodiments of the first aspect of the invention are fully characterised by the term (a$^i$b$^i$c$^i$d$^i$) if for each letter i in this term an individual figure is given. Indices i vary independently from each other. All individual embodiments described by the term in brackets with full permutation of indices i, referring to the above definitions, shall be comprised by the present invention.

The following table 1 shows, exemplary and in the order of increasing preference from the first line to the last line, such embodiments E-1 to E-15 of the invention that are considered preferred. This means that embodiment E-15, represented by the entries in the last row of table 1 is the most preferred embodiment:

TABLE 1

Preferred embodiments E-1 to E-15 of the invention

| | X | Y | W | $R^1, R^2, R^3, R^4, R^5$ |
|---|---|---|---|---|
| E-1 | $a^1$ | $b^1$ | $c^1$ | $d^2$ |
| E-2 | $a^2$ | $b^1$ | $c^1$ | $d^2$ |
| E-3 | $a^2$ | $b^2$ | $c^1$ | $d^2$ |
| E-4 | $a^2$ | $b^3$ | $c^1$ | $d^2$ |
| E-5 | $a^3$ | $b^3$ | $c^2$ | $d^2$ |
| E-6 | $a^3$ | $b^4$ | $c^2$ | $d^2$ |
| E-7 | $a^3$ | $b^4$ | $c^3$ | $d^2$ |
| E-8 | $a^4$ | $b^4$ | $c^3$ | $d^2$ |
| E-9 | $a^4$ | $b^5$ | $c^3$ | $d^2$ |
| E-10 | $a^5$ | $b^5$ | $c^3$ | $d^2$ |
| E-11 | $a^5$ | $b^5$ | $c^3$ | $d^3$ |
| E-12 | $a^6$ | $b^6$ | $c^3$ | $d^3$ |
| E-13 | $a^5$ | $b^6$ | $c^4$ | $d^2$ |
| E-14 | $a^6$ | $b^7$ | $c^4$ | $d^3$ |
| E-15 | $a^6$ | $b^7$ | $c^4$ | $d^4$ | including the tautomers, the stereoisomers, the mixtures, and the salts thereof.

Particular preferred embodiments of the invention are described in the Examples.

General Routes for Preparation

The compounds of general formula (I) may be prepared by the following methods, for example:

(a) In order to prepare compounds of general formula (I) wherein the group X is linked to the tricyclic core group via a N-atom:

reacting a compound of general formula

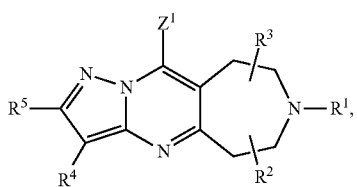

(XIV)

wherein $R^1$, with exception of the hydrogen atom, is defined as hereinbefore or represents a suitable protective group as a protected hydrogen equivalent resulting a hydrogen atom for $R^1$ after deprotection, preferably benzyl or tert-butoxycarbonyl (boc), $R^2$, $R^3$, $R^4$ and $R^5$ are defined as hereinbefore, and $Z^1$ denotes a leaving group such as a halogen atom, e.g. a chlorine or bromine atom, with a suitable nitrogen nucleophilic group of formula

(XV)

wherein X' denotes the meanings given for X hereinbefore, with the proviso that the H-atom in formula (XV) is attached to a N-atom, and Y and W are defined as mentioned hereinbefore, in a suitable solvent, such as ethanol at suitable temperatures, preferably at a temperature of 40-100° C., and, if necessary, cleaving concurrently or subsequently any protective group used in the reaction described above using standard techniques.

(b) In order to prepare compounds of general formula (I) wherein the group X is linked to the tricyclic core group via a C-atom:

reacting a compound of general formula

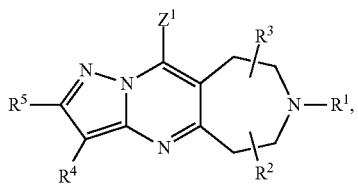

(XIV)

wherein $R^1$, with exception of the hydrogen atom, is defined as hereinbefore or represents a suitable protective group as a protected hydrogen equivalent resulting a hydrogen atom for $R^1$ after deprotection, preferably benzyl or tert-butoxycarbonyl (boc), $R^2$, $R^3$, $R^4$ and $R^5$ are defined as hereinbefore, and $Z^1$ denotes a leaving group such as a halogen atom, e.g. a chlorine or bromine atom, with a suitable carbon nucleophilic group of formula

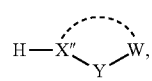

(XVI)

wherein X" denotes the meanings given for X hereinbefore, with the proviso that the H-atom in formula (XVI) is attached to a C-atom, and Y and W are defined as mentioned hereinbefore, in the presence of a suitable catalyst, such as Pd(0) catalysts, Pd(II) catalysts or Iron (III) catalysts, in a suitable solvent, such as methanol, tetrahydrofurane, dioxane at suitable temperatures, preferably 20° C. up to reflux of the solvent or solvent mixture and, if necessary cleaving concurrently or subsequently any protective group used in the reaction described above using standard techniques. Organo-magnesium reagents, organo-tin reagents, organo-zinc reagents, boronic acid or boronic ester derivatives may be used as carbon nucleophiles. In case the carbon nucleophile represents a boronic acid or a boronic ester, the reaction is carried out in a suitable solvent with a suitable base, such as cesium, sodium or potassium carbonate at suitable temperatures, preferably 20° C. up to reflux of the solvent or solvent mixture.

(c) In order to prepare compounds of general formula (I) wherein the group Y is linked via a carbonyl group to a N-atom of group W:

reacting a compound of general formula

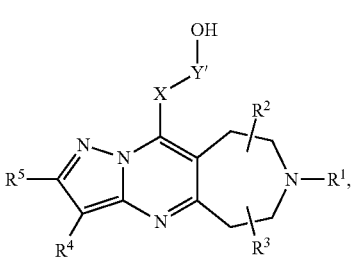

(XVII)

wherein $R^1$, with exception of the hydrogen atom, is defined as hereinbefore or represents a suitable protective group as a protected hydrogen equivalent resulting a hydrogen atom for $R^1$ after deprotection, R², R³, R⁴, R⁵ and X are as defined hereinbefore, and
Y' denotes the meanings given for Y hereinbefore, with the proviso that the OH group in formula (XVII) is attached to a carbonyl group,
with an amine of formula H—W' (XVIII),
wherein W' denotes the meanings given for W hereinbefore, with the proviso that the H-atom in formula (XVIII) is attached to a N-atom, thus resulting the corresponding amide, and, if necessary cleaving concurrently or subsequently any protective group used in the reaction described above using standard techniques, in case of boc e.g. by treatment with a mixture of dichloromethane and trifluoroacetic acid. The amidation can be carried out using standard procedures including a suitable activation reagent such as EDC, TBTU, PFTU or HATU in a solvent such as DMF and in the presence of a base such as triethyl amine or DIPEA upon treatment with the nucleophilic amine of formula (XVIII).

Compounds of general formula I thus obtained may be resolved into their stereoisomers, if applicable, or converted into the salts thereof, particularly for pharmaceutical use into the physiologically acceptable salts thereof.

The compounds of general formulas XIV, XV, XVI, XVII and XVIII used as starting or intermediate materials are available as described hereinafter or are either commercially available, known from the literature or may be obtained by methods known from the literature.

The compounds of formula (XIV) are available as follows:
(d) Reaction of a compound of formula Prep 1

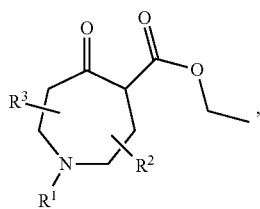

(Prep 1)

wherein R¹, R² and R³ are as defined herein, with a compound of formula Prep 2 or its tautomer:

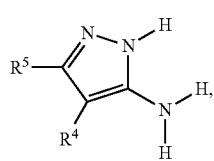

(Prep 2)

wherein R⁴ and R⁵ are as defined herein, using a suitable solvent, preferably acetic acid at a suitable temperature, preferably 50-100° C., to yield a compound of formula Prep 3 or its tautomer

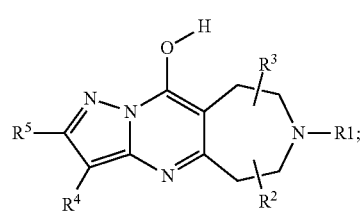

(Prep 3)

(e) Conversion of a compound of formula Prep 3 into a compound of formula (XIV) as defined hereinbefore, using a suitable chlorinating reagent, preferably phosphorus oxychloride, optionally in the presence of a base, preferably triethyl amine or ethyldiisopropylamine (DIPEA), at elevated temperature, preferably 40-120° C. In case the protection group is not stable under the reaction conditions a reprotection (preferably Pg=benzyl or boc) prior to further reactions may be required.

Compounds of formula (XV), wherein Y denotes an O-atom,
X denotes a divalent 4- to 10-membered monocylic, 7- to 12-membered spirocyclic or 6- to 12-membered bicyclic saturated, partially or fully unsaturated group selected from a monoaza-heterocycle and a diaza-heterocycle, and
W denotes an optionally substituted aryl or hetaryl group, an optionally substituted cyclo-$C_{3-8}$-alkyl-aryl or cyclo-$C_{3-8}$-alkyl-hetaryl group, wherein the cyclo-$C_{5-8}$-alkyl-submoieties one or two ring members optionally are replaced independently of each other by —NH— (or a N-atom for replacement of a —CH< member), >N($C_{1-3}$-alkyl), O, S, carbonyl, or sulfonyl,
are available according to the reaction sequence shown in scheme 1:

Scheme 1,

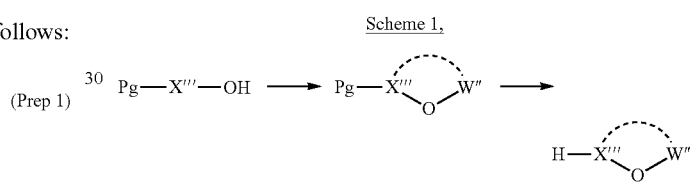

wherein
X''' denotes a divalent 4- to 10-membered monocylic, 7- to 12-membered spirocyclic or 6- to 12-membered bicyclic saturated, partially or fully unsaturated group selected from a monoaza-heterocycle and a diaza-heterocycle, e.g. an azetidine, pyrrolidine, piperidine or azepine ring,
W'' denotes an optionally substituted aryl or hetaryl group, an optionally substituted cyclo-$C_{3-8}$-alkyl-aryl or cyclo-$C_{3-8}$-alkyl-hetaryl group, wherein the cyclo-$C_{5-8}$-alkyl-submoieties one or two ring members optionally are replaced independently of each other by —NH— (or a N-atom for replacement of a —CH< member), >N($C_{1-3}$-alkyl), O, S, carbonyl, or sulfonyl, and Pg represents a suitable protection group attached to a nitrogen atom, resulting a hydrogen atom after deprotection.

In Scheme 1 the hydroxyl group is converted into the corresponding aryl or hetaryl ether by standard techniques using e.g. a Mitsunobu reaction or a nucleophilic substitution. In the latter case the hydroxyl group is transformed into a suitable leaving group such as mesylate or tosylate by standard techniques. The latter intermediates are then dissolved in a suitable solvent such as NMP, DMF or DMA and are treated with the appropriate aryl or hetaryl alcohol together with a suitable base such as cesium, sodium or potassium carbonate to yield Pg-X—O—W. The protection group is removed by standard techniques, in case of boc e.g. by treatment with a mixture of dichloromethane and trifluoroacetic acid.

As already mentioned, the compounds of general formula I according to the invention and the physiologically acceptable salts thereof have valuable pharmacological properties, particularly an agonistic activity at the human 5-HT2C receptor. In the literature, compounds which are 5-HT2C receptor ligands are proposed for the treatment of the metabolic syndrome, in particular diabetes type 2, obesity and dyslipidemia.

The biological properties of the new compounds may be investigated as follows:

A stable cell line was generated by transfecting CHO-K1 cells with plasmids containing the human 5-HT2C receptor cDNA (VSV RNA-edited isoform, NM_000868) in expression vector pcDNA3. Transfected cells were maintained in serum-free UltraCHO medium (Bio Whittaker) containing 400 µg/ml G418 at 37° C. in 10% $CO_2$ atmosphere. The ability of a compound to activate the 5-HT2C receptor was monitored in whole cells by measuring intracellular $Ca^{2+}$ release on a Fluorometric Imaging Plate Reader (FLIPR; Molecular Devices) using the FLIPR Calcium 3 no-wash Assay Kit (Molecular Devices). Cells were seeded overnight in 20 µL UltraCHO medium in black, collagen-coated 384-well plates (Becton Dickinson) at a density of 7.000 cells per well. After 24 h the cells were loaded with the fluorescence dye (Fluo-3) in Hanks buffered salt solution containing 50 mM HEPES and 2.5 mM Probenecid for 80 min at room temperature in the dark. Thereafter, test compound was added in 20 µl Hanks buffered salt solution in the FLIPR. $Ca^{2+}$-release was monitored over 30 sec with a time resolution of 5 sec before the addition of compound and for 90 sec with a 1 sec time resolution after the addition of compound. The fluorescence signal obtained with 1 µM 5-HT as a positive control was set to 100% maximal efficacy (Emax). Data were fitted to a sigmoidal dose-response model using the XLfit4 software (IDBS) and potency of a compound is expressed as EC50 value giving 50% of maximal activation.

The compounds of formula (I) according to the invention, including the physiologically acceptable salts thereof, are suitable for the prevention or treatment of metabolic and CNS-related disorders. More specifically, the compounds of formula (I) are useful for the treatment and/or prevention of disorders involving elevated plasma blood glucose, particularly diabetes mellitus (including Type II or non-insulin dependent diabetes mellitus (NIDDM); Type I or insulin dependent diabetes mellitus (IDDM); and Type III or malnutrition-related diabetes), or of diabetic complications. obesity and dyslipidemia. Furthermore, the compounds of formula (I) are suitable for the treatment and/or prevention of CNS-related disorders such as depression, schizophrenia, obsessive-compulsive disorder, drug abuse, sleep disorders, anxiety and epilepsy.

The dosage required to achieve the corresponding activity for treatment or prevention usually depends on the compound which is to be administered, the patient, the nature and gravity of the illness or condition and the method and frequency of administration and is for the patient's doctor to decide. Expediently, the dosage may be from 1 to 100 mg, preferably 1 to 30 mg, by intravenous route, and 1 to 1000 mg, preferably 1 to 100 mg, by oral route, in each case administered 1 to 4 times a day. For this purpose, the compounds of formula I prepared according to the invention may be formulated, optionally together with other active substances, together with one or more inert conventional carriers and/or diluents, e.g. with corn starch, lactose, glucose, microcrystalline cellulose, magnesium stearate, polyvinylpyrrolidone, citric acid, tartaric acid, water, water/ethanol, water/glycerol, water/sorbitol, water/polyethylene glycol, propylene glycol, cetylstearyl alcohol, carboxymethylcellulose or fatty substances such as hard fat or suitable mixtures thereof, to produce conventional galenic preparations such as plain or coated tablets, capsules, powders, suspensions or suppositories.

The compounds according to the invention may also be used in conjunction with other active substances, particularly for the treatment and/or prevention of the diseases and conditions mentioned above. Other active substances which are suitable for such combinations include for example those which potentiate the therapeutic effect of a 5-HT2C receptor agonist according to the invention with respect to one of the indications mentioned and/or which allow the dosage of a 5-HT2C receptor agonist according to the invention to be reduced. Therapeutic agents which are suitable for such a combination include, for example, antidiabetic agents such as metformin, sulfonylureas (e.g. glibenclamide, tolbutamide, glimepiride), nateglinide, repaglinide, thiazolidinediones (e.g. rosiglitazone, pioglitazone), SGLT 2 inhibitors (e.g. dapagliflozin, sergliflozin), PPAR-gamma-agonists (e.g. GI 262570) and antagonists, PPAR-gamma/alpha modulators (e.g. KRP 297), alpha-glucosidase inhibitors (e.g. acarbose, voglibose), DPPIV inhibitors (e.g. Sitagliptin, Vildagliptin, Saxagliptin, Alogliptin, BI 1356), alpha2-antagonists, insulin and insulin analogues, GLP-1 and GLP-1 analogues (e.g. exendin-4) or amylin. The list also includes inhibitors of protein tyrosinephosphatase 1, substances that affect deregulated glucose production in the liver, such as e.g. inhibitors of glucose-6-phosphatase, or fructose-1,6-bisphosphatase, glycogen phosphorylase, glucagon receptor antagonists and inhibitors of phosphoenol pyruvate carboxykinase, glycogen synthase kinase or pyruvate dehydrokinase and glucokinase activators, lipid lowering agents such as for example HMG-CoA-reductase inhibitors (e.g. simvastatin, atorvastatin), fibrates (e.g. bezafibrate, fenofibrate), nicotinic acid and the derivatives thereof, PPAR-alpha agonists, PPAR-delta agonists, ACAT inhibitors (e.g. avasimibe) or cholesterol absorption inhibitors such as, for example, ezetimibe, bile acid-binding substances such as, for example, cholestyramine, inhibitors of ileac bile acid transport, HDL-raising compounds such as CETP inhibitors or ABC1 regulators.

Moreover, therapeutic agents which are suitable for such a combination include active substances for treating obesity, such as sibutramine or tetrahydrolipostatin, SDRIs, axokine, leptin, leptin mimetics, antagonists of the cannabinoid1 receptor, MCH-1 receptor antagonists, MC4 receptor agonists, NPY5 or NPY2 antagonists or β3-agonists such as SB-418790 or AD-9677 and agonists of the 5HT2c receptor.

Moreover, combinations with drugs for influencing high blood pressure, chronic heart failure or atherosclerosis such as e.g. A-II antagonists or ACE inhibitors, ECE inhibitors, diuretics, β-blockers, Ca-antagonists, centrally acting antihypertensives, antagonists of the alpha-2-adrenergic receptor, inhibitors of neutral endopeptidase, thrombocyte aggregation inhibitors and others or combinations thereof are suitable. Examples of angiotensin II receptor antagonists are candesartan cilexetil, potassium losartan, eprosartan mesylate, valsartan, telmisartan, irbesartan, EXP-3174, L-158809, EXP-3312, olmesartan, medoxomil, tasosartan, KT-3-671, GA-0113, RU-64276, EMD-90423, BR-9701, etc. Angiotensin II receptor antagonists are preferably used for the treatment or prevention of high blood pressure and complications of diabetes, often combined with a diuretic such as hydrochlorothiazide.

A combination with uric acid synthesis inhibitors or uricosurics is suitable for the treatment or prevention of gout.

A combination with GABA-receptor antagonists, Na-channel blockers, topiramat, protein-kinase C inhibitors, advanced glycation end product inhibitors or aldose reductase inhibitors may be used for the treatment or prevention of complications of diabetes.

The dosage for the combination partners mentioned above is usefully ⅕ of the lowest dose normally recommended up to 1/1 of the normally recommended dose.

Therefore, in another aspect, this invention relates to the use of a compound according to the invention or a physiologically acceptable salt of such a compound combined with at least one of the active substances described above as a combination partner, for preparing a pharmaceutical composition which is suitable for the treatment or prevention of diseases or conditions which can be affected by modulating 5-HT2C receptor activity. These are preferably metabolic diseases and CNS-related diseases, particularly one of the diseases or conditions listed above, most particularly Type II diabetes or obesity.

The use of the compound according to the invention, or a physiologically acceptable salt thereof, in combination with another active substance may take place simultaneously or at staggered times, but particularly within a short space of time. If they are administered simultaneously, the two active substances are given to the patient together; while if they are used at staggered times the two active substances are given to the patient within a period of less than or equal to 12 hours, but particularly less than or equal to 6 hours.

Consequently, in another aspect, this invention relates to a pharmaceutical composition which comprises a compound according to the invention or a physiologically acceptable salt of such a compound and at least one of the active substances described above as combination partners, optionally together with one or more inert carriers and/or diluents.

Thus, for example, a pharmaceutical composition according to the invention comprises a combination of a compound of formula I according to the invention or a physiologically acceptable salt of such a compound and at least one angiotensin II receptor antagonist optionally together with one or more inert carriers and/or diluents.

The compound according to the invention, or a physiologically acceptable salt thereof, and the additional active substance to be combined therewith may both be present together in one formulation, for example a tablet or capsule, or separately in two identical or different formulations, for example as a so-called kit-of-parts.

The Examples that follow are intended to illustrate the present invention without restricting it. The terms "ambient temperature" and "room temperature" are used interchangeably and designate a temperature of about 20° C.

EXPERIMENTAL PART

Definitions

| | |
|---|---|
| (aq.) | aqueous |
| (w/w) | Weight:weight ratio |
| DCM | Dichloromethane |
| DIAD | Diisopropyl azodicarboxylate |
| DIPEA | N,N-Diisopropylethylamine |
| DMA | Dimethylacetamide |
| DMF | Dimethylformamide |
| EtOAc | Ethyl acetate |
| $H_2O$ | water |
| KOH | Potassium hydroxide |
| MeOH | Methanol |
| $MgSO_4$ | Magnesium sulfate |
| $Na_2S_2O_3$ | Sodium thiosulfate |
| $Na_2SO_4$ | Sodium sulfate |
| NMP | 1-Methyl-2-pyrrolidon |
| TBME | tert-Butyl methyl ether |
| BOP | Benzotriazole-1-yl-oxy-tris-(dimethylamino)-phosphonium hexafluorophosphate |
| TBTU | O-(Benztriazol-1-yl)-N,N,N',N'-tetramethyluroniumhexafluoroborat |
| $Cs_2CO_3$ | Caesium Carbonate |
| DME | Dimethoxyethane |
| CuI | copper(I) iodide |
| TF/TFA | Trifluoroacetic acid |
| $NaHCO_3$ | sodium hydrogen carbonate |
| NaH | Sodium hydride |
| HCl | hydrochloric acid |
| AIBN | Azobisisobutyronitrile |
| $^nBu_3SnH$ | Tributyltin hydride |
| THF | Tetrahydrofuran |

HPLC-Methods

Method A:

| | MET/CR/1278<br>Standard 3.5 minute method |
|---|---|
| Column | Atlantis dC18<br>2.1 × 50 mm, 5 um |
| Mobile phase | A = Formic acid (aq) 0.1%<br>B = Formic acid (acetonitrile) 0.1% |
| Flow rate | 1 mL/min |
| Injection volume | 3 ul |
| Detector | 215 nm (nominal) |

| Gradient | Time (mins) | % Organic |
|---|---|---|
| | 0 | 5 |
| | 2.5 | 100 |
| | 2.7 | 100 |
| | 2.71 | 5 |
| | 3.0 | 5 |

Method B:

| | MET/CR/0990<br>High pH method |
|---|---|
| Column | Zorbax Extend C18<br>2.1 × 50 mm, 5 um |
| Mobile phase | A = 2 mM Amm. Bicarbonate, buffered to pH10<br>B = Acetonitrile:2 mM Amm. Bicarbonate 95:5 |
| Flow rate | 1 mL/min |
| Injection volume | 3 ul |
| Detector | 215 nm (nominal) |

| Gradient | Time (mins) | % Organic |
|---|---|---|
| | 0 | 1 |
| | 1.80 | 100 |
| | 2.10 | 100 |
| | 2.30 | 1 |
| | 2.39 | 1 |

Method C:

| | MET/CR/1600<br>High pH method, high resolution |
|---|---|
| Column | Phenomenex Gemini C18<br>2.0 × 100 mm, 3 um 50 C |

MET/CR/1600
High pH method, high resolution

| | |
|---|---|
| Mobile phase | A = 2 mM Amm. Bicarbonate, buffered to pH10<br>B = Acetonitrile:2 mM Amm. Bicarbonate 95:5 |
| Flow rate | 0.5 mL/min |
| Injection volume | 3 ul |
| Detector | 215 nm (nominal) |

| Gradient | Time (mins) | % Organic |
|---|---|---|
| | 0 | 5 |
| | 5.50 | 100 |
| | 5.90 | 100 |
| | 5.92 | 5 |

Method D:

MET/CR/1673
Generic 2 minutes method

| | |
|---|---|
| Column | Atlantis dC18<br>2.1 × 30 mm, 3 um |
| Mobile phase | A = Formic acid (aq) 0.1%<br>B = Formic acid (acetonitrile) 0.1% |
| Flow rate | 1 mL/min |
| Injection volume | 3 ul |
| Detector | 215 nm (nominal) |

| Gradient | Time (mins) | % Organic |
|---|---|---|
| | 0 | 5 |
| | 1.50 | 100 |
| | 1.60 | 100 |
| | 1.61 | 5 |

Method F:

| time (min) | Vol % water (incl. 0.1% TFA) | Vol % acetonitrile (incl. 0.1% TFA) |
|---|---|---|
| 0 | 95 | 5 |
| 2 | 0 | 100 |
| 2.5 | 0 | 100 |
| 2.6 | 95 | 5 |

Analytical column: Sunfire C18 (Waters); 3.5 μm; 4.6×50 mm; column temperature: 40° C.; flow: 1.5 mL/min; injection volume: 20 μL; detection 210-500 nm Method G:

| time (min) | Vol % water (incl. 0.1% TFA) | Vol % acetonitrile (incl. 0.1% TFA) |
|---|---|---|
| 0 | 95 | 5 |
| 2 | 0 | 100 |
| 2.49 | 0 | 100 |
| 2.5 | 95 | 5 |

Analytical column: X-Terra MS C18; 3.5 μm; 4.6×50 mm; column temperature: 40° C.; flow: 1.5 mL/min; injection volume: 20 μL; detection 210-500 nm Method H:

| time (min) | Vol % water (incl. 0.1% TFA) | Vol % acetonitrile (incl. 0.1% TFA) |
|---|---|---|
| 0 | 95 | 5 |
| 2 | 2 | 98 |
| 2.5 | 2 | 98 |
| 2.9 | 95 | 5 |

Analytical column: Sunfire C18 (Waters); 3.5 μm; 4.6×50 mm; column temperature: 40° C.; flow: 1.5 mL/min; injection volume: 60 μL; detection 210-500 nm.

Method I:

| time (min) | Vol % water (incl. 0.1% TFA) | Vol % acetonitrile (incl. 0.1% TFA) |
|---|---|---|
| 0 | 95 | 5 |
| 2 | 0 | 100 |
| 3 | 0 | 100 |
| 5.5 | 95 | 5 |

Analytical column: Sunfire C18 (Waters); 3.5 μm; 4.6×50 mm; column temperature: 40° C.; flow: 1.5 mL/min; injection volume: 20 μL; detection 210-500 nm.

Method J:

| time (min) | Vol % water (incl. 0.1% TFA) | Vol % acetonitrile (incl. 0.1% TFA) |
|---|---|---|
| 0 | 95 | 5 |
| 2 | 2 | 98 |
| 3 | 2 | 98 |
| 3.4 | 95 | 5 |

Analytical column: Sunfire C18 (Waters); 3.5 μm; 4.6×50 mm; column temperature: 40° C.; flow: 1.5 mL/min; injection volume: 20 μL; detection 210-500 nm.

Method K

| time (min) | Vol % water (incl. 0.1% NH$_4$OH) | Vol % acetonitrile (incl. 0.1% NH$_4$OH) |
|---|---|---|
| 0 | 95 | 5 |
| 1.8 | 10 | 90 |
| 2 | 10 | 90 |
| 2.2 | 95 | 5 |

Analytical column: XBridge (Waters); 2.5 μm; 3×30 mm; column temperature: room temperature; flow: 1.4 mL/min; injection volume: 1 μL; detection 190-400 nm.

Method L

| time (min) | Vol % water (incl. 0.1% NH$_4$OH) | Vol % acetonitrile (incl. 0.1% NH$_4$OH) |
|---|---|---|
| 0 | 95 | 5 |
| 1.8 | 10 | 90 |
| 2 | 10 | 90 |
| 2.2 | 95 | 5 |

Analytical column: XBridge (Waters); 3.5 μm; 4.6×75 mm; column temperature: room temperature; flow: 1.4 mL/min; injection volume: 1 μL; detection 190-400 nm.

Method M

| time (min) | Vol % water (incl. 0.1% NH₄OH) | Vol % acetonitrile (incl. 0.1% NH₄OH) |
|---|---|---|
| 0 | 95 | 5 |
| 0.8 | 10 | 90 |
| 2 | 10 | 90 |
| 2.2 | 95 | 5 |

Analytical column: XBridge (Waters); 2.5 µm; 3×30 mm; column temperature: room temperature; flow: 1.4 mL/min; injection volume: 1 µL; detection 190-400 nm.

Method N

| time (min) | Vol % water (incl. 0.1% formic acid) | Vol % acetonitrile (incl. 0.1% formic acid) |
|---|---|---|
| 0 | 95 | 5 |
| 1 | 95 | 5 |
| 4 | 70 | 30 |
| 4.5 | 10 | 90 |
| 5 | 10 | 90 |
| 5.5 | 95 | 5 |

Analytical column: Symmetry (Waters); 3.5 µm; 4.6×75 mm; column temperature: room temperature; flow: 1.6 mL/min; injection volume: 5 µL; detection 190-400 nm.

Method O

| time (min) | Vol % water (incl. 0.1% formic acid) | Vol % acetonitrile (incl. 0.1% formic acid) |
|---|---|---|
| 0 | 95 | 5 |
| 4.5 | 5 | 95 |
| 5 | 5 | 95 |
| 5.5 | 95 | 5 |

Analytical column: Zorbax Stable Bond; 3.5 µm; 4.6×75 mm; column temperature: room temperature; flow: 1.6 mL/min; injection volume: 5 µL; detection 190-400 nm.

Method P

| time (min) | Vol % water (incl. 0.1% formic acid) | Vol % acetonitrile (incl. 0.1% formic acid) |
|---|---|---|
| 0 | 95 | 5 |
| 0.1 | 95 | 5 |
| 1.75 | 5 | 95 |
| 1.9 | 5 | 95 |
| 1.95 | 95 | 5 |
| 2 | 95 | 5 |

Analytical column: Zorbax Stable Bond; 1.8 µm; 3×30 mm; column temperature: room temperature; flow: 1.6 mL/min; injection volume: 5 µL; detection 190-400 nm.

Method Q

| time (min) | Vol % water (incl. 0.032% NH₄OH) | Vol % acetonitrile |
|---|---|---|
| 0 | 95 | 5 |
| 2.0 | 0 | 100 |
| 2.5 | 0 | 100 |
| 2.6 | 95 | 5 |

Analytical column: XBridge C18 (Waters); 1.7 µm; 2.1×50 mm; column temperature: 60° C.; flow: 1.3 mL/min; injection volume: 1 µL; detection 210-500 nm.

Method R

| time (min) | Vol % water (incl. 0.1% HCOOH) | Vol % acetonitrile (incl. 0.1% HCOOH) |
|---|---|---|
| 0 | 95 | 5 |
| 4.5 | 10 | 90 |
| 5.0 | 10 | 90 |
| 5.5 | 95 | 5 |

Analytical column: Symmetry C18 (Waters); 3.5 µm; 4.6×75 mm; column temperature: 60° C.; flow: 1.6 mL/min; injection volume: 1 µL; detection 210-500 nm.

Route 1

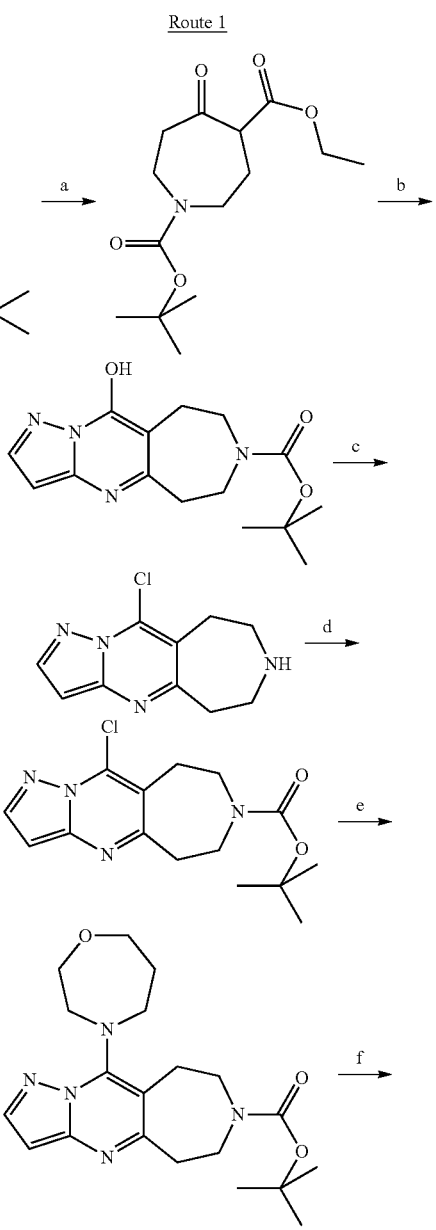

Example 1

10-[1,4]Oxazepan-4-yl-6,7,8,9-tetrahydro-5H-1,4,7,10a-tetraaza-cyclohepta[f]indene

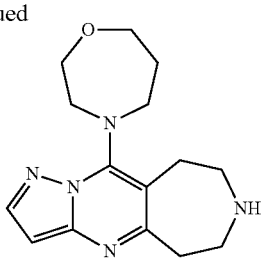

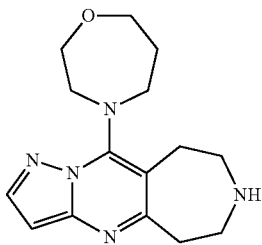 [SMILES: c1cc2nc3c(c(N4CCCOCC4)n2n1)CCNCC3]

1a 5-Oxo-azepane-1,4-dicarboxylic acid 1-tert-butyl ester 4-ethyl ester

To 10.0 g (50.18 mmol) 4-oxo-piperidine-1-carboxylic acid tert-butyl ester in 60 mL anhydrous ether maintained between −25° C. and −30° C. were added, over 20 minutes, solutions of 8.2 mL (65.23 mmol) boron trifluoride diethyl etherate in 17 mL anhydrous ether, followed by 6.85 mL (65.23 mmol) ethyl diazoacetate in 17 mL anhydrous ether, and the reaction was maintained between −25° C. and −30° C. for 1 hour. The mixture was allowed to warm to room temperature, 30 mL 30% potassium carbonate solution was added and the mixture extracted with EtOAc (3×30 mL), the organic layers were combined and dried with MgSO$_4$. After filtration, the solvent was evaporated to give the desired product.

Yield: 14.31 g (100% of theory)
$C_{14}H_{23}NO_5$ (M=285.34)
predicted: Molecular ion (M+H)$^+$: 286 observed: Molecular ion (M+H)$^+$: 286
HPLC-MS: 1.92 minutes (Method A)

1b 10-Hydroxy-5,6,8,9-tetrahydro-1,4,7,10a-tetraaza-cyclohepta[f]indene-7-carboxylic acid tert-butyl ester To 13.3 g (46.61 mmol) 5-oxo-azepane-1,4-dicarboxylic acid 1-tert-butyl ester 4-ethyl ester in 8 mL acetic acid was added 3.87 g (46.61 mmol) 3-aminopyrazole and the reaction mixture was heated at 80° C. for 15 minutes. The resulting solid was collected by filtration and washed with TBME (3×10 mL) to give the desired product.

Yield: 14.18 g (100% of theory)
$C_{15}H_{20}N_4O_3$ (M=304.35)
predicted: Molecular ion (M+H)$^+$: 305 observed: Molecular ion (M+H)$^+$: 305
HPLC-MS: 1.43 minutes (Method A)

1c 10-Chloro-6,7,8,9-tetrahydro-5H-1,4,7,10a-tetraaza-cyclohepta[f]indene

To 5 g (16.43 mmol) 10-hydroxy-5,6,8,9-tetrahydro-1,4,7,10a-tetraaza-cyclohepta[f]indene-7-carboxylic acid tert-butyl ester was added 15.2 mL (160.8 mmol) of phosphorus oxychloride followed by 2.85 mL (16.43 mmol) of DIPEA. The reaction mixture was stirred at room temperature for 10 minutes, then heated at 90° C. for 1 hour, and allowed to cool to room temperature. 30 mL DCM was added to the mixture and the solid was collected by filtration and washed with DCM (2×10 mL) to give the desired product as a HCl salt.

Yield: 2.24 g (46% of theory)
$C_{10}H_{11}ClN_4$ (M=222.68)
predicted: Molecular ion (M+H)$^+$: 223 observed: Molecular ion (M+H)$^+$: 223
HPLC-MS: 0.28 minutes (Method A)

1d 10-Chloro-5,6,8,9-tetrahydro-1,4,7,10a-tetraaza-cyclohepta[f]indene-7-carboxylic acid tert-butyl ester To 2.24 g (8.64 mmol) 10-chloro-6,7,8,9-tetrahydro-5H-1,4,7,10a-tetraaza-cyclohepta[f]indene in 20 mL DCM was added 3.5 mL (25.12 mmol) of triethylamine followed by 2.41 g (11.06 mmol) di-tert-butyl dicarbonate and the reaction was stirred at room temperature for 2 hours. 10 mL of H$_2$O was added and the mixture was extracted with DCM (2×20 mL), the organic layers were combined and dried with MgSO$_4$. After filtration and evaporation of the solvent the product was purified by column chromatography (silica, hexane/EtOAc 9:1 to 7:3).

Yield: 2.2 g (90% of theory)
$C_{15}H_{19}ClN_4O_2$ (M=322.80)
predicted: Molecular ion (M+H)$^+$: 323/325 observed: Molecular ion (M+H)$^+$: 323/325
HPLC-MS: 1.92 minutes (Method A)
Rf: 0.54 (hexane/EtOAc 6:4)

1e 10-[1,4]Oxazepan-4-yl-5,6,8,9-tetrahydro-1,4,7,10a-tetraaza-cyclohepta[f]indene-7-carboxylic acid tert-butyl ester To 0.1 g (0.31 mmol) 10-chloro-5,6,8,9-tetrahydro-1,4,7,10a-tetraaza-cyclohepta[f]indene-7-carboxylic acid tert-butyl ester, in a sealed tube in 4 mL ethanol, was added 0.2 mL (1.12 mmol) DIPEA followed by 47 mg (0.34 mmol) homomorpholine hydrochloride, and the reaction was heated at 80° C. for 16 hours. 5 mL of H$_2$O was added and the mixture was extracted with EtOAc (2×10 mL), the organic layers were combined and dried with MgSO$_4$. After filtration and evaporation of the solvent the product was purified by column chromatography (silica, hexane/EtOAc 10:0 to 6:4).

Yield: 88 mg (73% of theory)
$C_{20}H_{29}N_5O_3$ (M=387.49)
predicted: Molecular ion (M+H)$^+$: 388 observed: Molecular ion (M+H)$^+$: 388
HPLC-MS: 1.85 minutes (Method A)
Rf: 0.4 (hexane/EtOAc 6:4)

1f 10-[1,4]Oxazepan-4-yl-6,7,8,9-tetrahydro-5H-1,4,7,10a-tetraaza-cyclohepta[f]indene To 88 mg (0.23 mmol) 10-[1,4]oxazepan-4-yl-5,6,8,9-tetrahydro-1,4,7,10a-tetraaza-cyclohepta[f]indene-7-carboxylic acid tert-butyl ester in 3 mL DCM, was added 1.13 mL (4.5 mmol) HCl in dioxane (4 M), and the reaction was stirred at room temperature for 16 hours. The solvent was evaporated to give the desired product as a HCl salt.

Yield: 52.2 mg (64% of theory)

$C_{15}H_{21}N_5O$ (M=287.37)

predicted: Molecular ion $(M+H)^+$: 288 observed: Molecular ion $(M+H)^+$: 288

HPLC-MS: 1.18 minutes (Method B)

In case that TF salts are listed a mixture of dichloromethane and TFA (1/1) was used to remove the boc-protection group.

TABLE 1

| Example | Structure | Yield of final steps or last two steps (%) | Salt type | Mass spec result | HPLC retention time (method) |
|---|---|---|---|---|---|
| 1.1 | 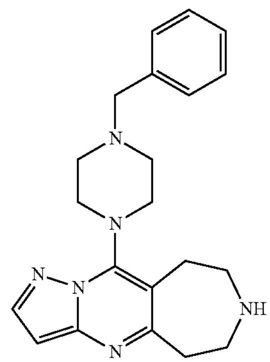 [SMILES: c1ccc(CN2CCN(c3c4c(nc5ccnn35)CCNCC4)CC2)cc1] | 69 | HCl | 363 $[M + H]^+$ | 1.67 (B) |
| 1.2 | 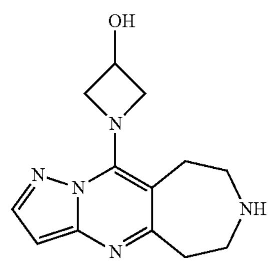 [SMILES: OC1CN(c2c3c(nc4ccnn24)CCNCC3)C1] | 74 | HCl | 260 $[M + H]^+$ | 0.92 (B) |
| 1.3 | 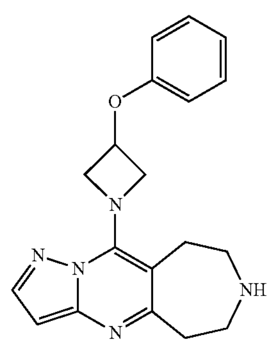 [SMILES: c1ccc(OC2CN(c3c4c(nc5ccnn35)CCNCC4)C2)cc1] | 80 | HCl | 336 $[M + H]^+$ | 1.49 (B) |
| 1.4 | 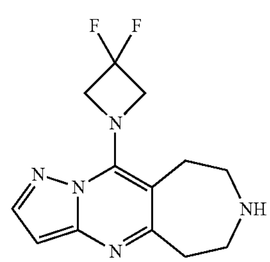 [SMILES: FC1(F)CN(c2c3c(nc4ccnn24)CCNCC3)C1] | 42 | HCl | 280 $[M + H]^+$ | 1.25 (B) |

TABLE 1-continued

| Example | Structure | Yield of final steps or last two steps (%) | Salt type | Mass spec result | HPLC retention time (method) |
|---|---|---|---|---|---|
| 1.5 | 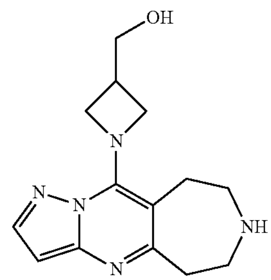 [SMILES: OCC1CN(c2c3c(nc4ccnn24)CCNCC3)C1] | 70 | HCl | 274 [M + H]+ | 1.01 (B) |
| 1.6 | 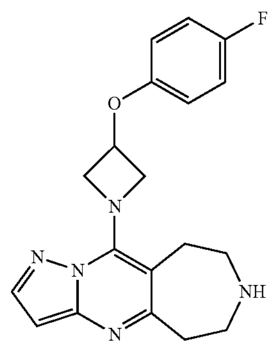 [SMILES: Fc1ccc(OC2CN(c3c4c(nc5ccnn35)CCNCC4)C2)cc1] | 66 | HCl | 354 [M + H]+ | 1.52 (B) |
| 1.7 | 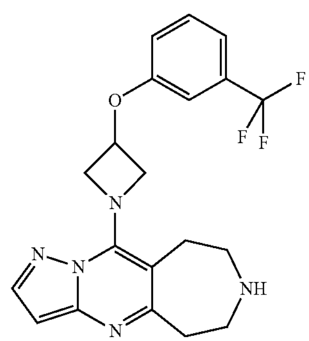 [SMILES: FC(F)(F)c1cccc(OC2CN(c3c4c(nc5ccnn35)CCNCC4)C2)c1] | 81 | HCl | 404 [M + H]+ | 1.88 (B) |
| 1.8 | 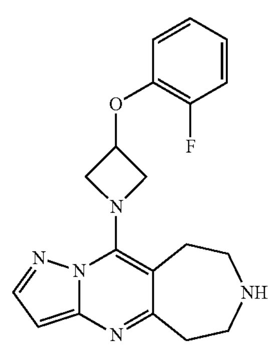 [SMILES: Fc1ccccc1OC1CN(c2c3c(nc4ccnn24)CCNCC3)C1] | 58 | HCl | 354 [M + H]+ | 1.62 (B) |

TABLE 1-continued

| Example | Structure | Yield of final steps or last two steps (%) | Salt type | Mass spec result | HPLC retention time (method) |
|---|---|---|---|---|---|
| 1.9 | 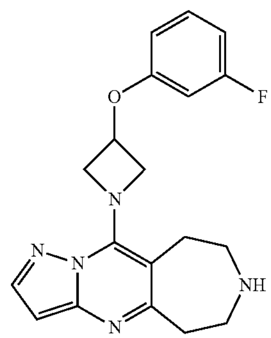 [SMILES: Fc1cccc(OC2CN(c3c4c(nc5ccnn35)CCNCC4)C2)c1] | 92 | HCl | 354 [M + H]+ | 1.63 (B) |
| 1.10 | 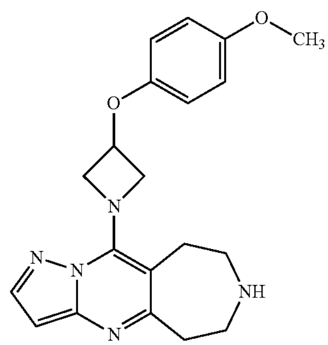 [SMILES: COc1ccc(OC2CN(c3c4c(nc5ccnn35)CCNCC4)C2)cc1] | 99 | HCl | 366 [M + H]+ | 1.63 (B) |
| 1.11 | 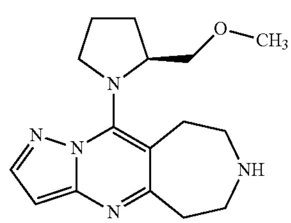 [SMILES: COC[C@@H]1CCCN1c1c2c(nc3ccnn13)CCNCC2] | 100 | HCl | 302 [M + H]+ | 1.21 (B) |
| 1.12 | 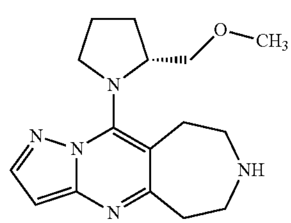 [SMILES: COC[C@H]1CCCN1c1c2c(nc3ccnn13)CCNCC2] | 100 | HCl | 302 [M + H]+ | 1.24 (B) |
| 1.13 | 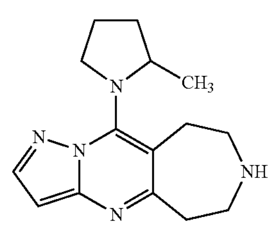 [SMILES: CC1CCCN1c1c2c(nc3ccnn13)CCNCC2] | 98 | HCl | 272 [M + H]+ | 1.52 (B) |

TABLE 1-continued

| Example | Structure | Yield of final steps or last two steps (%) | Salt type | Mass spec result | HPLC retention time (method) |
|---|---|---|---|---|---|
| 1.14 | 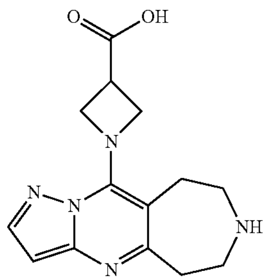 [SMILES: O=C(O)C1CN(c2c3c(nc4ccnn24)CCNCC3)C1] | 100 | TF | 288 [M + H]⁺ | 1.78 (C) |
| 1.15 | 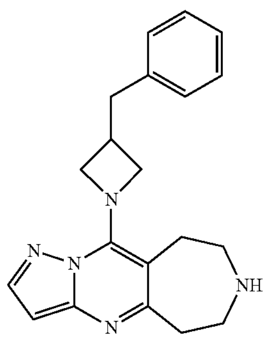 | 99 | TF | 334 [M + H]⁺ | 4.66 (C) |
| 1.16 | 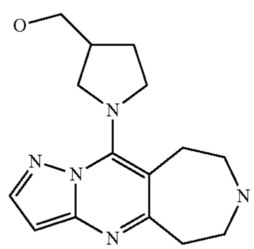 [SMILES: OCC1CCN(c2c3c(nc4ccnn24)CCNCC3)C1] | 38 | TF | 288.2 [M + H]⁺ | 2.26 (G) |
| 1.17 | 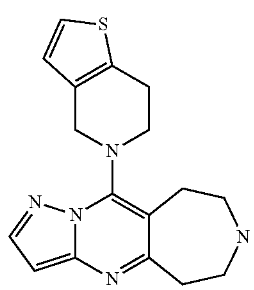 [SMILES: c1cc2nc3c(c(N4CCc5sccc5C4)n2n1)CCNCC3] | 23 | TF | 326.1 [M + H]⁺ | 1.69 (G) |
| 1.18 | 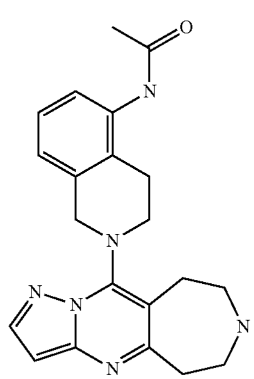 [SMILES: CC(=O)Nc1cccc2c1CCN(c1c3c(nc4ccnn14)CCNCC3)C2] | 15 | TF | 377.2 [M + H]⁺ | 1.46 (G) |

TABLE 1-continued
| Example | Structure | Yield of final steps or last two steps (%) | Salt type | Mass spec result | HPLC retention time (method) |
|---|---|---|---|---|---|
| 1.19 | 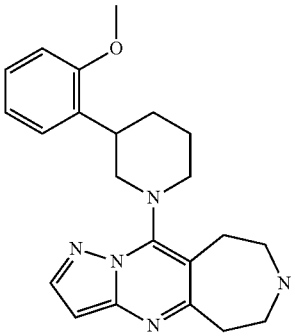 [SMILES: COc1ccccc1C1CCCN(c2c3c(nc4ccnn24)CCNCC3)C1] | 33 | TF | 378.3 [M + H]+ | 1.83 (G) |
| 1.20 | 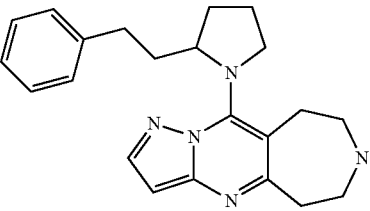 [SMILES: c1ccc(CCC2CCCN2c2c3c(nc4ccnn24)CCNCC3)cc1] | 33 | TF | 362.2 [M + H]+ | 1.78 (G) |
| 1.21 | 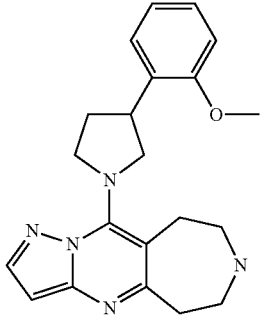 [SMILES: COc1ccccc1C1CCN(c2c3c(nc4ccnn24)CCNCC3)C1] | 24 | TF | 364.2 [M + H]+ | 1.69 (G) |
| 1.22 | 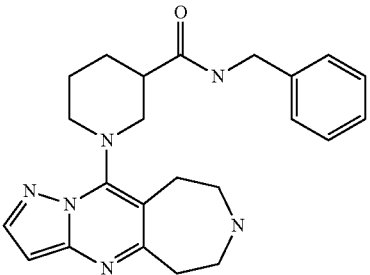 [SMILES: O=C(NCc1ccccc1)C1CCCN(c2c3c(nc4ccnn24)CCNCC3)C1] | 38 | TF | 405.3 [M + H]+ | 1.64 (G) |
| 1.23 | 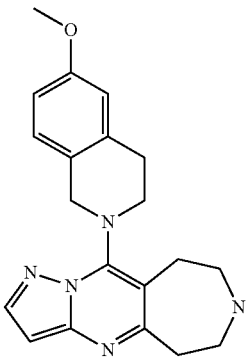 [SMILES: COc1ccc2c(c1)CCN(c1c3c(nc4ccnn14)CCNCC3)C2] | 7 | BS | 350.2 [M + H]+ | 1.7 (G) |

TABLE 1-continued

| Example | Structure | Yield of final steps or last two steps (%) | Salt type | Mass spec result | HPLC retention time (method) |
|---|---|---|---|---|---|
| 1.24 | 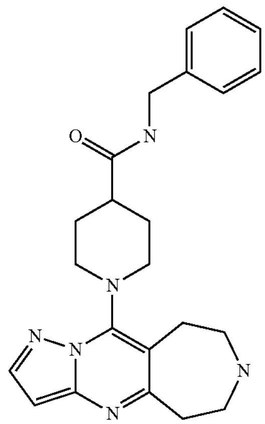 [SMILES: O=C(NCc1ccccc1)C1CCN(c2c3c(nc4ccnn24)CCNCC3)CC1] | 30 | TF | 405.3 [M + H]+ | 1.61 (G) |
| 1.25 | 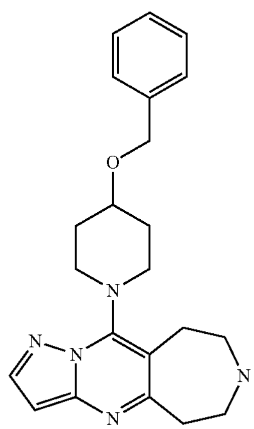 [SMILES: c1ccc(COC2CCN(c3c4c(nc5ccnn35)CCNCC4)CC2)cc1] | 29 | TF | 378.2 [M + H]+ | 1.78 (G) |
| 1.26 | 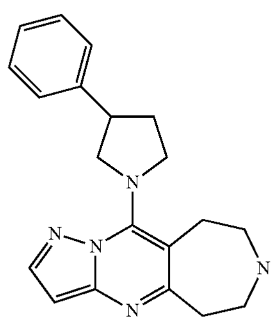 [SMILES: c1ccc(C2CCN(c3c4c(nc5ccnn35)CCNCC4)C2)cc1] | 49 | TF | 334.2 [M + H]+ | 1.64 (G) |
| 1.27 | 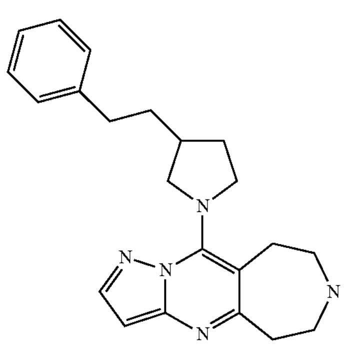 [SMILES: c1ccc(CCC2CCN(c3c4c(nc5ccnn35)CCNCC4)C2)cc1] | 47 | TF | 362.2 [M + H]+ | 1.76 (G) |

TABLE 1-continued

| Example | Structure | Yield of final steps or last two steps (%) | Salt type | Mass spec result | HPLC retention time (method) |
| --- | --- | --- | --- | --- | --- |
| 1.28 | 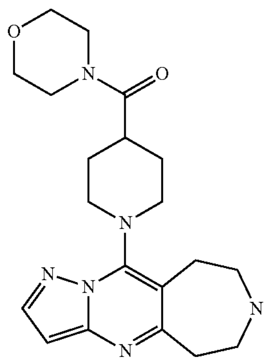 [SMILES: O=C(C1CCN(c2c3c(nc4ccnn24)CCNCC3)CC1)N1CCOCC1] | 43 | TF | 385.3 [M + H]+ | 1.36 (G) |
| 1.29 | 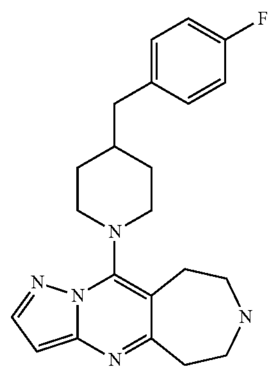 [SMILES: Fc1ccc(CC2CCN(c3c4c(nc5ccnn35)CCNCC4)CC2)cc1] | 64 | TF | 380.2 [M + H]+ | 1.87 (G) |
| 1.30 | 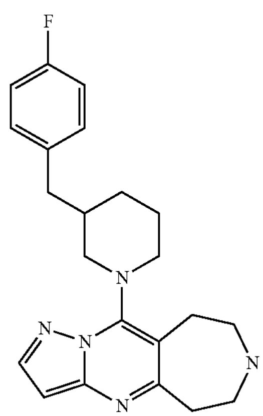 [SMILES: Fc1ccc(CC2CCCN(c3c4c(nc5ccnn35)CCNCC4)C2)cc1] | 67 | TF | 380.2 [M + H]+ | 1.86 (G) |
| 1.31 | 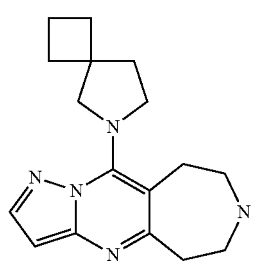 [SMILES: c1cc2nc3c(c(N4CCC5(CCC5)C4)n2n1)CCNCC3] | 69 | TF | 298.2 [M + H]+ | 1.53 (G) |

TABLE 1-continued

| Example | Structure | Yield of final steps or last two steps (%) | Salt type | Mass spec result | HPLC retention time (method) |
|---|---|---|---|---|---|
| 1.32 | 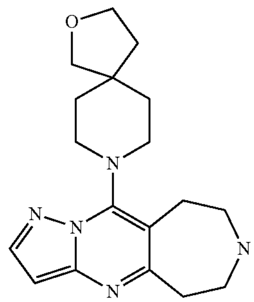 [SMILES: c1cc2nc3c(c(N4CCC5(CCOC5)CC4)n2n1)CCNCC3] | 51 | TF | 328.2 [M + H]⁺ | 1.45 (G) |
| 1.33 | 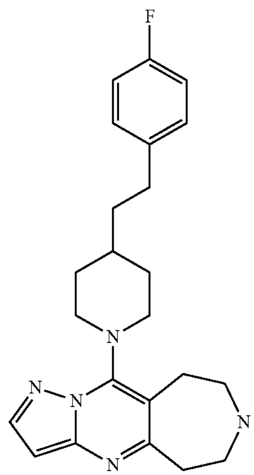 [SMILES: Fc1ccc(CCC2CCN(c3c4c(nc5ccnn35)CCNCC4)CC2)cc1] | 75 | TF | 394.3 [M + H]⁺ | 1.95 (G) |
| 1.34 | 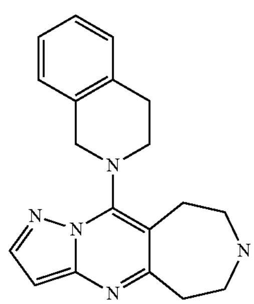 [SMILES: c1ccc2c(c1)CCN(c1c3c(nc4ccnn14)CCNCC3)C2] | 50 | TF | 320.2 [M + H]⁺ | 1.7 (G) |
| 1.35 | 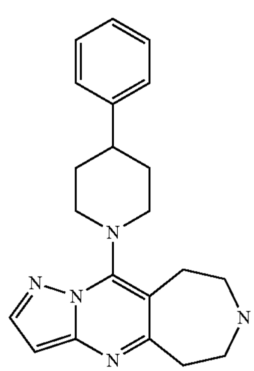 [SMILES: c1ccc(C2CCN(c3c4c(nc5ccnn35)CCNCC4)CC2)cc1] | 69 | TF | 348.2 [M + H]⁺ | 1.79 (G) |

TABLE 1-continued
| Example | Structure | Yield of final steps or last two steps (%) | Salt type | Mass spec result | HPLC retention time (method) |
|---|---|---|---|---|---|
| 1.36 | 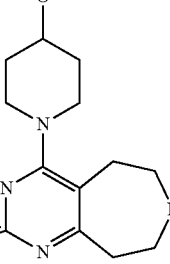 | 85 | TF | 288 [M + H]+ | 1.3 (G) |
| 1.37 | 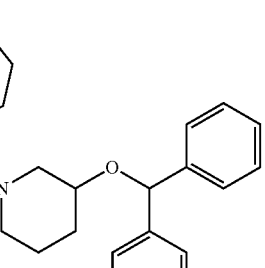 | 1 | TF | 455 [M + H]+ | 1.97 (G) |
| 1.38 | 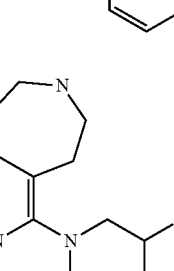 | 58 | TF | 288 [M + H]+ | 1.43 (G) |
| 1.39 | 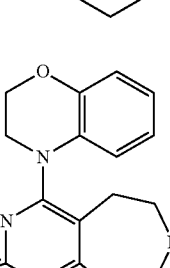 | 22 | TF | 322 [M + H]+ | 1.62 (G) |
| 1.40 | 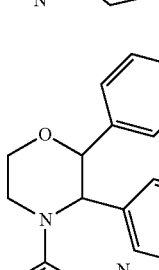 | 4 | TF | 426 [M + H]+ | 1.93 (G) |

TABLE 1-continued

| Example | Structure | Yield of final steps or last two steps (%) | Salt type | Mass spec result | HPLC retention time (method) |
|---|---|---|---|---|---|
| 1.41 | 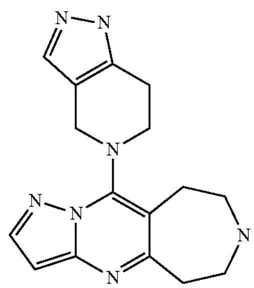 [SMILES: c1cc2nc3c(c(N4CCc5[nH]ncc5C4)n2n1)CCNCC3] | 36 | TF | 310.2 [M + H]+ | 1.35 (H) |
| 1.42 | 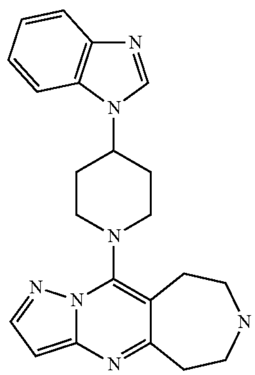 [SMILES: c1ccc2c(c1)ncn2C1CCN(c2c3c(nc4ccnn24)CCNCC3)CC1] | 15 | TF | 388 [M + H]+ | 1.45 (H) |
| 1.43 | 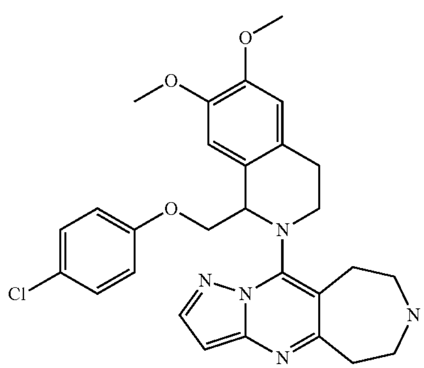 [SMILES: COc1cc2c(cc1OC)C(COc1ccc(Cl)cc1)N(c1c3c(nc4ccnn14)CCNCC3)CC2] | 23 | TF | 520.2 [M + H]+ | 1.91 (H) |
| 1.44 | 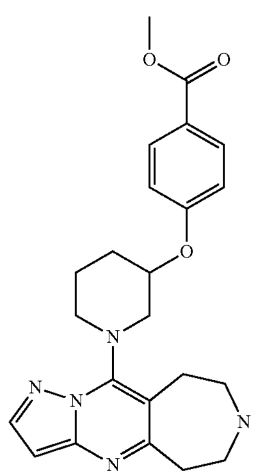 [SMILES: COC(=O)c1ccc(OC2CCCN(c3c4c(nc5ccnn35)CCNCC4)C2)cc1] | 61 | TF | 422.2 [M + H]+ | 1.8 (H) |

TABLE 1-continued

| Example | Structure | Yield of final steps or last two steps (%) | Salt type | Mass spec result | HPLC retention time (method) |
|---|---|---|---|---|---|
| 1.45 | 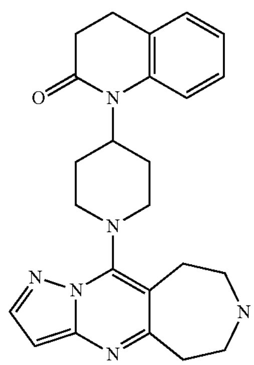 [SMILES: O=C1CCc2ccccc2N1C1CCN(c2c3c(nc4ccnn24)CCNCC3)CC1] | 73 | TF | 417.2 [M + H]+ | 1.71 (H) |
| 1.46 | 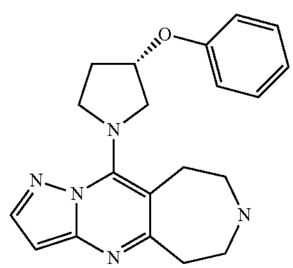 [SMILES: c1ccc(O[C@H]2CCN(c3c4c(nc5ccnn35)CCNCC4)C2)cc1] | 63 | TF | 350.2 [M + H]+ | 1.65 (H) |
| 1.47 | 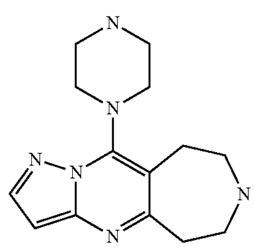 [SMILES: c1cc2nc3c(c(N4CCNCC4)n2n1)CCNCC3] | 24 | BS | 273 [M + H]+ | 1.03 (K) |
| 1.48 | 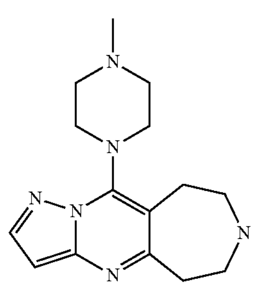 [SMILES: CN1CCN(c2c3c(nc4ccnn24)CCNCC3)CC1] | 24 | BS | 287 [M + H]+ | 1.61 (L) |
| 1.49 | 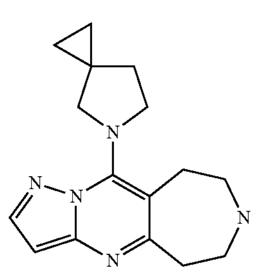 [SMILES: c1cc2nc3c(c(N4CCC5(CC5)C4)n2n1)CCNCC3] | 88 | TF2 | 284 [M + H]+ | 1.55 (J) |

TABLE 1-continued
| Example | Structure | Yield of final steps or last two steps (%) | Salt type | Mass spec result | HPLC retention time (method) |
|---|---|---|---|---|---|
| 1.50 | 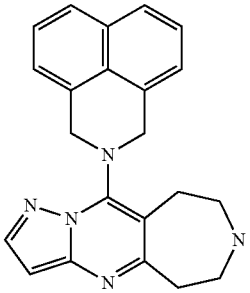 [SMILES: c1cc2c3c(cccc3c1)CN(c1c3c(nc4ccnn14)CCNCC3)C2] | 19 | TF | 356.2 [M + H]⁺ | 1.82 (G) |
| 1.51 | 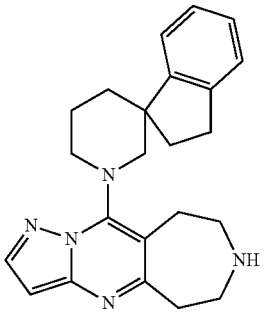 [SMILES: c1ccc2c(c1)CCC21CCCN(c2c3c(nc4ccnn24)CCNCC3)C1] | 56 | TF | 374.2 [M + H]⁺ | 1.64 (H) |
| 1.52 | 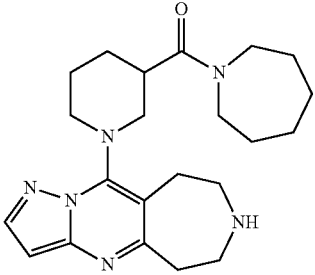 [SMILES: O=C(C1CCCN(c2c3c(nc4ccnn24)CCNCC3)C1)N1CCCCCC1] | 39 | TF | 397.2 [M + H]⁺ | 1.43 (H) |
| 1.53 | 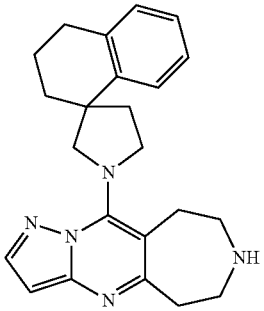 [SMILES: c1ccc2c(c1)CCCC21CCN(c2c3c(nc4ccnn24)CCNCC3)C1] | 38 | TF | 374.2 [M + H]⁺ | 1.53 (H) |
| 1.54 | 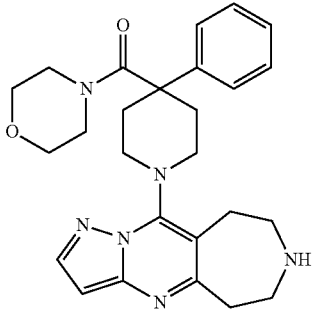 [SMILES: O=C(N1CCOCC1)C1(c2ccccc2)CCN(c2c3c(nc4ccnn24)CCNCC3)CC1] | 51 | TF | 461.2 [M + H]⁺ | 1.45 (H) |

TABLE 1-continued

| Example | Structure | Yield of final steps or last two steps (%) | Salt type | Mass spec result | HPLC retention time (method) |
|---|---|---|---|---|---|
| 1.55 | 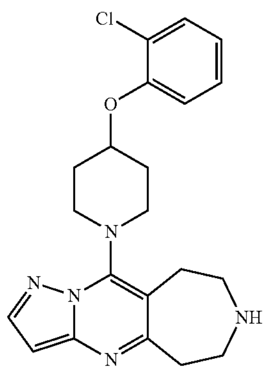 [SMILES: Clc1ccccc1OC1CCN(c2c3c(nc4ccnn24)CCNCC3)CC1] | 57 | TF | 398.1 [M + H]⁺ | 1.61 (H) |
| 1.56 | 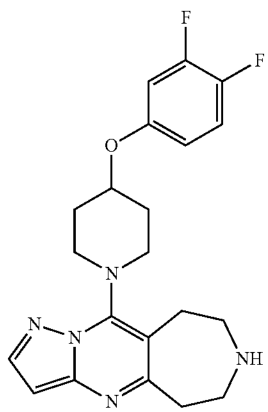 [SMILES: Fc1ccc(OC2CCN(c3c4c(nc5ccnn35)CCNCC4)CC2)cc1F] | 51 | TF | 400.1 [M + H]⁺ | 1.63 (H) |
| 1.57 | 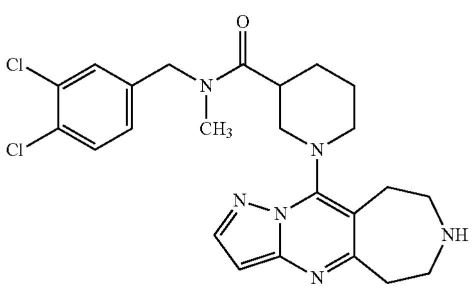 [SMILES: CN(Cc1ccc(Cl)c(Cl)c1)C(=O)C1CCCN(c2c3c(nc4ccnn24)CCNCC3)C1] | 58 | TF | 487.2 [M + H]⁺ | 1.62 (H) |
| 1.58 | 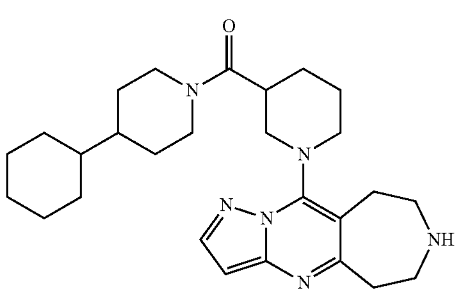 [SMILES: O=C(C1CCCN(c2c3c(nc4ccnn24)CCNCC3)C1)N1CCC(C2CCCCC2)CC1] | 39 | TF | 465.3 [M + H]⁺ | 1.73 (H) |

TABLE 1-continued

| Example | Structure | Yield of final steps or last two steps (%) | Salt type | Mass spec result | HPLC retention time (method) |
|---|---|---|---|---|---|
| 1.59 | 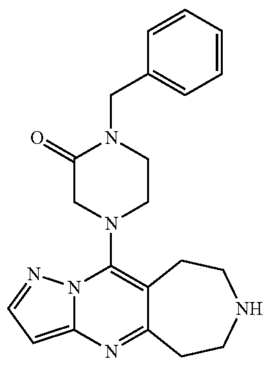 [SMILES: O=C1CN(c2c3c(nc4ccnn24)CCNCC3)CCN1Cc1ccccc1] | 4 | BS | 377.1 [M + H]+ | 1.43 (H) |
| 1.60 | 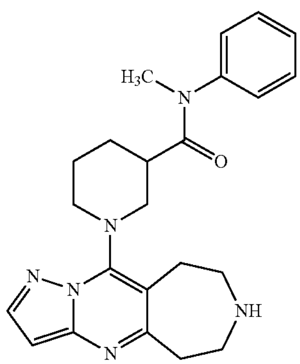 [SMILES: CN(C(=O)C1CCCN(c2c3c(nc4ccnn24)CCNCC3)C1)c1ccccc1] | 44 | TF | 405.2 [M + H]+ | 1.43 (H) |
| 1.61 | 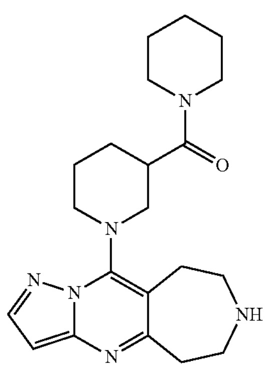 [SMILES: O=C(C1CCCN(c2c3c(nc4ccnn24)CCNCC3)C1)N1CCCCC1] | 28 | TF | 383.2 [M + H]+ | 1.38 (H) |
| 1.62 | 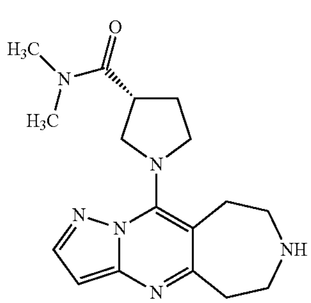 [SMILES: CN(C)C(=O)[C@@H]1CCN(c2c3c(nc4ccnn24)CCNCC3)C1] | 1 | TF | 329.2 [M + H]+ | 1.16 (H) |

TABLE 1-continued

| Example | Structure | Yield of final steps or last two steps (%) | Salt type | Mass spec result | HPLC retention time (method) |
| --- | --- | --- | --- | --- | --- |
| 1.63 | 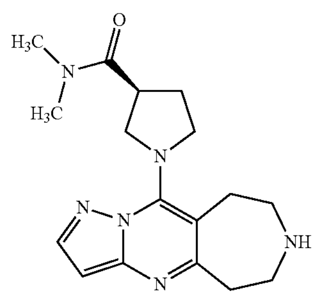 [SMILES: CN(C)C(=O)[C@H]1CCN(c2c3c(nc4ccnn24)CCNCC3)C1] | 14 | TF | 329.2 [M + H]+ | 1.16 (H) |
| 1.64 | 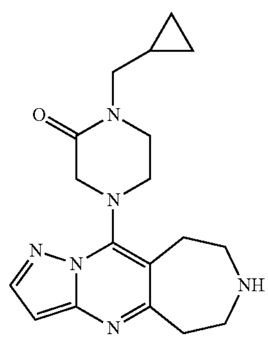 [SMILES: O=C1CN(c2c3c(nc4ccnn24)CCNCC3)CCN1CC1CC1] | 24 | TF | 341.2 [M + H]+ | 1.33 (H) |
| 1.65 | 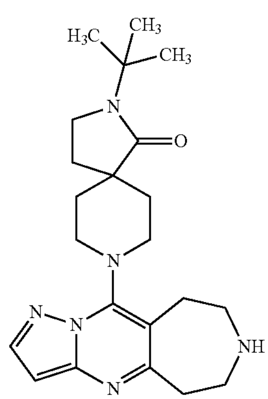 [SMILES: CC(C)(C)N1CCC2(CCN(c3c4c(nc5ccnn35)CCNCC4)CC2)C1=O] | 31 | TF | 397.2 [M + H]+ | 1.45 (H) |
| 1.66 | 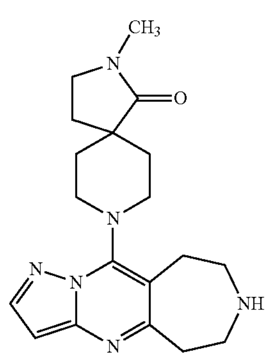 [SMILES: CN1CCC2(CCN(c3c4c(nc5ccnn35)CCNCC4)CC2)C1=O] | 18 | TF | 355.2 [M + H]+ | 1.24 (H) |

TABLE 1-continued
| Example | Structure | Yield of final steps or last two steps (%) | Salt type | Mass spec result | HPLC retention time (method) |
| --- | --- | --- | --- | --- | --- |
| 1.67 | 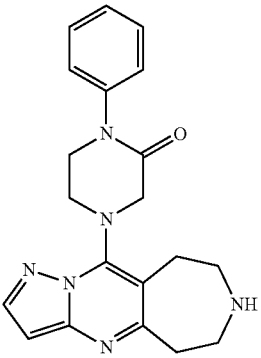 [SMILES: O=C1CN(c2c3c(nc4ccnn24)CCNCC3)CCN1c1ccccc1] | 3 | BS | 363.1 [M + H]+ | 1.37 (H) |
| 1.68 | 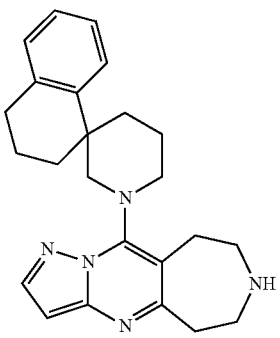 [SMILES: c1ccc2c(c1)CCCC21CCCN(c2c3c(nc4ccnn24)CCNCC3)C1] | 59 | TF | 388.2 [M + H]+ | 1.66 (H) |
Route 2
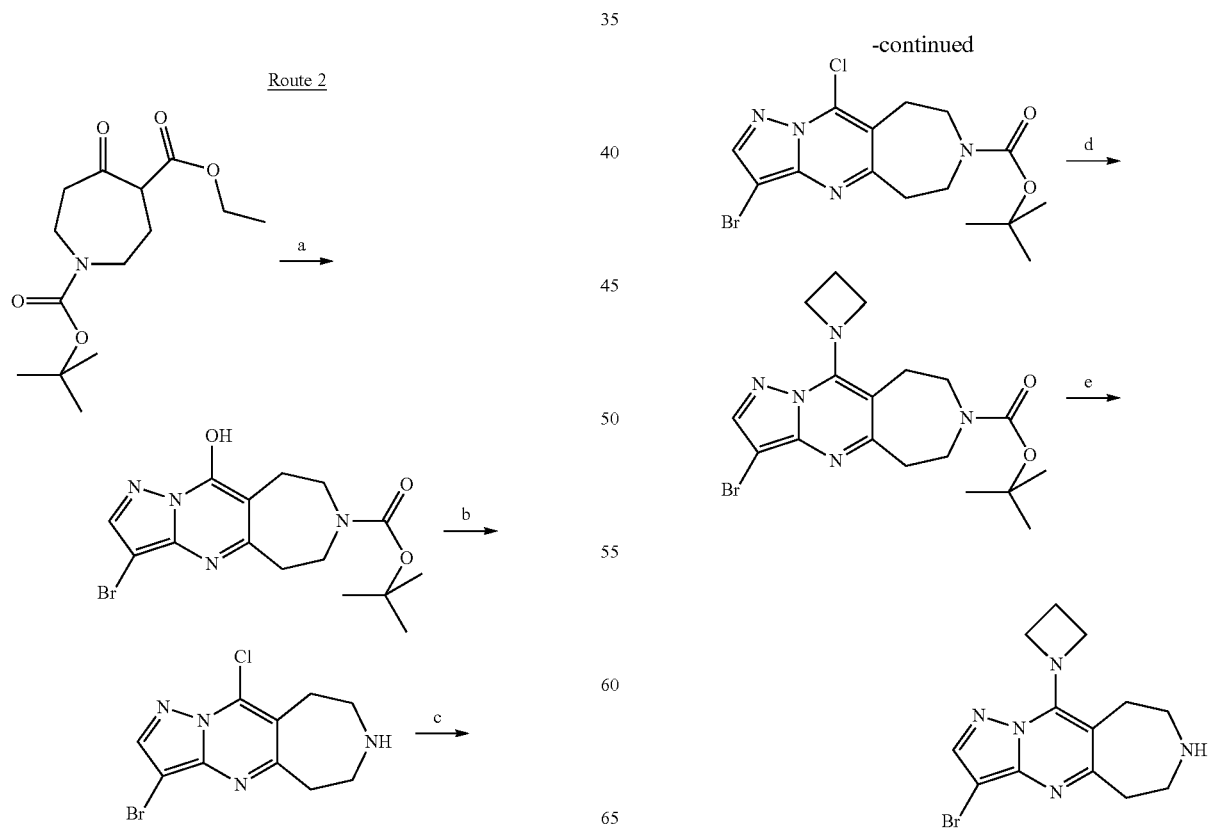

Example 2

10-Azetidin-1-yl-3-bromo-6,7,8,9-tetrahydro-5H-1,4,7,10a-tetraaza-cyclohepta[f]indene

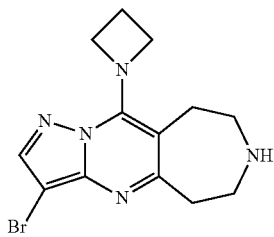 [SMILES: Brc1cnn2c(N3CCC3)c3c(nc12)CCNCC3]

Route 3

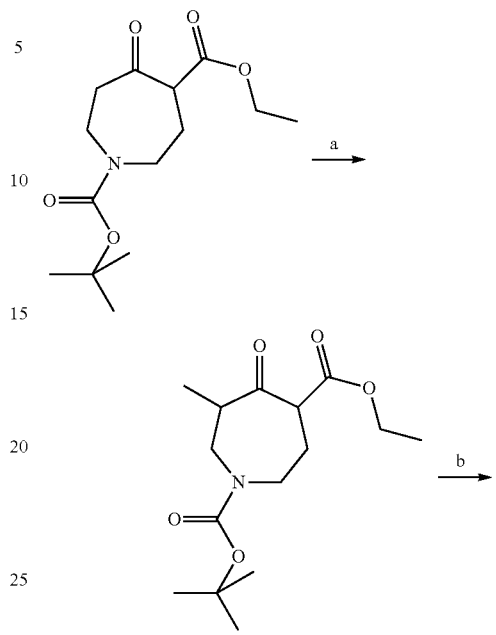

2e 10-Azetidin-1-yl-3-bromo-6,7,8,9-tetrahydro-5H-1,4,7,10a-tetraaza-cyclohepta[f]indene The product was prepared using route 1, in step b (route 1) 4-bromo-1H-pyrazol-5-amine was used, in step e (route 1) azetidine hydrochloride was used as the amine.

Yield: 80.4 mg (100% of theory)

$C_{13}H_{16}BrN_5$ (M=322.21)

predicted: Molecular ion (M+H)$^+$: 322/324 observed: Molecular ion (M+H)$^+$: 322/324

HPLC-MS: 1.36 minutes (Method B)

TABLE 2

| Example | Structure | Yield of final step (%) | Salt type | Mass spec result | HPLC retention time (method) |
|---|---|---|---|---|---|
| 2.1 | 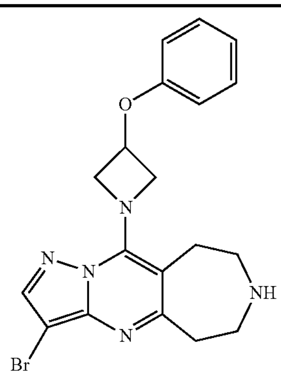 | 79 | HCl | 414/416 [M + H]$^+$ | 1.79 (B) |
| 2.2 | 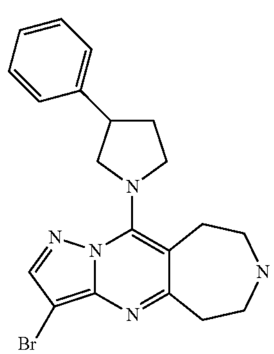 [SMILES: Brc1cnn2c(N3CCC(c4ccccc4)C3)c3c(nc12)CCNCC3] | 54 | TF | 414.1 [M + H]$^+$ | 1.89 (G) |

-continued

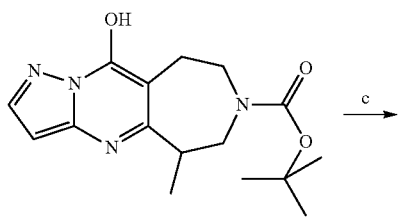

c

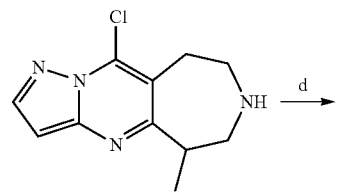

d

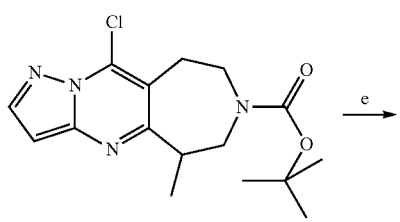

e

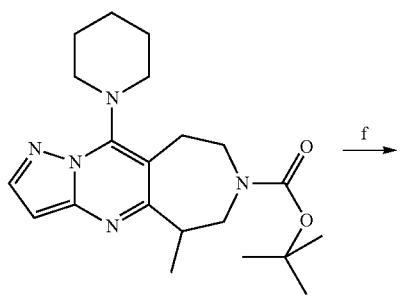

f

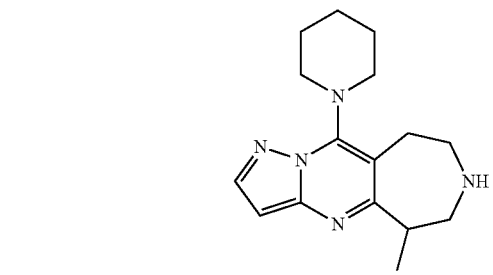

Example 3

5-Methyl-10-piperidin-1-yl-6,7,8,9-tetrahydro-5H-1,4,7,10a-tetraaza-cyclohepta[f]indene

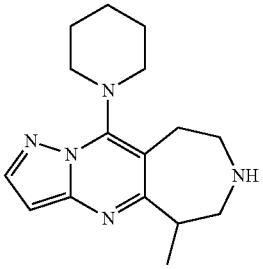 [SMILES: CC1CNCCc2c1nc1ccnn1c2N1CCCCC1]

3a 6-Methyl-5-oxo-azepane-1,4-dicarboxylic acid 1-tert-butyl ester 4-ethyl ester To 2 g (7.01 mmol) 5-oxo-azepane-1,4-dicarboxylic acid 1-tert-butyl ester 4-ethyl ester (route 1 step a) in 25 mL anhydrous THF at −78° C. was added 9.7 mL (17.46 mmol) of a 1.8 M solution of lithium diisopropylamide in heptane/THF dropwise under an atmosphere of nitrogen. The reaction mixture was stirred at −78° C. for 30 minutes and then warmed up to 0° C. 0.48 mL (7.70 mmol) iodomethane was added at 0° C. and the reaction was left to warm up to room temperature over a period of 2 hours. 100 mL of $H_2O$ was added and the mixture was extracted with EtOAc (3×100 mL), the organic layers were combined, washed with $H_2O$ (2×100 mL) and saturated brine (100 mL) and dried over $MgSO_4$. After filtration and evaporation of the solvent the product was purified by column chromatography (silica, hexane/EtOAc 9:1).

Yield: 1.25 g (60% of theory)
$C_{15}H_{25}NO_5$ (M=299.37)
predicted: Molecular ion (M+H)⁺: 300 observed: Molecular ion (M+H)⁺: 300
HPLC-MS: 1.98 minutes (Method A)
$R_f$: 0.32 (silica, hexane/EtOAc 8:2)

3f 5-Methyl-10-piperidin-1-yl-6,7,8,9-tetrahydro-5H-1,4,7,10a-tetraaza-cyclohepta[f]indene The product was prepared using 6-methyl-5-oxo-azepane-1,4-dicarboxylic acid 1-tert-butyl ester 4-ethyl ester in route 1 (from step b to step f), in step e (route 1) piperidine was used as the amine.

Yield: 100% of theory
$C_{16}H_{23}N_5$ (M=285.40)
predicted: Molecular ion (M+H)⁺: 286 observed: Molecular ion (M+H)⁺: 286
HPLC-MS: 1.68 minutes (Method B)

TABLE 3

| Example | Structure | Yield of final step (%) | Salt type | Mass spec result | HPLC retention time (method) |
|---|---|---|---|---|---|
| 3.1 | 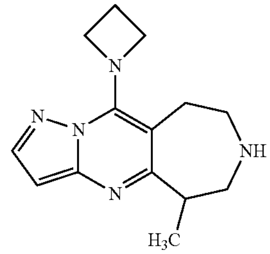 [SMILES: CC1CNCCc2c1nc1ccnn1c2N1CCC1] | 98 | TF | 258 [M + H]⁺ | 1.36 (B) |

Route 4

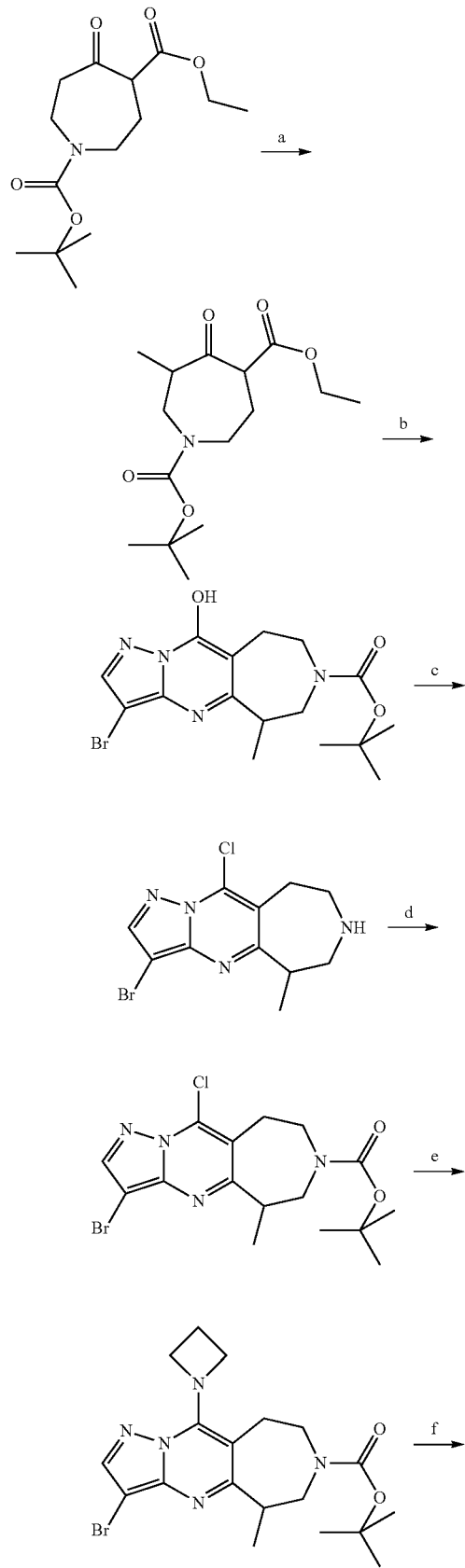

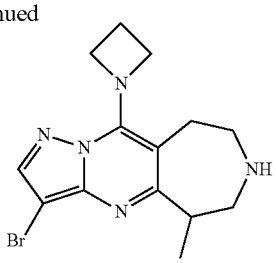

Example 4

10-Azetidin-1-yl-3-bromo-5-methyl-6,7,8,9-tetrahydro-5H-1,4,7,10a-tetraaza-cyclohepta[f]indene

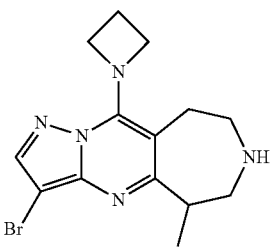 [SMILES: CC1CNCCc2c1nc1c(Br)cnn1c2N1CCC1]

4f 10-Azetidin-1-yl-3-bromo-5-methyl-6,7,8,9-tetrahydro-5H-1,4,7,10a-tetraaza-cyclohepta[f]indene The product was prepared using route 3 (step a), route 2 (step a), and route 1 (from step c to step f) with azetidine as the amine in step e (route 1).

Yield: 92% of theory $C_{14}H_{18}BrN_5$ (M=336.24)

predicted: Molecular ion (M+H)$^+$: 336/338 observed: Molecular ion (M+H)$^+$: 336/338

HPLC-MS: 1.59 minutes (Method B)

Route 5

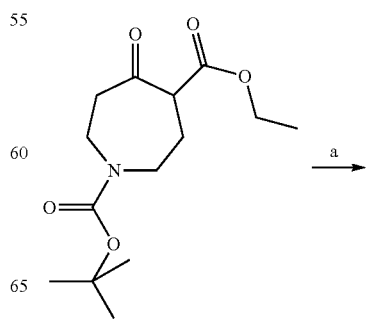

77
-continued

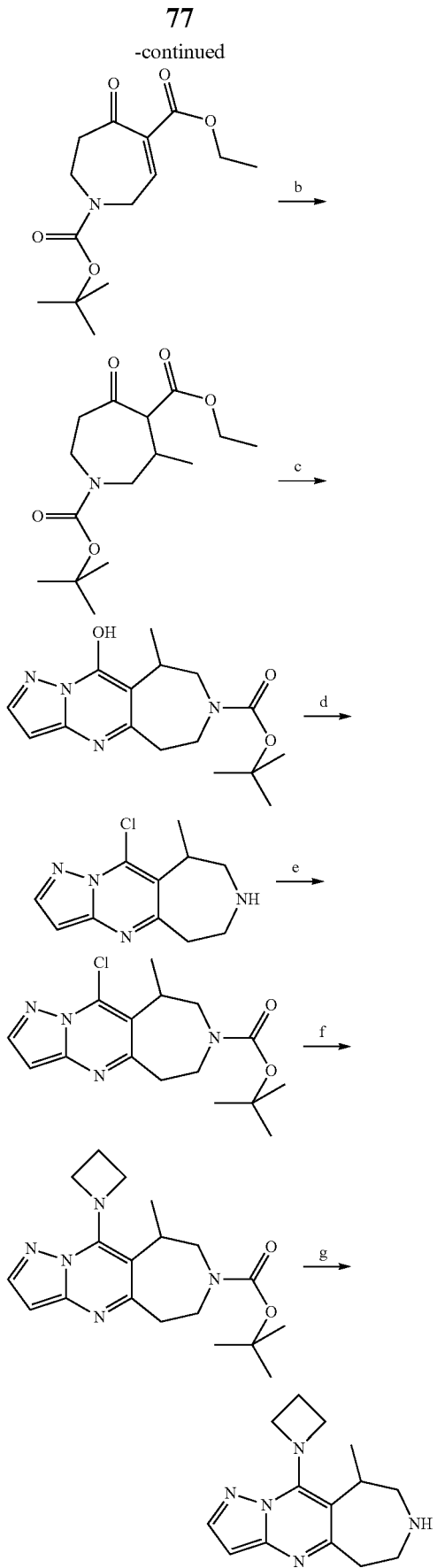

78

Example 5

10-Azetidin-1-yl-9-methyl-6,7,8,9-tetrahydro-5H-1,4,7,10a-tetraaza-cyclohepta[f]indene

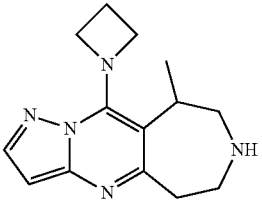 [SMILES: CC1CNCCc2nc3ccnn3c(N3CCC3)c21]

5a
5-Oxo-2,5,6,7-tetrahydro-azepine-1,4-dicarboxylic acid 1-tert-butyl ester 4-ethyl ester To 4.64 g (16.26 mmol) 5-oxo-azepane-1,4-dicarboxylic acid 1-tert-butyl ester 4-ethyl ester (route 1 step a) in 200 mL benzene at room temperature was added 1.47 g (8.13 mmol) copper (II) acetate and the resulting reaction mixture was stirred at room temperature for 30 minutes. 7.21 g (16.26 mmol) lead (IV) tetraacetate was added and the reaction was stirred at room temperature for 3 hours. After evaporation of the solvent, the material was partitioned between 250 mL EtOAc and 150 mL H$_2$O, the organic layer was separated and washed with H$_2$O (150 mL) and saturated brine (150 mL) and dried over MgSO$_4$. After filtration and evaporation of the solvent the resulting solid was used for the next step without further purification.

Yield: 3.85 g (crude)
C$_{14}$H$_{21}$NO$_5$ (M=283.33)
predicted: Molecular ion (M+H)$^+$: 284 observed: Molecular ion (M+H)$^+$: 284
HPLC-MS: 1.88 minutes (Method A)
R$_f$: 0.27 (silica, hexane/EtOAc 6:4)

5b 3-Methyl-5-oxo-azepane-1,4-dicarboxylic acid 1-tert-butyl ester 4-ethyl ester To a suspension of 5.18 g (27.18 mmol) CuI in 85 mL anhydrous THF at −78° C. was added 24 mL (34 mmol) of a 1.4 M solution of methyl magnesium bromide in THF/toluene dropwise under an atmosphere of nitrogen, the reaction was left to warm up to −15° C. and then stirred at this temperature for 45 minutes. It was cooled again at −78° C. and a solution of 3.85 g (13.59 mmol) 5-oxo-2,5,6,7-tetrahydro-azepine-1,4-dicarboxylic acid 1-tert-butyl ester 4-ethyl ester in 30 mL anhydrous THF was added dropwise. The resulting reaction mixture was stirred at −78° C. for 30 minutes and then left to warm up to room temperature over a period of 60 minutes. 100 mL saturated aqueous ammonium chloride was added and the resulting mixture was extracted with EtOAc (3×150 mL), the organic layers were combined, washed with H$_2$O (2×200 mL) and saturated brine (200 mL) and dried over MgSO$_4$. After filtration and evaporation of the solvent the product was purified by column chromatography (silica, hexane/EtOAc 8:2) to give crude material that was used in the next step.

5c 10-Hydroxy-9-methyl-5,6,8,9-tetrahydro-1,4,7,10a-tetraaza-cyclohepta[f]indene-7-carboxylic acid tert-butyl ester To a solution of 1.95 g (6.23 mmol) 3-methyl-5-oxo-azepane-1,4-dicarboxylic acid 1-tert-butyl ester 4-ethyl ester in 10 mL acetic acid was added 0.52 g (6.23 mmol) 3-aminopyrazole and the reaction mixture was heated at 80° C. for 3 hours. After the reaction was cooled at room temperature, the solvent was evaporated and the product purified by column chromatography (silica, DCM/MeOH 95:5).

Yield: 1.98 g (38% of theory for three steps)

$C_{16}H_{22}N_4O_3$ (M=318.38)

predicted: Molecular ion (M+H)$^+$: 319 observed: Molecular ion (M+H)$^+$: 319

HPLC-MS: 1.54 minutes (Method A)

$R_f$: 0.42 (silica, DCM/MeOH 9:1)

5 g 10-Azetidin-1-yl-9-methyl-6,7,8,9-tetrahydro-5H-1,4,7,10a-tetraaza-cyclohepta[f]indene The product was prepared using 10-hydroxy-9-methyl-5,6,8,9-tetrahydro-1,4,7,10a-tetraaza-cyclohepta[f]indene-7-carboxylic acid tert-butyl ester in route 1 (from step c to f), in step e (route 1) azetidine was used as the amine.

Yield: 100% of theory $C_{14}H_{19}N_5$ (M=257.34)

predicted: Molecular ion (M+H)$^+$: 258 observed: Molecular ion (M+H)$^+$: 258

HPLC-MS: 1.23 minutes (Method B)

Route 6

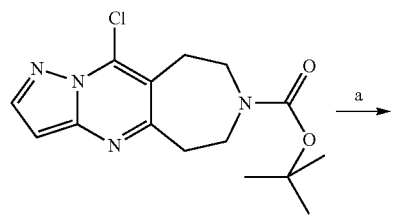

a →

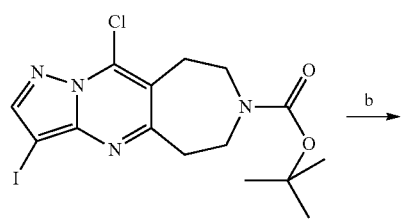

b →

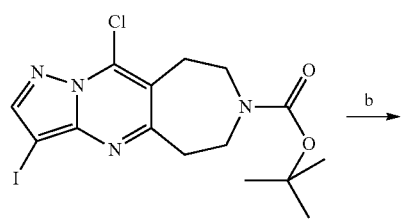

c →

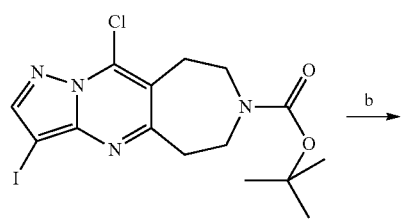

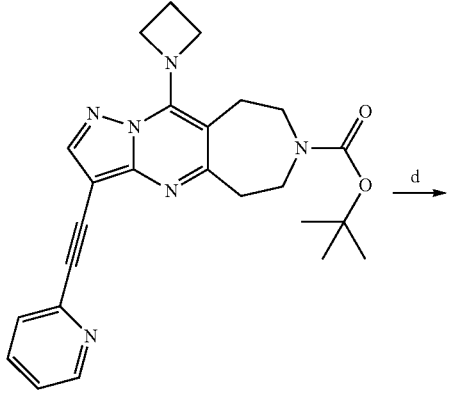

d →

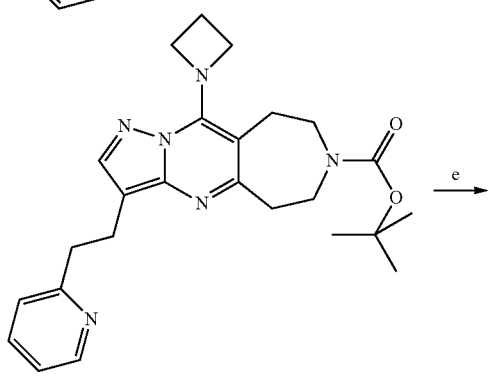

e →

Example 6

10-Azetidin-1-yl-3-(2-pyridin-2-yl-ethyl)-6,7,8,9-tetrahydro-5H-1,4,7,10a-tetraaza-cyclohepta[f]indene

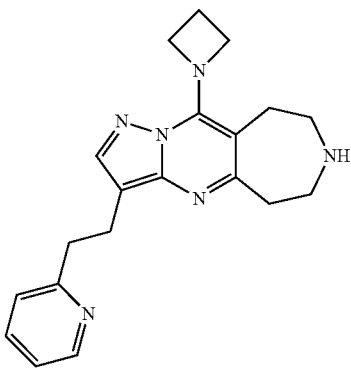 [SMILES: c1ccc(CCc2cnn3c(N4CCC4)c4c(nc23)CCNCC4)nc1]

6a 10-Chloro-3-iodo-5,6,8,9-tetrahydro-1,4,7,10a-tetraaza-cyclohepta[f]indene-7-carboxylic acid tert-butyl ester To 0.1 g (0.31 mmol) 10-chloro-5,6,8,9-tetrahydro-1,4,7,10a-tetraaza-cyclohepta[f]indene-7-carboxylic acid tert-butyl ester (route 1, step a to d) in 2 mL DMF, under nitrogen, was added 0.104 g (0.46 mmol) N-iodosuccinimide, and the reaction was stirred at room temperature for 16 hours. 20 mL EtOAc was added and the mixture was washed with a 10% solution of $Na_2S_2O_3$ (2×5 mL). The aqueous layers were combined and extracted with EtOAc (2×10 mL). The organic layers were combined, washed with 10 mL saturated brine, and dried with $MgSO_4$. After filtration and evaporation of the solvent the product was purified by column chromatography (silica, heptane/EtOAc 9:1).
Yield: 139 mg (100% of theory)
$C_{15}H_{18}ClIN_4O_2$ (M=448.69)
predicted: Molecular ion (M+H)$^+$: 449/451 observed: Molecular ion (M+H)$^+$: 449/451
HPLC-MS: 2.25 minutes (Method A)
$R_f$: 0.46 (heptane/EtOAc 7:3)

6b 10-Azetidin-1-yl-3-iodo-5,6,8,9-tetrahydro-1,4,7,10a-tetraaza-cyclohepta[f]indene-7-carboxylic acid tert-butyl ester The product was prepared using 10-chloro-3-iodo-5,6,8,9-tetrahydro-1,4,7,10a-tetraaza-cyclohepta[f]indene-7-carboxylic acid tert-butyl ester and azetidine as the amine in route 1 (step e).
Yield: 0.35 g (98% crude)
$C_{18}H_{24}IN_5O_2$ (M=469.33)
predicted: Molecular ion (M+H)$^+$: 470 observed: Molecular ion (M+H)$^+$: 470
HPLC-MS: 1.27 minutes (Method A)

6c 10-Azetidin-1-yl-3-pyridin-2-ylethynyl-5,6,8,9-tetrahydro-1,4,7,10a-tetraaza-cyclohepta[f]indene-7-carboxylic acid tert-butyl ester To 0.1 g (0.21 mmol) 10-azetidin-1-yl-3-iodo-5,6,8,9-tetrahydro-1,4,7,10a-tetraaza-cyclohepta[f]indene-7-carboxylic acid tert-butyl ester in a sealed tube under nitrogen was added 3 mL of dioxane and the mixture was degassed with nitrogen for 3 minutes. 14.7 mg (0.02 mmol) 1,1'-bis-(diphenylphosphino)-ferrocenedichloro palladium (II) was added and the reaction mixture was stirred at room temperature for 30 minutes. 86 μL (0.85 mmol) 2-ethynyl pyridine was added followed by 0.53 mL (3.8 mmol) triethylamine and 4 mg (0.02 mmol) CuI, and the reaction was stirred at 60° C. for 16 hours under nitrogen. The mixture was cooled to room temperature and partitioned between 20 mL EtOAc and 20 mL saturated ammonium chloride. The mixture was extracted with EtOAc (3×10 mL), the organic layers combined, washed with 20 mL brine, and dried with $MgSO_4$. After filtration and evaporation of the solvent the desired product was purified by column chromatography (silica, heptane/EtOAc 9:1 to 3:7).
Yield: 87 mg (92% of theory)
$C_{25}H_{28}N_6O_2$ (M=444.54)
predicted: Molecular ion (M+H)$^+$: 445 observed: Molecular ion (M+H)$^+$: 445
HPLC-MS: 1.28 minutes (Method A)

6d 10-Azetidin-1-yl-3-(2-pyridin-2-yl-ethyl)-5,6,8,9-tetrahydro-1,4,7,10a-tetraaza-cyclohepta[f]indene-7-carboxylic acid tert-butyl ester To 87 mg (0.2 mmol) 10-azetidin-1-yl-3-pyridin-2-ylethynyl-5,6,8,9-tetrahydro-1,4,7,10a-tetraaza-cyclohepta[f]indene-7-carboxylic acid tert-butyl ester in 3 mL ethanol was added 11 mg (20% weight) palladium hydroxide, the reaction was purged 3 times with nitrogen then 3 times with hydrogen and was stirred at room temperature under a balloon of hydrogen for 16 hours. The mixture was purged twice with nitrogen, then the solution was filtered through a pad of celite. After evaporation of the solvent the product was purified by column chromatography (silica, heptane/EtOAc 9:1 to 3:7).
Yield: 71 mg (81% of theory)
$C_{25}H_{32}N_6O_2$ (M=448.57)
predicted: Molecular ion (M+H)$^+$: 449 observed: Molecular ion (M+H)$^+$: 449
HPLC-MS: 0.95 minutes (Method D)

6e 10-Azetidin-1-yl-3-(2-pyridin-2-yl-ethyl)-6,7,8,9-tetrahydro-5H-1,4,7,10a-tetraaza-cyclohepta[f]indene The product was prepared using 10-azetidin-1-yl-3-(2-pyridin-2-yl-ethyl)-5,6,8,9-tetrahydro-1,4,7,10a-tetraaza-cyclohepta[f]indene-7-carboxylic acid tert-butyl ester in route 1 (step f).
Yield: 60.1 mg (90% of theory)
$C_{20}H_{24}N_6$ (M=348.45)
predicted: Molecular ion (M+H)$^+$: 349 observed: Molecular ion (M+H)$^+$: 349
HPLC-MS: 3.75 minutes (Method C)

TABLE 4

| Example | Structure | Yield of final step (%) | Salt type | Mass spec result | HPLC retention time (method) |
|---|---|---|---|---|---|
| 6.1 | 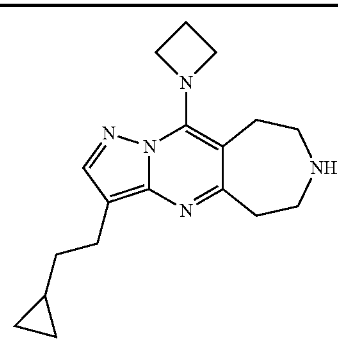 | 22 | none | 312 [M + H]$^+$ | 4.60 (C) |

Route 7

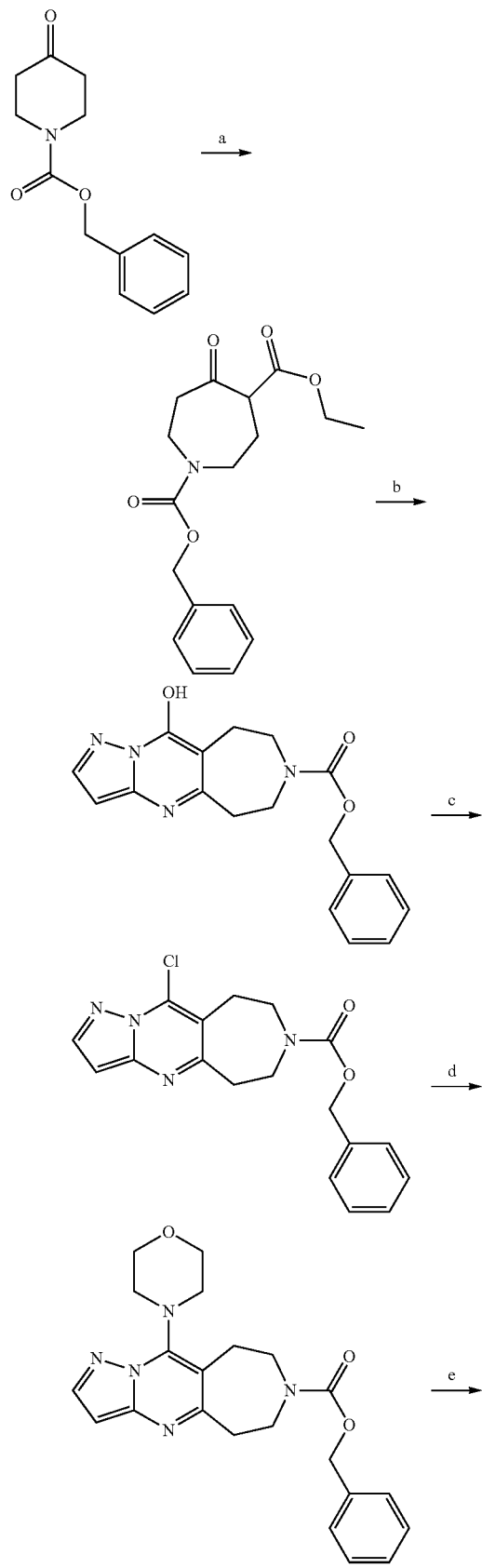

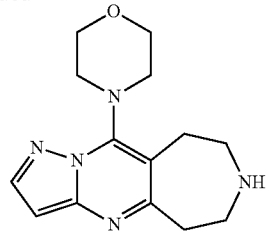 [SMILES: c1cc2nc3c(c(N4CCOCC4)n2n1)CCNCC3]

Example 7

10-Morpholin-4-yl-6,7,8,9-tetrahydro-5H-1,4,7,10a-tetraaza-cyclohepta[f]indene

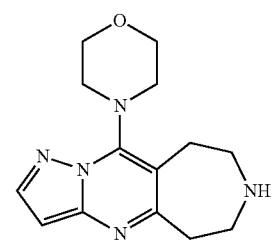 [SMILES: c1cc2nc3c(c(N4CCOCC4)n2n1)CCNCC3]

7a 5-Oxo-azepane-1,4-dicarboxylic acid 1-benzyl ester 4-ethyl ester

To 1.0 g (4.28 mmol) 4-oxo-piperidine-1-carboxylic acid benzyl ester in 5 mL anhydrous ether maintained between −25° C. and −30° C. were added, over 20 minutes, solutions of 0.7 mL (5.56 mmol) $BF_3Et_2O$ in 1.5 mL anhydrous ether, followed by 0.67 mL (6.42 mmol) ethyl diazoacetate in 1.5 mL anhydrous ether, and the reaction was maintained between −25° C. and −30° C. for 1 hour. The mixture was allowed to warm up to room temperature, 10 mL 30% potassium carbonate solution was added and the mixture extracted with EtOAc (3×15 mL), the organic layers were combined and dried with $MgSO_4$. After filtration and evaporation of the solvent the product was purified by flash column chromatography (silica, hexane/EtOAc 9:1 to 8:2).

Yield: 1.1 g (80% of theory)
$C_{17}H_{21}NO_5$ (M=319.36)
predicted: Molecular ion $(M+H)^+$: 320 observed: Molecular ion $(M+H)^+$: 320
HPLC-MS: 1.97 minutes (Method A)
$R_f$: 0.35 (hexane/EtOAc 7:3)

7b 10-Hydroxy-5,6,8,9-tetrahydro-1,4,7,10a-tetraaza-cyclohepta[f]indene-7-carboxylic acid benzyl ester To 5.87 g (18.38 mmol) 5-oxo-azepane-1,4-dicarboxylic acid 1-benzyl ester 4-ethyl ester in 3 mL acetic acid was added 1.53 g (18.38 mmol) 3-aminopyrazole and the reaction mixture was heated at 80° C. for 15 minutes. The resulting solid was collected by filtration and washed with TBME (3×10 mL) to give the desired product.

Yield: 5.9 g (95% of theory)
$C_{18}H_{18}N_4O_3$ (M=338.37)

predicted: Molecular ion (M+H)⁺: 339 observed: Molecular ion (M+H)⁺: 339
HPLC-MS: 1.5 minutes (Method A)

7c 10-Chloro-5,6,8,9-tetrahydro-1,4,7,10a-tetraaza-cyclohepta[f]indene-7-carboxylic acid benzyl ester To a suspension of 3.0 g (8.86 mmol) 10-hydroxy-5,6,8,9-tetrahydro-1,4,7,10a-tetraaza-cyclohepta[f]indene-7-carboxylic acid benzyl ester in 6 mL toluene was added 7 mL (74.06 mmol) of phosphorus oxychloride and 1.28 mL (7.35 mmol) of DIPEA, and the reaction was heated at reflux for 40 minutes. The mixture was cooled to room temperature and poured into ice. The aqueous phase was extracted with DCM (3×20 mL) and the combined organic layers were dried over MgSO₄. After filtration and evaporation of the solvent the product was purified by column chromatography (silica, heptane/EtOAc 9:1 to 7:3).
Yield: 2.0 g (63% of theory)
$C_{18}H_{17}ClN_4O_2$ (M=356.81)
predicted: Molecular ion (M+H)⁺: 357/359 observed: Molecular ion (M+H)⁺: 357/359
HPLC-MS: 1.99 minutes (Method A)
$R_f$: 0.4 (heptane/EtOAc 7:3)

7d 10-Morpholin-4-yl-5,6,8,9-tetrahydro-1,4,7,10a-tetraaza-cyclohepta[f]indene-7-carboxylic acid benzyl ester To 0.15 g 10-chloro-5,6,8,9-tetrahydro-1,4,7,10a-tetraaza-cyclohepta[f]indene-7-carboxylic acid benzyl ester (0.42 mmol), in a sealed tube in 8 mL ethanol, was added 78 μL (0.88 mmol) morpholine, and the reaction was heated at 60° C. for 16 hours. 5 mL of H₂O was added and the mixture was extracted with EtOAc (2×10 mL), the organic layers were combined and dried with MgSO₄. After filtration and evaporation of the solvent the product was purified by column chromatography (silica, DCM/MeOH 2%).
Yield: 0.15 g (88% of theory)
$C_{22}H_{25}N_5O_3$ (M=407.48)
predicted: Molecular ion (M+H)⁺: 408 observed: Molecular ion (M+H)⁺: 408
HPLC-MS: 1.88 minutes (Method A)

7e 10-Morpholin-4-yl-6,7,8,9-tetrahydro-5H-1,4,7,10a-tetraaza-cyclohepta[f]indene To 0.15 g (0.37 mmol) 10-morpholin-4-yl-5,6,8,9-tetrahydro-1,4,7,10a-tetraaza-cyclohepta[f]indene-7-carboxylic acid benzyl ester in 8 mL ethanol was added 30 mg (20% weight) palladium hydroxide, the reaction was purged 3 times with nitrogen then 3 times with hydrogen and was stirred at room temperature under a balloon of hydrogen for 4 hours. The mixture was purged twice with nitrogen, then the solution was filtered through a pad of celite and the solvent was evaporated to give the desired product.
Yield: 96 mg (95% of theory)
$C_{14}H_{19}N_5O$ (M=273.34)
predicted: Molecular ion (M+H)⁺: 274 observed: Molecular ion (M+H)⁺: 274
HPLC-MS: 1.08 minutes (Method B)

TABLE 5

| Example | Structure | Yield of final step (%) | Mass spec result | HPLC retention time (method) |
|---|---|---|---|---|
| 7.1 | 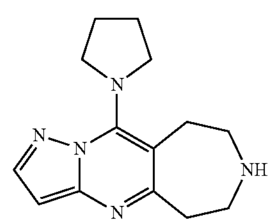 [SMILES: c1cc2nc3c(c(N4CCCC4)n2n1)CCNCC3] | 100 | 258 [M + H]⁺ | 1.29 (B) |
| 7.2 | 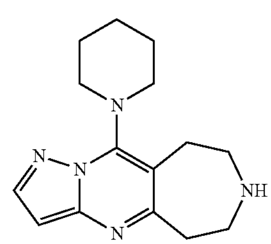 [SMILES: c1cc2nc3c(c(N4CCCCC4)n2n1)CCNCC3] | 98 | 272 [M + H]⁺ | 1.44 (B) |

TABLE 5-continued
| Example | Structure | Yield of final step (%) | Mass spec result | HPLC retention time (method) |
|---|---|---|---|---|
| 7.3 | 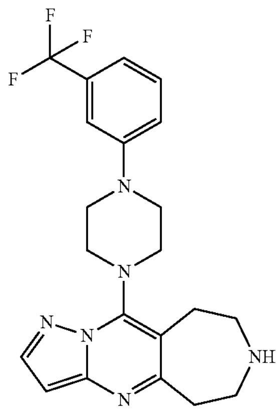 [SMILES: FC(F)(F)c1cccc(N2CCN(c3c4c(nc5ccnn35)CCNCC4)CC2)c1] | 41 | 417 [M + H]+ | 1.94 (B) |
| 7.4 | 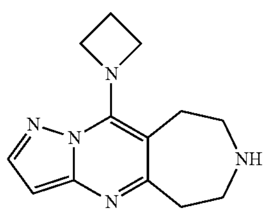 | 89 | 244 [M + H]+ | 1.39 (B) |
| 7.5 | 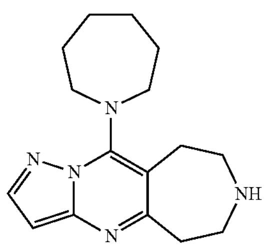 [SMILES: c1cc2nc3c(c(N4CCCCCC4)n2n1)CCNCC3] | 82 | 286 [M + H]+ | 1.71 (B) |
Route 8
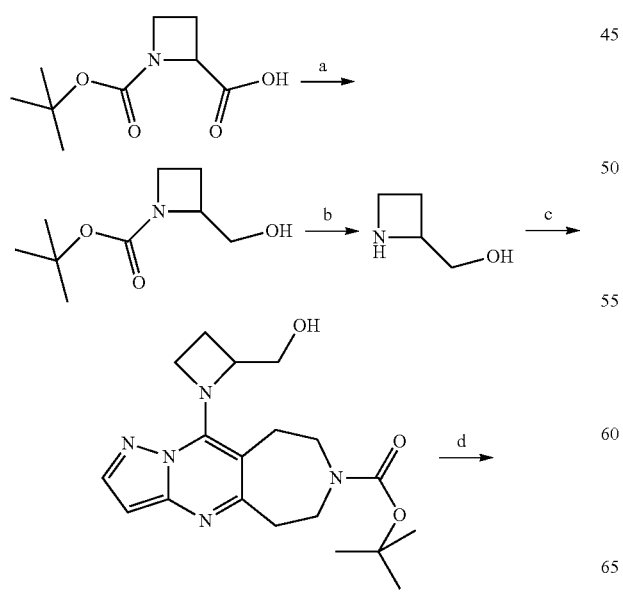
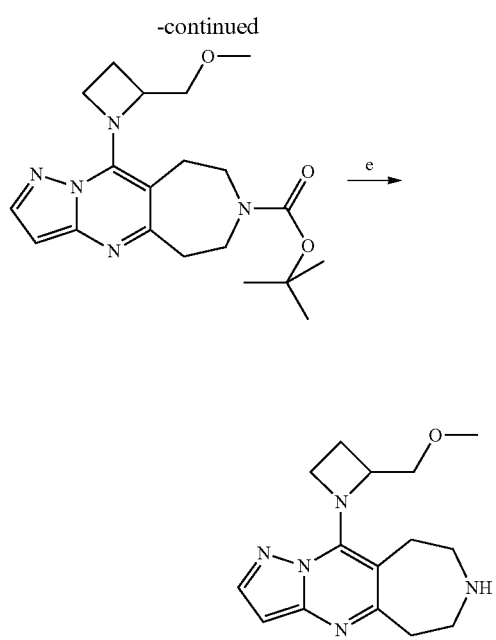
-continued

Example 8

(S)-10-(2-Methoxymethyl-azetidin-1-yl)-6,7,8,9-tetrahydro-5H-1,4,7,10a-tetraaza-cyclohepta[f]indene

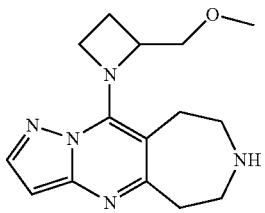 [SMILES: COCC1CCN1c1c2c(nc3ccnn13)CCNCC2]

8a (S)-2-Hydroxymethyl-azetidine-1-carboxylic acid tert-butyl ester

To 699 mg (18.48 mmol) sodium borohydride in 20 mL dry THF under nitrogen, was added 1.15 g (5.74 mmol) (S)-azetidine-1,2-dicarboxylic acid 1-tert-butyl ester and the reaction was cooled to 0° C., 1.72 g (6.78 mmol) iodine in 10 mL dry THF was added dropwise over 30 minutes, the reaction mixture was allowed to warm to room temperature, and was heated under reflux for 19 hours. The mixture was cooled to room temperature and 25 mL MeOH was added dropwise over 15 minutes. After evaporation of the solvent, 30 mL KOH (1 M) was added and the mixture was stirred at room temperature for 2 hours. The aqueous phase was extracted with DCM (2×75 mL) and the combined organic layers were washed with saturated brine (3×50 mL), then dried over $MgSO_4$. After filtration, the solvent was evaporated to give the desired product, which was used for the next step without further purification.

8b (S)-Azetidin-2-yl-methanol hydrogen chloride

To 756.2 mg (4.04 mmol) (S)-2-hydroxymethyl-azetidine-1-carboxylic acid tert-butyl ester in 3 mL DCM was added 2 mL (8 mmol) HCl in dioxane (4 M) and the reaction was stirred at room temperature for 5 hours. The solvent evaporated to give the desired product as a HCl salt, which was used for the next step without further purification.

8c (S)-10-(2-Hydroxymethyl-azetidin-1-yl)-5,6,8,9-tetrahydro-1,4,7,10a-tetraaza-cyclohepta[f]indene-7-carboxylicacid tert-butyl ester To 50 mg (0.155 mmol) 10-chloro-5,6,8,9-tetrahydro-1,4,7,10a-tetraaza-cyclohepta[f]indene-7-carboxylic acid tert-butyl ester (route 1, from step a to d) and 22 mg (0.17 mmol) (S)-azetidin-2-yl-methanol hydrogen chloride in 2 mL ethanol was added 2 mL (0.31 mmol) DIPEA, and the reaction mixture was heated at 80° C. for 19 hours. The reaction was cooled to room temperature and 20 mL EtOAc was added. The organic layer was washed with 10 mL citric acid (1 M), $H_2O$ (2×10 mL), 10 mL saturated brine, and dried over $MgSO_4$. After evaporation of the solvent the product was purified by column chromatography (silica, heptane/EtOAc 1:5).

Yield: 25.33 mg (44% of theory)
$C_{19}H_{27}N_5O_3$ (M=373.46)
predicted: Molecular ion $(M+H)^+$: 374 observed: Molecular ion $(M+H)^+$: 374
HPLC-MS: 1.26 minutes (Method A)

8d (S)-10-(2-Methoxymethyl-azetidin-1-yl)-5,6,8,9-tetrahydro-1,4,7,10a-tetraaza-cyclohepta[f]indene-7-carboxylic acid tert-butyl ester To 57.9 mg (0.155 mmol) (S)-10-(2-hydroxymethyl-azetidin-1-yl)-5,6,8,9-tetrahydro-1,4,7,10a-tetraaza-cyclohepta[f]indene-7-carboxylic acid tert-butyl ester in 10 mL anhydrous THF was added 29.8 mg (1.24 mmol, 60% dispersion in mineral oil) NaH and the reaction was cooled to 0° C. 0.4 mL (1.24 mmol) methyl iodide was added and the reaction was stirred at room temperature for 6 hours. 25 mL EtOAc was added and the organic layer was washed with $H_2O$ (2×20 mL), 20 mL saturated brine, and dried over $MgSO_4$. After evaporation of the solvent the product was purified by column chromatography (silica, heptane/EtOAc 2:3).

Yield: 60.1 mg (100% of theory)
$C_{20}H_{29}N_5O_3$ (M=387.49)
predicted: Molecular ion $(M+H)^+$: 388 observed: Molecular ion $(M+H)^+$: 388
HPLC-MS: 1.41 minutes (Method A)
$R_f$: 0.25 (heptane/EtOAc 2:3)

8e (S)-10-(2-Methoxymethyl-azetidin-1-yl)-6,7,8,9-tetrahydro-5H-1,4,7,10a-tetraaza-cyclohepta[f]indene To 60.1 mg (0.155 mmol) (S)-10-(2-methoxymethyl-azetidin-1-yl)-5,6,8,9-tetrahydro-1,4,7,10a-tetraaza-cyclohepta[f]indene-7-carboxylic acid tert-butyl ester in 3 mL DCM was added 2 mL (3.1 mmol) HCl in dioxane (4 M) and the reaction was stirred at room temperature for 5 hours. The solvent was evaporated to give the desired product as a HCl salt.

Yield: 48.8 mg (87% of theory)
$C_{15}H_{21}N_5O$ (M=287.37)
predicted: Molecular ion $(M+H)^+$: 288 observed: Molecular ion $(M+H)^+$: 288
HPLC-MS: 1.37 minutes (Method B)

TABLE 6

| Example | Structure | Yield of final step (%) | Salt type | Mass spec result | HPLC retention time (method) |
|---|---|---|---|---|---|
| 8.1 | 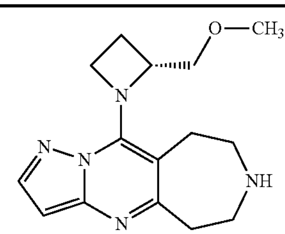 | 59 | HCl | 288 $[M + H]^+$ | 1.35 (B) |

TABLE 6-continued

| Example | Structure | Yield of final step (%) | Salt type | Mass spec result | HPLC retention time (method) |
|---|---|---|---|---|---|
| 8.2 | 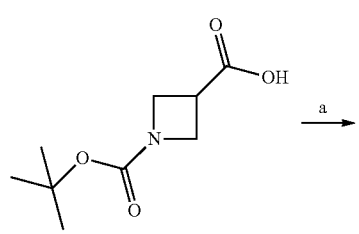 | 42 | TF | 274 [M + H]⁺ | 0.98 (B) |

Route 9

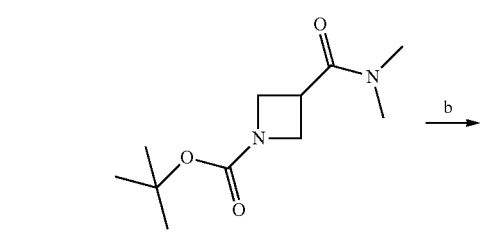

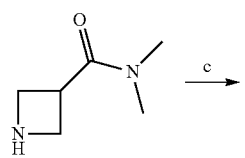

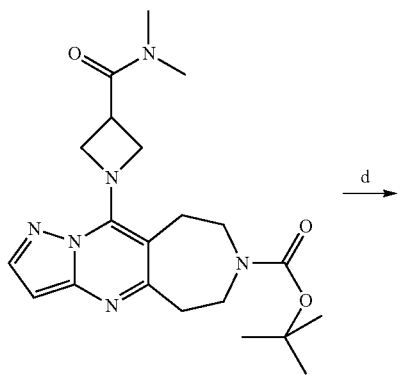

-continued

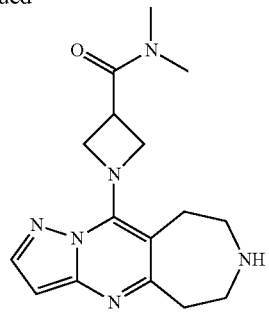

Example 9

1-(6,7,8,9-Tetrahydro-5H-1,4,7,10a-tetraaza-cyclohepta[f]inden-10-yl)-azetidine-3-carboxylic acid dimethylamide

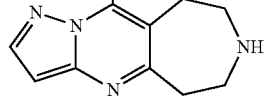

9a 3-Dimethylcarbamoyl-azetidine-1-carboxylic acid tert-butyl ester

To 300 mg (1.49 mmol) azetidine-1,3-dicarboxylic acid mono-tert-butyl ester and 241.6 mg (1.79 mmol) 1-hydroxybenzotriazole hydrate in 20 mL DMF at 0° C., was added 364.5 mg (4.47 mmol) dimethylamine hydrochloride, and the reaction was stirred for 30 minutes. 342.8 mg (1.79 mmol) N-(3-dimethylaminopropyl)-N'-ethylcarbodiimide hydrochloride, followed by 1.5 mL (8.94 mmol) DIPEA were added, and the reaction was stirred at room temperature for 3 hours. After evaporation of the solvent, the crude was diluted with 100 mL DCM. The organic phase was washed with a 2 M solution of HCl (2×50 mL), a saturated solution of NaHCO₃ (2×50 mL), brine (2×50 mL), and dried over Na₂SO₄. After filtration, the solvent was evaporated to give the desired product which was used for the next step without further purification.

9b Azetidine-3-carboxylic acid dimethylamide trifluoroacetate

To 324.3 mg (1.42 mmol) 3-dimethylcarbamoyl-azetidine-1-carboxylic acid tert-butyl ester in 7.5 mL DCM was added 2.5 mL TFA and the reaction was stirred at room temperature for 5 hours. The solvent was evaporated to give the desired product as a TFA salt, which was used for the next step without further purification.

9d 1-(6,7,8,9-Tetrahydro-5H-1,4,7,10a-tetraaza-cyclohepta[f]inden-10-yl)-azetidine-3-carboxylic acid dimethylamide The product was prepared by using route 1 (step e and f) using azetidine-3-carboxylic acid dimethylamide trifluoroacetate as the amine in step e (route 1).

Yield: 33% of theory
$C_{16}H_{22}N_6O$ (M=314.39)
predicted: Molecular ion $(M+H)^+$: 315 observed: Molecular ion $(M+H)^+$: 315
HPLC-MS: 1.19 minutes (Method B)

TABLE 7

| Example | Structure | Yield of final step (%) | Salt type | Mass spec result | HPLC retention time (method) |
|---|---|---|---|---|---|
| 9.1 | 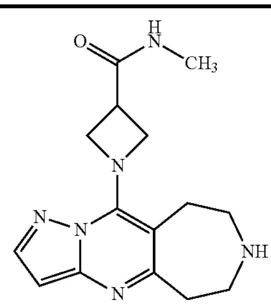 | 9 | base | 301 $[M + H]^+$ | 1.07 (B) |

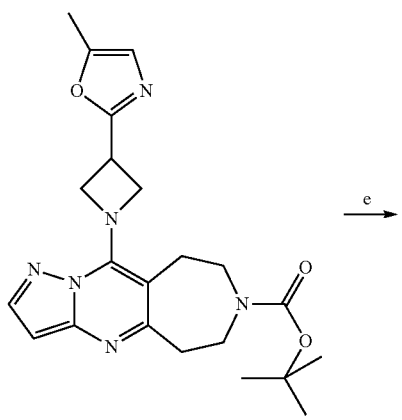

Route 10

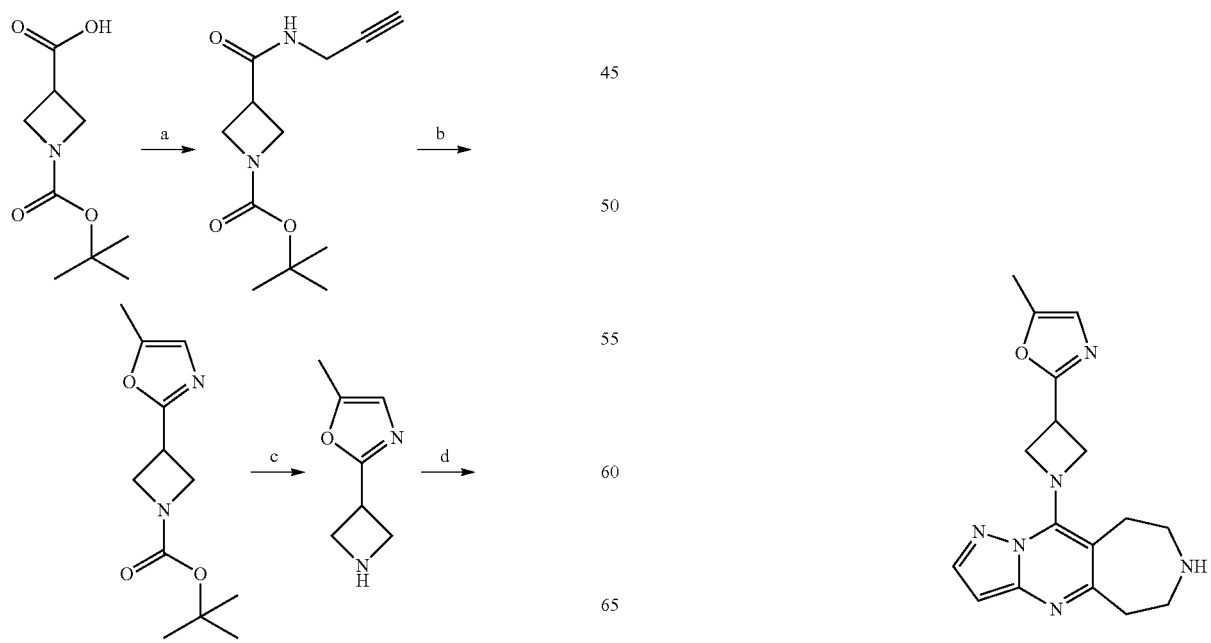

Example 10

10-[3-(5-Methyl-oxazol-2-yl)-azetidin-1-yl]-6,7,8,9-tetrahydro-5H-1,4,7,10a-tetraaza-cyclohepta[f]indene

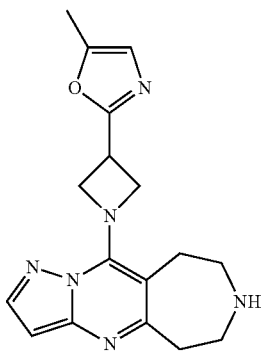 [SMILES: Cc1cnc(C2CN(c3c4c(nc5ccnn35)CCNCC4)C2)o1]

10a 3-Prop-2-ynylcarbamoyl-azetidine-1-carboxylic acid tert-butyl ester

To 0.5 g (2.48 mmol) boc-azetidine-3-carboxylic acid in 5 mL DCM were added 0.52 g (2.73 mmol) 1-(3-dimethylaminopropyl)-3-ethylcarbodiimide hydrochloride, 0.4 g (2.98 mmol) 1-hydroxybenzotriazole hydrate and 0.9 mL (5.47 mmol) DIPEA, and the reaction was stirred at room temperature for 30 minutes. 0.19 mL (2.73 mmol) propargylamine was added and the reaction was stirred for 16 hours at room temperature. 5 mL DCM was added and the mixture was washed with 10 mL aqueous HCl (1 M), then 10 mL aqueous NaHCO₃ (1 M) and 10 mL brine. The organic layer was dried over Na₂SO₄. After filtration and evaporation of the solvent the product was purified by column chromatography (silica, heptane/EtOAc 7:3).

Yield: 0.334 g (57% of theory)

$C_{12}H_{18}N_2O_3$ (M=238.29)

predicted: Molecular ion (M+H)⁺: 239 observed: Molecular ion (M+H)⁺: 239

HPLC-MS: 1.53 minutes (Method A)

10b 3-(5-Methyl-oxazol-2-yl)-azetidine-1-carboxylic acid tert-butyl ester

To 0.22 g (0.92 mmol) 3-prop-2-ynylcarbamoyl-azetidine-1-carboxylic acid tert-butyl ester in 4 mL anhydrous acetonitrile, under nitrogen, was added 14 mg (0.046 mmol) gold (III) chloride and the reaction mixture was stirred at 45° C. for 6 hours. After evaporation of the solvent, 20 mL DCM was added, the organic layer was washed with H₂O (2×10 mL) then dried over Na₂SO₄. After filtration and evaporation of the solvent the product was purified by column chromatography (silica, heptane/EtOAc 6:4 to 5:5), and used for the next step without further purification.

10c 2-Azetidin-3-yl-5-methyl-oxazole hydrochloride

To 57 mg (0.24 mmol) 3-(5-methyl-oxazol-2-yl)-azetidine-1-carboxylic acid tert-butyl ester was added 2 mL (8 mmol) HCl in dioxane (4 M), and the reaction was stirred at room temperature for 1 hour. The solvent was evaporated to give the desired product as a HCl salt, which was used for the next step without further purification.

10e 10-[3-(5-Methyl-oxazol-2-yl)-azetidin-1-yl]-6,7,8,9-tetrahydro-5H-1,4,7,10a-tetraaza-cyclohept[f]indene The product was prepared using route 1 (step e and f), in step e (route 1) 2-azetidin-3-yl-5-methyl-oxazole hydrochloride was used as the amine.

Yield: 77.3 mg (90% of theory)

$C_{17}H_{20}N_6O$ (M=324.39)

predicted: Molecular ion (M+H)⁺: 325 observed: Molecular ion (M+H)⁺: 325

HPLC-MS: 3.49 minutes (Method C)

Route 11

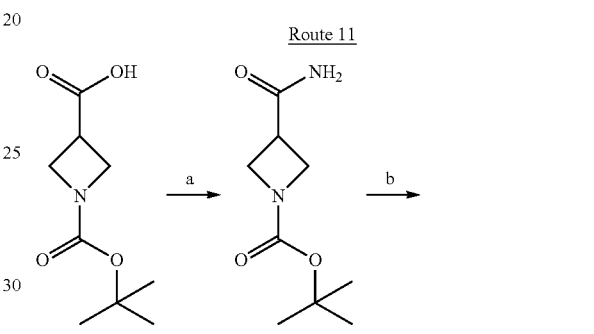

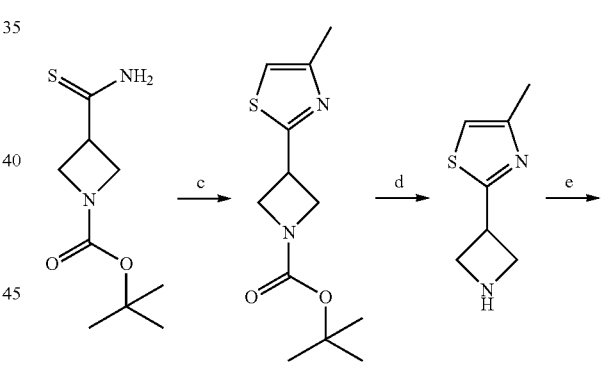

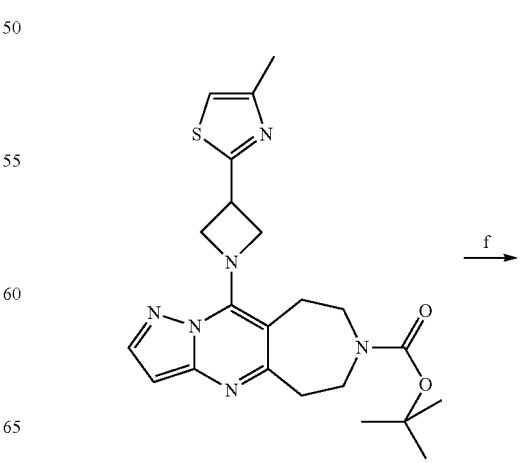

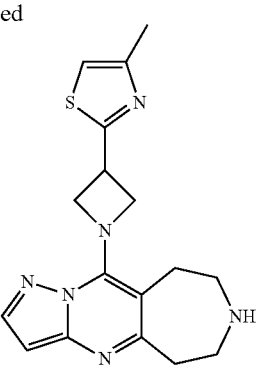

Example 11

10-[3-(4-Methyl-thiazol-2-yl)-azetidin-1-yl]-6,7,8,9-tetrahydro-5H-1,4,7,10a-tetraaza-cyclohepta[f]indene

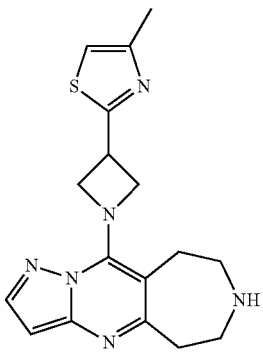 [SMILES: Cc1csc(C2CN(c3c4c(nc5ccnn35)CCNCC4)C2)n1]

11a 3-Carbamoyl-azetidine-1-carboxylic acid tert-butyl ester

To 1.0 g (4.97 mmol) boc-azetidine-3-carboxylic acid in 10 mL anhydrous THF was added 0.55 mL of 1-methyl-2-pyrrolidinone. The reaction mixture was cooled to −20° C., then 0.62 mL (4.72 mmol) isobutyl chloroformate was added and the reaction was stirred for 5 minutes. 1.51 mL (24.85 mmol) aqueous ammonia (28% w/w) was added and the mixture was stirred at −20° C. for 2 hours. 5 mL aqueous NaHCO$_3$ (1 M) was added and the mixture was allowed to reach room temperature over 1 hour. The mixture was extracted with DCM (3×10 mL), the organic layers were combined, washed with aqueous NaHCO$_3$ (1 M), aqueous citric acid (1 M) and dried over Na$_2$SO$_4$. After filtration and evaporation of the solvent the product was used in the next step without further purification.

Yield: 740 mg (74% crude)

11b 3-Thiocarbamoyl-azetidine-1-carboxylic acid tert-butyl ester

To 0.35 g (1.75 mmol) 3-carbamoyl-azetidine-1-carboxylic acid tert-butyl ester in 3.5 mL DCM was added 0.39 g (0.96 mmol) Laweson's reagent and the reaction mixture was stirred at room temperature for 16 hours. The solvent was removed and the product was purified twice by column chromatography (silica, heptane/EtOAc 8:2 to 5:5; silica, heptane/EtOAc 7:3 to 6.5:3.5).

Yield: 195 mg (52% of theory)
C$_9$H$_{16}$N$_2$O$_2$S (M=216.30)
predicted: Molecular ion (M+H)$^+$: 217 observed: Molecular ion (M+H)$^+$: 217
HPLC-MS: 1.59 minutes (Method A)

11c 3-(4-Methyl-thiazol-2-yl)-azetidine-1-carboxylic acid tert-butyl ester

To 145 mg (0.67 mmol) 3-thiocarbamoyl-azetidine-1-carboxylic acid tert-butyl ester in 3 mL MeOH in a sealed tube was added 64 μL (0.8 mmol) chloroacetone, and the reaction was stirred at 90° C. for 3 hours. After evaporation of the solvent the product was purified by column chromatography (silica, heptane/EtOAc 8:2 to 6:4).

Yield: 35 mg (21% of theory)
C$_{12}$H$_{18}$N$_2$O$_2$S (M=254.35)
predicted: Molecular ion (M+H)$^+$: 255 observed: Molecular ion (M+H)$^+$: 255
HPLC-MS: 1.91 minutes (Method A)

11d 2-Azetidin-3-yl-4-methyl-thiazole hydrochloride

To 47 mg (0.18 mmol) 3-(4-methyl-thiazol-2-yl)-azetidine-1-carboxylic acid tert-butyl ester was added 2 mL (8 mmol) HCl in dioxane (4 M), and the reaction was stirred at room temperature for 1 hour. The solvent was evaporated to give the desired product as a HCl salt, which was used in the next step without further purification.

11f 10-[3-(4-Methyl-thiazol-2-yl)-azetidin-1-yl]-6,7,8,9-tetrahydro-5H-1,4,7,10a-tetraaza-cyclohept[f]indene The product was prepared using route 1 (step e and f), in step e (route 1) 2-azetidin-3-yl-4-methyl-thiazole hydrochloride was used as the amine.

Yield: 66.4 mg (83% of theory)
C$_{17}$H$_{20}$N$_6$S (M=340.45)
predicted: Molecular ion (M+H)$^+$: 341 observed: Molecular ion (M+H)$^+$: 341
HPLC-MS: 3.69 minutes (Method C)

Route 12

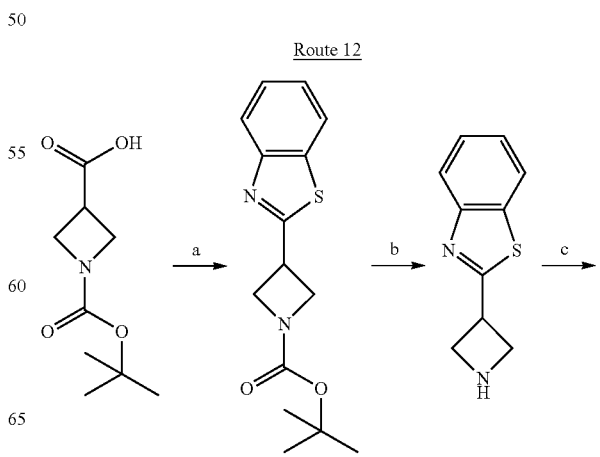

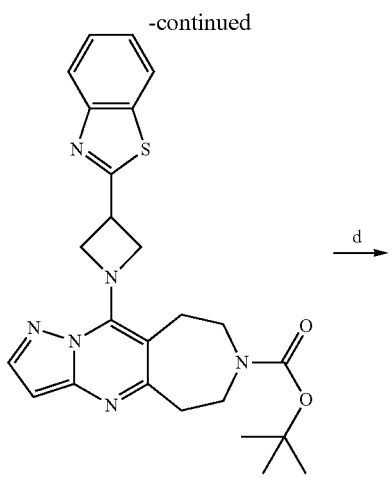

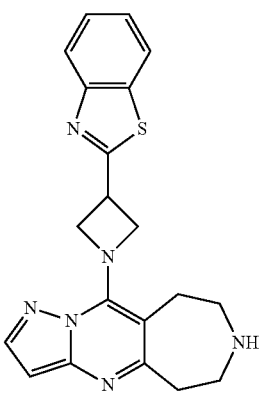 [SMILES: c1ccc2sc(C3CN(c4c5c(nc6ccnn46)CCNCC5)C3)nc2c1]

Example 12

10-(3-Benzothiazol-2-yl-azetidin-1-yl)-6,7,8,9-tetrahydro-5H-1,4,7,10a-tetraaza-cyclohepta[f]indene

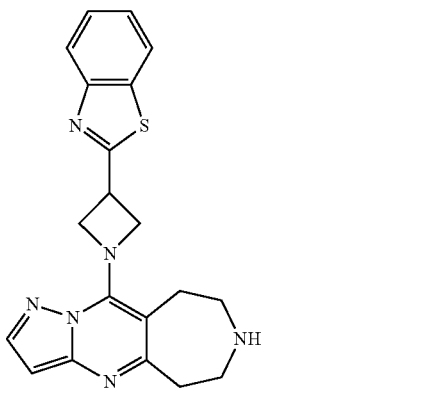

12a 3-Benzothiazol-2-yl-azetidine-1-carboxylic acid tert-butyl ester

To 10 mL DCE was added 533 mg (3.7 mmol) phosphorus pentoxide and 1.57 mL (7.36 mmol) bis-trimethylsilyl ether and the mixture was heated at 80° C. for 15 minutes. 0.19 g (0.92 mmol) N-boc-azetidine-3-carboxylic acid and 108 μL (1.01 mmol) 2-aminothiophenol were added and the mixture heated at 85° C. for 20 minutes. After cooling to room temperature the mixture was diluted with 20 mL DCM and washed with 1 M Na$_2$CO$_3$ (2×10 mL). The organic layer was dried with Na$_2$SO$_4$. After filtration and evaporation of the solvent the product was purified by column chromatography (silica, hexane/EtOAc 1:1).

Yield: 30 mg (11% of theory)

C$_{15}$H$_{18}$N$_2$O$_2$S (M=290.39)

predicted: Molecular ion (M+H)$^+$: 291 observed: Molecular ion (M+H)$^+$: 291

HPLC-MS: 1.49 minutes (Method A)

Rf: 0.50 (EtOAc)

12b 3-Benzothiazol-2-yl-azetidine trifluoroacetate

To 48 mg (166 μmol) 3-benzothiazol-2-yl-azetidine-1-carboxylic acid tert-butyl ester was added 5 mL DCM and 5 mL TFA. The resulting mixture was stirred at room temperature for 30 minutes. The solvent was evaporated to give the product as the TFA salt which was used in the next step without further purification.

12c 10-(3-Benzothiazol-2-yl-azetidin-1-yl)-6,7,8,9-tetrahydro-5H-1,4,7,10a-tetraaza-cyclohepta[f]indene The product was prepared using 10-chloro-5,6,8,9-tetrahydro-1,4,7,10a-tetraaza-cyclohepta[f]indene-7-carboxylic acid tert-butyl ester in route 1 (step e and f), in step e (route 1) 3-benzothiazol-2-yl-azetidine trifluoroacetate was used as the amine.

Yield: 68 mg (64% of theory)

C$_{20}$H$_{20}$N$_6$S (M=376.49)

predicted: Molecular ion (M+H)$^+$: 377 observed: Molecular ion (M+H)$^+$: 377

HPLC-MS: 4.27 minutes (Method C)

Route 13

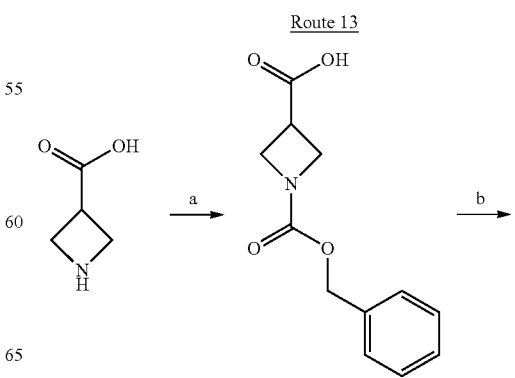

-continued

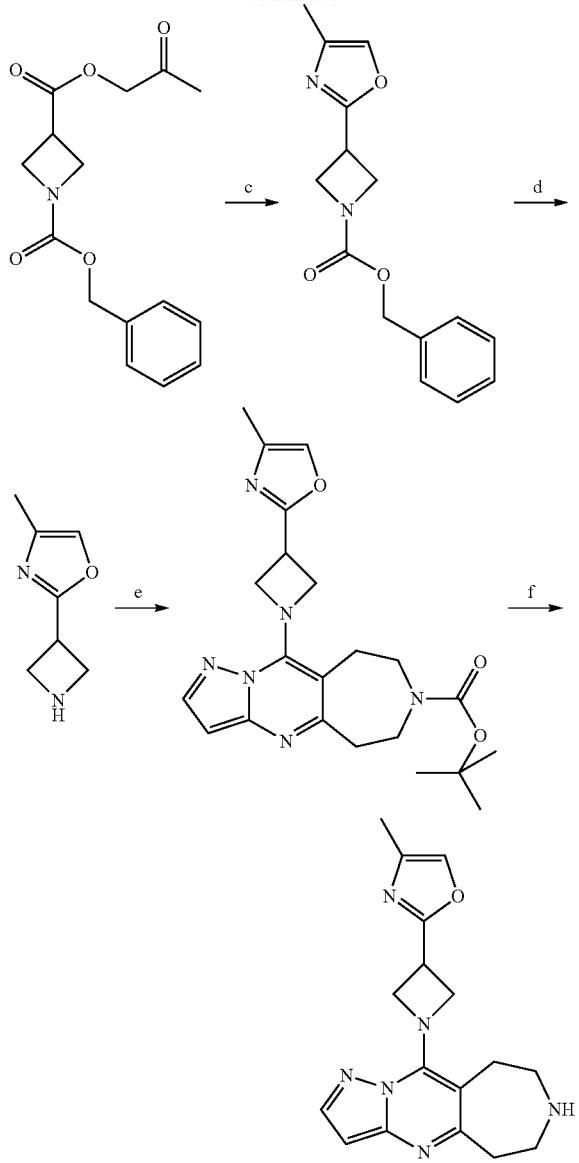

Example 13

113-[3-(4-Methyl-oxazol-2-yl)-azetidin-1-yl]-6,7,8,9-tetrahydro-5H-1,4,7,10a-tetraaza-cyclohepta[f]indene

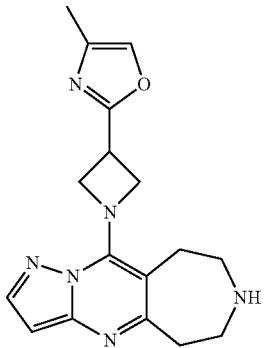 [SMILES: Cc1coc(C2CN(c3c4c(nc5ccnn35)CCNCC4)C2)n1]

13a Azetidine-1,3-dicarboxylic acid monobenzyl ester

To 500 mg (4.95 mmol) azetidine-3-carboxylic acid was added 10 mL dioxane and 10 mL H$_2$O and the solution cooled to 0° C. 1.38 g (10 mmol) potassium carbonate was added followed by 0.78 mL (11 mmol) benzylchloroformate, and the reaction stirred at room temperature for 18 hours. The mixture was acidified with 25 mL 1 M HCl, extracted with DCM (2×20 mL), the combined organic layers dried over Na$_2$SO$_4$. After filtration the solvent was evaporated to give the desired product which was used in the next step without further purification.

C$_{12}$H$_{13}$NO$_4$ (M=235.24)

predicted: Molecular ion (M+H)$^+$: 236 observed: Molecular ion (M+H)$^+$: 236

HPLC-MS: 1.14 minutes (Method A)

13b Azetidine-1,3-dicarboxylic acid 1-benzyl ester 3-(2-oxo-propyl)ester

To 321 mg (75% w/w, 1.37 mmol) azetidine-1,3-dicarboxylic acid monobenzyl ester in 10 mL dry THF were added 82 mg NaH (2.05 mmol, 60% dispersion in mineral oil), 182 mg 18-crown-6 (0.68 mmol), 328 µL chloroacetone (4.11 mmol), and the mixture was stirred at 60° C. for 6 hours. After cooling to room temperature, 10 mL 1 M sodium bicarbonate was added and the mixture was extracted with DCM (2×10 mL), the organic layers were combined and dried over Na$_2$SO$_4$. After filtration and evaporation of the solvent the product was purified by column chromatography (silica, heptane-EtOAc 1:1 to EtOAc).

Yield: 204 mg (51% of theory)

C$_{15}$H$_{17}$NO$_5$ (M=291.31)

predicted: Molecular ion (M+H)$^+$: 292 observed: Molecular ion (M+H)$^+$: 292

HPLC-MS: 1.14 minutes (Method A)

13c 3-(4-Methyl-oxazol-2-yl)-azetidine-1-carboxylic acid benzyl ester

To 130 mg (0.45 mmol) azetidine-1,3-dicarboxylic acid 1-benzyl ester 3-(2-oxo-propyl)ester in 4 mL xylene were added 132 mg (2.25 mmol) acetamide, 39 µL (0.31 mmol) boron trifluoride etherate and the mixture was heated at 130° C. for 24 hours. After cooling to room temperature and evaporation of the solvent the product was purified by chromatography (silica, hexane-EtOAc 6:4).

Yield: 19 mg (15% of theory)

C$_{15}$H$_{16}$N$_2$O$_3$ (M=272.31)

predicted: Molecular ion (M+H)$^+$: 273 observed: Molecular ion (M+H)$^+$: 273

HPLC-MS: 1.30 minutes (Method A)

13d 2-Azetidin-3-yl-4-methyl-oxazole

To 40 mg (0.15 mmol) 3-(4-methyl-oxazol-2-yl)-azetidine-1-carboxylic acid benzyl ester in 2 mL ethanol was added 4 mg (20% w/w on carbon) palladium hydroxide, the reaction was purged 3 times with nitrogen then 3 times with hydrogen and was stirred at 30° C. under a balloon of hydrogen for 18 hours. The mixture was purged twice with nitrogen, then the solution was filtered through a pad of celite. The solvent was evaporated to give the desired product, which was used in the next step without further purification.

13e 10-[3-(4-Methyl-oxazol-2-yl)-azetidin-1-yl]-6,7,8,9-tetrahydro-5H-1,4,7,10a-tetraaza-cyclohepta[f]indene The product was prepared using 10-chloro-5,6,8,9-tetrahydro-1,4,7,10a-tetraaza-cyclohepta[f]indene-7-carboxylic acid tert-butyl ester in route 1 (step e and f), in step e (route 1) 2-azetidin-3-yl-4-methyl-oxazole was used as the amine.

Yield: 4.8 mg (15% of theory)
$C_{17}H_{20}N_6O$ (M=324.39)
predicted: Molecular ion (M+H)$^+$: 325 observed: Molecular ion (M+H)$^+$: 325
HPLC-MS: 3.41 minutes (Method C)

Route 14

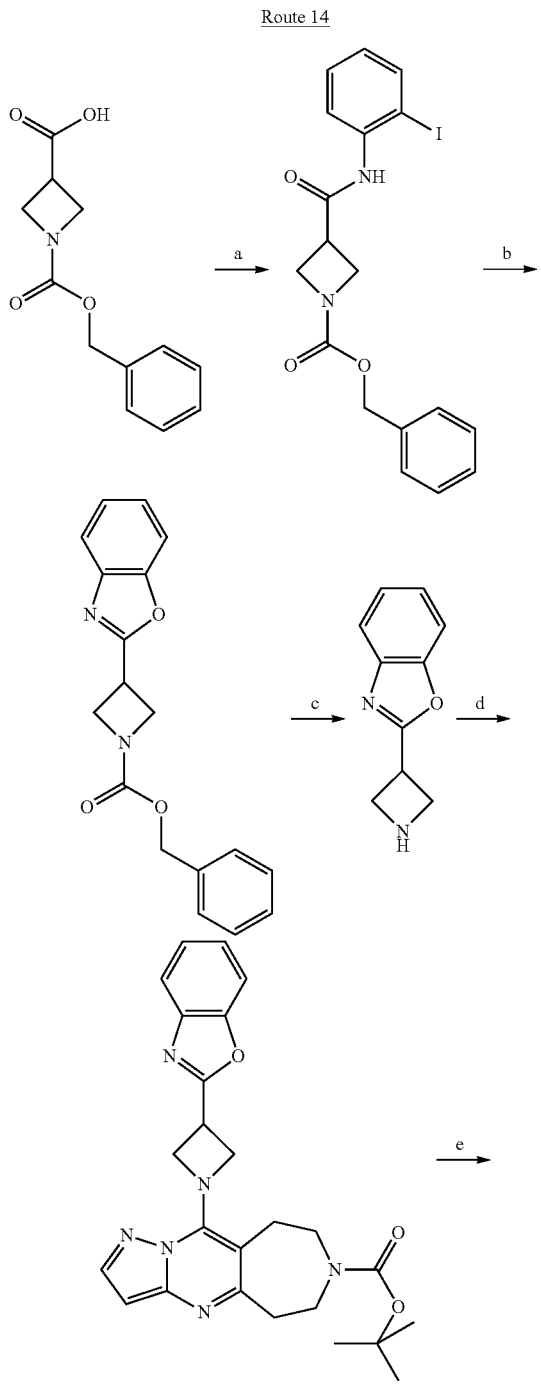

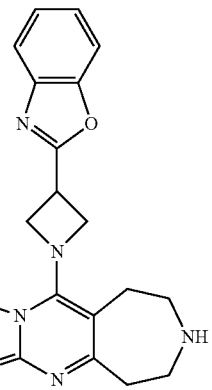

Example 14

10-(3-Benzooxazol-2-yl-azetidin-1-yl)-6,7,8,9-tetrahydro-5H-1,4,7,10a-tetraaza-cyclohepta[f]indene

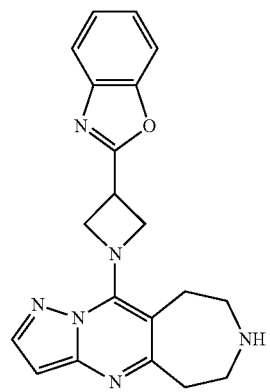 [SMILES: c1ccc2oc(C3CN(c4c5c(nc6ccnn46)CCNCC5)C3)nc2c1]

14a 3-(2-Iodo-phenylcarbamoyl)-azetidine-1-carboxylic acid benzyl ester

To 1.0 g (4.57 mmol) iodoaniline in 30 mL acetonitrile were added 2.22 g (5.02 mmol) BOP, 1.78 g (4.57 mmol) azetidine-1,3-dicarboxylic acid monobenzyl ester (route 13, step a), 0.6 mL (4.57 mmol) triethylamine, and the mixture was stirred at room temperature for 16 hours. 0.6 mL (4.57 mmol) triethylamine was added and the mixture was stirred for 2 hours. 2.22 g (5.02 mmol) BOP was added and the mixture was stirred at room temperature for 16 hours. 30 mL 1 M aqueous $Na_2CO_3$ was added and the mixture was extracted with EtOAc (2×30 mL), the organic layers were combined, washed with 30 mL brine then dried with $Na_2SO_4$. After filtration and evaporation of the solvent the product was purified by column chromatography (silica, heptane/EtOAc 7:3).

Yield: 0.47 g (24% of theory)
$C_{18}H_{17}IN_2O_3$ (M=436.25)
predicted: Molecular ion (M+H)$^+$: 437 observed: Molecular ion (M+H)$^+$: 437
HPLC-MS: 1.39 minutes (Method D)

14b 3-Benzooxazol-2-yl-azetidine-1-carboxylic acid benzyl ester

To 195 mg (0.45 mmol) 3-(2-iodo-phenylcarbamoyl)-azetidine-1-carboxylic acid benzyl ester in 4.5 mL DME in a sealed tube under nitrogen were added 291 mg (0.89 mmol) $Cs_2CO_3$, 8.1 mg (44.6 μmol) 1,10-phenanthroline, 4.3 mg (22.3 μmol) CuI, and the mixture was heated at 90° C. for 16 hours. After cooling to room temperature, 5 mL $H_2O$ was added followed by 4 drops 1 M HCl, 5 mL $NaHCO_3$ and the mixture was extracted with DCM (3×10 mL). The organic layers were combined and dried with $Na_2SO_4$. After filtration and evaporation of the solvent the product was purified by preparative HPLC.

Yield: 67 mg (49% of theory)
$C_{18}H_{16}N_2O_3$ (M=308.34)
predicted: Molecular ion $(M+H)^+$: 309 observed: Molecular ion $(M+H)^+$: 309
HPLC-MS: 1.42 minutes (Method D)

14c 2-Azetidin-3-yl-benzooxazole

The product was prepared using 3-benzooxazol-2-yl-azetidine-1-carboxylic acid benzyl ester in route 13 (step d).

Yield: 100% crude yield
$C_{10}H_{10}N_2O$ (M=174.20)
predicted: Molecular ion $(M+H)^+$: 175 observed: Molecular ion $(M+H)^+$: 175
HPLC-MS: 0.22 minutes (Method A)

14e 10-(3-Benzooxazol-2-yl-azetidin-1-yl)-6,7,8,9-tetrahydro-5H-1,4,7,10a-tetraaza-cyclohepta[f]indene The product was prepared using 10-chloro-5,6,8,9-tetrahydro-1,4,7,10a-tetraaza-cyclohepta[f]indene-7-carboxylic acid tert-butyl ester in route 1 (step e and f), in step e (route 1) 2-azetidin-3-yl-benzooxazole was used as the amine.

Yield: 66 mg (37% of theory)
$C_{20}H_{20}N_6O$ (M=360.42)
predicted: Molecular ion $(M+H)^+$: 361 observed: Molecular ion $(M+H)^+$: 361
HPLC-MS: 1.28 minutes (Method C)

Route 15

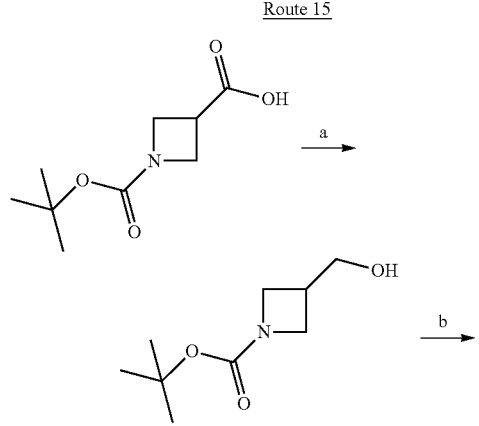

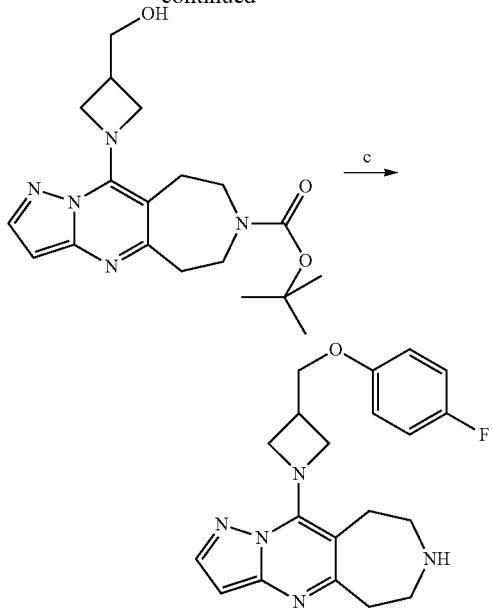

Example 15

10-[3-(4-Fluoro-phenoxymethyl)-azetidin-1-yl]-6,7,8,9-tetrahydro-5H-1,4,7,10a-tetraaza-cyclohepta[f]indene

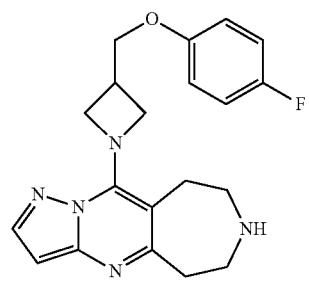 [SMILES: Fc1ccc(OCC2CN(c3c4c(nc5ccnn35)CCNCC4)C2)cc1]

15a 3-Hydroxymethyl-azetidine-1-carboxylic acid tert-butyl ester

To a stirred mixture of 0.56 g (14.91 mmol) sodium borohydride in 10 mL THF was added 1.0 g (4.97 mmol) 1-(tert-butoxycarbonyl)-3-azetidinecarboxylic acid, and the reaction mixture was cooled to 0° C. 1.26 g (4.97 mmol) iodine in 5 mL THF was added dropwise over 15 minutes and the reaction was stirred at 0° C. for 10 minutes, then heated under reflux for 18 hours. The mixture was allowed to cool to room temperature, diluted with 80 mL MeOH and stirred until all effervescence ceased. After evaporation of the solvent, 25 mL 20% (w/w) KOH was added to the residue and the mixture was stirred for 4.5 hours. The mixture was extracted with DCM (3×100 mL) and the combined organic layers were dried over $MgSO_4$. After filtration, the solvent was evaporated to give the desired product, which was used for the next step without further purification.

Yield: 0.84 g (90% of theory)
$C_9H_{17}NO_3$ (M=187.24)

predicted: Molecular ion (M+H—CH$_2$=C(CH$_3$)$_2$)$^+$: 132
observed: Molecular ion (M+H—CH$_2$=C(CH$_3$)$_2$)$^+$: 132
HPLC-MS: 1.34 minutes (Method A)

15b 10-(3-Hydroxymethyl-azetidin-1-yl)-5,6,8,9-tetrahydro-1,4,7,10a-tetraaza-cyclohepta[f]indene-7-carboxylic acid tert-butyl ester A mixture of 2.57 g (13.75 mmol) 3-hydroxymethyl-azetidine-1-carboxylic acid tert-butyl ester and 2.62 g (13.75 mmol) para-toluenesulfonic acid monohydrate in 14 mL DCM was stirred at room temperature for 16 hours. After evaporation of the solvent, the residue was dissolved in 28 mL EtOH, then 4.8 mL (27.5 mmol) DIPEA followed by 4.03 g (12.5 mmol) 10-chloro-5,6,8,9-tetrahydro-1,4,7,10a-tetraaza-cyclohepta[f]indene-7-carboxylic acid tert-butyl ester were added and the reaction mixture was heated under reflux for 24 hours. The mixture was allowed to cool to room temperature and the solvent was evaporated. 300 mL DCM was added to the mixture, the organic layer was washed sequentially with 100 mL saturated solution of NaHCO$_3$, a mixture of 1.94 g (9.23 mmol) citric acid monohydrate in 100 mL H$_2$O and 100 mL saturated brine, then was dried over MgSO$_4$. After filtration and evaporation of the solvent the product was purified by column chromatography (Biotage silica 40+M, heptane/EtOAc 1:1 to EtOAc).

Yield: 2.59 g (56% of theory)
C$_{19}$H$_{27}$N$_5$O$_3$ (M=373.46)
predicted: Molecular ion (M+H)$^+$: 374 observed: Molecular ion (M+H)$^+$: 374
HPLC-MS: 1.20 minutes (Method A)

15c 10-[3-(4-Fluoro-phenoxymethyl)-azetidin-1-yl]-6,7,8,9-tetrahydro-5H-1,4,7,10a-tetraaza-cyclohepta[f]indene To 0.1 g (0.268 mmol) 10-(3-hydroxymethyl-azetidin-1-yl)-5,6,8,9-tetrahydro-1,4,7,10a-tetraaza-cyclohepta[f]indene-7-carboxylic acid tert-butyl ester in 0.3 mL THF, was added 30 mg (0.268 mmol) 4-fluorophenol followed by 74 mg (0.281 mmol) triphenylphosphine and the reaction mixture was sonicated for 5 minutes. 55 µL (0.278 mmol) DIAD was added, the reaction mixture was sonicated for 5 minutes, then allowed to stand at room temperature for 17 hours. The solvent was evaporated under a stream of N$_2$ gas and the residue was redissolved in 2 mL DCM. The mixture was adsorbed on 0.43 g (1.3 mmol) macroporous polymer supported sulfonic acid and the resin was washed with 5 mL MeOH. The resin was eluted with 2×4 mL NH$_3$ (2 M in MeOH), the eluted mixtures were combined and concentrated. The residue was redissolved in 3 mL DCM and 1 mL TFA was added to the mixture. After evaporation, the product was purified by preparative HPLC (high-pH method). The purified product was dissolved in 3 mL DCM, 1 mL TFA was added and the mixture was stirred at room temperature for 2 hours. The mixture was evaporated to give the desired product as a TFA salt.

Yield: 85 mg (53% of theory)
C$_{20}$H$_{22}$FN$_5$O (M=367.43)
predicted: Molecular ion (M+H)$^+$: 368 observed: Molecular ion (M+H)$^+$: 368
HPLC-MS: 1.62 minutes (Method B)

TABLE 8

| Example | Structure | Yield of final step (%) | Salt type | Mass spec result | HPLC retention time (method) |
|---|---|---|---|---|---|
| 15.1 | 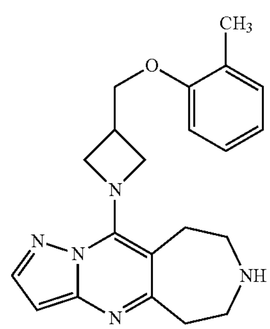 | 64 | TF | 364 [M + H]$^+$ | 1.58 (B) |
| 15.2 | 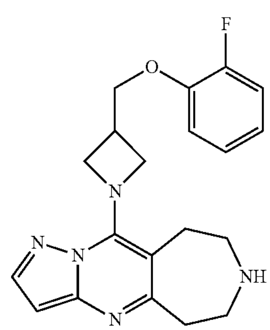 [SMILES: Fc1ccccc1OCC1CN(c2c3c(nc4ccnn24)CCNCC3)C1] | 99 | TF | 368 [M + H]$^+$ | 1.45 (B) |

TABLE 8-continued

| Example | Structure | Yield of final step (%) | Salt type | Mass spec result | HPLC retention time (method) |
|---|---|---|---|---|---|
| 15.3 | 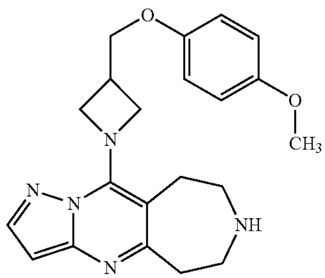 [SMILES: COc1ccc(OCC2CN(c3c4c(nc5ccnn35)CCNCC4)C2)cc1] | 99 | TF | 380 [M + H]⁺ | 1.43 (B) |
| 15.4 | 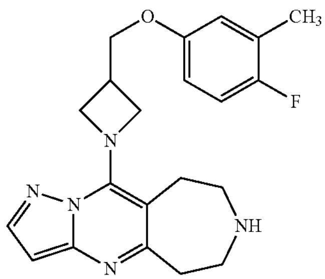 [SMILES: Cc1cc(OCC2CN(c3c4c(nc5ccnn35)CCNCC4)C2)ccc1F] | 99 | TF | 382 [M + H]⁺ | 1.70 (B) |
| 15.5 | 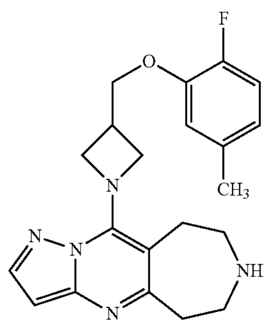 [SMILES: Cc1ccc(F)c(OCC2CN(c3c4c(nc5ccnn35)CCNCC4)C2)c1] | 57 | TF | 382 [M + H]⁺ | 1.57 (B) |
| 15.6 | 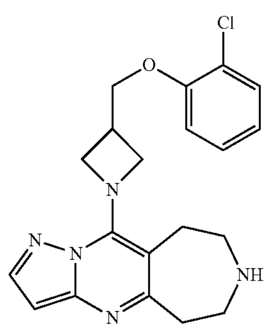 [SMILES: Clc1ccccc1OCC1CN(c2c3c(nc4ccnn24)CCNCC3)C1] | 99 | TF | 384/386 [M + H]⁺ | 1.49 (B) |
| 15.7 | 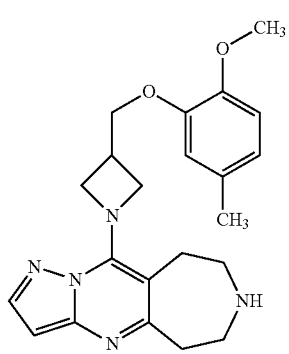 [SMILES: COc1ccc(C)cc1OCC1CN(c2c3c(nc4ccnn24)CCNCC3)C1] | 99 | TF | 394 [M + H]⁺ | 1.46 (B) |

TABLE 8-continued
| Example | Structure | Yield of final step (%) | Salt type | Mass spec result | HPLC retention time (method) |
|---|---|---|---|---|---|
| 15.8 | 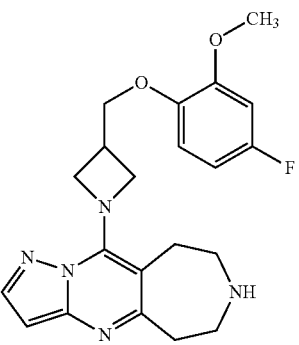 [SMILES: COc1cc(F)ccc1OCC1CN(c2c3c(nc4ccnn24)CCNCC3)C1] | 99 | TF | 398 [M + H]+ | 1.44 (B) |
| 15.9 | 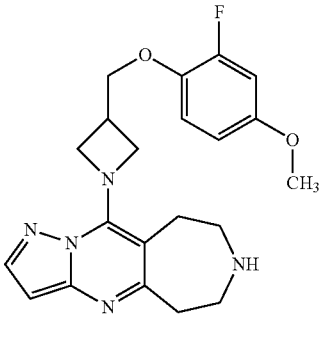 [SMILES: COc1ccc(OCC2CN(c3c4c(nc5ccnn35)CCNCC4)C2)c(F)c1] | 56 | TF | 398 [M + H]+ | 1.46 (B) |
| 15.10 | 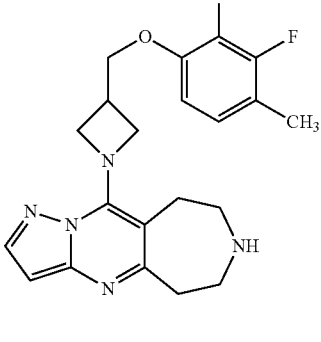 | 99 | TF | 400 [M + H]+ | 1.62 (B) |
| 15.11 | 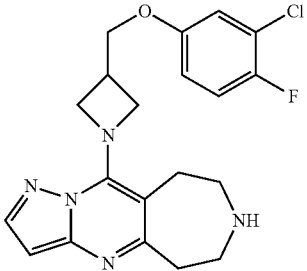 | 99 | TF | 402/404 [M + H]+ | 1.62 (B) |

TABLE 8-continued

| Example | Structure | Yield of final step (%) | Salt type | Mass spec result | HPLC retention time (method) |
|---|---|---|---|---|---|
| 15.12 | 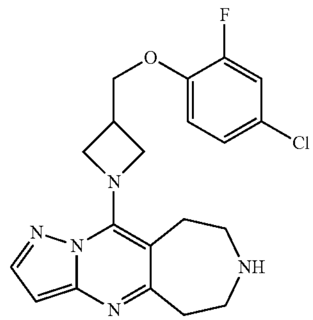 [SMILES: Fc1cc(Cl)ccc1OCC1CN(c2c3c(nc4ccnn24)CCNCC3)C1] | 99 | TF | 402/404 [M + H]⁺ | 1.63 (B) |
| 15.13 | 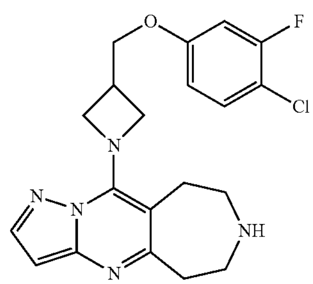 [SMILES: Fc1cc(OCC2CN(c3c4c(nc5ccnn35)CCNCC4)C2)ccc1Cl] | 55 | TF | 402/404 [M + H]⁺ | 1.64 (B) |
| 15.14 | 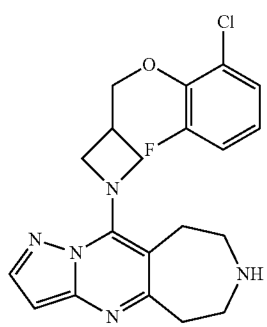 [SMILES: Fc1cccc(Cl)c1OCC1CN(c2c3c(nc4ccnn24)CCNCC3)C1] | 99 | TF | 402/404 [M + H]⁺ | 1.52 (B) |
| 15.15 | 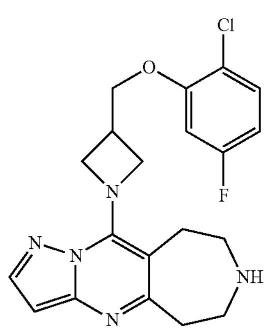 [SMILES: Fc1ccc(Cl)c(OCC2CN(c3c4c(nc5ccnn35)CCNCC4)C2)c1] | 99 | TF | 402/404 [M + H]⁺ | 1.51 (B) |

TABLE 8-continued

| Example | Structure | Yield of final step (%) | Salt type | Mass spec result | HPLC retention time (method) |
|---------|-----------|-------------------------|-----------|------------------|------------------------------|
| 15.16 | 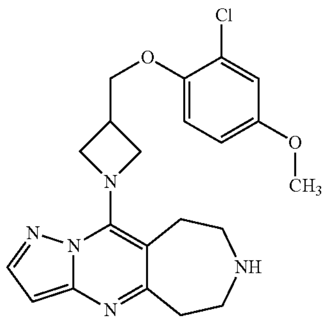 | 99 | TF | 414/416 $[M + H]^+$ | 1.53 (B) |
| 15.17 | 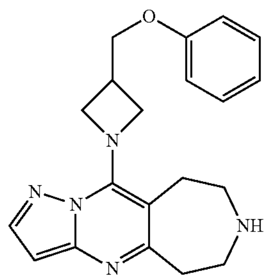 [SMILES: c1ccc(OCC2CN(c3c4c(nc5ccnn35)CCNCC4)C2)cc1] | 41 | TF | 350 $[M + H]^+$ | 3.72 (C) |
| 15.18 | 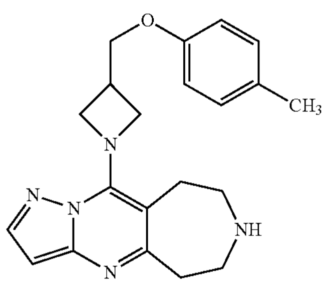 [SMILES: Cc1ccc(OCC2CN(c3c4c(nc5ccnn35)CCNCC4)C2)cc1] | 49 | TF | 364 $[M + H]^+$ | 4.03 (C) |
| 15.19 | 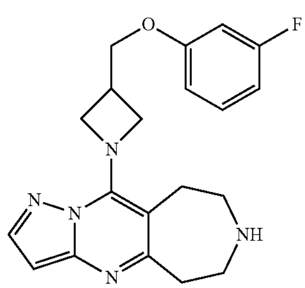 [SMILES: Fc1cccc(OCC2CN(c3c4c(nc5ccnn35)CCNCC4)C2)c1] | 40 | TF | 368 $[M + H]^+$ | 3.85 (C) |
| 15.20 | 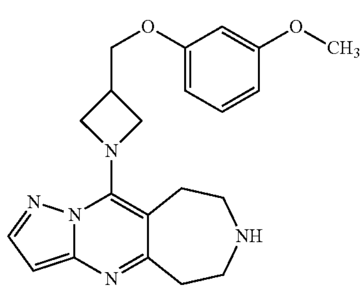 [SMILES: COc1cccc(OCC2CN(c3c4c(nc5ccnn35)CCNCC4)C2)c1] | 37 | TF | 380 $[M + H]^+$ | 3.74 (C) |

TABLE 8-continued

| Example | Structure | Yield of final step (%) | Salt type | Mass spec result | HPLC retention time (method) |
|---------|-----------|-------------------------|-----------|------------------|------------------------------|
| 15.21 | 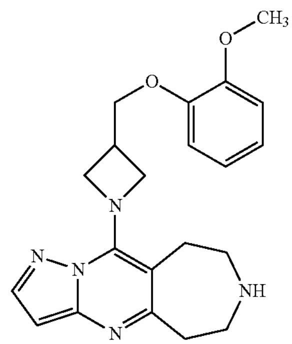 [SMILES: COc1ccccc1OCC1CN(c2c3c(nc4ccnn24)CCNCC3)C1] | 18 | TF | 380 [M + H]⁺ | 3.52 (C) |
| 15.22 | 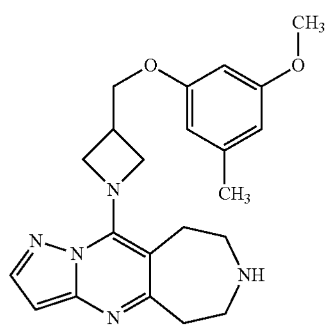 [SMILES: COc1cc(C)cc(OCC2CN(c3c4c(nc5ccnn35)CCNCC4)C2)c1] | 42 | TF | 394 [M + H]⁺ | 3.99 (C) |
| 15.23 | 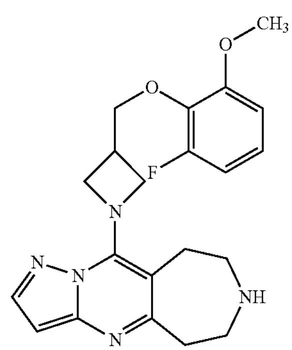 [SMILES: COc1cccc(F)c1OCC1CN(c2c3c(nc4ccnn24)CCNCC3)C1] | 37 | TF | 398 [M + H]⁺ | 3.72 (C) |
| 15.24 | 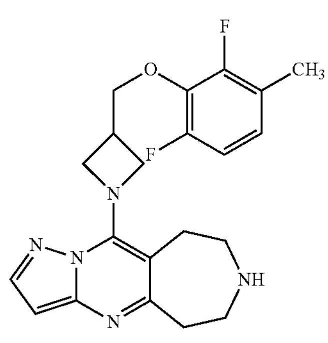 [SMILES: Cc1ccc(F)c(OCC2CN(c3c4c(nc5ccnn35)CCNCC4)C2)c1F] | 22 | TF | 400 [M + H]⁺ | 4.11 (C) |

TABLE 8-continued

| Example | Structure | Yield of final step (%) | Salt type | Mass spec result | HPLC retention time (method) |
|---------|-----------|------------------------|-----------|------------------|------------------------------|
| 15.25 | 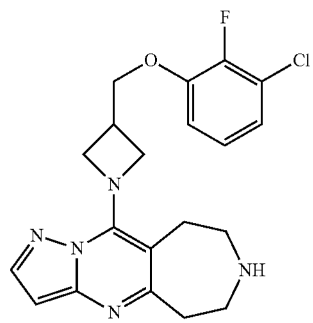 [SMILES: Fc1c(Cl)cccc1OCC1CN(c2c3c(nc4ccnn24)CCNCC3)C1] | 21 | TF | 402/404 [M + H]+ | 4.09 (C) |
| 15.26 | 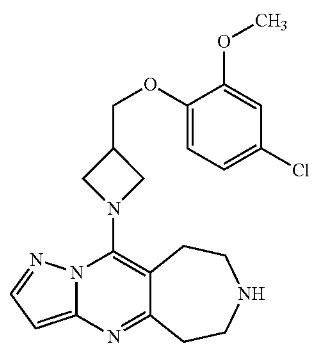 [SMILES: COc1cc(Cl)ccc1OCC1CN(c2c3c(nc4ccnn24)CCNCC3)C1] | 38 | TF | 414/416 [M + H]+ | 3.94 (C) |
| 15.27 | 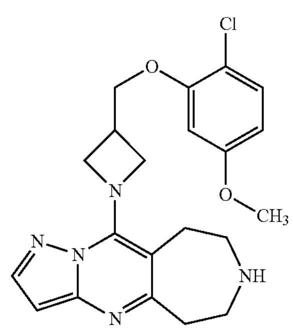 [SMILES: COc1ccc(Cl)c(OCC2CN(c3c4c(nc5ccnn35)CCNCC4)C2)c1] | 9 | TF | 414/416 [M + H]+ | 3.92 (C) |
| 15.28 | 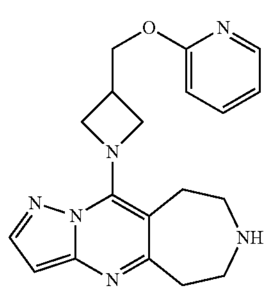 [SMILES: c1ccc(OCC2CN(c3c4c(nc5ccnn35)CCNCC4)C2)nc1] | 52 | none | 351 [M + H]+ | 4.20 (C) |

Example 16

10-(3-Methoxymethyl-azetidin-1-yl)-6,7,8,9-tetrahydro-5H-1,4,7,10a-tetraaza-cyclohepta[f]indene

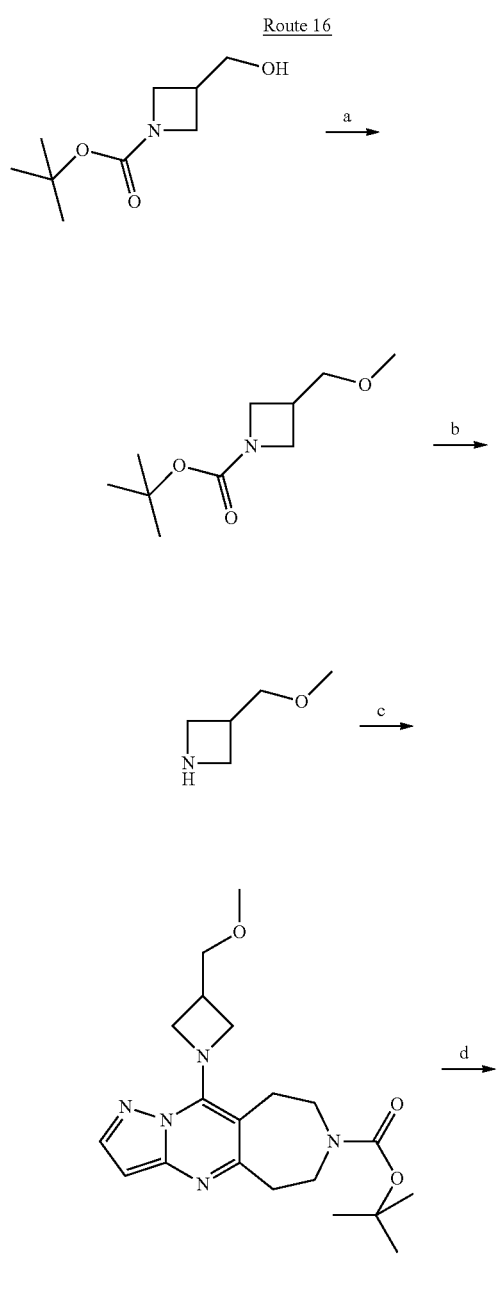

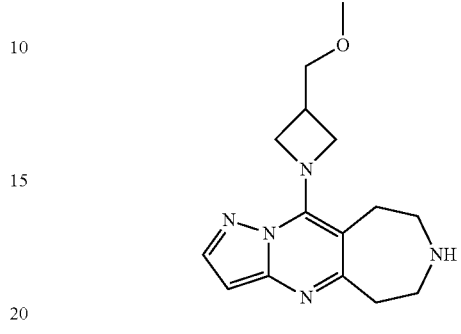

16a 3-Methoxymethyl-azetidine-1-carboxylic acid tert-butyl ester

To 24.6 mg (0.74 mmol, 60% dispersion in mineral oil) NaH in 5 mL THF at 0° C. was added 0.115 g (0.61 mmol) 3-hydroxymethyl-azetidine-1-carboxylic acid tert-butyl ester (prepared using route 15 step a) in 1 mL THF dropwise over 10 minutes, and the reaction was stirred at 0° C. for 30 minutes. 46 µL (0.74 mmol) methyl iodide was added and the reaction was stirred at room temperature for 2 hours. 20 mg (0.61 mmol, 60% dispersion in mineral oil) of NaH followed by 38 µL (0.61 mmol) of methyl iodide were added and the reaction mixture was stirred at room temperature for 16 hours. 5 mL of $H_2O$ was added and the mixture was extracted with EtOAc (2×10 mL), the organic layers were combined and dried with $MgSO_4$. After filtration, the solvent was evaporated to give the desired product which was used for the next step without further purification.

16b 3-Methoxymethyl-azetidine trifluoroacetate

To 0.123 g (0.61 mmol) 3-methoxymethyl-azetidine-1-carboxylic acid tert-butyl in 2 mL DCM was added 0.47 mL (6.1 mmol) TFA and the reaction mixture was stirred for 16 hours. The solvent was evaporated to give the desired product as a TFA salt, which was used for the next step without further purification.

16d 10-(3-Methoxymethyl-azetidin-1-yl)-6,7,8,9-tetrahydro-5H-1,4,7,10a-tetraaza-cyclohepta[f]indene

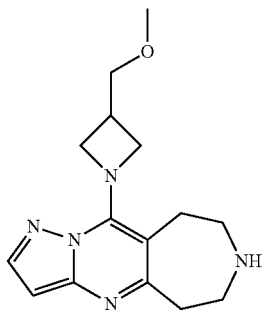 [SMILES: COCC1CN(c2c3c(nc4ccnn24)CCNCC3)C1]

The product was prepared by using route 1 (step e and f), using 3-methoxymethyl-azetidine trifluoroacetate as the amine in step e (route 1).

Yield: 52.5 mg (60% of theory)

$C_{15}H_{21}N_5O$ (M=287.37)

predicted: Molecular ion $(M+H)^+$: 288 observed: Molecular ion $(M+H)^+$: 288

HPLC-MS: 1.17 minutes (Method B)

TABLE 9

| Example | Structure | Yield of final step (%) | Salt type | Mass spec result | HPLC retention time (method) |
|---|---|---|---|---|---|
| 16.1 | 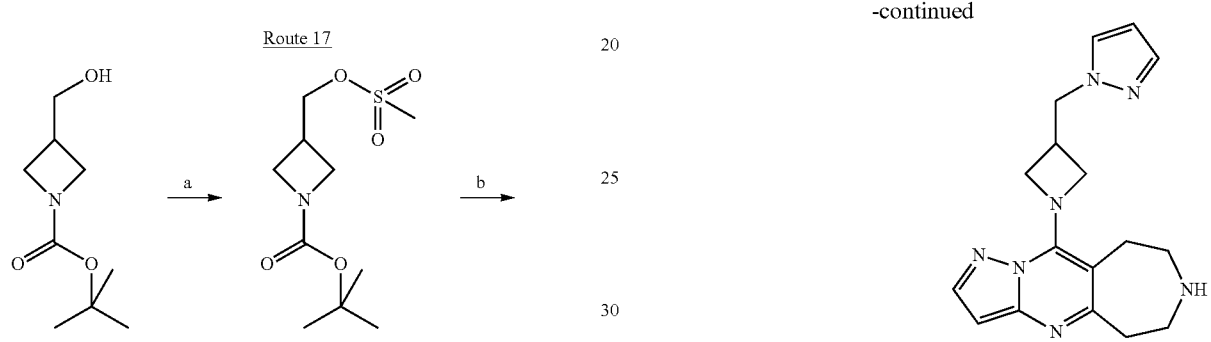 | 93 | HCl | 274 [M + H]⁺ | 1.17 (B) |

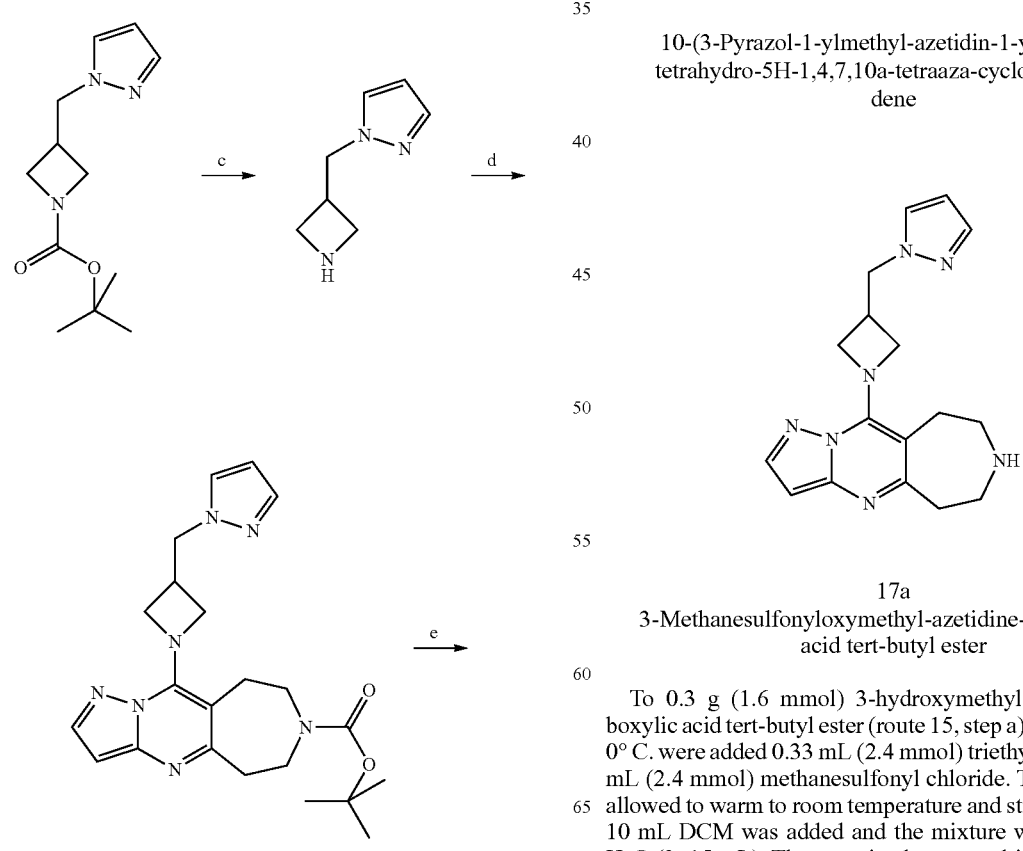

Example 17

10-(3-Pyrazol-1-ylmethyl-azetidin-1-yl)-6,7,8,9-tetrahydro-5H-1,4,7,10a-tetraaza-cyclohepta[f]indene

17a
3-Methanesulfonyloxymethyl-azetidine-1-carboxylic acid tert-butyl ester

To 0.3 g (1.6 mmol) 3-hydroxymethyl-azetidine-1-carboxylic acid tert-butyl ester (route 15, step a) in 3 mL DCM at 0° C. were added 0.33 mL (2.4 mmol) triethylamine and 0.19 mL (2.4 mmol) methanesulfonyl chloride. The reaction was allowed to warm to room temperature and stirred for 3 hours. 10 mL DCM was added and the mixture was washed with $H_2O$ (3×15 mL). The organic phase was dried over $Na_2SO_4$.

After filtration and evaporation of the solvent the product was purified by column chromatography (silica, heptane/EtOAc 7:3 to 6:4).

Yield: 0.37 g (87% of theory)
$C_{10}H_{19}NO_5S$ (M=265.33)
predicted: Molecular ion $(M+H)^+$: 266 observed: Molecular ion $(M+H)^+$: 266
HPLC-MS: 1.73 minutes (Method A)

17b 3-Pyrazol-1-ylmethyl-azetidine-1-carboxylic acid tert-butyl ester

To 17.9 mg (0.26 mmol) pyrazole in 2 mL dry THF at 0° C. was added 14 mg (0.35 mmol, 60% dispersion in mineral oil) NaH and the reaction was stirred for 30 minutes. 50 mg (0.17 mmol) 3-methanesulfonyloxymethyl-azetidine-1-carboxylic acid tert-butyl ester in 1 mL dry THF was added dropwise and the reaction was allowed to warm to room temperature for 16 hours. The solvent was evaporated and the remaining residue was partitioned between 25 mL $H_2O$ and 25 mL EtOAc. The organic phase was washed with 25 mL 1% citric acid solution, $H_2O$ (3×25 mL), 25 mL brine and dried with $Na_2SO_4$. After filtration and evaporation of the solvent the product was used in the next step without further purification.

Yield: 41.5 mg (100% of theory)
$C_{12}H_{19}N_3O_2$ (M=237.30)
predicted: Molecular ion $(M+H)^+$: 238 observed: Molecular ion $(M+H)^+$: 238
HPLC-MS: 1.71 minutes (Method A)

17c 1-Azetidin-3-ylmethyl-1H-pyrazole

To 41.5 mg (0.17 mmol) 3-pyrazol-1-ylmethyl-azetidine-1-carboxylic acid tert-butyl ester was added 2 mL of 25% TFA in DCM and the reaction was stirred at room temperature for 1 hour. The solvent was evaporated to give the desired product as a TFA salt, which was used in the next step without further purification.

17e 10-(3-Pyrazol-1-ylmethyl-azetidin-1-yl)-6,7,8,9-tetrahydro-5H-1,4,7,10a-tetraaza-cyclohepta[f]indene The product was prepared using 10-chloro-5,6,8,9-tetrahydro-1,4,7,10a-tetraaza-cyclohepta[f]indene-7-carboxylic acid tert-butyl ester in route 1 (step e and f), in step e (route 1) 1-azetidin-3-ylmethyl-1H-pyrazole was used as the amine.

Yield: 23.3 mg (90% of theory)
$C_{17}H_{21}N_7$ (M=323.40)
predicted: Molecular ion $(M+H)^+$: 324 observed: Molecular ion $(M+H)^+$: 324
HPLC-MS: 4.28 minutes (Method C)

Route 18

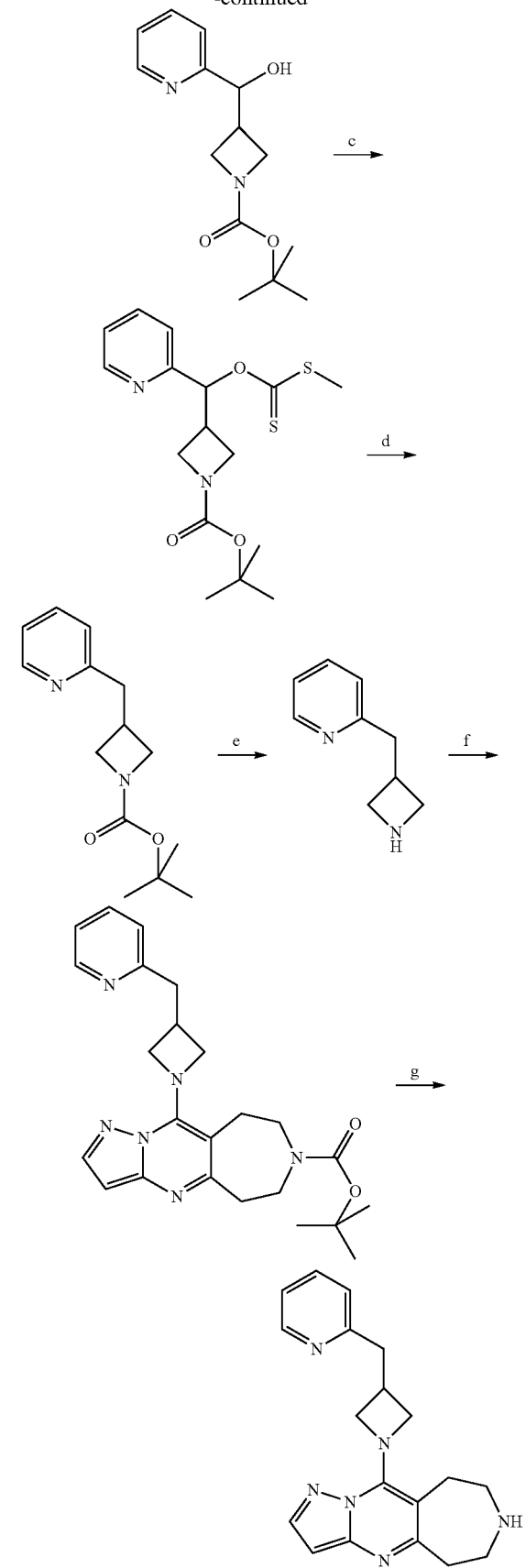

Example 18

10-(3-Pyridin-2-ylmethyl-azetidin-1-yl)-6,7,8,9-tetrahydro-5H-1,4,7,10a-tetraaza-cyclohepta[f]indene

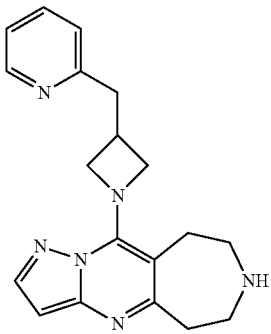 [SMILES: c1ccc(CC2CN(c3c4c(nc5ccnn35)CCNCC4)C2)nc1]

18a 3-Formyl-azetidine-1-carboxylic acid tert-butyl ester

To 40 mL dry DCM was added 2.19 mL (30.8 mmol) DMSO. The solution was cooled to −78° C. under nitrogen and 1.95 mL (23.1 mmol) oxalyl chloride was added dropwise. A solution of 2.88 g (15.4 mmol) 3-hydroxymethyl-azetidine-1-carboxylic acid tert-butyl ester in 20 mL dry DCM was added quickly via syringe followed by 10.5 mL (77 mmol) triethylamine. The mixture was allowed to warm to room temperature and then quenched by extraction with 1 M HCl (2×50 mL). The organic layer was dried over $Na_2SO_4$, filtered and evaporated to give the product which was used in the next step without further purification.

18b 3-(Hydroxy-pyridin-2-yl-methyl)-azetidine-1-carboxylic acid tert-butyl ester To 1.51 g (9.55 mmol) bromopyridine in 50 mL ether at −20° C. was added 6 mL (1.6 M in hexane, 9.6 mmol) n-butyl lithium, after 10 minutes the mixture was cooled to −78° C. and 1.61 g (8.7 mmol) 3-formyl-azetidine-1-carboxylic acid tert-butyl ester in 20 mL ether was added. The mixture was stirred and allowed to warm to room temperature, quenched with 50 mL 1 M sodium bicarbonate solution and then extracted with 50 mL DCM. The organic layer was dried over $Na_2SO_4$. After filtration and evaporation of the solvent the desired product was purified by column chromatography (silica, heptane/EtOAc 1:1 to EtOAc).

Yield: 0.5 g (22% of theory)
$C_{14}H_{20}N_2O_3$ (M=264.33)
predicted: Molecular ion $(M+H)^+$: 265 observed: Molecular ion $(M+H)^+$: 265
HPLC-MS: 0.93 minutes (Method D)

18c 3-(Methylsulfanylthiocarboxyoxy-pyridin-2-yl-methyl)-azetidine-1-carboxylic acid tert-butyl ester To 529 mg (2 mmol) 3-(hydroxy-pyridin-2-yl-methyl)-azetidine-1-carboxylic acid tert-butyl ester in 10 mL dry THF was added 88 mg (2.2 mmol, 60% dispersion in mineral oil) NaH, and the mixture was stirred at room temperature for 10 minutes. 133 μL (2.4 mmol) carbon disulfide was added and the mixture was stirred for 30 minutes. 162 μL (2.6 mmol) methyl iodide was added and the mixture was stirred for 2 hours. 10 mL 1 M aqueous sodium bicarbonate was added and the mixture extracted with EtOAc (2×10 mL), the organic layers were combined and dried over $Na_2SO_4$. After filtration and evaporation of the solvent the product was purified by column chromatography (silica, hexane/EtOAc 9:1 to 7:3).

Yield: 737 mg (72% of theory)
$C_{16}H_{22}N_2O_3S_2$ (M=354.49)
predicted: Molecular ion $(M+H)^+$: 355 observed: Molecular ion $(M+H)^+$: 355
HPLC-MS: 1.52 minutes (Method D)

18d 3-Pyridin-2-ylmethyl-azetidine-1-carboxylic acid tert-butyl ester

To 428 mg (1.21 mmol) 3-(methylsulfanylthiocarboxyoxy-pyridin-2-yl-methyl)-azetidine-1-carboxylic acid tert-butyl ester in 15 mL dry toluene was added 6 mg (36 μmol) AIBN followed by 508 mg (1.69 mmol) $^nBu_3SnH$, and the mixture was heated under nitrogen at 110° C. for 2 hours. After evaporation of the solvent the product was purified by column chromatography (silica, heptane/EtOAc 1:1 to EtOAc).

Yield: 257 mg (86% of theory)
$C_{14}H_{20}N_2O_2$ (M=248.33)
predicted: Molecular ion $(M+H)^+$: 249 observed: Molecular ion $(M+H)^+$: 249
HPLC-MS: 0.91 minutes (Method D)

18e 2-Azetidin-3-ylmethyl-pyridine trifluoroacetate

To 257 mg (1.04 mmol) 3-pyridin-2-ylmethyl-azetidine-1-carboxylic acid tert-butyl ester was added 2 mL DCM and 2 mL TFA. The mixture was stirred at room temperature for 30 minutes. The solvent was evaporated to give the desired product as a TFA salt, which was used in the next step without further purification.

$C_9H_{12}N_2$ (M=148.21)
predicted: Molecular ion $(M+H)^+$: 149 observed: Molecular ion $(M+H)^+$: 149
HPLC-MS: 0.23 minutes (Method D)

18 g 10-(3-Pyridin-2-ylmethyl-azetidin-1-yl)-6,7,8,9-tetrahydro-5H-1,4,7,10a tetraaza-cyclohepta[f]indene The product was prepared using 10-chloro-5,6,8,9-tetrahydro-1,4,7,10a-tetraaza-cyclohepta[f]indene-7-carboxylic acid tert-butyl ester in route 1 (step e and f), in step e (route 1) 2-azetidin-3-ylmethyl-pyridine trifluoroacetate was used as the amine.

Yield: 32 mg (4% of theory)
$C_{19}H_{22}N_6$ (M=334.43)
predicted: Molecular ion $(M+H)^+$: 335 observed: Molecular ion $(M+H)^+$: 335
HPLC-MS: 3.48 minutes (Method C)

TABLE 10
| Example | Structure | Yield of final step (%) | Salt type | Mass spec result | HPLC retention time (method) |
|---|---|---|---|---|---|
| 18.1 | 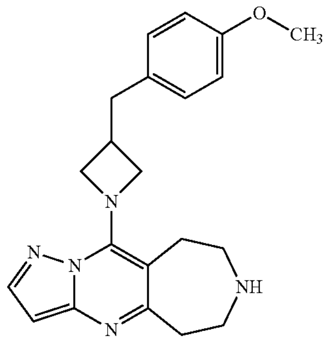 [SMILES: COc1ccc(CC2CN(c3c4c(nc5ccnn35)CCNCC4)C2)cc1] | 63 | TF | 364 [M + H]+ | 4.20 (C) |
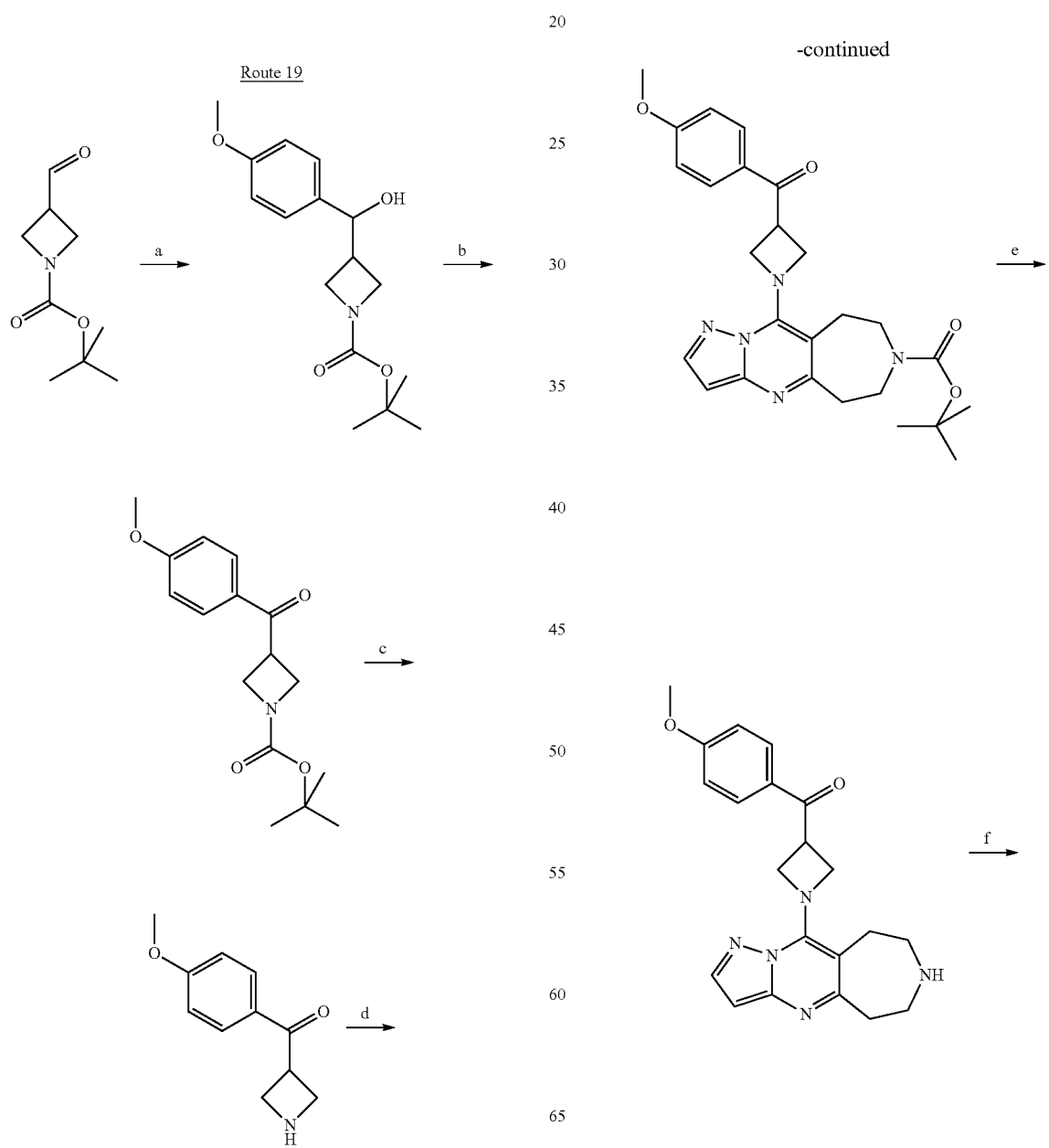

-continued

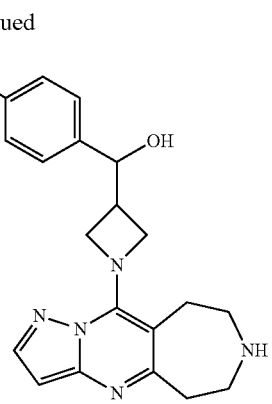

Example 19

(4-Methoxy-phenyl)-[1-(6,7,8,9-tetrahydro-5H-1,4,7,10a-tetraaza-cyclohepta[f]inden-10-yl)-azetidin-3-yl]-methanol

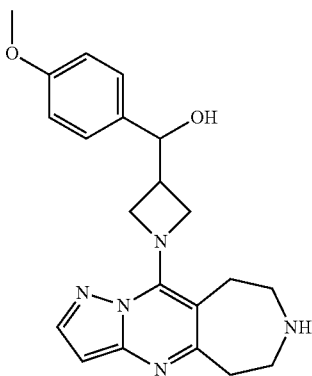 [SMILES: COc1ccc(C(O)C2CN(c3c4c(nc5ccnn35)CCNCC4)C2)cc1]

19a 3-[Hydroxy-(4-methoxy-phenyl)-methyl]azetidine-1-carboxylic acid tert-butyl ester To 2.2 g (11.8 mmol) 4-bromoanisole in 30 mL dry heptane under nitrogen was added 8.02 mL (1.6 M in hexane, 12.83 mmol) n-butyl lithium dropwise, and the mixture was stirred at room temperature for 30 minutes. The solution was then cooled to −78° C. and a solution of 2.0 g (10.7 mmol) 3-formyl-azetidine-1-carboxylic acid tert-butyl ester (route 18, step a) in 30 mL dry THF was added. The resultant mixture was allowed to warm to room temperature, quenched with 50 mL 1 M sodium bicarbonate and extracted with DCM (2×50 mL). The combined organic layers were dried over $Na_2SO_4$. After filtration and evaporation of the solvent the product was purified by column chromatography (silica, heptane/EtOAc 4:1 to 1:1).

Yield: 901 mg (29% of theory)

$C_{16}H_{23}NO_4$ (M=293.37)

predicted: Molecular ion (M+Na)$^+$: 316 observed: Molecular ion (M+Na)$^+$: 316

HPLC-MS: 1.30 minutes (Method D)

19b 3-(4-Methoxy-benzoyl)-azetidine-1-carboxylic acid tert-butyl ester

To 30 mL dry DCM was added 0.45 mL (6.28 mmol) DMSO and the mixture was cooled to −78° C., 0.4 mL (4.71 mmol) oxalyl chloride was added followed by a solution of 920 mg (3.14 mmol) 3-[hydroxy-(4-methoxy-phenyl)-methyl]-azetidine-1-carboxylic acid tert-butyl in 15 mL dry DCM. 2.14 mL (15.7 mmol) triethylamine was added, the mixture was allowed to warm to room temperature, washed with 1 M aqueous HCl (2×50 mL) and dried over $Na_2SO_4$. After filtration and evaporation of the solvent the product was purified by column chromatography (silica, heptane-EtOAc 7:3 to 1:1).

Yield: 714 mg (78% of theory)

$C_{16}H_{21}NO_4$ (M=291.35)

predicted: Molecular ion (M+Na)$^+$: 314 observed: Molecular ion (M+Na)$^+$: 314

HPLC-MS: 1.30 minutes (Method D)

19c Azetidin-3-yl-(4-methoxy-phenyl)-methanone trifluoroacetate

To 714 mg (2.45 mmol) 3-(4-methoxy-benzoyl)-azetidine-1-carboxylic acid tert-butyl ester in 10 mL DCM was added 10 mL TFA and the mixture was stirred at room temperature for 30 minutes. The solvent was evaporated to give the desired product as a TFA salt, which was used in the next step without further purification.

19e (4-Methoxy-phenyl)-[1-(6,7,8,9-tetrahydro-5H-1,4,7,10a-tetraaza-cyclohepta[f]inden-10-yl)-azetidin-3-yl]-methanone The product was prepared using 10-chloro-5,6,8,9-tetrahydro-1,4,7,10a-tetraaza-cyclohepta[f]indene-7-carboxylic acid tert-butyl ester in route 1 (step e and f), in step e (route 1) azetidin-3-yl-(4-methoxy-phenyl)-methanone trifluoroacetate was used as the amine.

Yield: 912 mg (100% of theory)

$C_{21}H_{23}N_5O_2$ (M=377.45)

predicted: Molecular ion (M+H)$^+$: 378 observed: Molecular ion (M+H)$^+$: 378

HPLC-MS: 3.91 minutes (Method C)

19f (4-Methoxy-phenyl)-[1-(6,7,8,9-tetrahydro-5H-1,4,7,10a-tetraaza-cyclohepta[f]inden-10-yl)-azetidin-3-yl]-methanol To 200 mg (0.53 mmol) (4-methoxy-phenyl)-[1-(6,7,8,9-tetrahydro-5H-1,4,7,10a-tetraaza-cyclohepta[f]inden-10-yl)-azetidin-3-yl]-methanone in 3 mL MeOH was added 20 mg (0.53 mmol) sodium borohydride and the mixture was stirred at room temperature for 30 minutes. 1 mL saturated brine was added and the mixture extracted with DCM (2×5 mL), the organic layers were combined and dried over sodium sulphate. After filtration the solvent was evaporated to give the desired product.

Yield: 183 mg (91% of theory)

$C_{21}H_{25}N_5O_2$ (M=379.47)

predicted: Molecular ion (M+H)$^+$: 380 observed: Molecular ion (M+H)$^+$: 380

HPLC-MS: 3.54 minutes (Method C)

Route 20

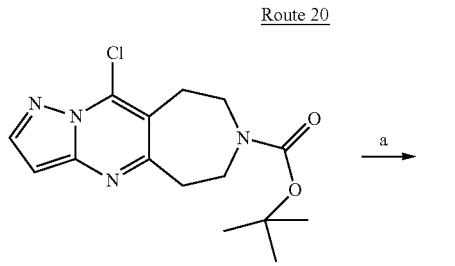

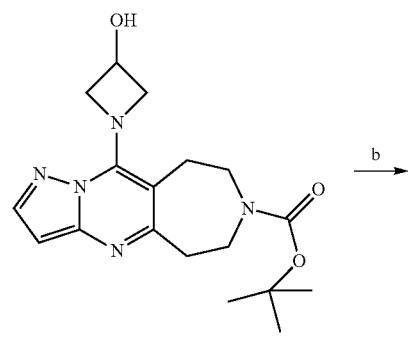

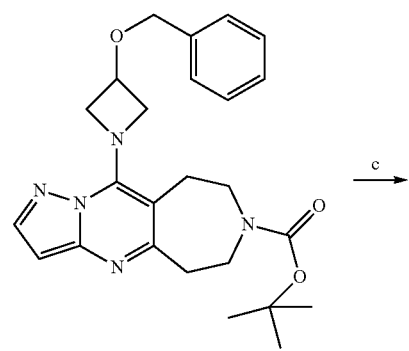

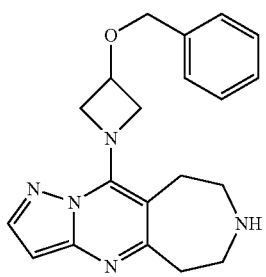

Example 20

10-(3-Benzyloxy-azetidin-1-yl)-6,7,8,9-tetrahydro-5H-1,4,7,10a-tetraaza-cyclohepta[f]indene

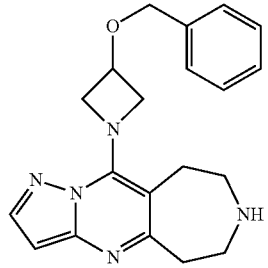 [SMILES: c1ccc(COC2CN(c3c4c(nc5ccnn35)CCNCC4)C2)cc1]

20a 10-(3-Hydroxy-azetidin-1-yl)-5,6,8,9-tetrahydro-1,4,7,10a-tetraaza-cyclohepta[f]indene-7-carboxylic acid tert-butyl ester The product was prepared using route 1 (step a to e), in step e (route 1) 3-hydroxyazetidine hydrochloride was used as the amine.
Yield: 212 mg (16% of theory)
$C_{18}H_{25}N_5O_3$ (M=359.43)
predicted: Molecular ion $(M+H)^+$: 360 observed: Molecular ion $(M+H)^+$: 360
HPLC-MS: 1.15 minutes (Method A)

20b 10-(3-Benzyloxy-azetidin-1-yl)-5,6,8,9-tetrahydro-1,4,7,10a-tetraaza-cyclohepta[f]indene-7-carboxylic acid tert-butyl ester To 200 mg (0.56 mmol) 10-(3-hydroxy-azetidin-1-yl)-5,6,8,9-tetrahydro-1,4,7,10a-tetraaza-cyclohepta[f]indene-7-carboxylic acid tert-butyl ester in 10 mL anhydrous THF maintained at 0° C. for 30 minutes was added 320 mg (6.72 mmol, 60% dispersion in mineral oil) NaH under an atmosphere of nitrogen and the reaction was stirred at 0° C. for 30 minutes. 0.8 mL (6.80 mmol) benzyl bromide was added and the reaction was heated at 65° C. for 16 hours. The reaction mixture was allowed to cool to room temperature and the solvent was evaporated. 25 mL EtOAc was added and the organic layer was washed with $H_2O$ (2×20 mL), and dried over $Na_2SO_4$. After filtration and evaporation the product was purified by column chromatography (silica, heptane/EtOAc 3:7).
Yield: 40 mg (16% of theory)
$C_{25}H_{31}N_5O_3$ (M=449.56)
predicted: Molecular ion $(M+H)^+$: 450 observed: Molecular ion $(M+H)^+$: 450
HPLC-MS: 1.67 minutes (Method A)
Rf: 0.30 (heptane/EtOAc 3:7)

20c 10-(3-Benzyloxy-azetidin-1-yl)-6,7,8,9-tetrahydro-5H-1,4,7,10a-tetraaza-cyclohepta[f]indene The product was prepared by using route 1 (step e) using 10-(3-benzyloxy-azetidin-1-yl)-5,6,8,9-tetrahydro-1,4,7,10a-tetraaza-cyclohepta[f]indene-7-carboxylic acid tert-butyl ester as the boc-protected amine.
Yield: 21 mg (40% of theory)
$C_{20}H_{23}N_5O$ (M=349.44)
predicted: Molecular ion $(M+H)^+$: 350 observed: Molecular ion $(M+H)^+$: 350
HPLC-MS: 3.83 minutes (Method C)

TABLE 11
| Example | Structure | Yield of final step (%) | Salt type | Mass spec result | HPLC retention time (method) |
|---|---|---|---|---|---|
| 20.1 | 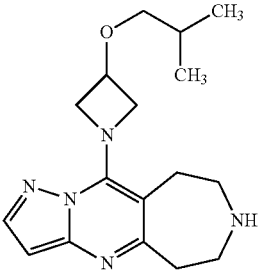 [SMILES: CC(C)COC1CN(c2c3c(nc4ccnn24)CCNCC3)C1] | 78 | TF | 316 [M + H]⁺ | 3.85 (C) |
| 20.2 | 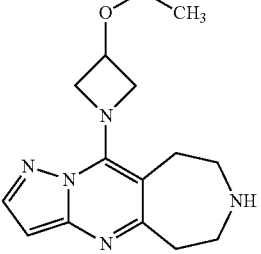 | 100 | TF | 288 [M + H]⁺ | 2.74 (C) |
| 20.3 | 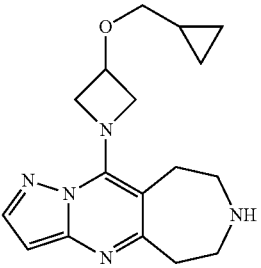 [SMILES: c1cc2nc3c(c(N4CC(OCC5CC5)C4)n2n1)CCNCC3] | 100 | TF | 314 [M + H]⁺ | 3.23 (C) |
| 20.4 | 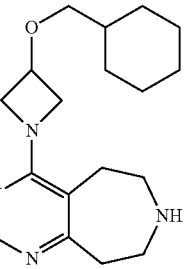 | 100 | TF | 356 [M + H]⁺ | 4.72 (C) |
| 20.5 | 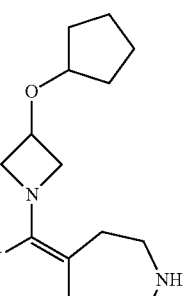 | 11 | TF | 328 [M + H]⁺ | 4.59 (C) |

TABLE 11-continued

| Example | Structure | Yield of final step (%) | Salt type | Mass spec result | HPLC retention time (method) |
|---|---|---|---|---|---|
| 20.6 | 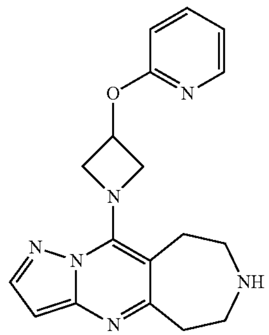 [SMILES: c1ccc(OC2CN(c3c4c(nc5ccnn35)CCNCC4)C2)nc1] | 93 | none | 337 [M + H]⁺ | 4.00 (C) |
| 20.7 | 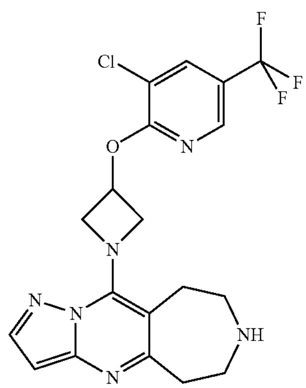 [SMILES: FC(F)(F)c1cnc(OC2CN(c3c4c(nc5ccnn35)CCNCC4)C2)c(Cl)c1] | 100 | TF | 439/441 [M + H]⁺ | 5.01 (C) |
| 20.8 | 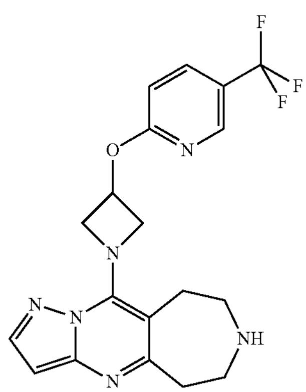 [SMILES: FC(F)(F)c1ccc(OC2CN(c3c4c(nc5ccnn35)CCNCC4)C2)nc1] | 91 | TF | 405 [M + H]⁺ | 4.73 (C) |
| 20.9 | 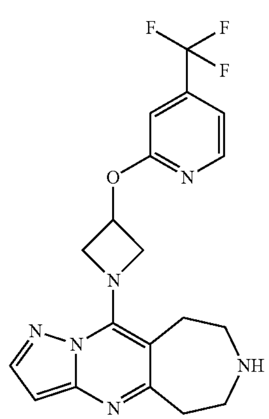 [SMILES: FC(F)(F)c1ccnc(OC2CN(c3c4c(nc5ccnn35)CCNCC4)C2)c1] | 95 | none | 405 [M + H]⁺ | 4.73 (C) |

TABLE 11-continued

| Example | Structure | Yield of final step (%) | Salt type | Mass spec result | HPLC retention time (method) |
|---|---|---|---|---|---|
| 20.10 | 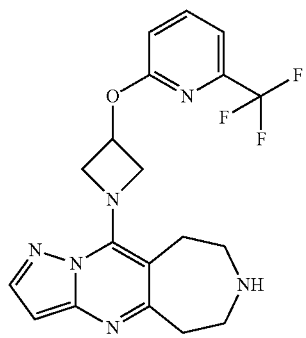 [SMILES: FC(F)(F)c1cccc(OC2CN(c3c4c(nc5ccnn35)CCNCC4)C2)n1] | 95 | TF | 405 [M + H]⁺ | 4.65 (C) |
| 20.11 | 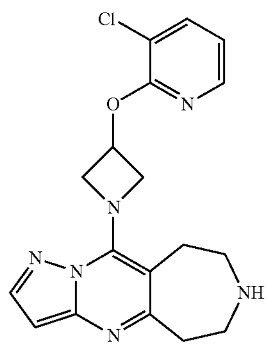 [SMILES: Clc1cccnc1OC1CN(c2c3c(nc4ccnn24)CCNCC3)C1] | 97 | none | 371/373 [M + H]⁺ | 4.39 (C) |
| 20.12 | 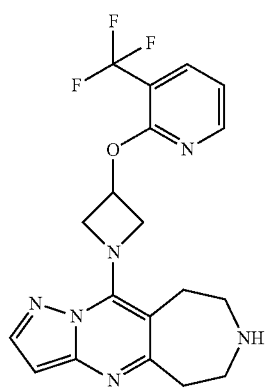 [SMILES: FC(F)(F)c1cccnc1OC1CN(c2c3c(nc4ccnn24)CCNCC3)C1] | 81 | none | 405 [M + H]⁺ | 4.55 (C) |
| 20.13 | 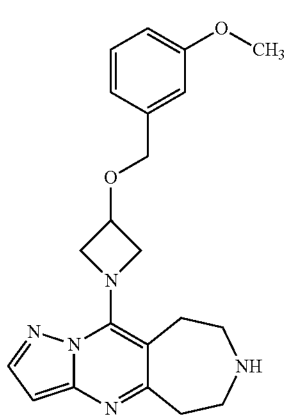 [SMILES: COc1cccc(COC2CN(c3c4c(nc5ccnn35)CCNCC4)C2)c1] | 93 | TF | 380 [M + H]⁺ | 4.13 (C) |

TABLE 11-continued

| Example | Structure | Yield of final step (%) | Salt type | Mass spec result | HPLC retention time (method) |
|---------|-----------|------------------------|-----------|------------------|------------------------------|
| 20.14 | 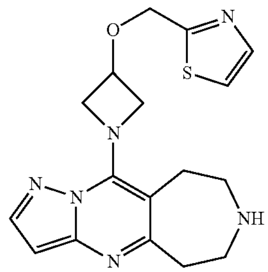 [SMILES: c1csc(COC2CN(c3c4c(nc5ccnn35)CCNCC4)C2)n1] | 44 | none | 357 [M + H]+ | 3.36 (C) |
| 20.15 | 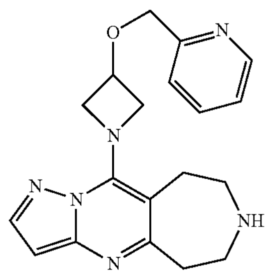 [SMILES: c1ccc(COC2CN(c3c4c(nc5ccnn35)CCNCC4)C2)nc1] | 87 | TF | 351 [M + H]+ | 3.25 (C) |

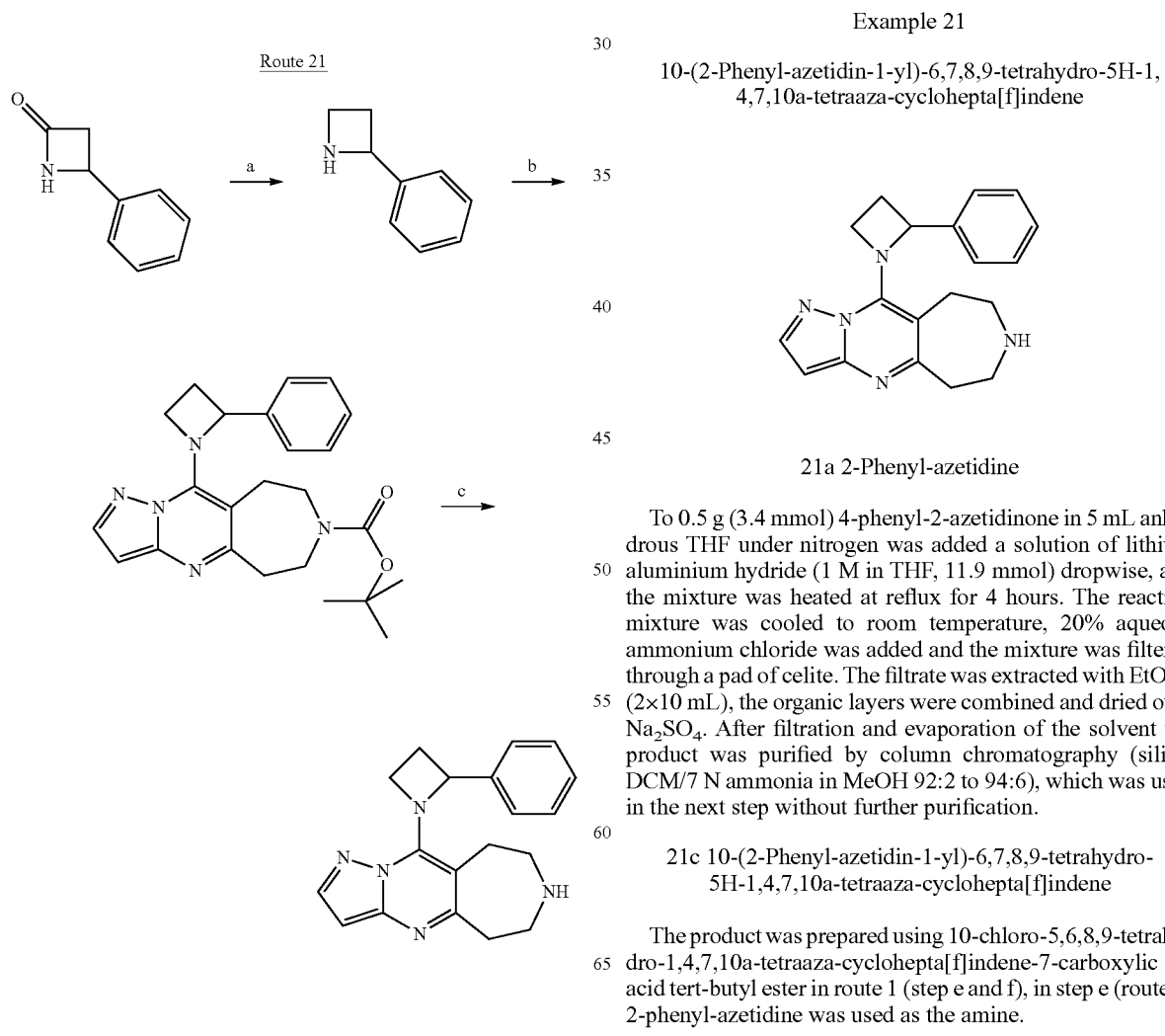

Example 21

10-(2-Phenyl-azetidin-1-yl)-6,7,8,9-tetrahydro-5H-1,4,7,10a-tetraaza-cyclohepta[f]indene

21a 2-Phenyl-azetidine

To 0.5 g (3.4 mmol) 4-phenyl-2-azetidinone in 5 mL anhydrous THF under nitrogen was added a solution of lithium aluminium hydride (1 M in THF, 11.9 mmol) dropwise, and the mixture was heated at reflux for 4 hours. The reaction mixture was cooled to room temperature, 20% aqueous ammonium chloride was added and the mixture was filtered through a pad of celite. The filtrate was extracted with EtOAc (2×10 mL), the organic layers were combined and dried over $Na_2SO_4$. After filtration and evaporation of the solvent the product was purified by column chromatography (silica, DCM/7 N ammonia in MeOH 92:2 to 94:6), which was used in the next step without further purification.

21c 10-(2-Phenyl-azetidin-1-yl)-6,7,8,9-tetrahydro-5H-1,4,7,10a-tetraaza-cyclohepta[f]indene The product was prepared using 10-chloro-5,6,8,9-tetrahydro-1,4,7,10a-tetraaza-cyclohepta[f]indene-7-carboxylic acid tert-butyl ester in route 1 (step e and f), in step e (route 1) 2-phenyl-azetidine was used as the amine.

143

Yield: 0.122 g (36% of theory)
$C_{19}H_{21}N_5$ (M=319.41)
predicted: Molecular ion (M+H)⁺: 320 observed: Molecular ion (M+H)⁺: 320
HPLC-MS: 3.24 minutes (Method C)

Route 22

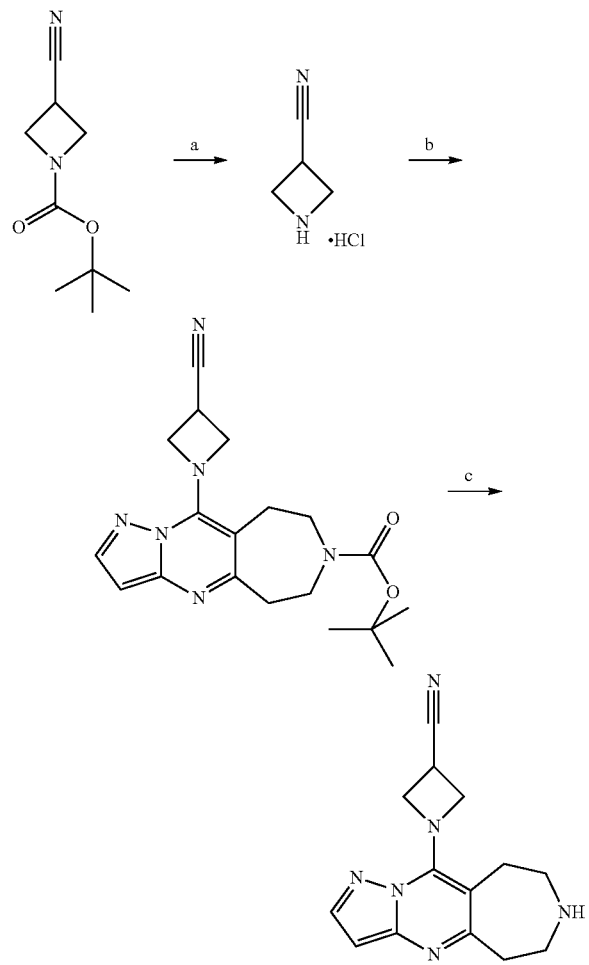

Example 22

1-(6,7,8,9-Tetrahydro-5H-1,4,7,10a-tetraaza-cyclohepta[f]inden-10-yl)-azetidine-3-carbonitrile

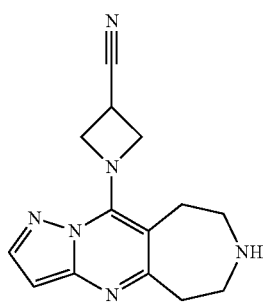 [SMILES: N#CC1CN(c2c3c(nc4ccnn24)CCNCC3)C1]

144

22a Azetidine-3-carbonitrile hydrochloride

To 0.3 g (1.64 mmol) 1-N-boc-3-cyanoazetidine, was added 8.23 mL (32.9 mmol) HCl in dioxane (4 M), and the reaction was stirred at room temperature for 2 hours. The solvent was evaporated to give the desired product as a HCl salt, which was used in the next step without further purification.

22c 1-(6,7,8,9-Tetrahydro-5H-1,4,7,10a-tetraaza-cyclohepta[f]inden-10-yl)-azetidine-3-carbonitrile The product was prepared using 10-chloro-5,6,8,9-tetrahydro-1,4,7,10a-tetraaza-cyclohepta[f]indene-7-carboxylic acid tert-butyl ester in route 1 (step e and f), in step e (route 1) azetidine-3-carbonitrile hydrochloride was used as the amine.

Yield: 0.2 g (87% of theory)
$C_{14}H_{16}N$ (M=268.3)
predicted: Molecular ion (M+H)⁺: 269 observed: Molecular ion (M+H)⁺: 269
HPLC-MS: 3.12 minutes (Method C)

Route 23

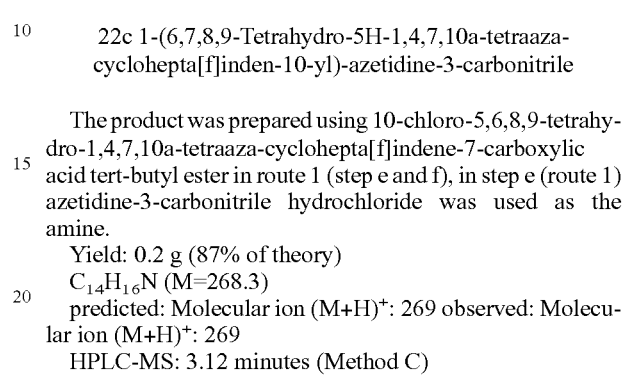

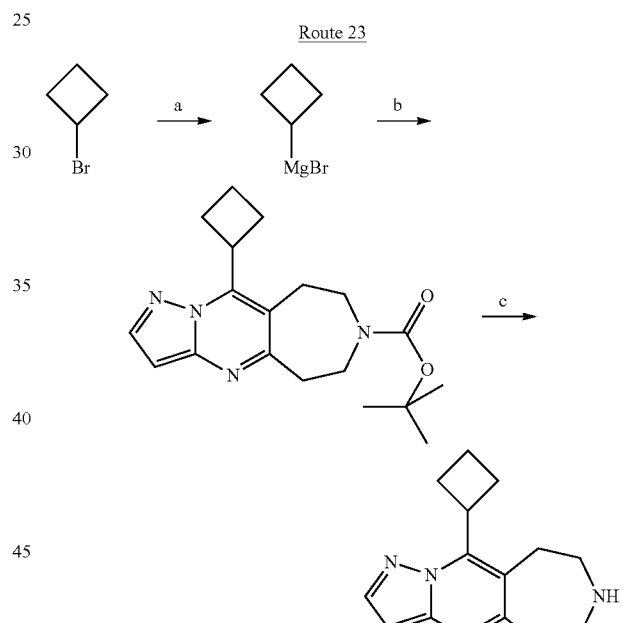

Example 23

10-Cyclobutyl-6,7,8,9-tetrahydro-5H-1,4,7,10a-tetraaza-cyclohepta[f]indene

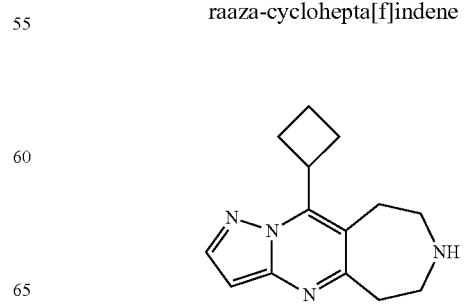

23a Cyclobutyl magnesium bromide

To 1.11 g (45.67 mmol) magnesium turnings in 5 mL THF was added 2 mg (7.9 µmol) iodine and the reaction was heated to 40° C. for 30 minutes. 0.5 g (3.7 mmol) cyclobutyl bromide was added and the reaction mixture was heated for 1.5 hours at 40° C. The mixture was cooled to room temperature and used in the next step.

23b 10-Cyclobutyl-5,6,8,9-tetrahydro-1,4,7,10a-tetraaza-cyclohepta[f]indene-7-carboxylic acid tert-butyl ester To a nitrogen purged mixture of 0.15 g (0.46 mmol) 10-chloro-5,6,8,9-tetrahydro-1,4,7,10a-tetraaza-cyclohepta[f]indene-7-carboxylic acid tert-butyl ester in 5 mL/0.5 mL THF/NMP in a sealed tube, was added 5.5 mg (0.022 mmol) iron (III) 2,4-pentanedionate. 0.5 mL (0.37 mmol) of cyclobutyl magnesium bromide in THF (23a) was added dropwise and the reaction was stirred at room temperature for 30 minutes. An extra 0.5 mL (0.37 mmol) of cyclobutyl magnesium bromide in THF (23a) was added and the reaction was stirred at room temperature for another 30 minutes. 5 mL EtOAc and 5 mL H$_2$O were added, and the mixture was extracted with EtOAc (2×10 mL), the organic layers were combined and dried with MgSO$_4$. After filtration and evaporation of the solvent the product was purified by preparative HPLC.

Yield: 0.021 g (13% of theory)

C$_{19}$H$_{26}$N$_4$O$_2$ (M=342.44)

predicted: Molecular ion (M+H)$^+$: 343 observed: Molecular ion (M+H)$^+$: 343

HPLC-MS: 2.17 minutes (Method A)

23c 10-Cyclobutyl-6,7,8,9-tetrahydro-5H-1,4,7,10a-tetraaza-cyclohepta[f]indene The product was prepared using 10-cyclobutyl-5,6,8,9-tetrahydro-1,4,7,10a-tetraaza-cyclohepta[f]indene-7-carboxylic acid tert-butyl ester in route 1 (step f).

Yield: 14.4 mg (74% of theory)

C$_{14}$H$_{18}$N$_4$ (M=242.33)

predicted: Molecular ion (M+H)$^+$: 243 observed: Molecular ion (M+H)$^+$: 243

HPLC-MS: 1.47 minutes (Method B)

Route 24

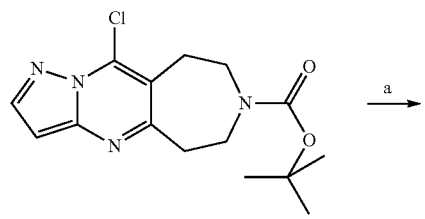

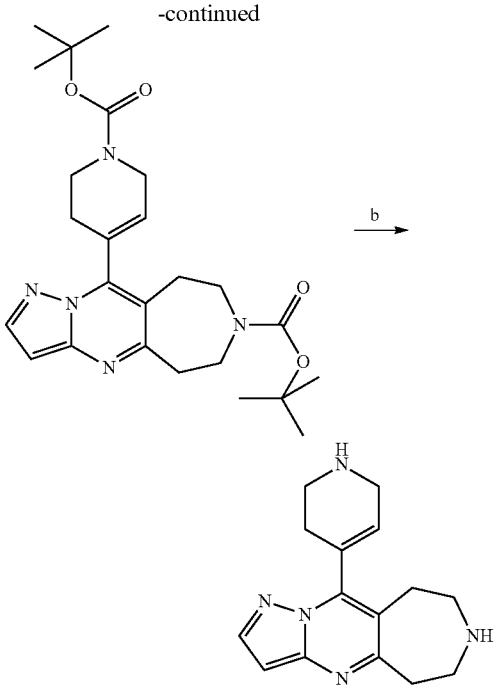

Example 24

10-(1,2,3,6-Tetrahydro-pyridin-4-yl)-6,7,8,9-tetrahydro-5H-1,4,7,10a-tetraaza-cyclohepta[f]indene

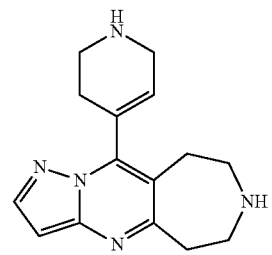 [SMILES: C1=C(c2c3c(nc4ccnn24)CCNCC3)CCNC1]

24a 10-(1-tert-Butoxycarbonyl-1,2,3,6-tetrahydro-pyridin-4-yl)-5,6,8,9-tetrahydro-1,4,7,10a-tetraaza-cyclohepta[f]indene-7-carboxylic acid tert-butyl ester To 0.075 g (0.23 mmol) 10-chloro-5,6,8,9-tetrahydro-1,4,7,10a-tetraaza-cyclohepta[f]indene-7-carboxylic acid tert-butyl ester in a microwave tube were added 3 mL dioxane, 1 mL MeOH, 79 mg (0.25 mmol) (N-tert-butoxycarbonyl)-1,2,3,6-tetrahydropyridine-4-boronic acid pinacol ester, 0.6 mL aqueous Na$_2$CO$_3$ (2 M), 19 mg (0.023 mmol) 1,1'-bis(diphenylphosphino)ferrocenedichloro palladium (II) under nitrogen and the reaction was subjected to microwave irradiation (discoverer, 100° C., 250 Watts) for 15 minutes. After evaporation of the solvent the product was purified by column chromatography (silica, DCM/MeOH 100:2).

Yield: 33 mg (30% of theory)

C$_{25}$H$_{35}$N$_5$O$_4$ (M=469.59)

147

24b 10-(1,2,3,6-Tetrahydro-pyridin-4-yl)-6,7,8,9-tetrahydro-5H-1,4,7,10a-tetraaza-cyclohepta[f]indene The product was prepared by using route 1 (step f).
Yield: 12.9 mg (37% of theory)
$C_{15}H_{19}N_5$ (M=269.35)
predicted: Molecular ion $(M+H)^+$: 270 observed: Molecular ion $(M+H)^+$: 270
HPLC-MS: 1.11 minutes (Method B)

Route 25

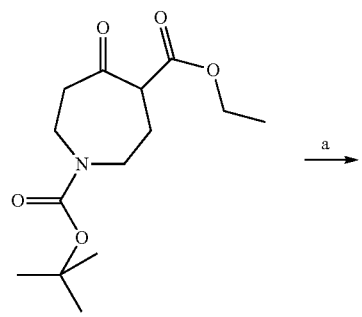

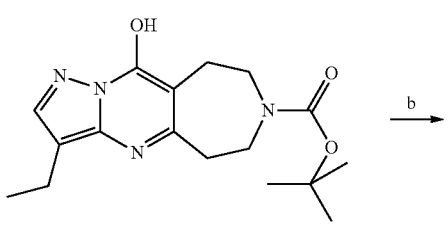

148

-continued

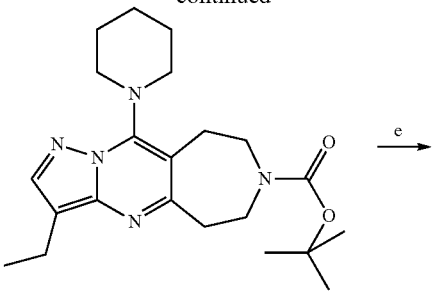

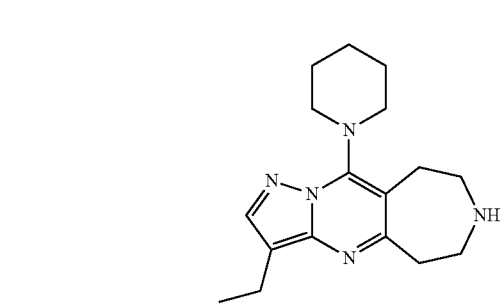

Example 25

3-Ethyl-10-piperidin-1-yl-6,7,8,9-tetrahydro-5H-1,4,7,10a-tetraaza-cyclohepta[f]indene

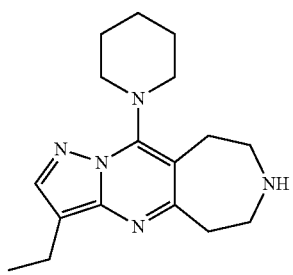 [SMILES: CCc1cnn2c(N3CCCCC3)c3c(nc12)CCNCC3]

25e 3-Ethyl-10-piperidin-1-yl-6,7,8,9-tetrahydro-5H-1,4,7,10a-tetraaza-cyclohepta[f]indene The product was prepared using route 1 (step a to e), in step b (route 1) 4-ethyl-2H-pyrazol-3-ylamine (prepared according to J. Med. Chem. 1982, 25, 235-242) was used, in step e (route 1) piperidine was used as the amine.
Yield: 126 mg (84% of theory)
$C_{17}H_{25}N_5$ (M=299.42)
predicted: Molecular ion $(M+H)^+$: 300 observed: Molecular ion $(M+H)^+$: 300
HPLC-MS: 4.61 minutes (Method C)

TABLE 12
| Example | Structure | Yield of final step (%) | Salt type | Mass spec result | HPLC retention time (method) |
|---|---|---|---|---|---|
| 25.1 | 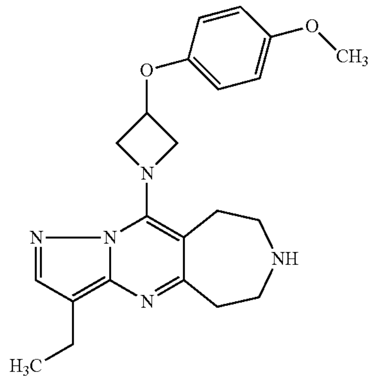 [SMILES: CCc1cnn2c(N3CC(Oc4ccc(OC)cc4)C3)c3c(nc12)CCNCC3] | 63 | TF | 394 [M + H]+ | 4.73 (C) |
| 25.2 | 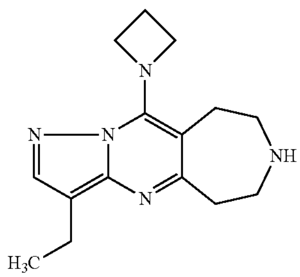 [SMILES: CCc1cnn2c(N3CCC3)c3c(nc12)CCNCC3] | 51 | TF | 272 [M + H]+ | 3.74 (C) |
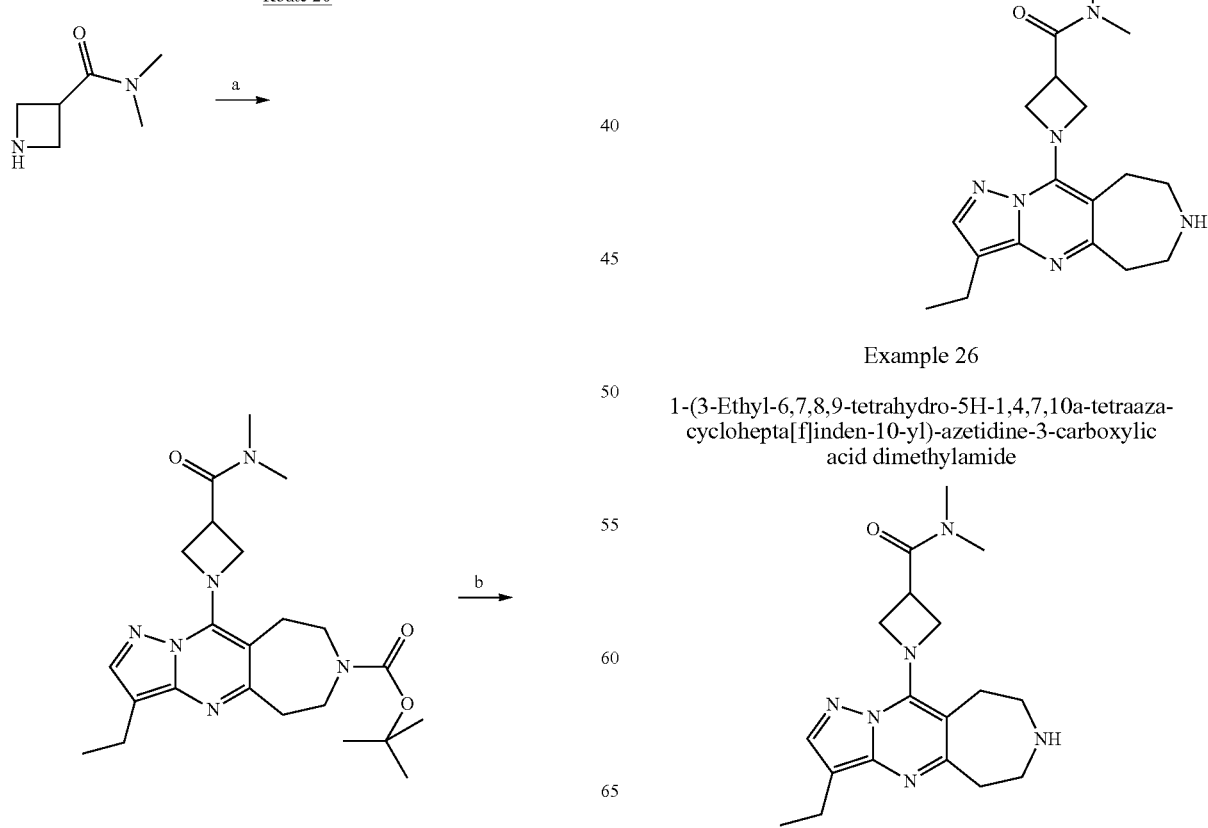
Example 26
1-(3-Ethyl-6,7,8,9-tetrahydro-5H-1,4,7,10a-tetraaza-cyclohepta[f]inden-10-yl)-azetidine-3-carboxylic acid dimethylamide

26b 1-(3-Ethyl-6,7,8,9-tetrahydro-5H-1,4,7,10a-tetraaza-cyclohepta[f]inden-10-yl)-azetidine-3-carboxylic acid dimethylamide The product was prepared using route 25 (step a to e), in step d (route 25) azetidine-3-carboxylic acid dimethylamide (route 9, step a and b) was used as the amine.

Yield: 161 mg (99% of theory)
$C_{18}H_{26}N_6O$ (M=342.45)
predicted: Molecular ion (M+H)$^+$: 343 observed: Molecular ion (M+H)$^+$: 343
HPLC-MS: 3.51 minutes (Method C)

Route 27

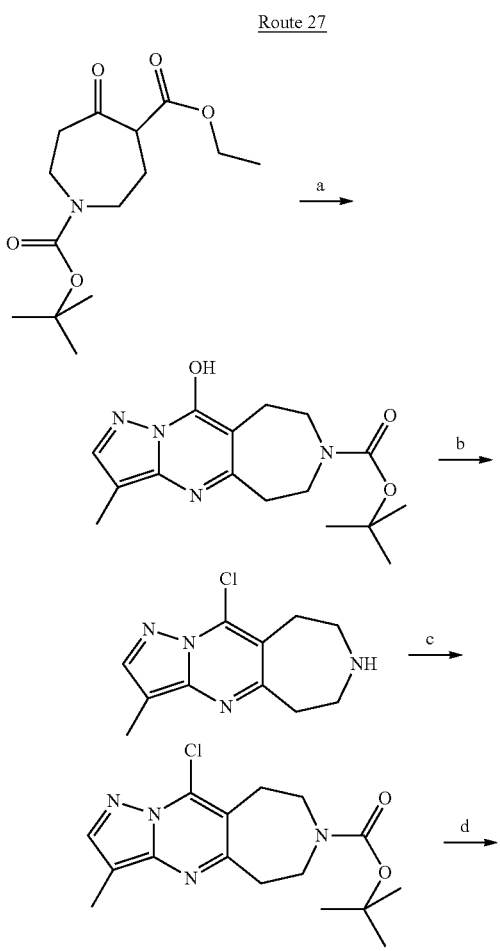

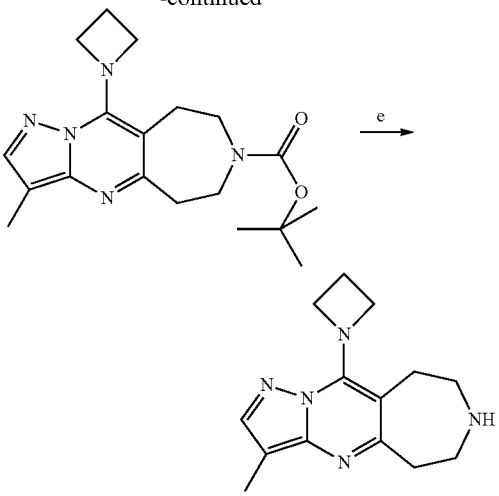

Example 27

10-Azetidin-1-yl-3-methyl-6,7,8,9-tetrahydro-5H-1,4,7,10a-tetraaza-cyclohepta[f]indene

27e 10-Azetidin-1-yl-3-methyl-6,7,8,9-tetrahydro-5H-1,4,7,10a-tetraaza-cyclohepta[f]indene The product was prepared using route 1 (from step a to f), in step b (route 1) 4-methyl-2H-pyrazol-3-ylamine was used, in step e (route 1) azetidine was used as the amine.

$C_{14}H_{19}N_5$ (M=257.34)
predicted: Molecular ion (M+H)$^+$: 258 observed: Molecular ion (M+H)$^+$: 258
HPLC-MS: 3.52 minutes (Method C)

TABLE 13

| Example | Structure | Yield of final step (%) | Salt type | Mass spec result | HPLC retention time (method) |
|---|---|---|---|---|---|
| 27.1 | 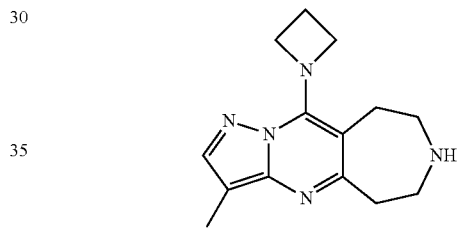 | 46 | TF | 286 [M + H]$^+$ | 4.30 (C) |

TABLE 13-continued

| Example | Structure | Yield of final step (%) | Salt type | Mass spec result | HPLC retention time (method) |
|---|---|---|---|---|---|
| 27.2 | 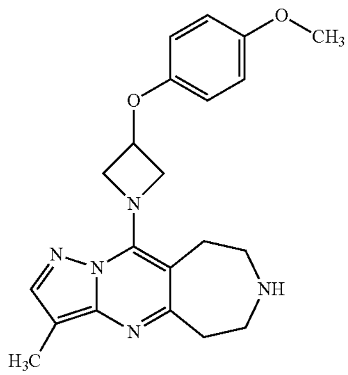 [SMILES: COc1ccc(OC2CN(c3c4c(nc5c(C)cnn35)CCNCC4)C2)cc1] | 68 | TF | 380 [M + H]⁺ | 4.44 (C) |

Route 28

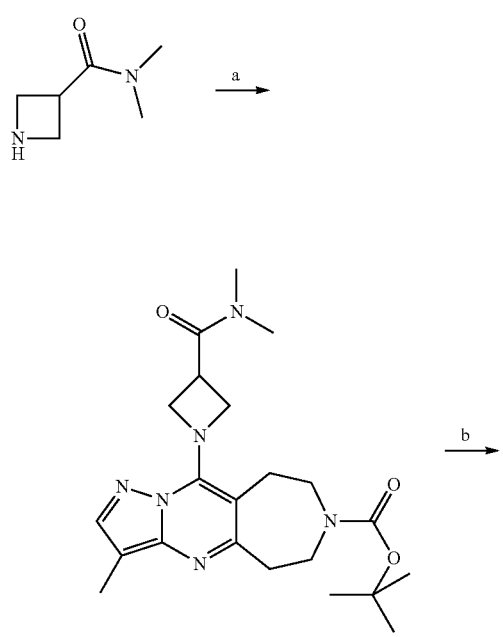

Example 28

1-(3-Methyl-6,7,8,9-tetrahydro-5H-1,4,7,10a-tetraaza-cyclohepta[f]inden-10-yl)-azetidine-3-carboxylic acid dimethylamide

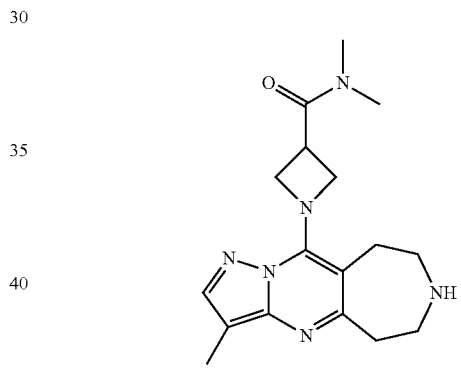

28b 1-(3-Methyl-6,7,8,9-tetrahydro-5H-1,4,7,10a-tetraaza-cyclohepta[f]inden-10-yl)-azetidine-3-carboxylic acid dimethylamide The product was prepared using route 27 (step a to e), in step d (route 27) azetidine-3-carboxylic acid dimethylamide (route 9, step a and b) was used as the amine.

C17H24N6O (M=328.42)

predicted: Molecular ion (M+H)⁺: 329 observed: Molecular ion (M+H)⁺: 329

HPLC-MS: 3.22 minutes (Method C)

Route 29

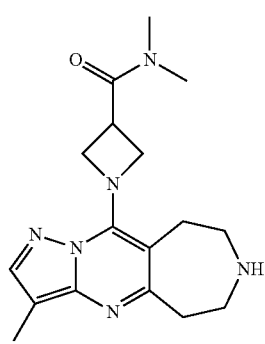 [SMILES: Cc1cnn2c(N3CC(C(=O)N(C)C)C3)c3c(nc12)CCNCC3]

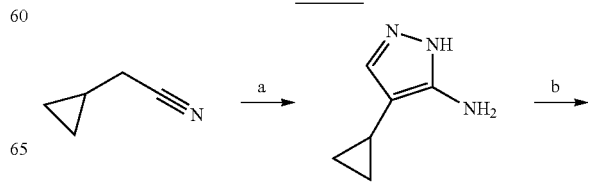

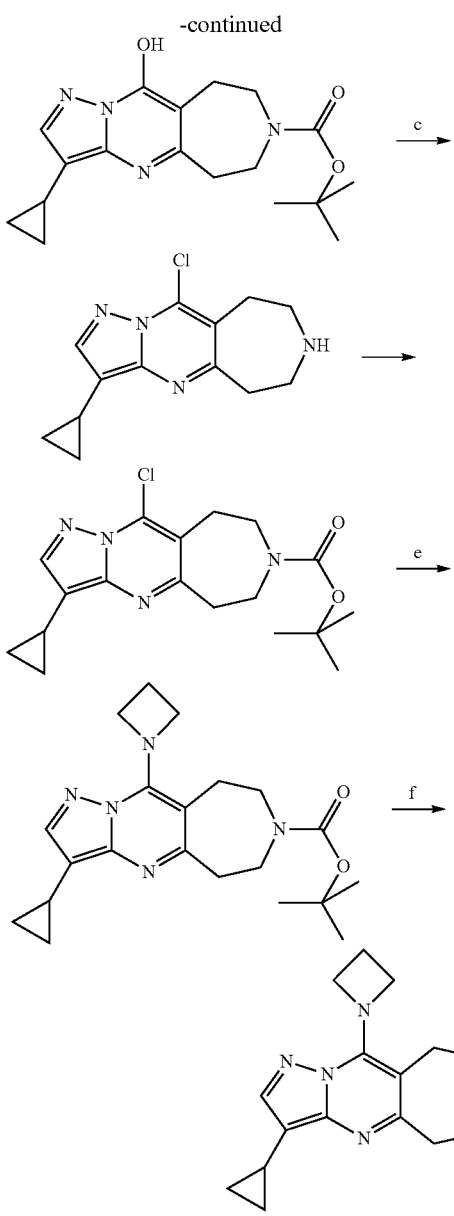

Example 29

10-Azetidin-1-yl-3-cyclopropyl-6,7,8,9-tetrahydro-5H-1,4,7,10a-tetraaza-cyclohepta[f]indene

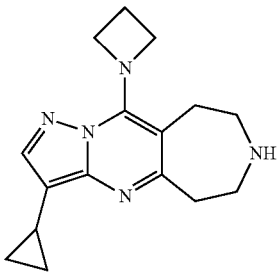 [SMILES: c1nn2c(N3CCC3)c3c(nc2c1C1CC1)CCNCC3]

29a 4-Cyclopropyl-2H-pyrazol-3-ylamine

To 7 g (0.3 mol) of freshly cut sodium chunks in 220 mL dry ether under nitrogen and external ice cooling was added a solution of 25 mL (0.3 mol) ethyl formate followed by a solution of 25 g (0.3 mol) cyclopropylacetonitrile in 50 mL dry ether, and the mixture was stirred at room temperature for 2 days. 19 mL (0.3 mol) glacial acetic acid was added whilst maintaining the internal temperature at 10-12° C., the solids were filtered off and the filtrate was concentrated at below 20° C. The residue was treated with 300 mL (0.6 mol) 2 M hydrazine in THF, 5 mL glacial acetic acid and heated at reflux for 2 hours. After cooling, the mixture was concentrated and the desired product was obtained by kugelrohr distillation. The product was used in the next step without further purification.

Yield: 6.9 g (18% of theory)
$C_6H_9N_3$ (M=123.16)

29f 10-Azetidin-1-yl-3-cyclopropyl-6,7,8,9-tetrahydro-5H-1,4,7,10a-tetraaza-cyclohepta[f]indene The product was prepared using route 1 (step b to f), in step b (route 1) 4-cyclopropyl-2H-pyrazol-3-ylamine was used, in step e (route 1) azetidine was used as the amine.

Yield: 81 mg (57% of theory)
$C_{16}H_{21}N_5$ (M=283.38)
predicted: Molecular ion (M+H)⁺: 284 observed: Molecular ion (M+H)⁺: 284
HPLC-MS: 3.81 minutes (Method C)

Route 30

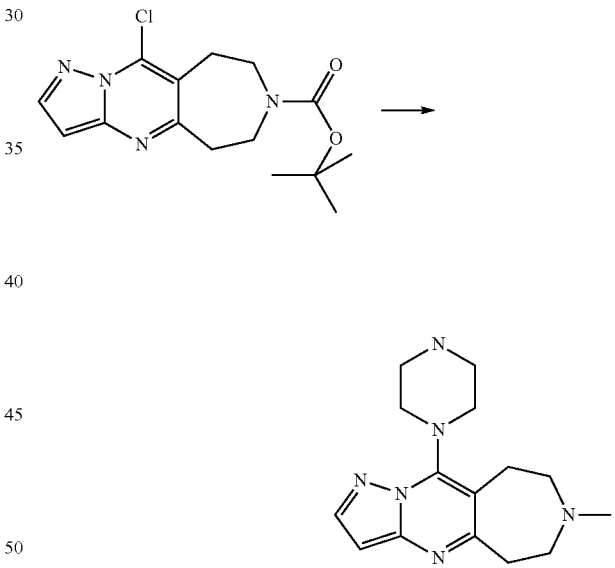

Example 30

7-Methyl-10-piperazin-1-yl-6,7,8,9-tetrahydro-5H-1,4,7,10a-tetraaza-cyclohepta[f]indene 0.2 g (0.62 mmol) 10-chloro-5,6,8,9-tetrahydro-1,4,7,10a-tetraaza-cyclohepta[f]indene-7-carboxylic acid tert-butyl ester were suspended in 5 mL acetonitrile. 0.23 mL HCl in dioxane (4 mol/l) were added and the reaction mixture was stirred at 60° C. over night. The solvents were removed to yield the desired product as a hydrochloride. Yield: 0.19 g (115% of theory). Subsequently 0.18 g of the intermediate, 59 µL formaldehyde (0.76 mmol) and 40 µL glacial acetic acid (0.7 mmol) were suspended in 20 mL THF. The reaction mixture was stirred at room temperature for 3 h. 0.34 g sodium cyanoborohydride (1.5 mmol) was added in portions and the mixture was stirred again at room temperature for 3 h. 20 mL aqueous potassium carbonate (15%) were added and the reaction was extracted with EtOAc. The organic layers were dried ($Na_2SO_4$), filtered, and the solvent was evaporated. The intermediate was purified by reversed phase prep. HPLC. Yield: 30 mg (18% of theory).

Subsequently the intermediate and 47 mg (0.25 mmol) piperazine-1-carboxylic acid tert-butyl ester were suspended in 2 mL NMP. The reaction mixture was stirred at 130° C. over night. The intermediate was purified by prep. HPLC and column chromatography (silica, EtOAc/MeOH/$NH_4OH$ 9/1/0.1). Yield: 10.6 mg (36% of theory).

7 mg of the intermediate were suspended in 2 mL aqueous HCl (2 mol/l) and stirred at room temperature for 3 h. The reaction mixture was freeze-dried to yield the desired product as a hydrochloride.

Yield: 5.2 mg (80% of theory)

$C_{15}H_{22}N_6 \times 2HCl$: 359.3 predicted: Molecular ion (M+H)$^+$: 287 observed: Molecular ion (M+H)$^+$: 287

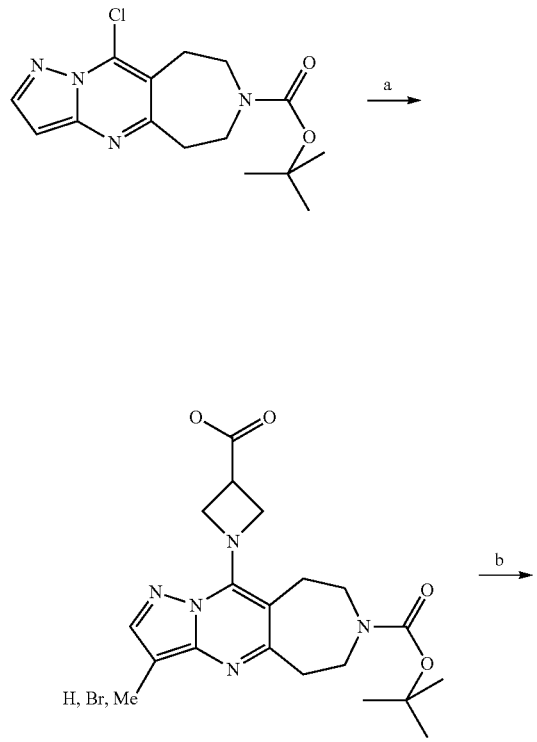

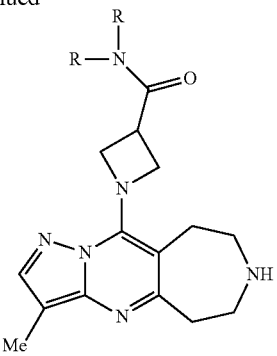

Example 31

31a 10-(3-Carboxy-azetidin-1-yl)-5,6,8,9-tetrahydro-1,4,7,10a-tetraaza-cyclohepta[f]indene-7-carboxylic acid tert-butyl ester 10 g (31 mmol) 10-Chloro-5,6,8,9-tetrahydro-1,4,7,10a-tetraaza-cyclohepta[f]indene-7-carboxylic acid tert-butyl ester were suspended in 750 mL ethanol. 13.2 g sodium hydrogencarbonate (155 mmol) and 3.6 g (36 mmol) azetidine-3-carboxylic acid were added and the reaction mixture was stirred at 70° C. for 36 h. After cooling down, the solvent was evaporated to 25 mL. The residue was washed several times with diethyl ether and the solvent was decanted. Then the residue was mixed again with 400 mL diethyl ether and the solid was filtered to yield the final product as a sodium salt.

Yield: 11.85 g (93% of theory)

$C_{19}H_{25}N_5O_4$. 387.4 predicted: Molecular ion (M+H)$^+$: 388 observed: Molecular ion (M+H)$^+$: 388

The 3-bromo and the 3-methyl derivatives were prepared following the same route using either 3-bromo-10-chloro-5,6,8,9-tetrahydro-1,4,7,10a-tetraaza-cyclohepta[f]indene-7-carboxylic acid tert-butyl ester (route 2 step a-c) or 3-methyl-10-chloro-5,6,8,9-tetrahydro-1,4,7,10a-tetraaza-cyclohepta[f]indene-7-carboxylic acid tert-butyl ester (route 27 step a-c) as starting materials.

31b (General Route)

10-(3-Carboxy-azetidin-1-yl)-5,6,8,9-tetrahydro-1,4,7,10a-tetraaza-cyclohepta[f]indene-7-carboxylic acid tert-butyl ester (1 eq) was suspended in 1 mL DMF. DIPEA (1.5 eq) and TBTU (1.1 eq) were added and the reaction mixture was stirred for 30 min. The amine (1 eq) was added and the reaction was stirred at room temperature till no further conversion was observed. The intermediate was purified by prep. HPLC and the fractions were freeze-dried. The residue was suspended in 1 mL DCM/TFA 1/1 and stirred for 2 h. The solvent was evaporated to yield the final product. Products with a purity lower than 90%, were purified again by prep. HPLC.

The 3-bromo and the 3-methyl derivatives were prepared following the same route using 3-bromo-10-(3-carboxy-azetidin-1-yl)-5,6,8,9-tetrahydro-1,4,7,10a-tetraaza-cyclohepta[f]indene-7-carboxylic acid tert-butyl ester or, respectively, 3-methyl-10-(3-carboxy-azetidin-1-yl)-5,6,8,9-tetrahydro-1,4,7,10a-tetraaza-cyclohepta[f]indene-7-carboxylic acid tert-butyl ester as starting materials.

TABLE 14

| Example | Structure | Yield of final step (%) | Salt type | Mass spec result | HPLC retention time (method) |
|---|---|---|---|---|---|
| 31.1 | 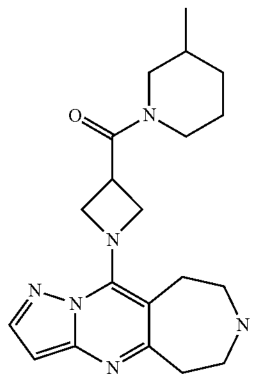 [SMILES: CC1CCCN(C(=O)C2CN(c3c4c(nc5ccnn35)CCNCC4)C2)C1] | 81 | TF | 369.3 [M + H]$^+$ | 1.38 (F) |
| 31.2 | 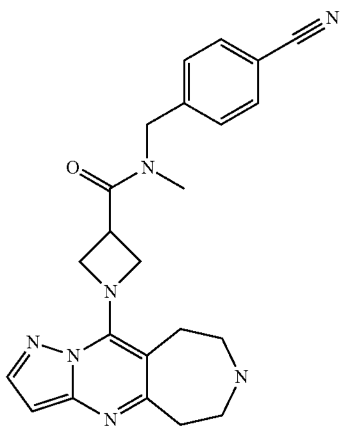 [SMILES: CN(Cc1ccc(C#N)cc1)C(=O)C1CN(c2c3c(nc4ccnn24)CCNCC3)C1] | 59 | TF | 416.2 [M + H]$^+$ | 1.38 (F) |
| 31.3 | 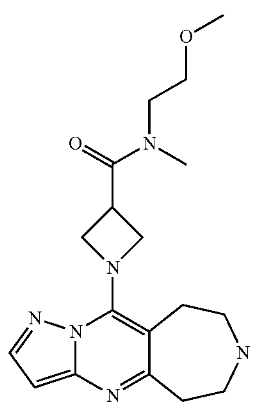 [SMILES: COCCN(C)C(=O)C1CN(c2c3c(nc4ccnn24)CCNCC3)C1] | 38 | TF | 359.5 [M + H]$^+$ | 1.4 (J) |
| 31.4 | 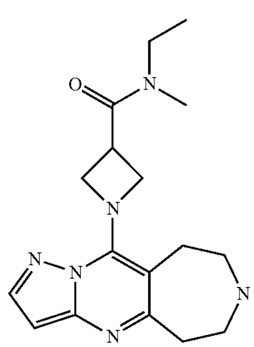 [SMILES: CCN(C)C(=O)C1CN(c2c3c(nc4ccnn24)CCNCC3)C1] | 21 | TF | 329.4 [M + H]$^+$ | 1.42 (J) |

TABLE 14-continued

| Example | Structure | Yield of final step (%) | Salt type | Mass spec result | HPLC retention time (method) |
|---|---|---|---|---|---|
| 31.5 | 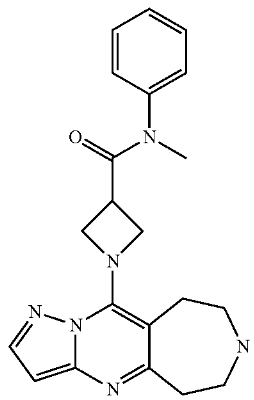 [SMILES: CN(C(=O)C1CN(c2c3c(nc4ccnn24)CCNCC3)C1)c1ccccc1] | 13 | TF | 377.5 [M + H]+ | 1.65 (J) |
| 31.6 | 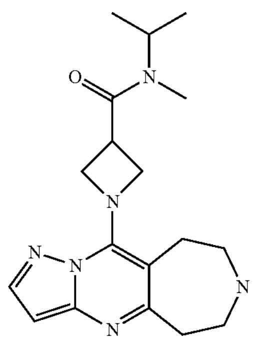 [SMILES: CC(C)N(C)C(=O)C1CN(c2c3c(nc4ccnn24)CCNCC3)C1] | 9 | TF | 343.2 [M + H]+ | 1.52 (J) |
| 31.7 | 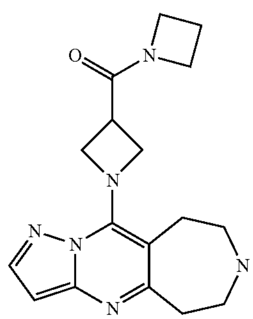 [SMILES: O=C(C1CN(c2c3c(nc4ccnn24)CCNCC3)C1)N1CCC1] | 26 | TF | 327.29 [M + H]+ | 1.35 (J) |
| 31.8 | 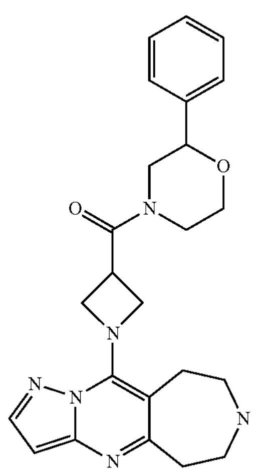 [SMILES: O=C(C1CN(c2c3c(nc4ccnn24)CCNCC3)C1)N1CCOC(c2ccccc2)C1] | 39 | TF | 433.3 [M + H]+ | 1.74 (J) |

TABLE 14-continued

| Example | Structure | Yield of final step (%) | Salt type | Mass spec result | HPLC retention time (method) |
|---|---|---|---|---|---|
| 31.9 | 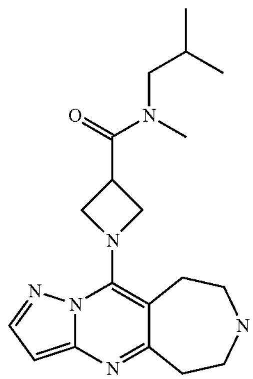 | 39 | TF | 367.36 [M + H]⁺ | 1.63 (J) |
| 31.10 | 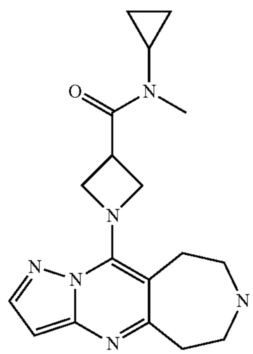 [SMILES: CN(C(=O)C1CN(c2c3c(nc4ccnn24)CCNCC3)C1)C1CC1] | 26 | TF | 341.28 [M + H]⁺ | 1.48 (J) |
| 31.11 | 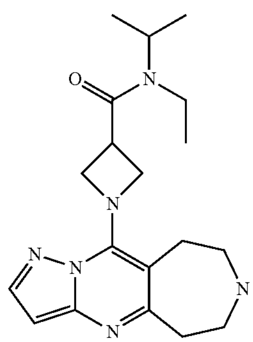 [SMILES: CCN(C(=O)C1CN(c2c3c(nc4ccnn24)CCNCC3)C1)C(C)C] | 26 | TF | 357.29 [M + H]⁺ | 1.61 (J) |
| 31.12 | 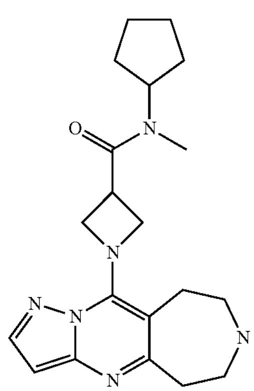 [SMILES: CN(C(=O)C1CN(c2c3c(nc4ccnn24)CCNCC3)C1)C1CCCC1] | 31 | TF | 369.35 [M + H]⁺ | 1.65 (J) |

TABLE 14-continued

| Example | Structure | Yield of final step (%) | Salt type | Mass spec result | HPLC retention time (method) |
|---|---|---|---|---|---|
| 31.13 | 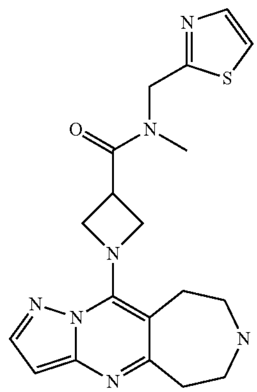 [SMILES: CN(Cc1nccs1)C(=O)C1CN(c2c3c(nc4ccnn24)CCNCC3)C1] | 27 | TF | 398.32 [M + H]+ | 1.46 (J) |
| 31.14 | 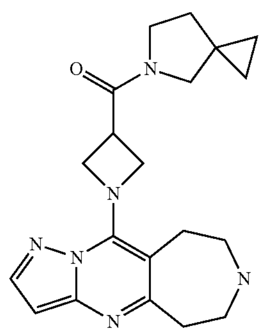 [SMILES: O=C(C1CN(c2c3c(nc4ccnn24)CCNCC3)C1)N1CCC2(CC2)C1] | 49 | TF | 367.36 [M + H]+ | 1.58 (J) |
| 31.15 | 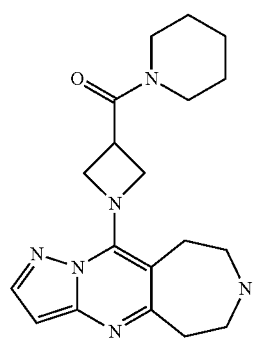 [SMILES: O=C(C1CN(c2c3c(nc4ccnn24)CCNCC3)C1)N1CCCCC1] | 55 | TF | 355.35 [M + H]+ | 1.54 (J) |
| 31.16 | 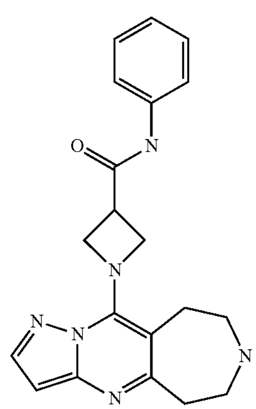 [SMILES: O=C(Nc1ccccc1)C1CN(c2c3c(nc4ccnn24)CCNCC3)C1] | 40 | TF | 363.33 [M + H]+ | 1.65 (J) |

TABLE 14-continued

| Example | Structure | Yield of final step (%) | Salt type | Mass spec result | HPLC retention time (method) |
|---------|-----------|------------------------|-----------|------------------|------------------------------|
| 31.17 | 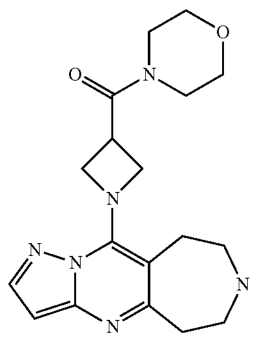 [SMILES: O=C(C1CN(c2c3c(nc4ccnn24)CCNCC3)C1)N1CCOCC1] | 35 | TF | 357.3 [M + H]$^+$ | 1.35 (J) |
| 31.18 | 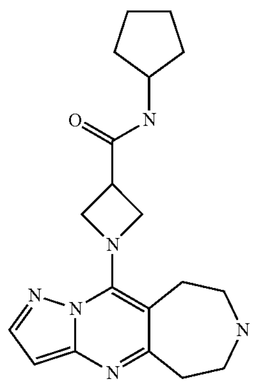 [SMILES: O=C(NC1CCCC1)C1CN(c2c3c(nc4ccnn24)CCNCC3)C1] | 37 | TF | 355.36 [M + H]$^+$ | 1.57 (J) |
| 31.19 | 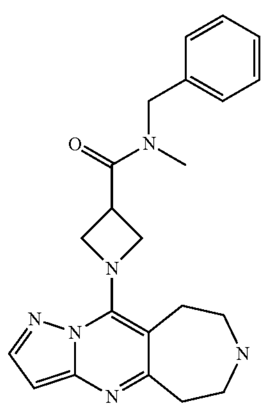 [SMILES: CN(Cc1ccccc1)C(=O)C1CN(c2c3c(nc4ccnn24)CCNCC3)C1] | 38 | TF | 391.36 [M + H]$^+$ | 1.7 (J) |
| 31.20 | 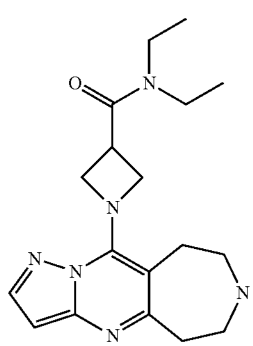 [SMILES: CCN(CC)C(=O)C1CN(c2c3c(nc4ccnn24)CCNCC3)C1] | 11 | TF | 343.34 [M + H]$^+$ | 1.52 (J) |

TABLE 14-continued

| Example | Structure | Yield of final step (%) | Salt type | Mass spec result | HPLC retention time (method) |
|---|---|---|---|---|---|
| 31.21 | 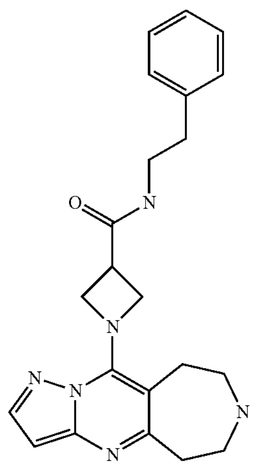 [SMILES: O=C(NCCc1ccccc1)C1CN(c2c3c(nc4ccnn24)CCNCC3)C1] | 46 | TF | 391.37 [M + H]⁺ | 1.69 (J) |
| 31.22 | 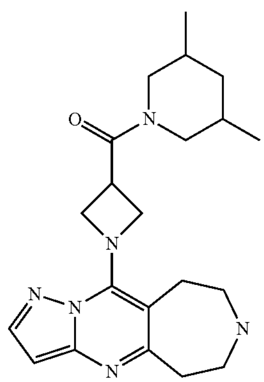 [SMILES: CC1CC(C)CN(C(=O)C2CN(c3c4c(nc5ccnn35)CCNCC4)C2)C1] | 87 | TF | 383.3 [M + H]⁺ | 1.45 (F) |
| 31.23 | 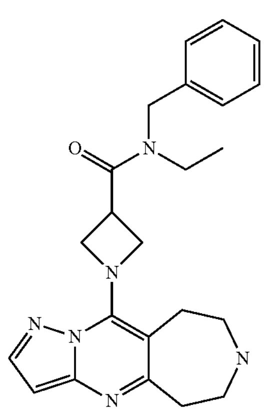 [SMILES: CCN(Cc1ccccc1)C(=O)C1CN(c2c3c(nc4ccnn24)CCNCC3)C1] | 75 | TF | 405.3 [M + H]⁺ | 1.46 (F) |

TABLE 14-continued
| Example | Structure | Yield of final step (%) | Salt type | Mass spec result | HPLC retention time (method) |
|---|---|---|---|---|---|
| 31.24 | 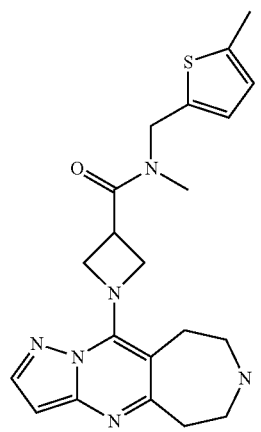 [SMILES: Cc1ccc(CN(C)C(=O)C2CN(c3c4c(nc5ccnn35)CCNCC4)C2)s1] | 40 | TF | 411.2 [M + H]⁺ | 1.44 (F) |
| 31.25 | 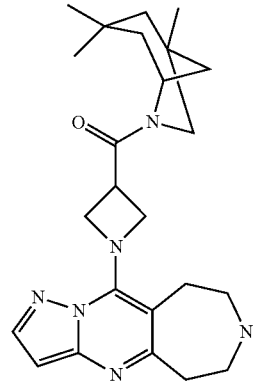 [SMILES: CC1(C)CC2CC(C)(CN2C(=O)C2CN(c3c4c(nc5ccnn35)CCNCC4)C2)C1] | 95 | TF | 423.3 [M + H]⁺ | 1.49 (F) |
| 31.26 | 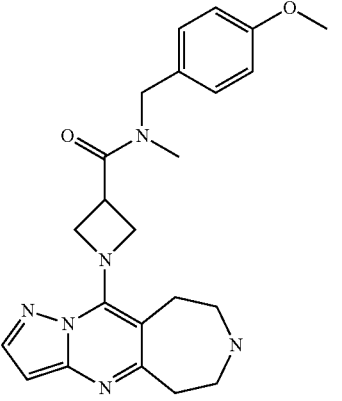 [SMILES: COc1ccc(CN(C)C(=O)C2CN(c3c4c(nc5ccnn35)CCNCC4)C2)cc1] | 88 | TF | 421.2 [M + H]⁺ | 1.4 (F) |

TABLE 14-continued

| Example | Structure | Yield of final step (%) | Salt type | Mass spec result | HPLC retention time (method) |
|---|---|---|---|---|---|
| 31.27 | 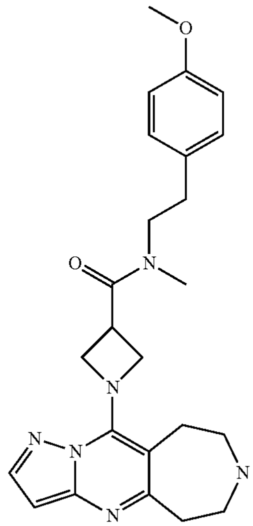 [SMILES: COc1ccc(CCN(C)C(=O)C2CN(c3c4c(nc5ccnn35)CCNCC4)C2)cc1] | 88 | TF | 435.3 [M + H]+ | 1.41 (F) |
| 31.28 | 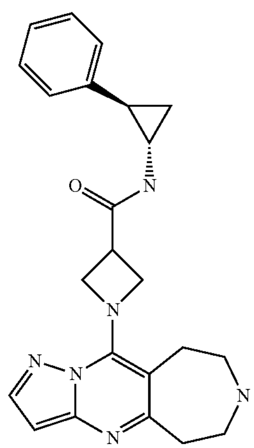 [SMILES: O=C(N[C@H]1C[C@@H]1c1ccccc1)C1CN(c2c3c(nc4ccnn24)CCNCC3)C1] | 98 | TF | 403.2 [M + H]+ | 1.44 (F) |
| 31.29 | 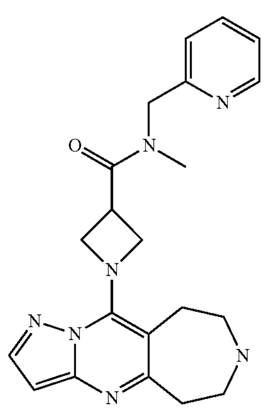 [SMILES: CN(Cc1ccccn1)C(=O)C1CN(c2c3c(nc4ccnn24)CCNCC3)C1] | 134 | TF | 392.2 [M + H]+ | 1.07 (F) |

TABLE 14-continued
| Example | Structure | Yield of final step (%) | Salt type | Mass spec result | HPLC retention time (method) |
|---|---|---|---|---|---|
| 31.30 | 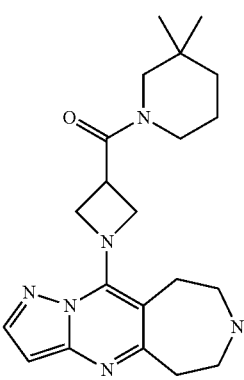 [SMILES: CC1(C)CCCN(C(=O)C2CN(c3c4c(nc5ccnn35)CCNCC4)C2)C1] | 98 | TF | 383.3 [M + H]+ | 1.41 (F) |
| 31.31 | 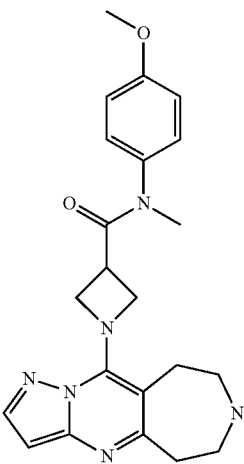 [SMILES: COc1ccc(N(C)C(=O)C2CN(c3c4c(nc5ccnn35)CCNCC4)C2)cc1] | 90 | TF | 407.2 [M + H]+ | 1.38 (F) |
| 31.32 | 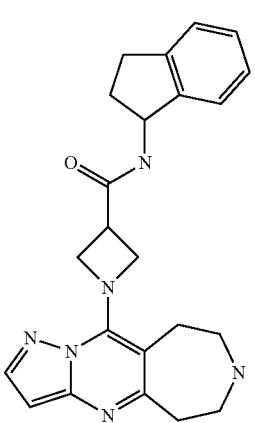 [SMILES: O=C(NC1CCc2ccccc21)C1CN(c2c3c(nc4ccnn24)CCNCC3)C1] | 80 | TF | 403.2 [M + H]+ | 1.43 (F) |

TABLE 14-continued

| Example | Structure | Yield of final step (%) | Salt type | Mass spec result | HPLC retention time (method) |
|---|---|---|---|---|---|
| 31.33 | 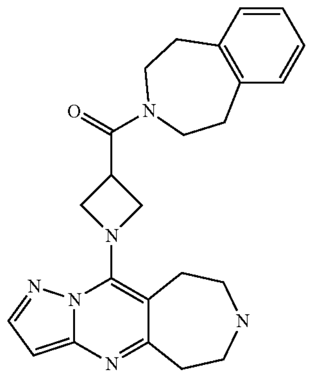 [SMILES: O=C(C1CN(c2c3c(nc4ccnn24)CCNCC3)C1)N1CCc2ccccc2CC1] | 70 | TF | 417.2 [M + H]⁺ | 1.45 (F) |
| 31.34 | 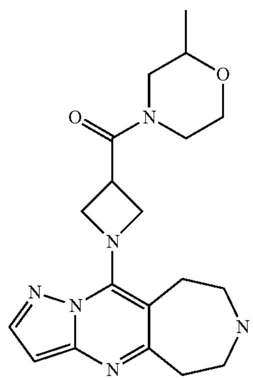 [SMILES: CC1CN(C(=O)C2CN(c3c4c(nc5ccnn35)CCNCC4)C2)CCO1] | 107 | TF | 371.2 [M + H]⁺ | 1.21 (F) |
| 31.35 | 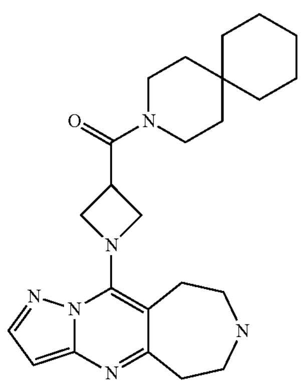 [SMILES: O=C(C1CN(c2c3c(nc4ccnn24)CCNCC3)C1)N1CCC2(CCCCC2)CC1] | 101 | TF | 423.3 [M + H]⁺ | 1.55 (F) |
| 31.36 | 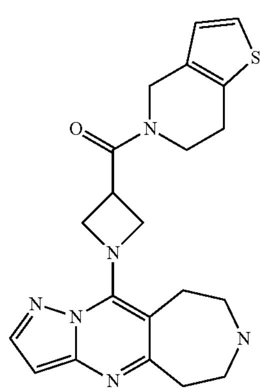 [SMILES: O=C(C1CN(c2c3c(nc4ccnn24)CCNCC3)C1)N1CCc2sccc2C1] | 89 | TF | 409.2 [M + H]⁺ | 1.42 (F) |

TABLE 14-continued

| Example | Structure | Yield of final step (%) | Salt type | Mass spec result | HPLC retention time (method) |
|---------|-----------|------------------------|-----------|------------------|------------------------------|
| 31.37 | 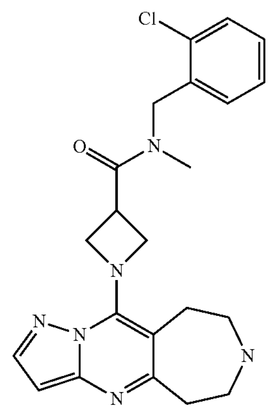 [SMILES: CN(Cc1ccccc1Cl)C(=O)C1CN(c2c3c(nc4ccnn24)CCNCC3)C1] | 72 | TF | 425.2 [M + H]⁺ | 1.47 (F) |
| 31.38 | 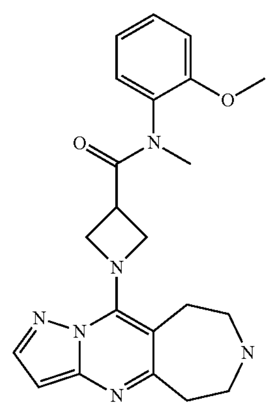 [SMILES: COc1ccccc1N(C)C(=O)C1CN(c2c3c(nc4ccnn24)CCNCC3)C1] | 25 | TF | 407.2 [M + H]⁺ | 1.4 (F) |
| 31.39 | 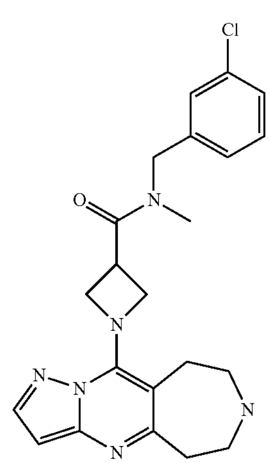 | 90 | TF | 425.2 [M + H]⁺ | 1.48 (F) |

TABLE 14-continued

| Example | Structure | Yield of final step (%) | Salt type | Mass spec result | HPLC retention time (method) |
| --- | --- | --- | --- | --- | --- |
| 31.40 | 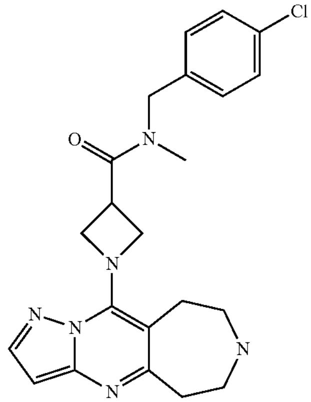 [SMILES: CN(Cc1ccc(Cl)cc1)C(=O)C1CN(c2c3c(nc4ccnn24)CCNCC3)C1] | 76 | TF | 425.2 [M + H]+ | 1.49 (F) |
| 31.41 | 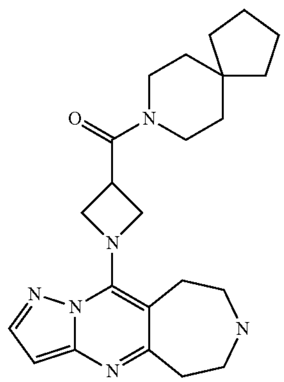 [SMILES: O=C(C1CN(c2c3c(nc4ccnn24)CCNCC3)C1)N1CCC2(CCCC2)CC1] | 93 | TF | 409.3 [M + H]+ | 1.51 (F) |
| 31.42 | 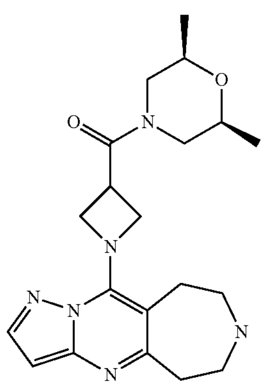 [SMILES: C[C@@H]1CN(C(=O)C2CN(c3c4c(nc5ccnn35)CCNCC4)C2)C[C@H](C)O1] | 104 | TF | 385.2 [M + H]+ | 1.27 (F) |
| 31.43 | 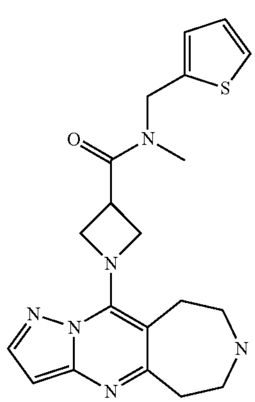 [SMILES: CN(Cc1cccs1)C(=O)C1CN(c2c3c(nc4ccnn24)CCNCC3)C1] | 16 | TF | 397.2 [M + H]+ | 1.38 (F) |

TABLE 14-continued

| Example | Structure | Yield of final step (%) | Salt type | Mass spec result | HPLC retention time (method) |
|---|---|---|---|---|---|
| 31.44 | 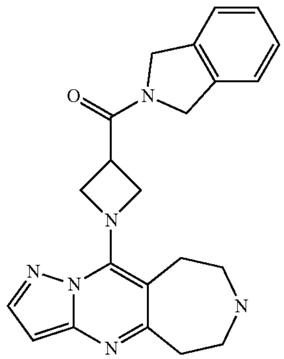 [SMILES: O=C(C1CN(c2c3c(nc4ccnn24)CCNCC3)C1)N1Cc2ccccc2C1] | 76 | TF | 389.2 [M + H]+ | 1.39 (F) |
| 31.45 | 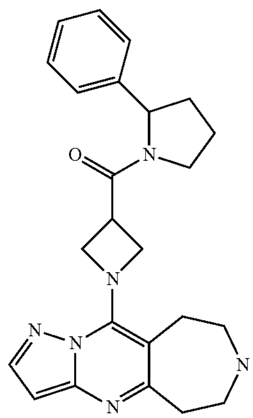 [SMILES: O=C(C1CN(c2c3c(nc4ccnn24)CCNCC3)C1)N1CCCC1c1ccccc1] | 90 | TF | 417.3 [M + H]+ | 1.43 (F) |
| 31.46 | 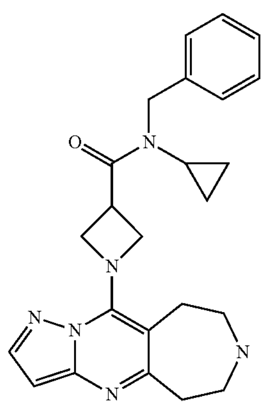 [SMILES: O=C(C1CN(c2c3c(nc4ccnn24)CCNCC3)C1)N(Cc1ccccc1)C1CC1] | 31 | TF | 417.3 [M + H]+ | 1.48 (F) |
| 31.47 | 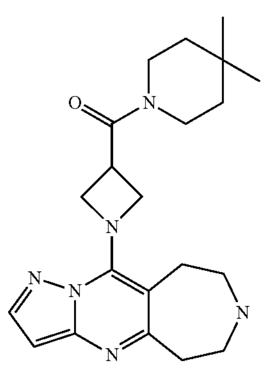 [SMILES: CC1(C)CCN(C(=O)C2CN(c3c4c(nc5ccnn35)CCNCC4)C2)CC1] | 28 | TF | 383.3 [M + H]+ | 1.44 (F) |

TABLE 14-continued

| Example | Structure | Yield of final step (%) | Salt type | Mass spec result | HPLC retention time (method) |
|---|---|---|---|---|---|
| 31.48 | 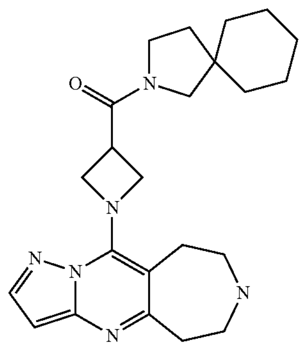 [SMILES: O=C(C1CN(c2c3c(nc4ccnn24)CCNCC3)C1)N1CCC2(CCCCC2)C1] | 90 | TF | 409.3 [M + H]+ | 1.49 (F) |
| 31.49 | 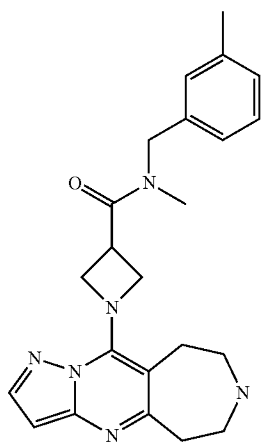 [SMILES: Cc1cccc(CN(C)C(=O)C2CN(c3c4c(nc5ccnn35)CCNCC4)C2)c1] | 91 | TF | 405.3 [M + H]+ | 1.47 (F) |
| 31.50 | 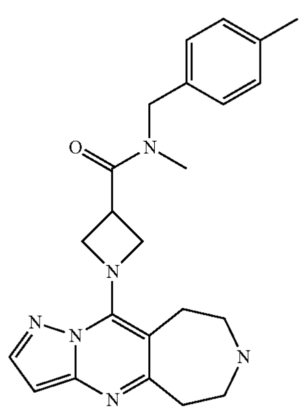 [SMILES: Cc1ccc(CN(C)C(=O)C2CN(c3c4c(nc5ccnn35)CCNCC4)C2)cc1] | 95 | TF | 405.3 [M + H]+ | 1.47 (F) |

TABLE 14-continued

| Example | Structure | Yield of final step (%) | Salt type | Mass spec result | HPLC retention time (method) |
|---------|-----------|-------------------------|-----------|------------------|------------------------------|
| 31.51 | 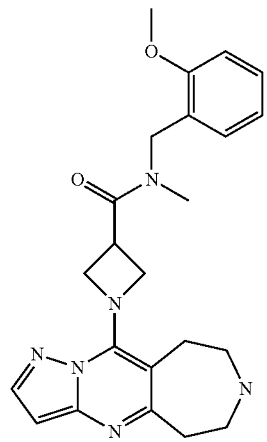 [SMILES: COc1ccccc1CN(C)C(=O)C1CN(c2c3c(nc4ccnn24)CCNCC3)C1] | 89 | TF | 421.2 [M + H]⁺ | 1.44 (F) |
| 31.52 | 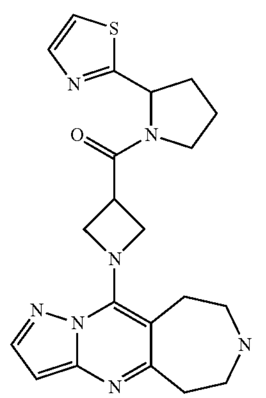 [SMILES: O=C(C1CN(c2c3c(nc4ccnn24)CCNCC3)C1)N1CCCC1c1nccs1] | 115 | TF | 424.2 [M + H]⁺ | 1.28 (F) |
| 31.53 | 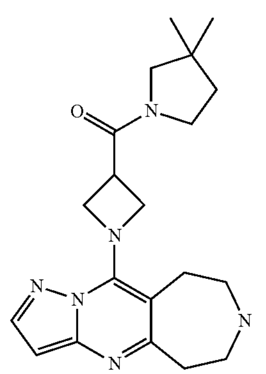 [SMILES: CC1(C)CCN(C(=O)C2CN(c3c4c(nc5ccnn35)CCNCC4)C2)C1] | 80 | TF | 369 [M + H]⁺ | 1.41 (K) |

TABLE 14-continued

| Example | Structure | Yield of final step (%) | Salt type | Mass spec result | HPLC retention time (method) |
|---|---|---|---|---|---|
| 31.54 | 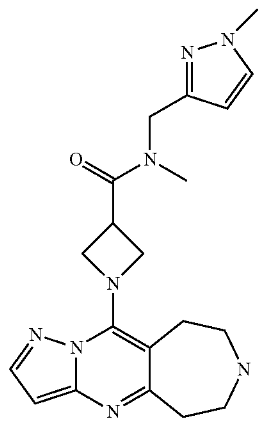 [SMILES: CN(Cc1ccn(C)n1)C(=O)C1CN(c2c3c(nc4ccnn24)CCNCC3)C1] | 122 | TF | 395.2 [M + H]⁺ | 1.23 (F) |
| 31.55 | 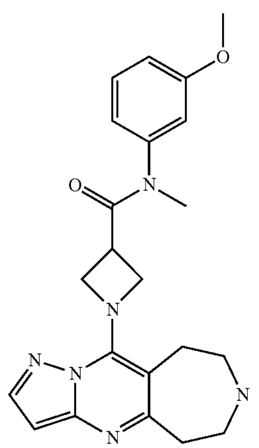 [SMILES: COc1cccc(N(C)C(=O)C2CN(c3c4c(nc5ccnn35)CCNCC4)C2)c1] | 20 | TF | 407.2 [M + H]⁺ | 1.41 (F) |
| 31.56 | 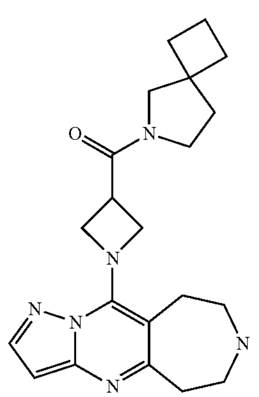 [SMILES: O=C(C1CN(c2c3c(nc4ccnn24)CCNCC3)C1)N1CCC2(CCC2)C1] | 72 | BS | 381 [M + H]⁺ | 1.09 (M) |

TABLE 14-continued

| Example | Structure | Yield of final step (%) | Salt type | Mass spec result | HPLC retention time (method) |
|---|---|---|---|---|---|
| 31.57 | 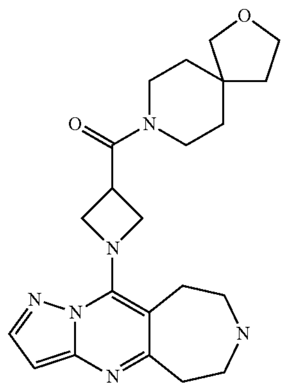 [SMILES: O=C(C1CN(c2c3c(nc4ccnn24)CCNCC3)C1)N1CCC2(CCOC2)CC1] | 96 | TF | 411.3 [M + H]+ | 1.26 (F) |
| 31.58 | 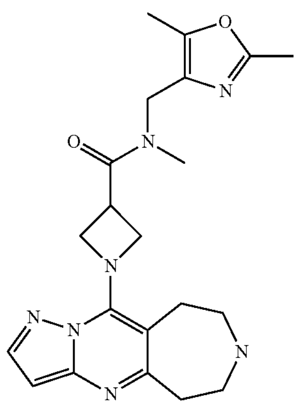 [SMILES: Cc1nc(CN(C)C(=O)C2CN(c3c4c(nc5ccnn35)CCNCC4)C2)c(C)o1] | 123 | TF | 410.3 [M + H]+ | 1.29 (F) |
| 31.59 | 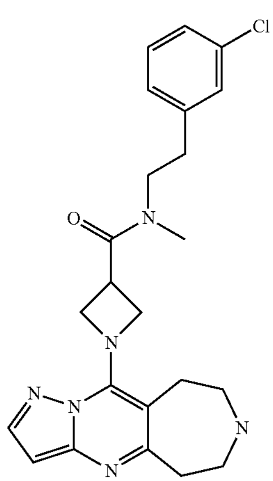 [SMILES: CN(CCc1cccc(Cl)c1)C(=O)C1CN(c2c3c(nc4ccnn24)CCNCC3)C1] | 65 | TF | 439.2 [M + H]+ | 1.49 (F) |

TABLE 14-continued

| Example | Structure | Yield of final step (%) | Salt type | Mass spec result | HPLC retention time (method) |
| --- | --- | --- | --- | --- | --- |
| 31.60 | 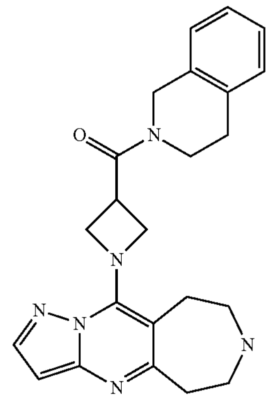 [SMILES: O=C(C1CN(c2c3c(nc4ccnn24)CCNCC3)C1)N1CCc2ccccc2C1] | 49 | TF | 403.2 [M + H]+ | 1.43 (F) |
| 31.61 | 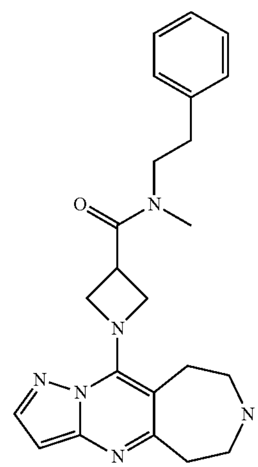 [SMILES: CN(CCc1ccccc1)C(=O)C1CN(c2c3c(nc4ccnn24)CCNCC3)C1] | 45 | TF | 405.3 [M + H]+ | 1.43 (F) |
| 31.62 | 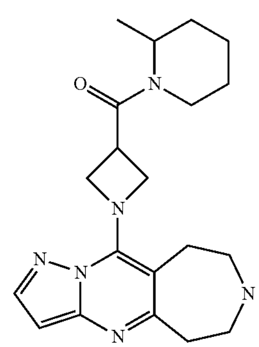 [SMILES: CC1CCCCN1C(=O)C1CN(c2c3c(nc4ccnn24)CCNCC3)C1] | 70 | TF | 369.3 [M + H]+ | 1.36 (F) |

TABLE 14-continued

| Example | Structure | Yield of final step (%) | Salt type | Mass spec result | HPLC retention time (method) |
|---|---|---|---|---|---|
| 31.63 | 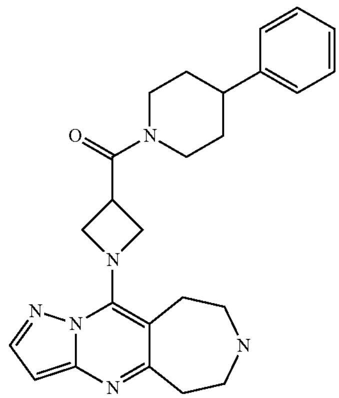 [SMILES: O=C(C1CN(c2c3c(nc4ccnn24)CCNCC3)C1)N1CCC(c2ccccc2)CC1] | 91 | TF | 431.3 [M + H]⁺ | 1.51 (F) |
| 31.64 | 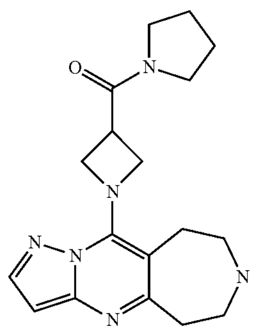 [SMILES: O=C(C1CN(c2c3c(nc4ccnn24)CCNCC3)C1)N1CCCC1] | 75 | TF | 341.2 [M + H]⁺ | 1.22 (F) |
| 31.65 | 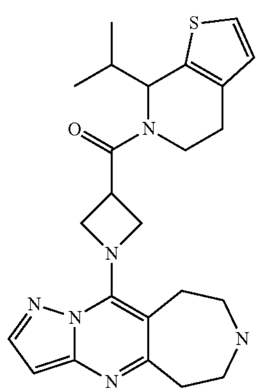 [SMILES: CC(C)C1c2sccc2CCN1C(=O)C1CN(c2c3c(nc4ccnn24)CCNCC3)C1] | 63 | TF | 451.3 [M + H]⁺ | 1.54 (F) |
| 31.66 | 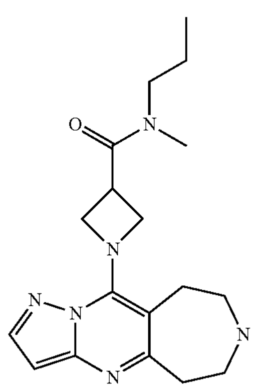 [SMILES: CCCN(C)C(=O)C1CN(c2c3c(nc4ccnn24)CCNCC3)C1] | 38 | TF | 343.2 [M + H]⁺ | 1.28 (F) |

TABLE 14-continued

| Example | Structure | Yield of final step (%) | Salt type | Mass spec result | HPLC retention time (method) |
| --- | --- | --- | --- | --- | --- |
| 31.67 | Chiral | 48 | BS | 423 [M + H]⁺ | 0.75 (P) |
| 31.68 | 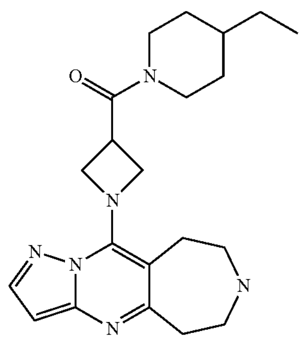 [SMILES: CCC1CCN(C(=O)C2CN(c3c4c(nc5ccnn35)CCNCC4)C2)CC1] | 30 | TF | 383.2 [M + H]⁺ | 1.57 (F) |
| 31.69 | 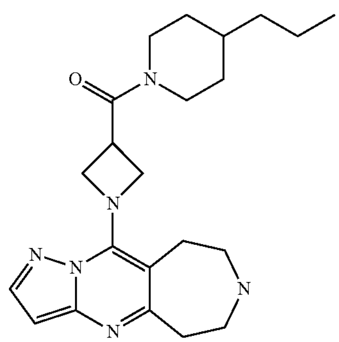 [SMILES: CCCC1CCN(C(=O)C2CN(c3c4c(nc5ccnn35)CCNCC4)C2)CC1] | 31 | TF | 397.3 [M + H]⁺ | 1.64 (F) |
| 31.70 | 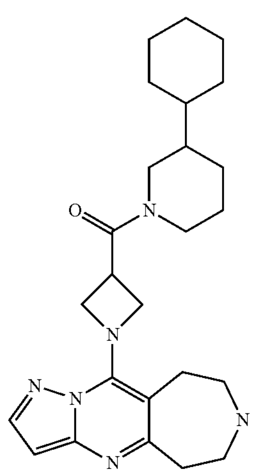 [SMILES: O=C(C1CN(c2c3c(nc4ccnn24)CCNCC3)C1)N1CCCC(C2CCCCC2)C1] | 24 | TF | 437.2 [M + H]⁺ | 1.76 (F) |

TABLE 14-continued

| Example | Structure | Yield of final step (%) | Salt type | Mass spec result | HPLC retention time (method) |
|---|---|---|---|---|---|
| 31.71 | 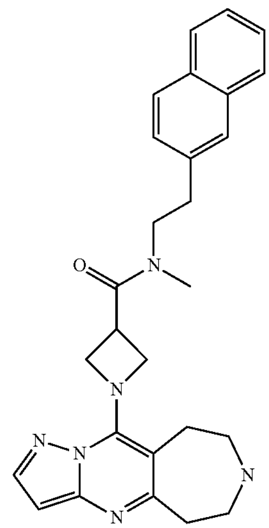 [SMILES: CN(CCc1ccc2ccccc2c1)C(=O)C1CN(c2c3c(nc4ccnn24)CCNCC3)C1] | 22 | TF | 455.2 [M + H]+ | 1.64 (F) |
| 31.72 | 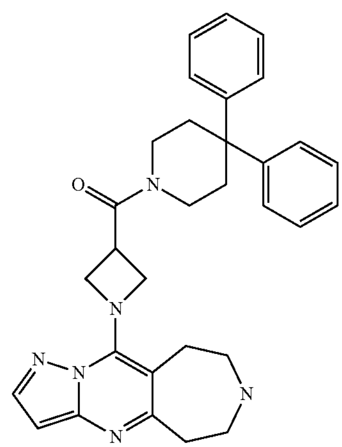 [SMILES: O=C(C1CN(c2c3c(nc4ccnn24)CCNCC3)C1)N1CCC(c2ccccc2)(c2ccccc2)CC1] | 26 | TF | 507.2 [M + H]+ | 1.75 (F) |
| 31.73 | 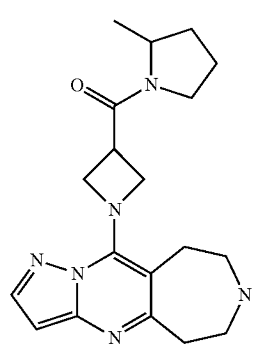 [SMILES: CC1CCCN1C(=O)C1CN(c2c3c(nc4ccnn24)CCNCC3)C1] | 22 | TF | 355.2 [M + H]+ | 1.45 (F) |

TABLE 14-continued

| Example | Structure | Yield of final step (%) | Salt type | Mass spec result | HPLC retention time (method) |
|---|---|---|---|---|---|
| 31.74 | 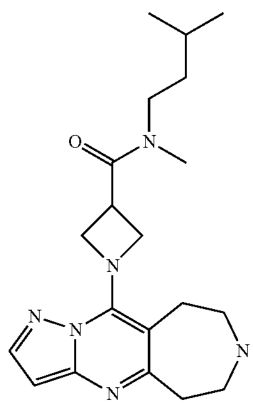 [SMILES: CC(C)CCN(C)C(=O)C1CN(c2c3c(nc4ccnn24)CCNCC3)C1] | 23 | TF | 371.2 [M + H]⁺ | 1.54 (F) |
| 31.75 | 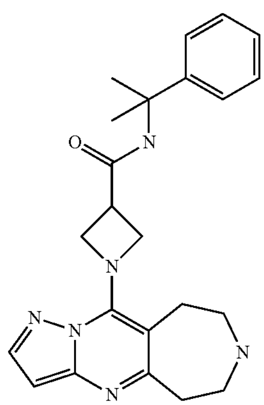 [SMILES: CC(C)(NC(=O)C1CN(c2c3c(nc4ccnn24)CCNCC3)C1)c1ccccc1] | 35 | TF | 405.2 [M + H]⁺ | 1.62 (F) |
| 31.76 | 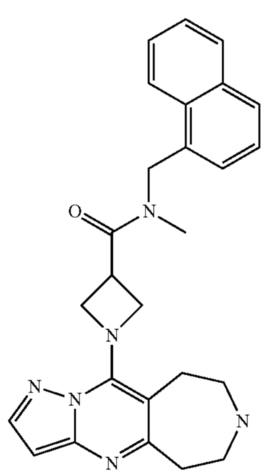 [SMILES: CN(Cc1cccc2ccccc12)C(=O)C1CN(c2c3c(nc4ccnn24)CCNCC3)C1] | 30 | TF | 441.2 [M + H]⁺ | 1.63 (F) |

TABLE 14-continued

| Example | Structure | Yield of final step (%) | Salt type | Mass spec result | HPLC retention time (method) |
|---|---|---|---|---|---|
| 31.77 | 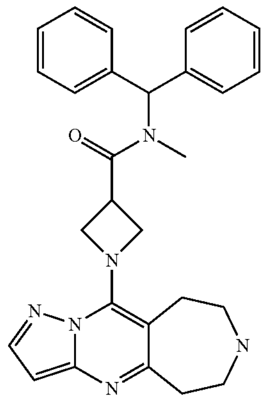 [SMILES: CN(C(=O)C1CN(c2c3c(nc4ccnn24)CCNCC3)C1)C(c1ccccc1)c1ccccc1] | 17 | TF | 467.2 [M + H]⁺ | 1.71 (F) |
| 31.78 | 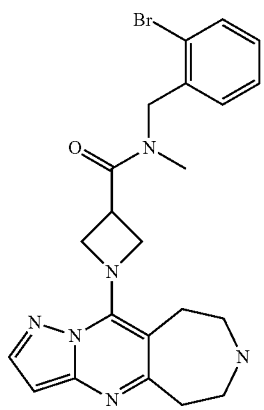 [SMILES: CN(Cc1ccccc1Br)C(=O)C1CN(c2c3c(nc4ccnn24)CCNCC3)C1] | 25 | TF | 470 [M + H]⁺ | 1.67 (F) |
| 31.79 | 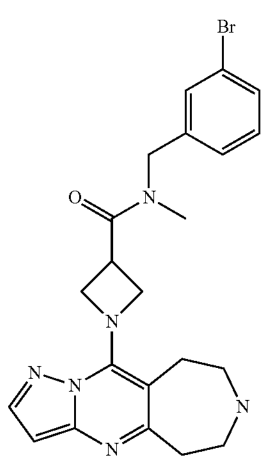 [SMILES: CN(Cc1cccc(Br)c1)C(=O)C1CN(c2c3c(nc4ccnn24)CCNCC3)C1] | 15 | TF | 471.1 [M + H]⁺ | 1.61 (F) |

TABLE 14-continued

| Example | Structure | Yield of final step (%) | Salt type | Mass spec result | HPLC retention time (method) |
| --- | --- | --- | --- | --- | --- |
| 31.80 | 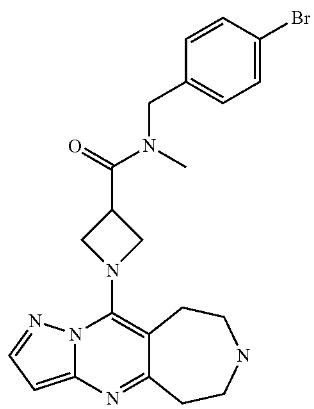 [SMILES: CN(Cc1ccc(Br)cc1)C(=O)C1CN(c2c3c(nc4ccnn24)CCNCC3)C1] | 22 | TF | 471.1 [M + H]+ | 1.62 (F) |
| 31.81 | 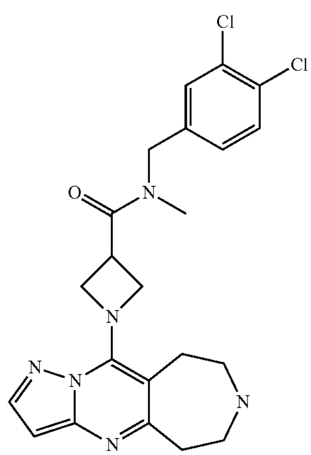 [SMILES: CN(Cc1ccc(Cl)c(Cl)c1)C(=O)C1CN(c2c3c(nc4ccnn24)CCNCC3)C1] | 18 | TF | 459.1 [M + H]+ | 1.74 (F) |
| 31.82 | 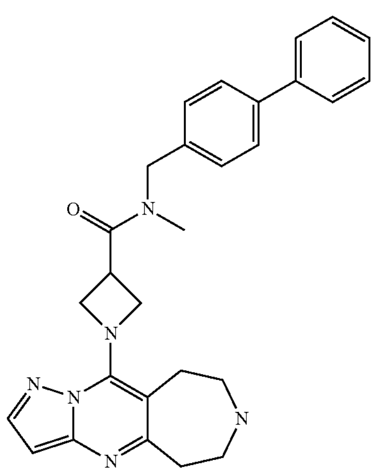 [SMILES: CN(Cc1ccc(-c2ccccc2)cc1)C(=O)C1CN(c2c3c(nc4ccnn24)CCNCC3)C1] | 30 | TF | 467.2 [M + H]+ | 1.72 (F) |

TABLE 14-continued

| Example | Structure | Yield of final step (%) | Salt type | Mass spec result | HPLC retention time (method) |
|---|---|---|---|---|---|
| 31.83 | 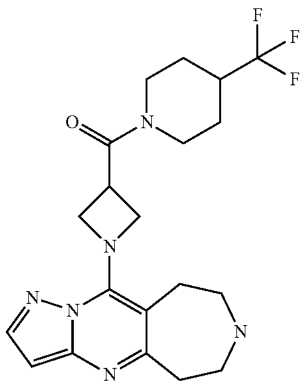 [SMILES: O=C(C1CN(c2c3c(nc4ccnn24)CCNCC3)C1)N1CCC(C(F)(F)F)CC1] | 24 | TF | 423.2 [M + H]+ | 1.35 (F) |
| 31.84 | 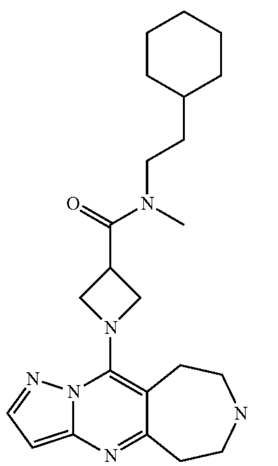 [SMILES: CN(CCC1CCCCC1)C(=O)C1CN(c2c3c(nc4ccnn24)CCNCC3)C1] | 21 | TF | 411.3 [M + H]+ | 1.76 (F) |
| 31.85 | 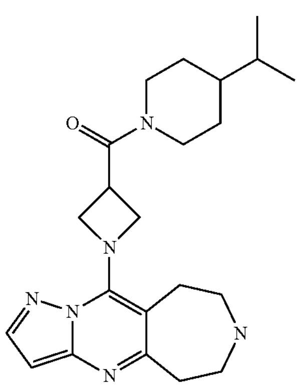 [SMILES: CC(C)C1CCN(C(=O)C2CN(c3c4c(nc5ccnn35)CCNCC4)C2)CC1] | 30 | TF | 397.2 [M + H]+ | 1.61 (F) |

TABLE 14-continued

| Example | Structure | Yield of final step (%) | Salt type | Mass spec result | HPLC retention time (method) |
|---------|-----------|-------------------------|-----------|------------------|------------------------------|
| 31.86 | 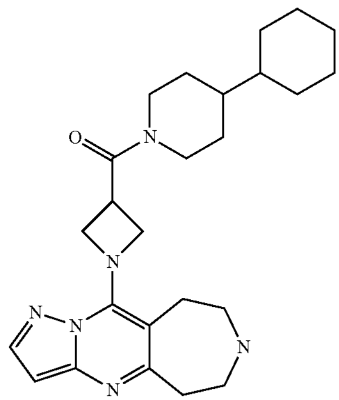 [SMILES: O=C(C1CN(c2c3c(nc4ccnn24)CCNCC3)C1)N1CCC(C2CCCCC2)CC1] | 23 | TF | 467.2 [M + H]+ | 1.77 (F) |
| 31.87 | 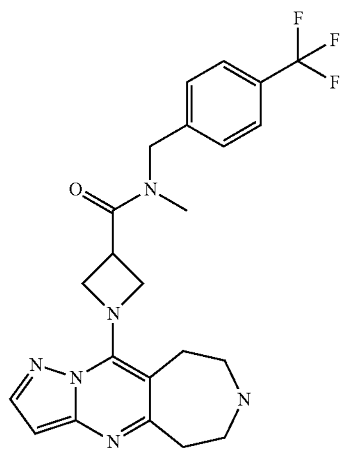 [SMILES: CN(Cc1ccc(C(F)(F)F)cc1)C(=O)C1CN(c2c3c(nc4ccnn24)CCNCC3)C1] | 29 | TF | 459.2 [M + H]+ | 1.72 (F) |
| 31.88 | 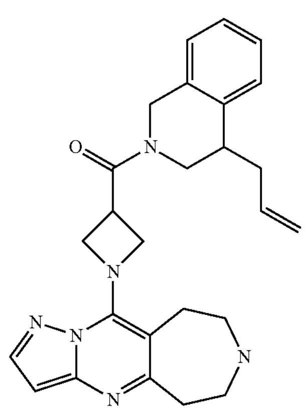 [SMILES: C=CCC1CN(C(=O)C2CN(c3c4c(nc5ccnn35)CCNCC4)C2)Cc2ccccc21] | 28 | TF | 443.2 [M + H]+ | 1.66 (F) |

TABLE 14-continued

| Example | Structure | Yield of final step (%) | Salt type | Mass spec result | HPLC retention time (method) |
|---|---|---|---|---|---|
| 31.89 | 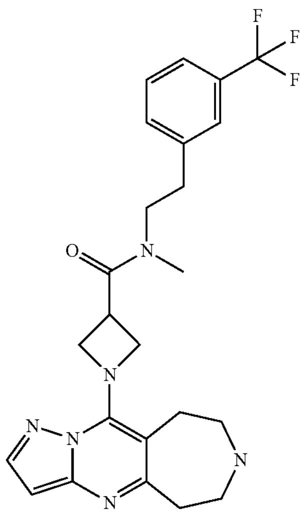 [SMILES: CN(CCc1cccc(C(F)(F)F)c1)C(=O)C1CN(c2c3c(nc4ccnn24)CCNCC3)C1] | 19 | TF | 473.2 [M + H]+ | 1.65 (F) |
| 31.90 | Chiral | 30 | TF | 405.2 [M + H]+ | 1.56 (F) |
| 31.91 | Chiral | 27 | TF | 405.2 [M + H]+ | 1.56 (F) |

TABLE 14-continued

| Example | Structure | Yield of final step (%) | Salt type | Mass spec result | HPLC retention time (method) |
|---|---|---|---|---|---|
| 31.92 | 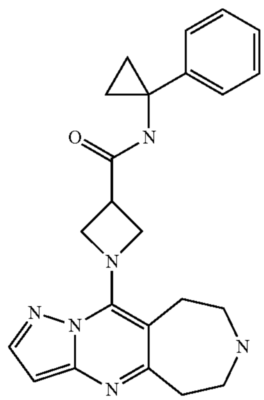 [SMILES: O=C(NC1(c2ccccc2)CC1)C1CN(c2c3c(nc4ccnn24)CCNCC3)C1] | 28 | TF | 403.2 [M + H]+ | 1.51 (F) |
| 31.93 | 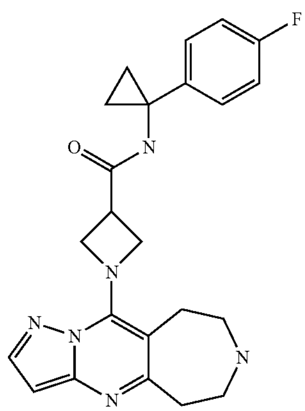 [SMILES: O=C(NC1(c2ccc(F)cc2)CC1)C1CN(c2c3c(nc4ccnn24)CCNCC3)C1] | 34 | TF | 421.2 [M + H]+ | 1.61 (F) |
| 31.94 | 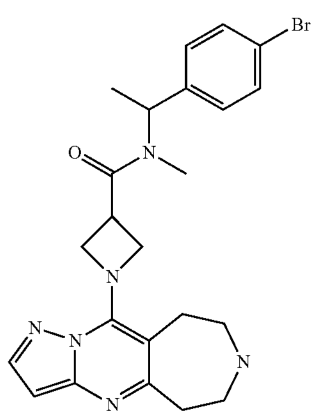 | 19 | TF | 301.1 [M + H]+ | 1.66 (F) |

TABLE 14-continued

| Example | Structure | Yield of final step (%) | Salt type | Mass spec result | HPLC retention time (method) |
| --- | --- | --- | --- | --- | --- |
| 31.95 | 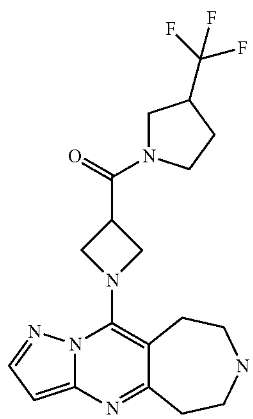 [SMILES: O=C(C1CN(c2c3c(nc4ccnn24)CCNCC3)C1)N1CCC(C(F)(F)F)C1] | 21 | TF | 409.2 [M + H]⁺ | 1.51 (F) |
| 31.96 | 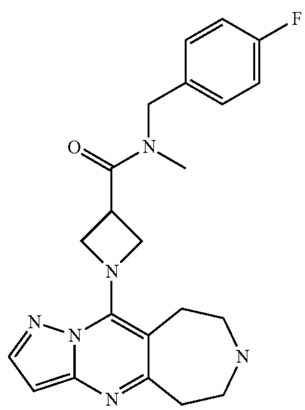 [SMILES: CN(Cc1ccc(F)cc1)C(=O)C1CN(c2c3c(nc4ccnn24)CCNCC3)C1] | 27 | TF | 409.2 [M + H]⁺ | 1.54 (F) |
| 31.97 | 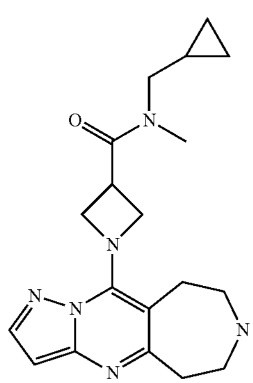 [SMILES: CN(CC1CC1)C(=O)C1CN(c2c3c(nc4ccnn24)CCNCC3)C1] | 28 | TF | 355.2 [M + H]⁺ | 1.42 (F) |

TABLE 14-continued
| Example | Structure | Yield of final step (%) | Salt type | Mass spec result | HPLC retention time (method) |
|---|---|---|---|---|---|
| 31.98 | 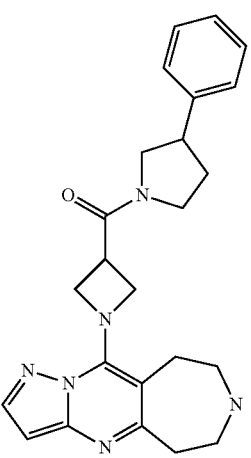 [SMILES: O=C(C1CN(c2c3c(nc4ccnn24)CCNCC3)C1)N1CCC(c2ccccc2)C1] | 26 | TF | 417.2 [M + H]⁺ | 1.57 (F) |
| 31.99 | 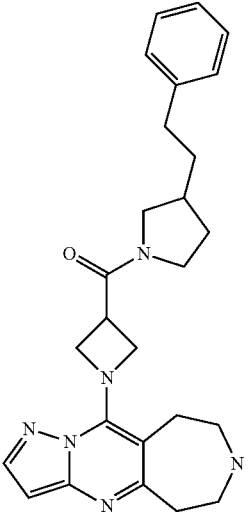 [SMILES: O=C(C1CN(c2c3c(nc4ccnn24)CCNCC3)C1)N1CCC(CCc2ccccc2)C1] | 27 | TF | 445.2 [M + H]⁺ | 1.67 (F) |
| 31.100 | 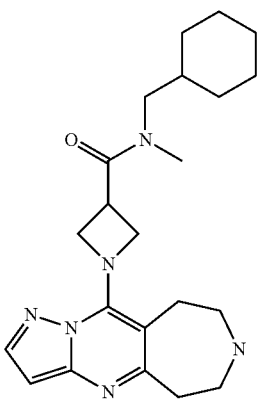 [SMILES: CN(CC1CCCCC1)C(=O)C1CN(c2c3c(nc4ccnn24)CCNCC3)C1] | 23 | TF | 397.2 [M + H]⁺ | 1.62 (F) |

TABLE 14-continued

| Example | Structure | Yield of final step (%) | Salt type | Mass spec result | HPLC retention time (method) |
|---|---|---|---|---|---|
| 31.101 | 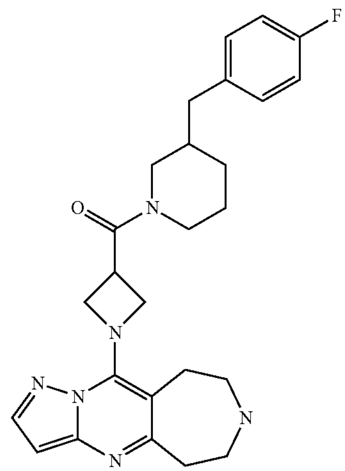 [SMILES: O=C(C1CN(c2c3c(nc4ccnn24)CCNCC3)C1)N1CCCC(Cc2ccc(F)cc2)C1] | 30 | TF | 463.2 [M + H]+ | 1.67 (F) |
| 31.102 | 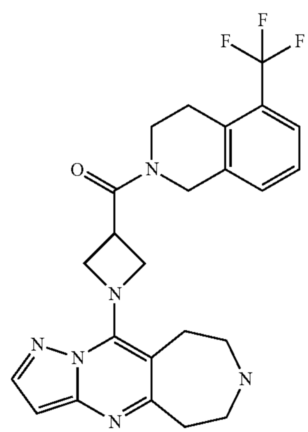 [SMILES: O=C(C1CN(c2c3c(nc4ccnn24)CCNCC3)C1)N1CCc2c(cccc2C(F)(F)F)C1] | 28 | TF | 471.2 [M + H]+ | 1.66 (F) |
| 31.103 | 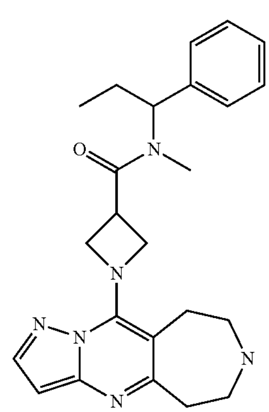 [SMILES: CCC(c1ccccc1)N(C)C(=O)C1CN(c2c3c(nc4ccnn24)CCNCC3)C1] | 18 | TF | 419.2 [M + H]+ | 1.61 (F) |

TABLE 14-continued

| Example | Structure | Yield of final step (%) | Salt type | Mass spec result | HPLC retention time (method) |
|---|---|---|---|---|---|
| 31.104 | 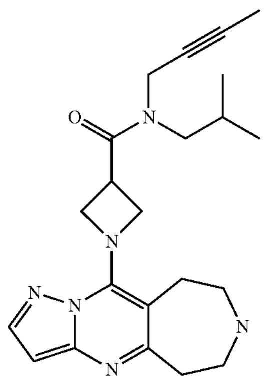 [SMILES: CC#CCN(CC(C)C)C(=O)C1CN(c2c3c(nc4ccnn24)CCNCC3)C1] | 24 | TF | 395.2 [M + H]⁺ | 1.59 (F) |
| 31.105 | 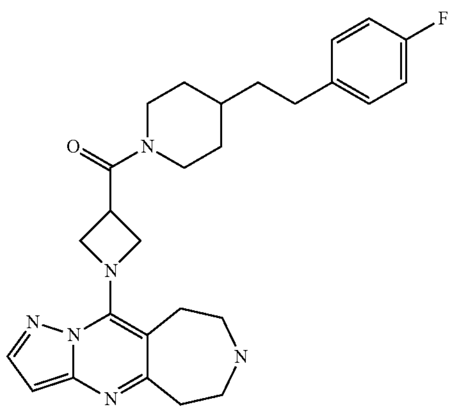 [SMILES: O=C(C1CN(c2c3c(nc4ccnn24)CCNCC3)C1)N1CCC(CCc2ccc(F)cc2)CC1] | 26 | TF | 477.2 [M + H]⁺ | 1.75 (F) |
| 31.106 | 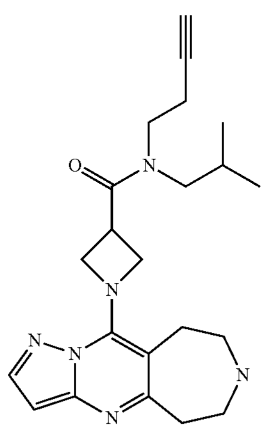 [SMILES: C#CCCN(CC(C)C)C(=O)C1CN(c2c3c(nc4ccnn24)CCNCC3)C1] | 13 | TF | 395.2 [M + H]⁺ | 1.57 (F) |

TABLE 14-continued

| Example | Structure | Yield of final step (%) | Salt type | Mass spec result | HPLC retention time (method) |
|---------|-----------|------|------|--------|--------|
| 31.107 | 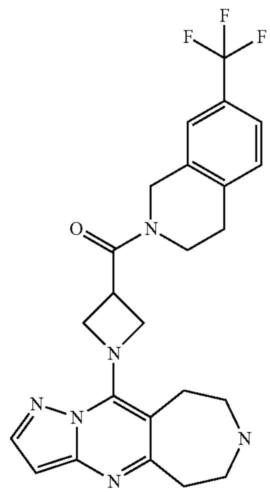 [SMILES: O=C(C1CN(c2c3c(nc4ccnn24)CCNCC3)C1)N1CCc2ccc(C(F)(F)F)cc2C1] | 25 | TF | 471.2 [M + H]⁺ | 1.68 (F) |
| 31.108 | 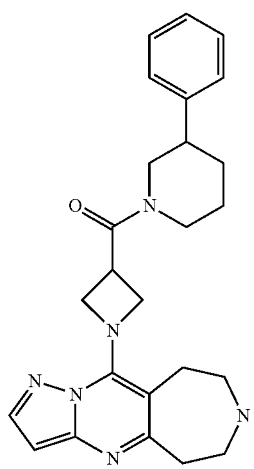 [SMILES: O=C(C1CN(c2c3c(nc4ccnn24)CCNCC3)C1)N1CCCC(c2ccccc2)C1] | 29 | TF | 431.2 [M + H]⁺ | 1.63 (F) |
| 31.109 | 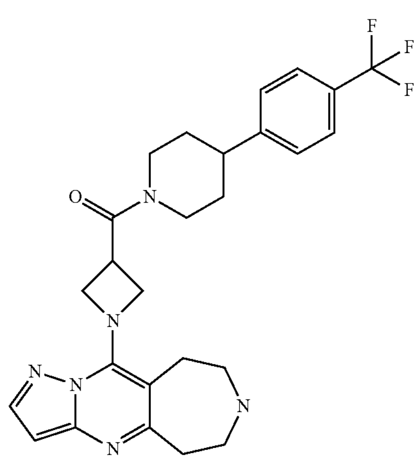 [SMILES: O=C(C1CN(c2c3c(nc4ccnn24)CCNCC3)C1)N1CCC(c2ccc(C(F)(F)F)cc2)CC1] | 25 | TF | 499.1 [M + H]⁺ | 1.74 (F) |

TABLE 14-continued

| Example | Structure | Yield of final step (%) | Salt type | Mass spec result | HPLC retention time (method) |
| --- | --- | --- | --- | --- | --- |
| 31.110 | 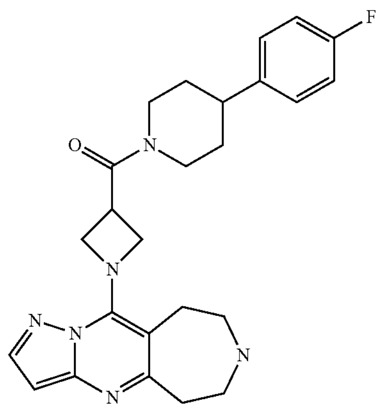 [SMILES: O=C(C1CN(c2c3c(nc4ccnn24)CCNCC3)C1)N1CCC(c2ccc(F)cc2)CC1] | 28 | TF | 449.2 [M + H]$^+$ | 1.65 (F) |
| 31.111 | 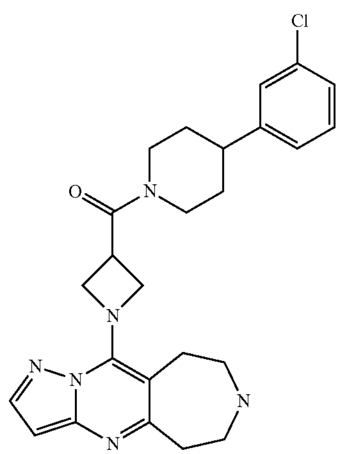 [SMILES: O=C(C1CN(c2c3c(nc4ccnn24)CCNCC3)C1)N1CCC(c2cccc(Cl)c2)CC1] | 28 | TF | 465.2 [M + H]$^+$ | 1.69 (F) |
| 31.112 | 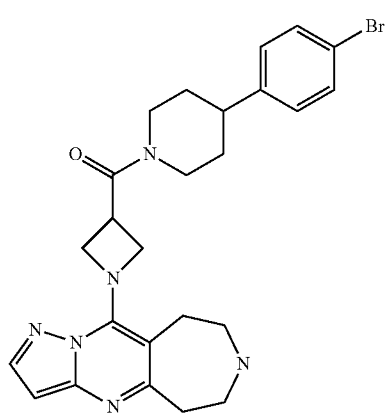 [SMILES: O=C(C1CN(c2c3c(nc4ccnn24)CCNCC3)C1)N1CCC(c2ccc(Br)cc2)CC1] | 18 | TF | 511.1 [M + H]$^+$ | 1.73 (F) |

TABLE 14-continued
| Example | Structure | Yield of final step (%) | Salt type | Mass spec result | HPLC retention time (method) |
|---|---|---|---|---|---|
| 31.113 | 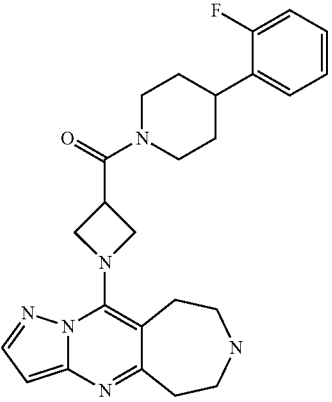 [SMILES: O=C(C1CN(c2c3c(nc4ccnn24)CCNCC3)C1)N1CCC(c2ccccc2F)CC1] | 29 | TF | 449.2 [M + H]+ | 1.63 (F) |
| 31.114 | 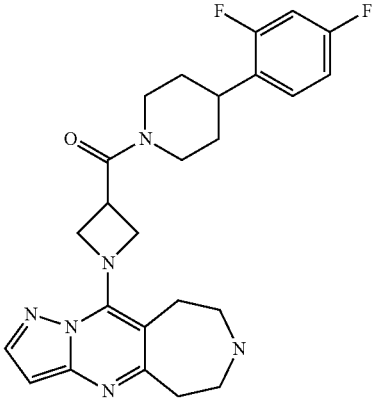 [SMILES: O=C(C1CN(c2c3c(nc4ccnn24)CCNCC3)C1)N1CCC(c2ccc(F)cc2F)CC1] | 24 | TF | 467.1 [M + H]+ | 1.68 (F) |
| 31.115 | 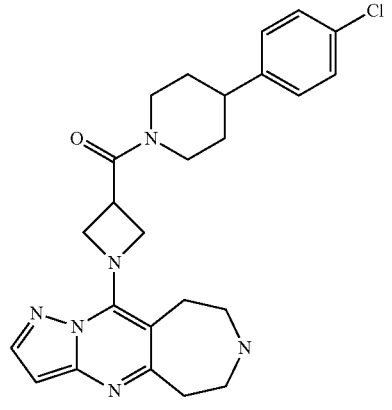 [SMILES: O=C(C1CN(c2c3c(nc4ccnn24)CCNCC3)C1)N1CCC(c2ccc(Cl)cc2)CC1] | 29 | TF | 465.2 [M + H]+ | 1.7 (F) |

TABLE 14-continued
| Example | Structure | Yield of final step (%) | Salt type | Mass spec result | HPLC retention time (method) |
|---------|-----------|------------------------|-----------|------------------|------------------------------|
| 31.116 | 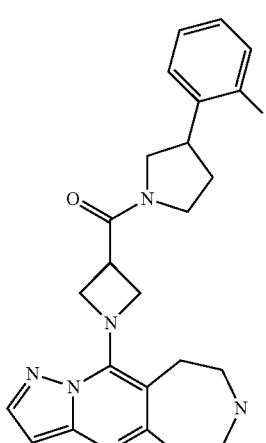 | 32 | TF | 435.2 [M + H]⁺ | 1.58 (F) |
| 31.117 | 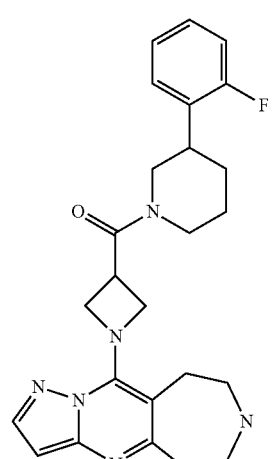 | 32 | TF | 449.2 [M + H]⁺ | 1.63 (F) |
| 31.118 | 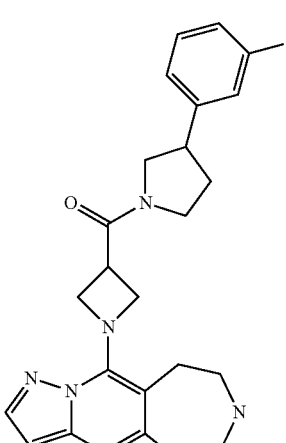 | 30 | TF | 435.2 [M + H]⁺ | 1.59 (F) |

TABLE 14-continued
| Example | Structure | Yield of final step (%) | Salt type | Mass spec result | HPLC retention time (method) |
|---|---|---|---|---|---|
| 31.119 | 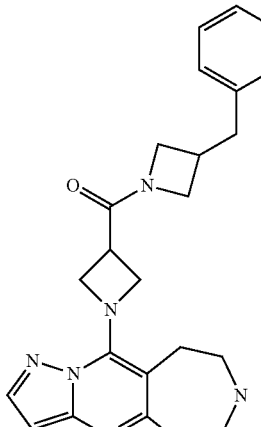 | 28 | TF | 417.2 [M + H]⁺ | 1.55 (F) |
| 31.120 | 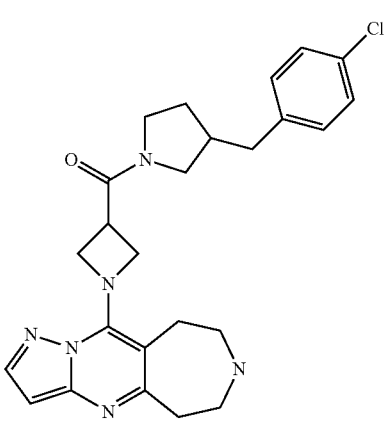 [SMILES: O=C(C1CN(c2c3c(nc4ccnn24)CCNCC3)C1)N1CCC(Cc2ccc(Cl)cc2)C1] | 23 | TF | 465.2 [M + H]⁺ | 1.77 (F) |
| 31.121 | 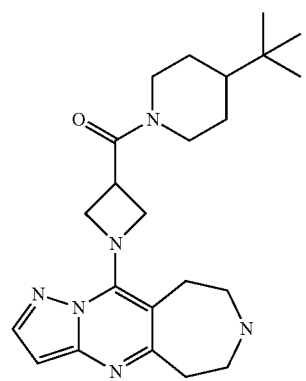 [SMILES: CC(C)(C)C1CCN(C(=O)C2CN(c3c4c(nc5ccnn35)CCNCC4)C2)CC1] | 26 | TF | 411.3 [M + H]⁺ | 1.8 (F) |

TABLE 14-continued

| Example | Structure | Yield of final step (%) | Salt type | Mass spec result | HPLC retention time (method) |
|---|---|---|---|---|---|
| 31.122 | 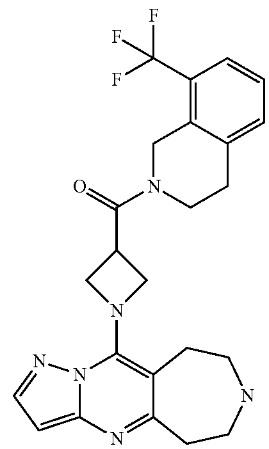 [SMILES: O=C(C1CN(c2c3c(nc4ccnn24)CCNCC3)C1)N1CCc2cccc(C(F)(F)F)c2C1] | 30 | TF | 471.1 [M + H]⁺ | 1.64 (F) |
| 31.123 | 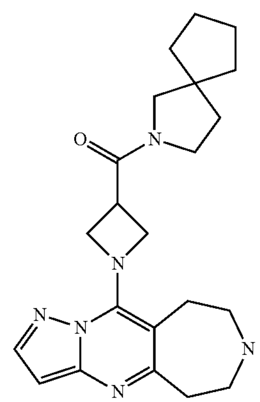 [SMILES: O=C(C1CN(c2c3c(nc4ccnn24)CCNCC3)C1)N1CCC2(CCCC2)C1] | 32 | TF | 395.2 [M + H]⁺ | 1.55 (F) |
| 31.124 | 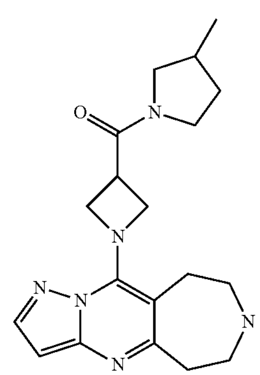 [SMILES: CC1CCN(C(=O)C2CN(c3c4c(nc5ccnn35)CCNCC4)C2)C1] | 38 | TF | 355.2 [M + H]⁺ | 1.4 (F) |

TABLE 14-continued
| Example | Structure | Yield of final step (%) | Salt type | Mass spec result | HPLC retention time (method) |
|---|---|---|---|---|---|
| 31.125 | 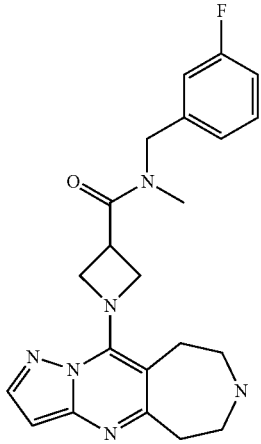 [SMILES: CN(Cc1cccc(F)c1)C(=O)C1CN(c2c3c(nc4ccnn24)CCNCC3)C1] | 28 | TF | 409.2 [M + H]+ | 1.54 (F) |
| 31.126 | 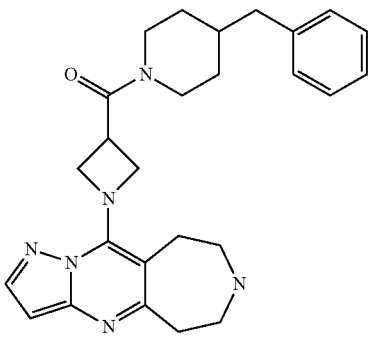 [SMILES: O=C(C1CN(c2c3c(nc4ccnn24)CCNCC3)C1)N1CCC(Cc2ccccc2)CC1] | 35 | TF | 445.2 [M + H]+ | 1.68 (F) |
| 31.127 | 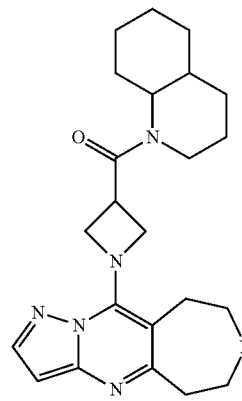 | 28 | TF | 409.2 [M + H]+ | 1.6 (F) |
| 31.128 | 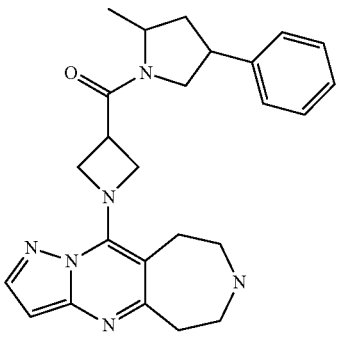 [SMILES: CC1CC(c2ccccc2)CN1C(=O)C1CN(c2c3c(nc4ccnn24)CCNCC3)C1] | 24 | TF | 431.2 [M + H]+ | 1.63 (F) |

TABLE 14-continued

| Example | Structure | Yield of final step (%) | Salt type | Mass spec result | HPLC retention time (method) |
|---------|-----------|-------------------------|-----------|------------------|------------------------------|
| 31.129  | 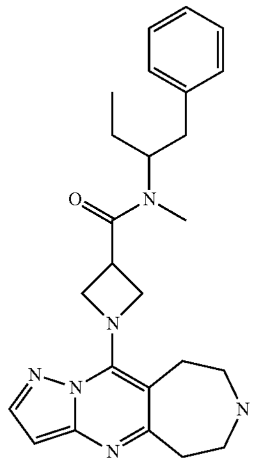 [SMILES: CCC(Cc1ccccc1)N(C)C(=O)C1CN(c2c3c(nc4ccnn24)CCNCC3)C1]          | 19                      | TF        | 433.2 [M + H]⁺   | 1.6 (F)                      |
| 31.130  | 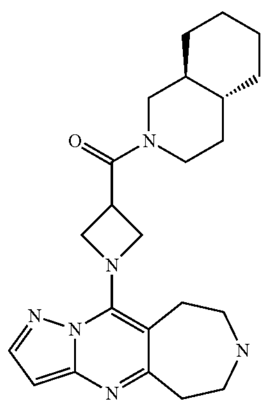 [SMILES: O=C(C1CN(c2c3c(nc4ccnn24)CCNCC3)C1)N1CC[C@H]2CCCC[C@@H]2C1]          | 34                      | TF        | 409.2 [M + H]⁺   | 1.63 (F)                     |
| 31.131  | 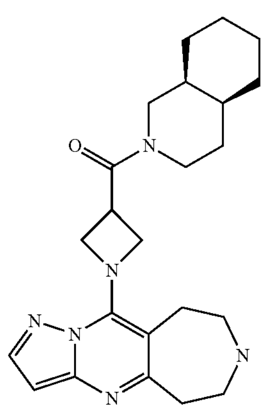 [SMILES: O=C(C1CN(c2c3c(nc4ccnn24)CCNCC3)C1)N1CC[C@@H]2CCCC[C@@H]2C1]          | 24                      | TF        | 409.2 [M + H]⁺   | 1.61 (F)                     |

TABLE 14-continued
| Example | Structure | Yield of final step (%) | Salt type | Mass spec result | HPLC retention time (method) |
|---|---|---|---|---|---|
| 31.132 | 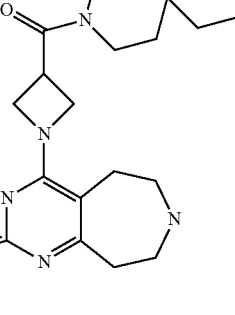 | 15 | TF | 501/503 [M + H]+ | 1.75 (G) |
| 31.133 | 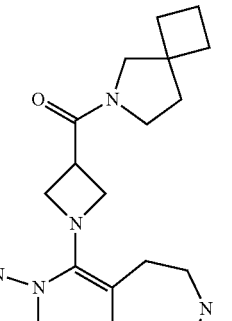 | 21 | TF | 459/461 [M + H]+ | 1.55 (G) |
| 31.134 | 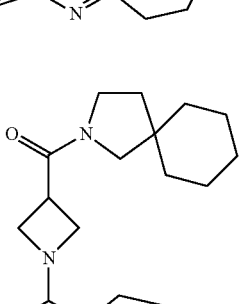 | 24 | TF | 487/489 [M + H]+ | 1.51 (G) |
| 31.135 | 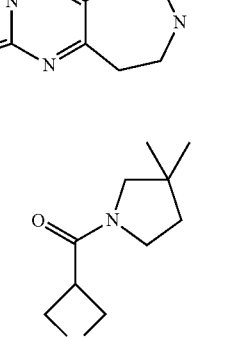 | 28 | TF | 447/449 [M + H]+ | 1.51 (G) |

TABLE 14-continued
| Example | Structure | Yield of final step (%) | Salt type | Mass spec result | HPLC retention time (method) |
|---|---|---|---|---|---|
| 31.136 | 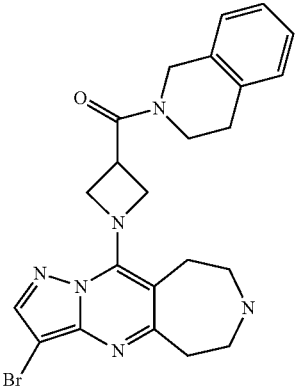 [SMILES: O=C(C1CN(c2c3c(nc4c(Br)cnn24)CCNCC3)C1)N1CCc2ccccc2C1] | 28 | TF | 481/483 [M + H]+ | 1.59 (G) |
| 31.137 | 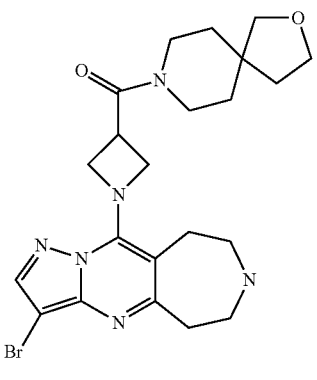 [SMILES: O=C(C1CN(c2c3c(nc4c(Br)cnn24)CCNCC3)C1)N1CCC2(CCOC2)CC1] | 24 | TF | 489/491 [M + H]+ | 1.41 (G) |
| 31.138 | 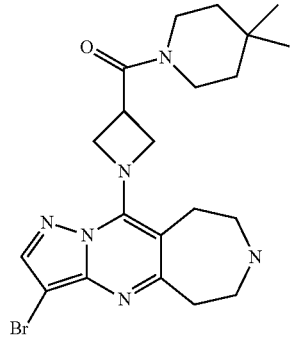 [SMILES: CC1(C)CCN(C(=O)C2CN(c3c4c(nc5c(Br)cnn35)CCNCC4)C2)CC1] | 19 | TF | 461/463 [M + H]+ | 1.6 (G) |
| 31.139 | 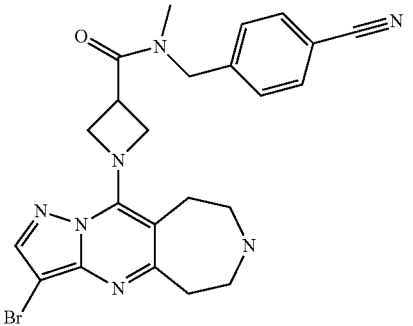 [SMILES: CN(Cc1ccc(C#N)cc1)C(=O)C1CN(c2c3c(nc4c(Br)cnn24)CCNCC3)C1] | 15 | TF | 494/496 [M + H]+ | 1.53 (G) |

TABLE 14-continued

| Example | Structure | Yield of final step (%) | Salt type | Mass spec result | HPLC retention time (method) |
|---|---|---|---|---|---|
| 31.140 | 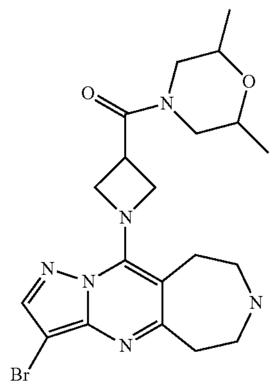 [SMILES: CC1CN(C(=O)C2CN(c3c4c(nc5c(Br)cnn35)CCNCC4)C2)CC(C)O1] | 16 | TF | 463/465 [M + H]+ | 1.43 (G) |
| 31.141 | 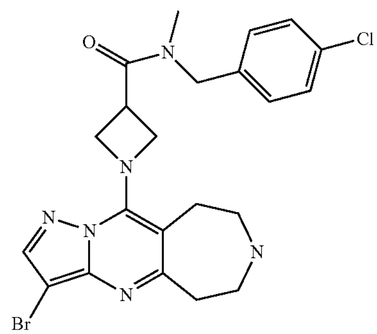 [SMILES: CN(Cc1ccc(Cl)cc1)C(=O)C1CN(c2c3c(nc4c(Br)cnn24)CCNCC3)C1] | 19 | TF | 503/505/ 507 [M + H]+ | 1.65 (G) |
| 31.142 | 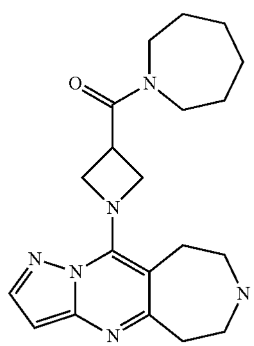 [SMILES: O=C(C1CN(c2c3c(nc4ccnn24)CCNCC3)C1)N1CCCCCC1] | 18 | TF | 369.1 [M + H]+ | 1.31 (F) |
| 31.143 | 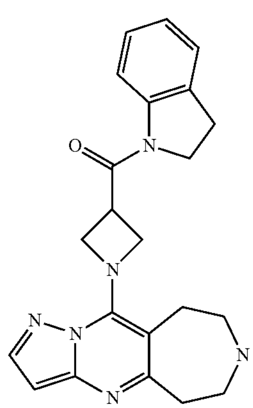 [SMILES: O=C(C1CN(c2c3c(nc4ccnn24)CCNCC3)C1)N1CCc2ccccc21] | 21 | TF | 389.1 [M + H]+ | 1.38 (F) |

TABLE 14-continued
| Example | Structure | Yield of final step (%) | Salt type | Mass spec result | HPLC retention time (method) |
|---|---|---|---|---|---|
| 31.144 | 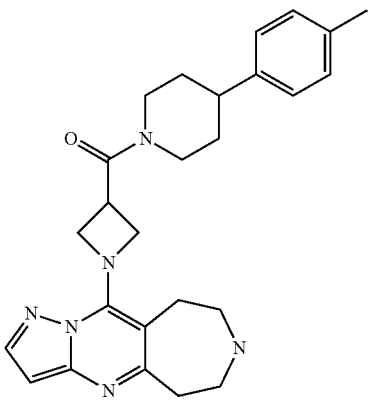 [SMILES: Cc1ccc(C2CCN(C(=O)C3CN(c4c5c(nc6ccnn46)CCNCC5)C3)CC2)cc1] | 15 | TF | 445.2 [M + H]+ | 1.53 (F) |
| 31.145 | 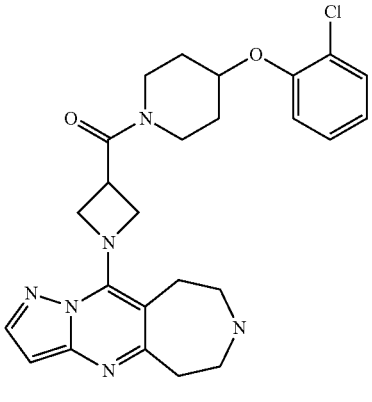 [SMILES: O=C(C1CN(c2c3c(nc4ccnn24)CCNCC3)C1)N1CCC(Oc2ccccc2Cl)CC1] | 17 | TF | 481.1 [M + H]+ | 1.52 (F) |
| 31.146 | 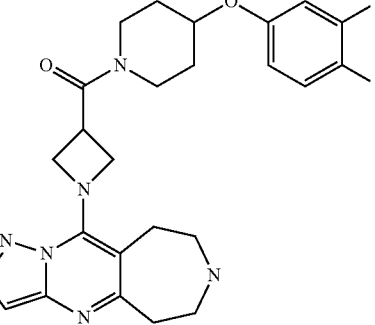 | 16 | TF | 483.2 [M + H]+ | 1.53 (F) |
| 31.147 | 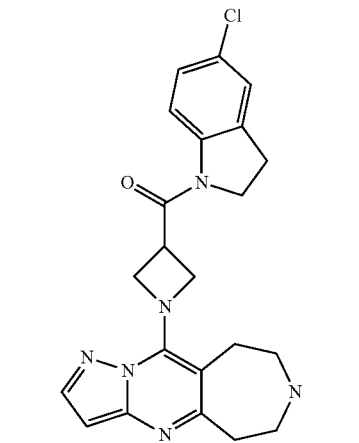 [SMILES: O=C(C1CN(c2c3c(nc4ccnn24)CCNCC3)C1)N1CCc2cc(Cl)ccc21] | 17 | TF | 423.1 [M + H]+ | 1.48 (F) |

TABLE 14-continued

| Example | Structure | Yield of final step (%) | Salt type | Mass spec result | HPLC retention time (method) |
|---|---|---|---|---|---|
| 31.148 | 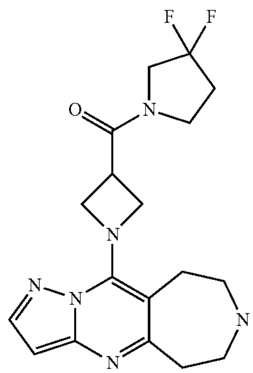 [SMILES: O=C(C1CN(c2c3c(nc4ccnn24)CCNCC3)C1)N1CCC(F)(F)C1] | 18 | TF | 377.1 [M + H]⁺ | 1.25 (F) |
| 31.149 | 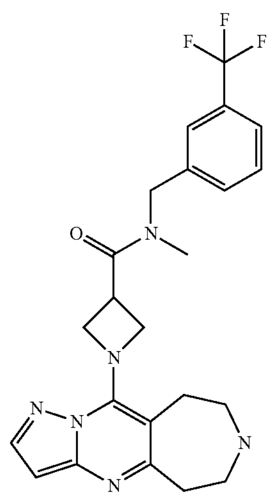 [SMILES: CN(Cc1cccc(C(F)(F)F)c1)C(=O)C1CN(c2c3c(nc4ccnn24)CCNCC3)C1] | 18 | TF | 459.1 [M + H]⁺ | 1.49 (F) |
| 31.150 | 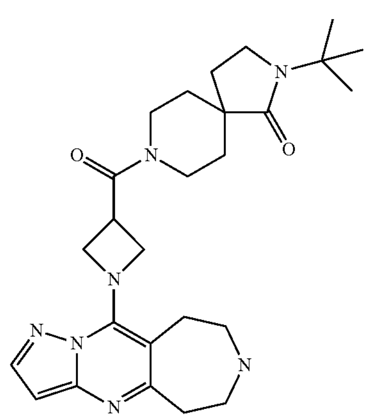 [SMILES: CC(C)(C)N1CCC2(CCN(C(=O)C3CN(c4c5c(nc6ccnn46)CCNCC5)C3)CC2)C1=O] | 19 | TF | 480.2 [M + H]⁺ | 1.38 (F) |

TABLE 14-continued

| Example | Structure | Yield of final step (%) | Salt type | Mass spec result | HPLC retention time (method) |
|---|---|---|---|---|---|
| 31.151 | 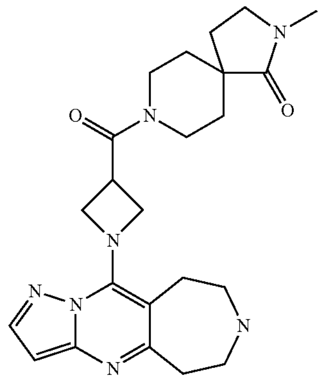 [SMILES: CN1CCC2(CCN(C(=O)C3CN(c4c5c(nc6ccnn46)CCNCC5)C3)CC2)C1=O] | 21 | TF | 438.2 [M + H]⁺ | 1.19 (F) |
| 31.152 | 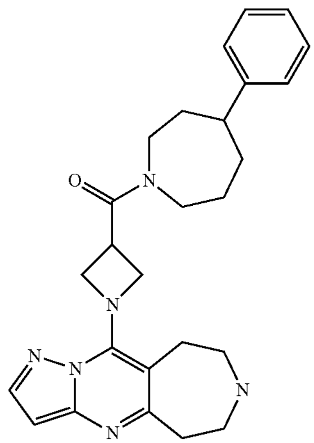 [SMILES: O=C(C1CN(c2c3c(nc4ccnn24)CCNCC3)C1)N1CCCC(c2ccccc2)CC1] | 20 | TF | 445.2 [M + H]⁺ | 1.5 (F) |
| 31.153 | 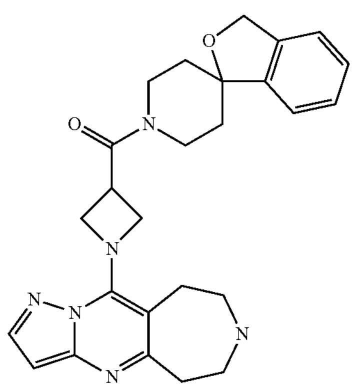 [SMILES: O=C(C1CN(c2c3c(nc4ccnn24)CCNCC3)C1)N1CCC2(CC1)OCc1ccccc12] | 17 | TF | 459.2 [M + H]⁺ | 1.43 (F) |
| 31.154 | 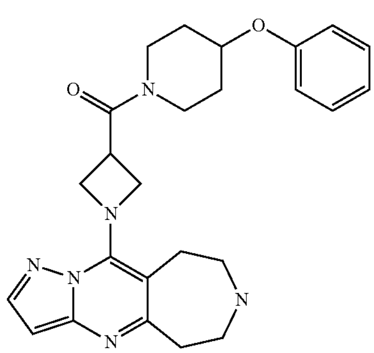 [SMILES: O=C(C1CN(c2c3c(nc4ccnn24)CCNCC3)C1)N1CCC(Oc2ccccc2)CC1] | 20 | TF | 447.2 [M + H]⁺ | 1.48 (F) |

TABLE 14-continued
| Example | Structure | Yield of final step (%) | Salt type | Mass spec result | HPLC retention time (method) |
|---|---|---|---|---|---|
| 31.155 | 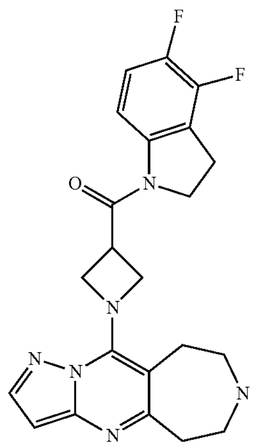 [SMILES: O=C(C1CN(c2c3c(nc4ccnn24)CCNCC3)C1)N1CCc2c1ccc(F)c2F] | 19 | TF | 425.1 [M + H]⁺ | 1.46 (F) |
| 31.156 | 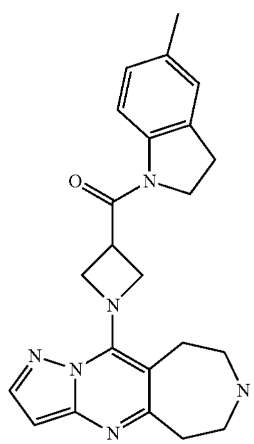 [SMILES: Cc1ccc2c(c1)CCN2C(=O)C1CN(c2c3c(nc4ccnn24)CCNCC3)C1] | 26 | TF | 403.1 [M + H]⁺ | 1.46 (F) |
| 31.157 | 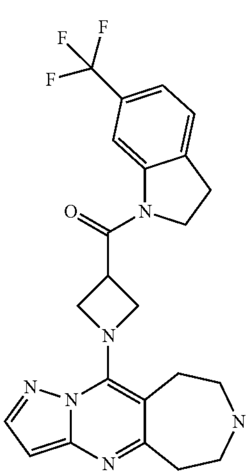 [SMILES: O=C(C1CN(c2c3c(nc4ccnn24)CCNCC3)C1)N1CCc2ccc(C(F)(F)F)cc21] | 10 | TF | 457.1 [M + H]⁺ | 1.52 (F) |

TABLE 14-continued

| Example | Structure | Yield of final step (%) | Salt type | Mass spec result | HPLC retention time (method) |
|---|---|---|---|---|---|
| 31.158 | 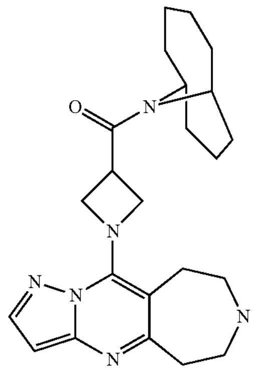 [SMILES: O=C(C1CN(c2c3c(nc4ccnn24)CCNCC3)C1)N1C2CCCCC1CCC2] | 22 | TF | 409.2 [M + H]⁺ | 1.43 (F) |
| 31.159 | 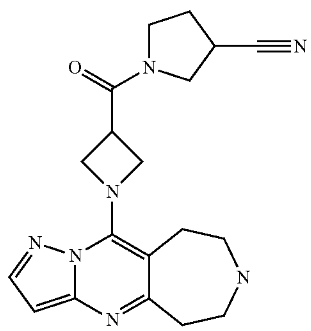 [SMILES: N#CC1CCN(C(=O)C2CN(c3c4c(nc5ccnn35)CCNCC4)C2)C1] | 12 | TF | 366.1 [M + H]⁺ | 1.14 (F) |
| 31.160 | 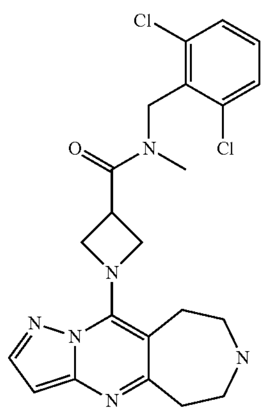 [SMILES: CN(Cc1c(Cl)cccc1Cl)C(=O)C1CN(c2c3c(nc4ccnn24)CCNCC3)C1] | 17 | TF | 459.1 [M + H]⁺ | 1.46 (F) |
| 31.161 | 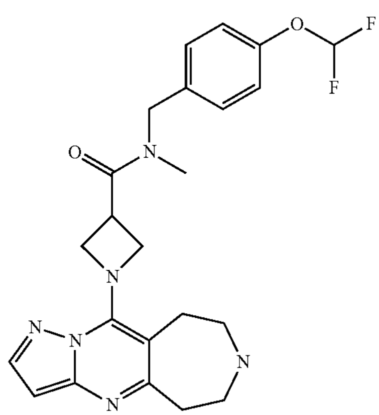 [SMILES: CN(Cc1ccc(OC(F)F)cc1)C(=O)C1CN(c2c3c(nc4ccnn24)CCNCC3)C1] | 18 | TF | 457.1 [M + H]⁺ | 1.45 (F) |

TABLE 14-continued

| Example | Structure | Yield of final step (%) | Salt type | Mass spec result | HPLC retention time (method) |
|---|---|---|---|---|---|
| 31.162 | 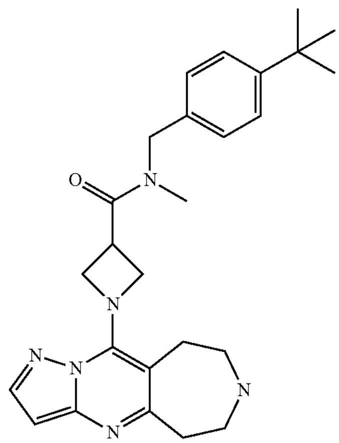 [SMILES: CN(Cc1ccc(C(C)(C)C)cc1)C(=O)C1CN(c2c3c(nc4ccnn24)CCNCC3)C1] | 20 | TF | 447.2 [M + H]+ | 1.57 (F) |
| 31.163 | 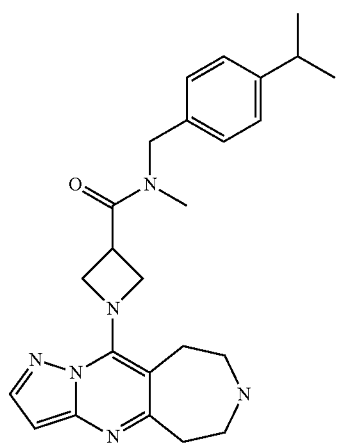 [SMILES: CC(C)c1ccc(CN(C)C(=O)C2CN(c3c4c(nc5ccnn35)CCNCC4)C2)cc1] | 17 | TF | 433.2 [M + H]+ | 1.53 (F) |
| 31.164 | 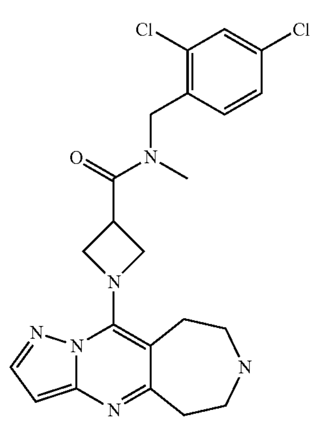 [SMILES: CN(Cc1ccc(Cl)cc1Cl)C(=O)C1CN(c2c3c(nc4ccnn24)CCNCC3)C1] | 14 | TF | 459.1 [M + H]+ | 1.51 (F) |

TABLE 14-continued

| Example | Structure | Yield of final step (%) | Salt type | Mass spec result | HPLC retention time (method) |
|---|---|---|---|---|---|
| 31.165 | 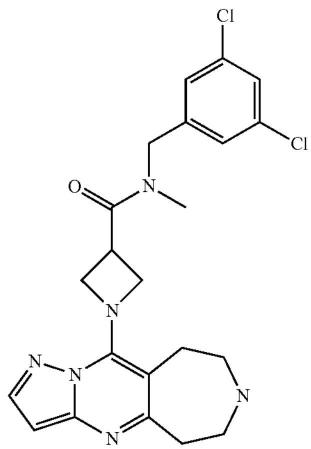 [SMILES: CN(Cc1cc(Cl)cc(Cl)c1)C(=O)C1CN(c2c3c(nc4ccnn24)CCNCC3)C1] | 11 | TF | 459.1 [M + H]⁺ | 1.52 (F) |
| 31.166 | 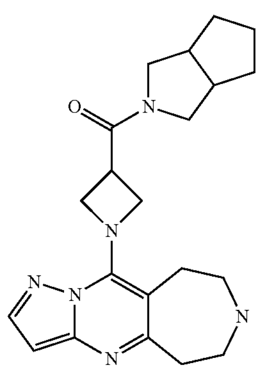 [SMILES: O=C(C1CN(c2c3c(nc4ccnn24)CCNCC3)C1)N1CC2CCCC2C1] | 22 | TF | 381.2 [M + H]⁺ | 1.35 (F) |
| 31.167 | 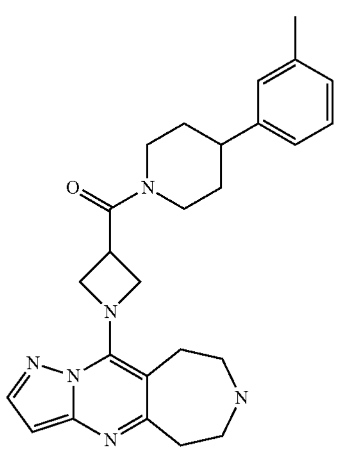 [SMILES: Cc1cccc(C2CCN(C(=O)C3CN(c4c5c(nc6ccnn46)CCNCC5)C3)CC2)c1] | 20 | TF | 445.2 [M + H]⁺ | 1.52 (F) |

TABLE 14-continued

| Example | Structure | Yield of final step (%) | Salt type | Mass spec result | HPLC retention time (method) |
|---|---|---|---|---|---|
| 31.168 | 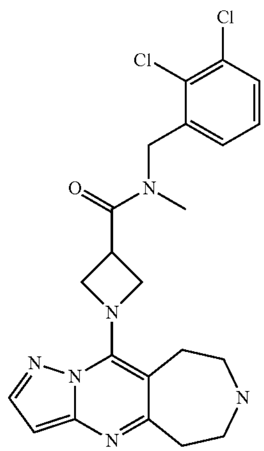 [SMILES: CN(Cc1cccc(Cl)c1Cl)C(=O)C1CN(c2c3c(nc4ccnn24)CCNCC3)C1] | 14 | TF | 459.1 [M + H]+ | 1.5 (F) |
| 31.169 | 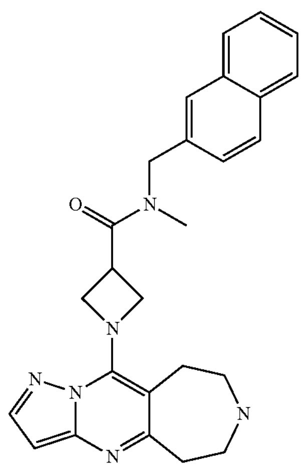 [SMILES: CN(Cc1ccc2ccccc2c1)C(=O)C1CN(c2c3c(nc4ccnn24)CCNCC3)C1] | 18 | TF | 441.2 [M + H]+ | 1.49 (F) |
| 31.170 | 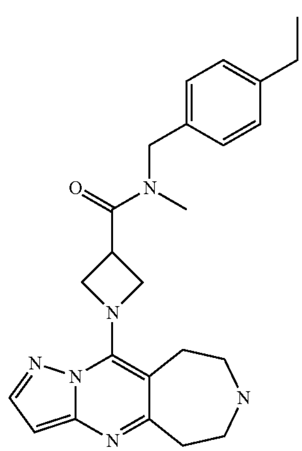 [SMILES: CCc1ccc(CN(C)C(=O)C2CN(c3c4c(nc5ccnn35)CCNCC4)C2)cc1] | 22 | TF | 419.2 [M + H]+ | 1.49 (F) |

TABLE 14-continued

| Example | Structure | Yield of final step (%) | Salt type | Mass spec result | HPLC retention time (method) |
|---|---|---|---|---|---|
| 31.171 | 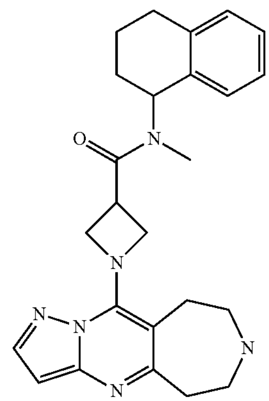 [SMILES: CN(C(=O)C1CN(c2c3c(nc4ccnn24)CCNCC3)C1)C1CCCc2ccccc21] | 10 | TF | 431.2 [M + H]⁺ | 1.47 (F) |
| 31.172 | 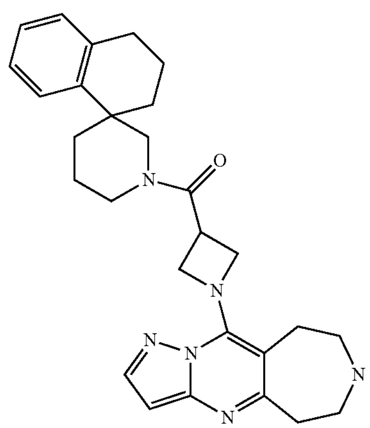 [SMILES: O=C(C1CN(c2c3c(nc4ccnn24)CCNCC3)C1)N1CCCC2(CCCc3ccccc32)C1] | 18 | TF | 471.3 [M + H]⁺ | 1.55 (F) |
| 31.173 | 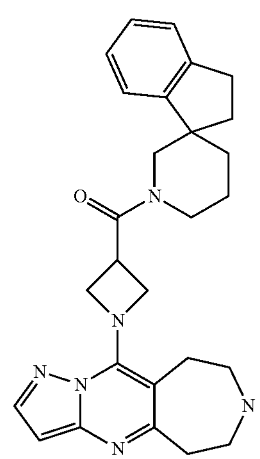 [SMILES: O=C(C1CN(c2c3c(nc4ccnn24)CCNCC3)C1)N1CCCC2(CCc3ccccc32)C1] | 20 | TF | 457.2 [M + H]⁺ | 1.52 (F) |

TABLE 14-continued

| Example | Structure | Yield of final step (%) | Salt type | Mass spec result | HPLC retention time (method) |
|---|---|---|---|---|---|
| 31.174 | 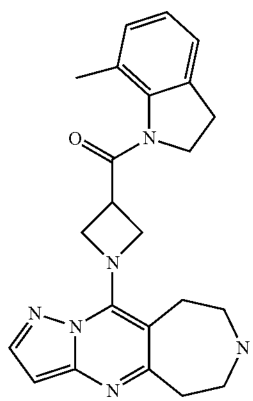 [SMILES: Cc1cccc2c1N(C(=O)C1CN(c3c4c(nc5ccnn35)CCNCC4)C1)CC2] | 15 | TF | 403.2 [M + H]⁺ | 1.43 (F) |
| 31.175 | 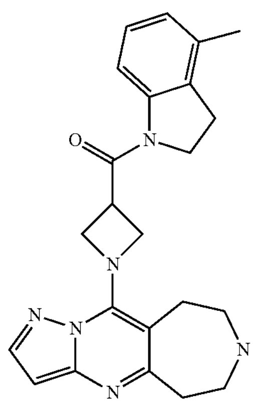 [SMILES: Cc1cccc2c1CCN2C(=O)C1CN(c2c3c(nc4ccnn24)CCNCC3)C1] | 20 | TF | 403.2 [M + H]⁺ | 1.44 (F) |
| 31.176 | 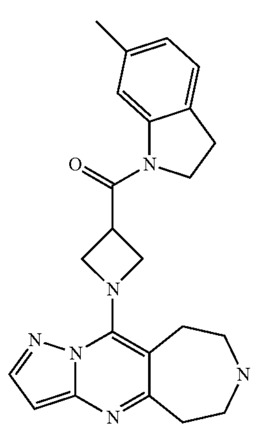 [SMILES: Cc1ccc2c(c1)N(C(=O)C1CN(c3c4c(nc5ccnn35)CCNCC4)C1)CC2] | 18 | TF | 403.2 [M + H]⁺ | 1.45 (F) |

TABLE 14-continued
| Example | Structure | Yield of final step (%) | Salt type | Mass spec result | HPLC retention time (method) |
|---|---|---|---|---|---|
| 31.177 | 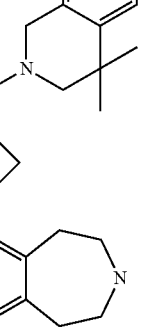 | 16 | TF | 431.2 [M + H]+ | 1.47 (F) |
| 31.178 | 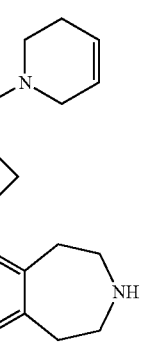 | 98 | TF | 353.3 [M + H]+ | 1.26 (G) |
| 31.179 | 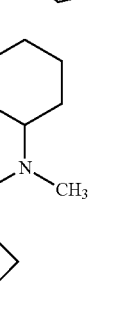 | 57 | TF | 383.4 [M + H]+ | 1.48 (G) |
| 31.180 | 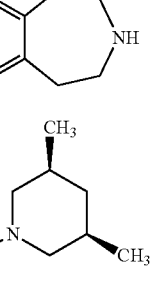 | 40 | TF | 383.4 [M + H]+ | 1.49 (G) |

TABLE 14-continued

| Example | Structure | Yield of final step (%) | Salt type | Mass spec result | HPLC retention time (method) |
|---|---|---|---|---|---|
| 31.181 | 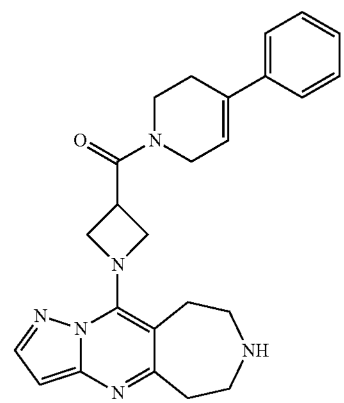 [SMILES: O=C(C1CN(c2c3c(nc4ccnn24)CCNCC3)C1)N1CC=C(c2ccccc2)CC1] | 37 | TF | 429.4 [M + H]+ | 1.54 (G) |
| 31.182 | 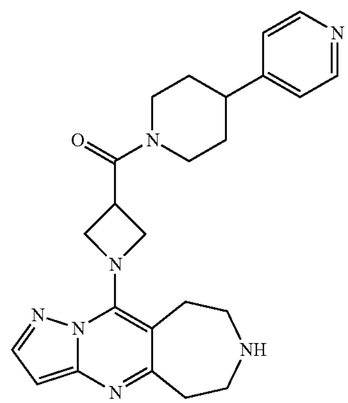 [SMILES: O=C(C1CN(c2c3c(nc4ccnn24)CCNCC3)C1)N1CCC(c2ccncc2)CC1] | 21 | TF | 432.6 [M + H]+ | 1.15 (G) |
| 31.183 | 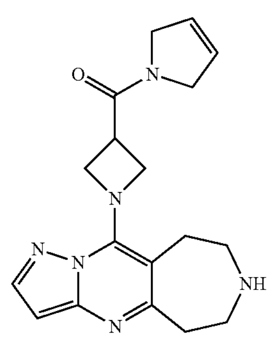 [SMILES: O=C(C1CN(c2c3c(nc4ccnn24)CCNCC3)C1)N1CC=CC1] | 77 | TF | 339.2 [M + H]+ | 1.23 (G) |
| 31.184 | 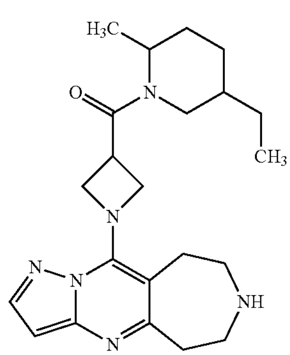 [SMILES: CCC1CCC(C)N(C(=O)C2CN(c3c4c(nc5ccnn35)CCNCC4)C2)C1] | 54 | TF | 397.4 [M + H]+ | 1.51 (G) |

TABLE 14-continued

| Example | Structure | Yield of final step (%) | Salt type | Mass spec result | HPLC retention time (method) |
|---------|-----------|-------------------------|-----------|------------------|------------------------------|
| 31.185 | 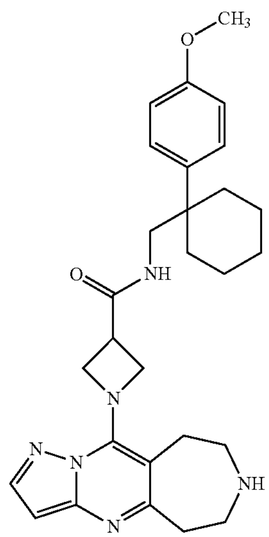 [SMILES: COc1ccc(C2(CNC(=O)C3CN(c4c5c(nc6ccnn46)CCNCC5)C3)CCCCC2)cc1] | 36 | TF | 489.5 [M + H]+ | 1.64 (G) |
| 31.186 | 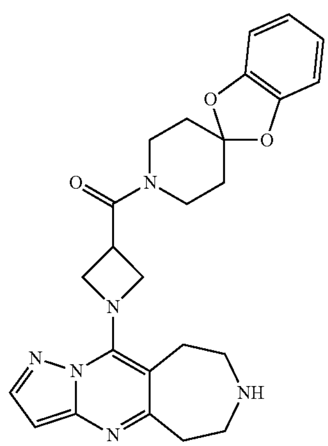 [SMILES: O=C(C1CN(c2c3c(nc4ccnn24)CCNCC3)C1)N1CCC2(CC1)Oc1ccccc1O2] | 58 | TF | 461.4 [M + H]+ | 1.54 (G) |
| 31.187 | 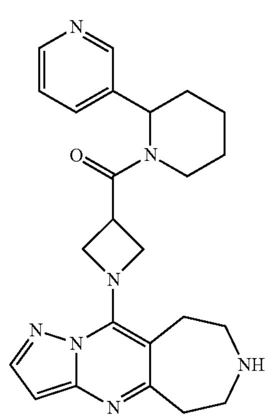 [SMILES: O=C(C1CN(c2c3c(nc4ccnn24)CCNCC3)C1)N1CCCCC1c1cccnc1] | 8 | TF | 432.6 [M + H]+ | 1.19 (G) |

TABLE 14-continued

| Example | Structure | Yield of final step (%) | Salt type | Mass spec result | HPLC retention time (method) |
|---|---|---|---|---|---|
| 31.188 | Chiral | 33 | TF | 397.4 [M + H]⁺ | 1.54 (G) |
| 31.189 | Chiral | 77 | TF | 397.4 [M + H]⁺ | 1.53 (G) |
| 31.190 | 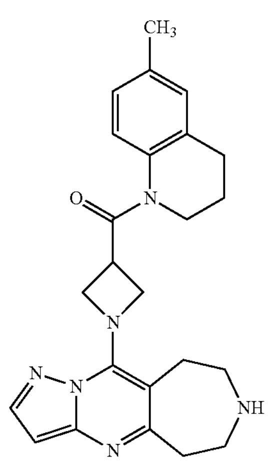 [SMILES: Cc1ccc2c(c1)CCCN2C(=O)C1CN(c2c3c(nc4ccnn24)CCNCC3)C1] | 3 | TF | 417.4 [M + H]⁺ | 1.53 (G) |

TABLE 14-continued

| Example | Structure | Yield of final step (%) | Salt type | Mass spec result | HPLC retention time (method) |
|---|---|---|---|---|---|
| 31.191 | 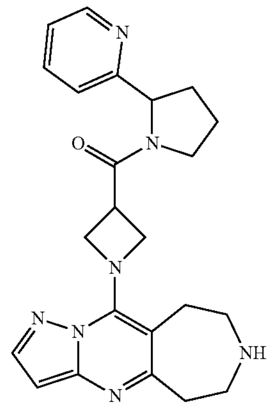 [SMILES: O=C(C1CN(c2c3c(nc4ccnn24)CCNCC3)C1)N1CCCC1c1ccccn1] | 38 | TF | 130.3 [M + H]+ | 1.14 (G) |
| 31.192 | 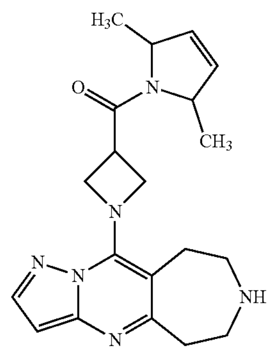 [SMILES: CC1C=CC(C)N1C(=O)C1CN(c2c3c(nc4ccnn24)CCNCC3)C1] | 21 | TF | 367.3 [M + H]+ | 1.37 (G) |
| 31.193 | 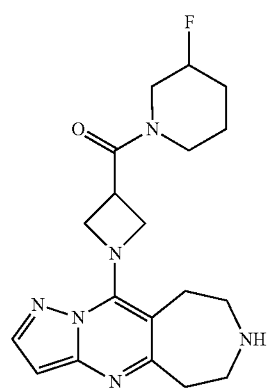 [SMILES: O=C(C1CN(c2c3c(nc4ccnn24)CCNCC3)C1)N1CCCC(F)C1] | 78 | TF | 373.3 [M + H]+ | 1.29 (G) |
| 31.194 | Chiral | 13 | TF | 399.4 [M + H]+ | 1.3 (G) |

TABLE 14-continued

| Example | Structure | Yield of final step (%) | Salt type | Mass spec result | HPLC retention time (method) |
|---|---|---|---|---|---|
| 31.195 | 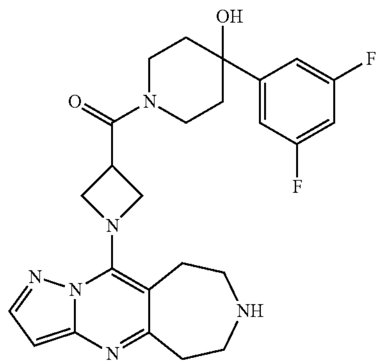 [SMILES: O=C(C1CN(c2c3c(nc4ccnn24)CCNCC3)C1)N1CCC(O)(c2cc(F)cc(F)c2)CC1] | 36 | TF | 483.5 [M + H]+ | 1.41 (G) |
| 31.196 | 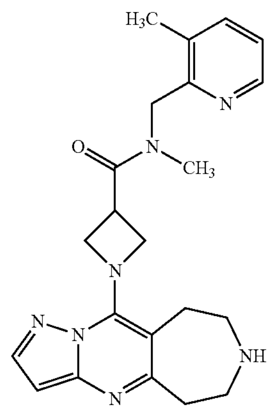 [SMILES: Cc1cccnc1CN(C)C(=O)C1CN(c2c3c(nc4ccnn24)CCNCC3)C1] | 69 | TF | 406.6 [M + H]+ | 1.13 (G) |
| 31.197 | 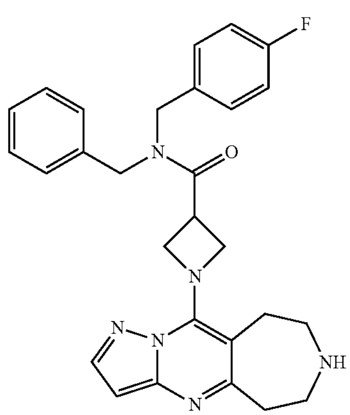 [SMILES: O=C(C1CN(c2c3c(nc4ccnn24)CCNCC3)C1)N(Cc1ccccc1)Cc1ccc(F)cc1] | 45 | TF | 485.5 [M + H]+ | 1.64 (G) |

TABLE 14-continued

| Example | Structure | Yield of final step (%) | Salt type | Mass spec result | HPLC retention time (method) |
|---------|-----------|------------------------|-----------|------------------|------------------------------|
| 31.198 | 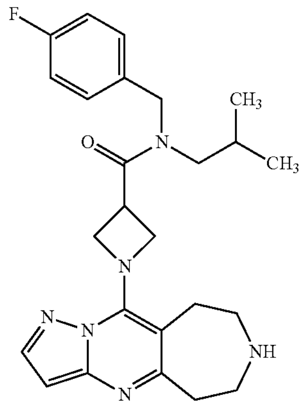 [SMILES: CC(C)CN(Cc1ccc(F)cc1)C(=O)C1CN(c2c3c(nc4ccnn24)CCNCC3)C1] | 34 | TF | 451.5 [M + H]⁺ | 1.61 (G) |
| 31.199 | 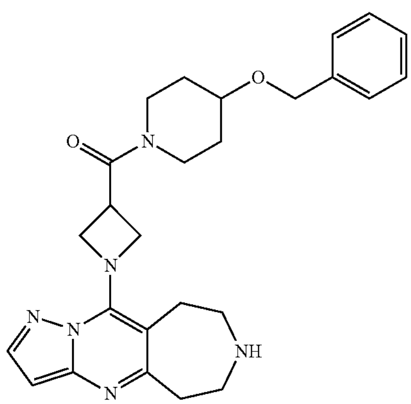 [SMILES: O=C(C1CN(c2c3c(nc4ccnn24)CCNCC3)C1)N1CCC(OCc2ccccc2)CC1] | 27 | TF | 461.5 [M + H]⁺ | 1.54 (G) |
| 31.200 | 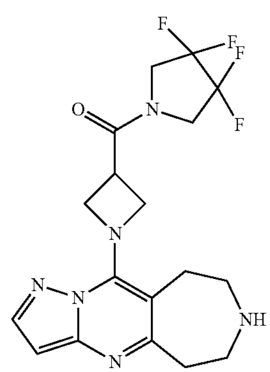 [SMILES: O=C(C1CN(c2c3c(nc4ccnn24)CCNCC3)C1)N1CC(F)(F)C(F)(F)C1] | 56 | TF | 413.3 [M + H]⁺ | 1.43 (G) |
| 31.201 | 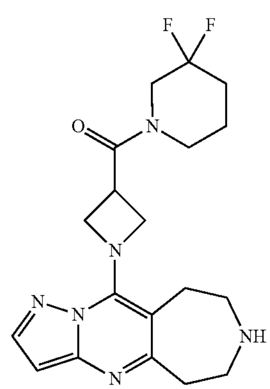 [SMILES: O=C(C1CN(c2c3c(nc4ccnn24)CCNCC3)C1)N1CCCC(F)(F)C1] | 46 | TF | 391.5 [M + H]⁺ | 1.35 (G) |

TABLE 14-continued
| Example | Structure | Yield of final step (%) | Salt type | Mass spec result | HPLC retention time (method) |
|---|---|---|---|---|---|
| 31.202 | Chiral 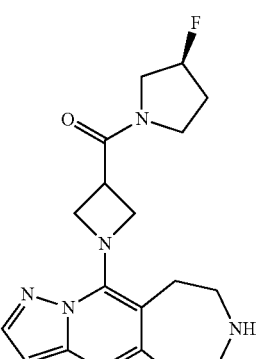 | 76 | TF | 359.5 [M + H]⁺ | 1.23 (G) |
| 31.203 | 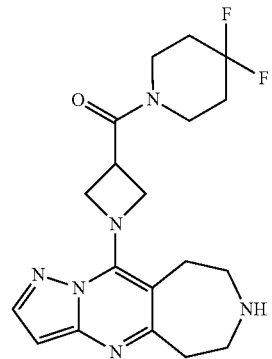 [SMILES: O=C(C1CN(c2c3c(nc4ccnn24)CCNCC3)C1)N1CCC(F)(F)CC1] | 57 | TF | 391.3 [M + H]⁺ | 1.36 (G) |
| 31.204 | 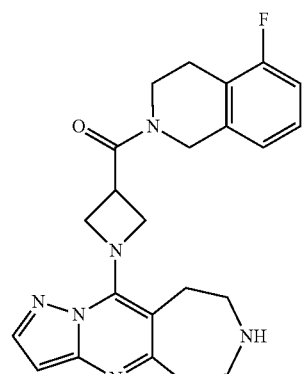 | 53 | TF | 421.4 [M + H]⁺ | 1.49 (G) |
| 31.205 | Chiral 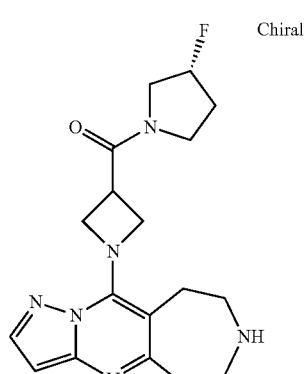 | 95 | TF | 359.5 [M + H]⁺ | 1.22 (G) |

TABLE 14-continued

| Example | Structure | Yield of final step (%) | Salt type | Mass spec result | HPLC retention time (method) |
| --- | --- | --- | --- | --- | --- |
| 31.206 | 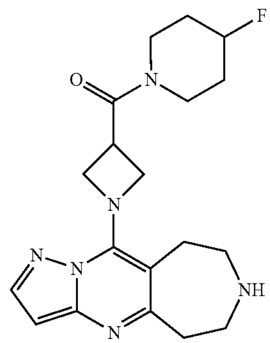 [SMILES: O=C(C1CN(c2c3c(nc4ccnn24)CCNCC3)C1)N1CCC(F)CC1] | 68 | TF | 373.4 [M + H]⁺ | 1.3 (G) |
| 31.207 | 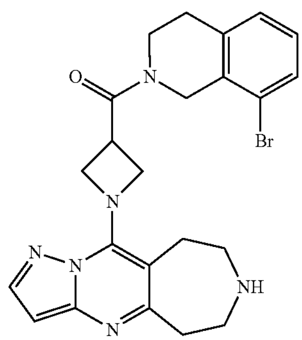 [SMILES: O=C(C1CN(c2c3c(nc4ccnn24)CCNCC3)C1)N1CCc2cccc(Br)c2C1] | 16 | TF | 483.3 [M + H]⁺ | 1.56 (G) |
| 31.208 | 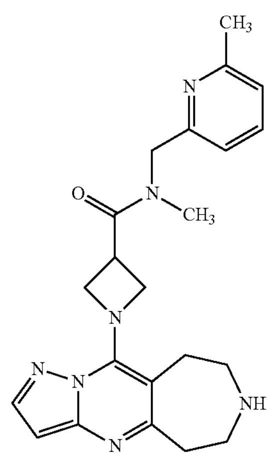 [SMILES: Cc1cccc(CN(C)C(=O)C2CN(c3c4c(nc5ccnn35)CCNCC4)C2)n1] | 73 | TF | 406.5 [M + H]⁺ | 1.12 (G) |
| 31.209 | 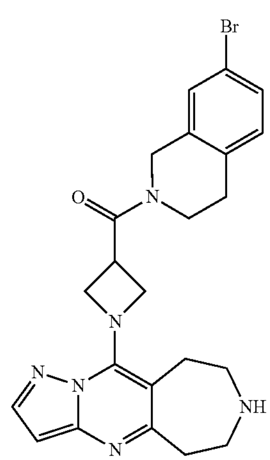 [SMILES: O=C(C1CN(c2c3c(nc4ccnn24)CCNCC3)C1)N1CCc2ccc(Br)cc2C1] | 31 | TF | 483.4 [M + H]⁺ | 1.57 (G) |

TABLE 14-continued

| Example | Structure | Yield of final step (%) | Salt type | Mass spec result | HPLC retention time (method) |
|---------|-----------|------------------------|-----------|------------------|------------------------------|
| 31.210 | 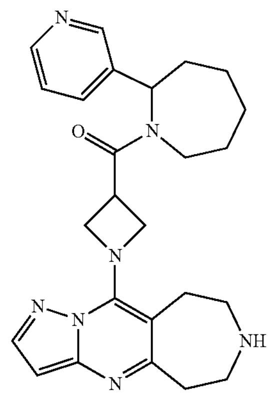 [SMILES: O=C(C1CN(c2c3c(nc4ccnn24)CCNCC3)C1)N1CCCCCC1c1cccnc1] | 5 | BS | 446.6 [M + H]⁺ | 1.25 (G) |
| 31.211 | 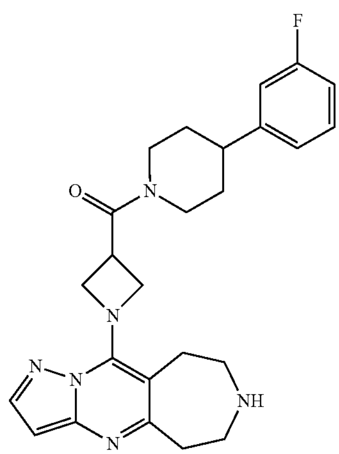 [SMILES: O=C(C1CN(c2c3c(nc4ccnn24)CCNCC3)C1)N1CCC(c2cccc(F)c2)CC1] | 50 | TF | 449.4 [M + H]⁺ | 1.58 (G) |
| 31.212 | Chiral | 30 | TF | 433.4 [M + H]⁺ | 1.49 (G) |
| 31.213 | Chiral | 42 | TF | 467.4 [M + H]⁺ | 1.57 (G) |

TABLE 14-continued

| Example | Structure | Yield of final step (%) | Salt type | Mass spec result | HPLC retention time (method) |
|---|---|---|---|---|---|
| 31.214 | 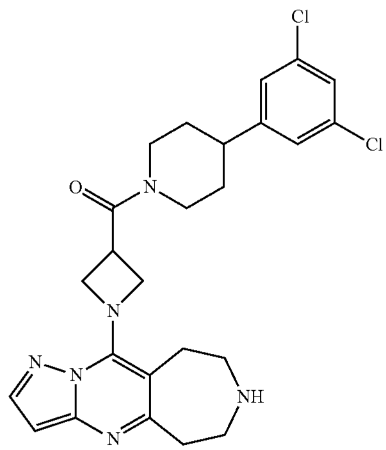 [SMILES: O=C(C1CN(c2c3c(nc4ccnn24)CCNCC3)C1)N1CCC(c2cc(Cl)cc(Cl)c2)CC1] | 31 | TF | 499.4 [M + H]⁺ | 1.71 (G) |
| 31.215 | 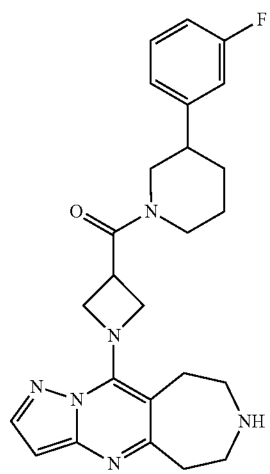 [SMILES: O=C(C1CN(c2c3c(nc4ccnn24)CCNCC3)C1)N1CCCC(c2cccc(F)c2)C1] | 48 | TF | 449.4 [M + H]⁺ | 1.57 (G) |
| 31.216 | 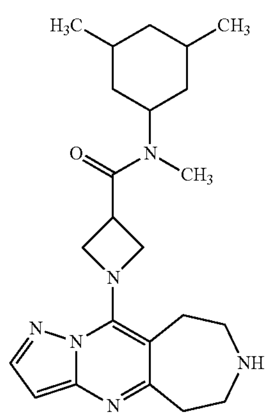 [SMILES: CC1CC(C)CC(N(C)C(=O)C2CN(c3c4c(nc5ccnn35)CCNCC4)C2)C1] | 40 | TF | 411.4 [M + H]⁺ | 1.61 (G) |

TABLE 14-continued

| Example | Structure | Yield of final step (%) | Salt type | Mass spec result | HPLC retention time (method) |
|---|---|---|---|---|---|
| 31.217 | 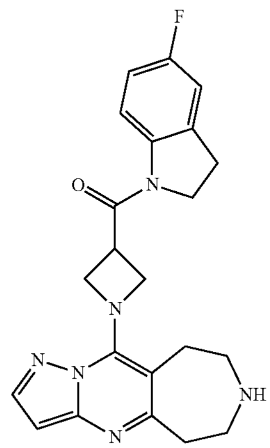 [SMILES: O=C(C1CN(c2c3c(nc4ccnn24)CCNCC3)C1)N1CCc2cc(F)ccc21] | 59 | TF | 407.4 [M + H]⁺ | 1.49 (G) |
| 31.218 | 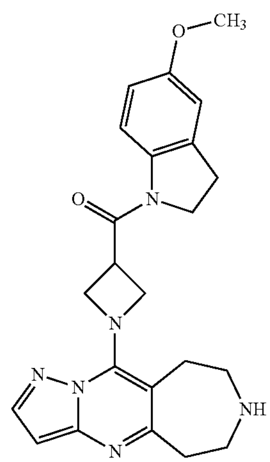 [SMILES: COc1ccc2c(c1)CCN2C(=O)C1CN(c2c3c(nc4ccnn24)CCNCC3)C1] | 44 | TF | 419.4 [M + H]⁺ | 1.47 (G) |
| 31.219 | 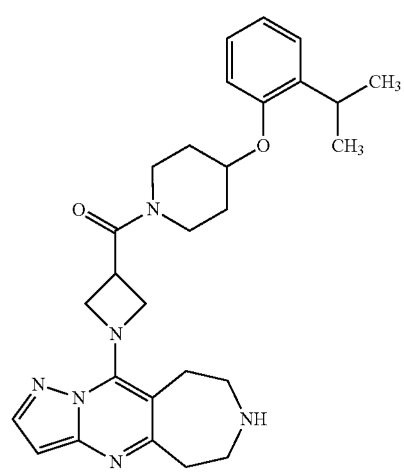 [SMILES: CC(C)c1ccccc1OC1CCN(C(=O)C2CN(c3c4c(nc5ccnn35)CCNCC4)C2)CC1] | 49 | TF | 489.5 [M + H]⁺ | 1.71 (G) |

TABLE 14-continued
| Example | Structure | Yield of final step (%) | Salt type | Mass spec result | HPLC retention time (method) |
|---|---|---|---|---|---|
| 31.220 | 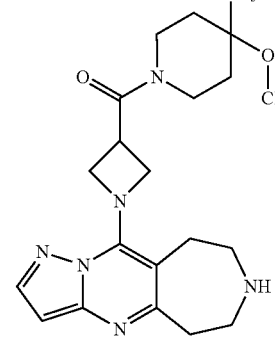 | 90 | TF | 399.4 [M + H]⁺ | 1.34 (G) |
| 31.221 | 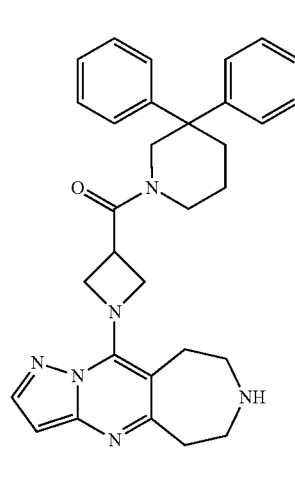 | 60 | TF | 507.5 [M + H]⁺ | 1.66 (G) |
| 31.222 | 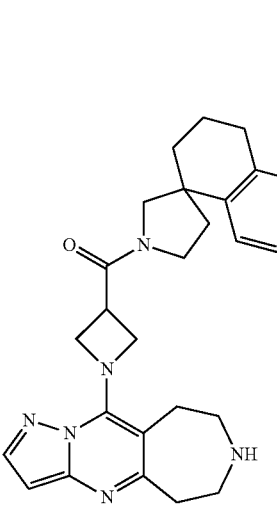 | 58 | TF | 457.5 [M + H]⁺ | 1.6 (G) |

TABLE 14-continued
| Example | Structure | | Yield of final step (%) | Salt type | Mass spec result | HPLC retention time (method) |
|---|---|---|---|---|---|---|
| 31.223 | 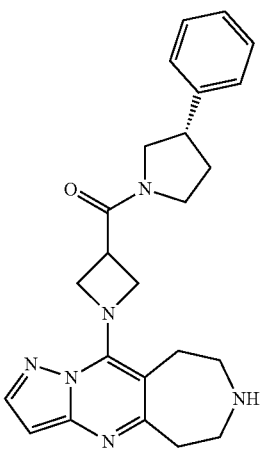 | Chiral | 65 | TF | 417.4 [M + H]+ | 1.5 (G) |
| 31.224 | 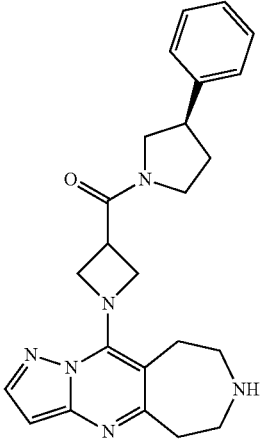 | Chiral | 46 | TF | 417.4 [M + H]+ | 1.5 (G) |
| 31.225 | 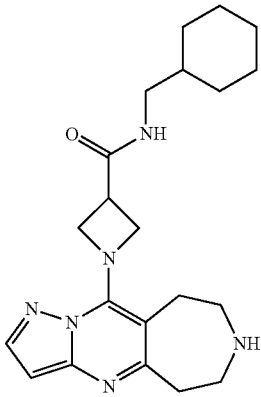 | | 59 | TF | 383.4 [M + H]+ | 1.5 (G) |

TABLE 14-continued

| Example | Structure | Yield of final step (%) | Salt type | Mass spec result | HPLC retention time (method) |
|---|---|---|---|---|---|
| 31.226 | 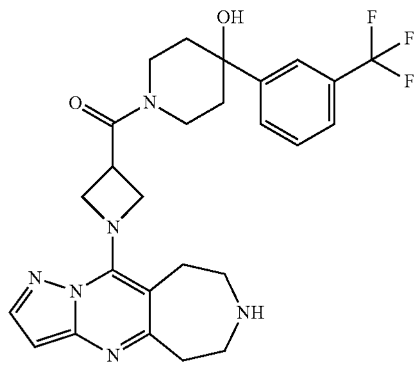 [SMILES: O=C(C1CN(c2c3c(nc4ccnn24)CCNCC3)C1)N1CCC(O)(c2cccc(C(F)(F)F)c2)CC1] | 38 | TF | 515.5 [M + H]⁺ | 1.55 (G) |
| 31.227 | 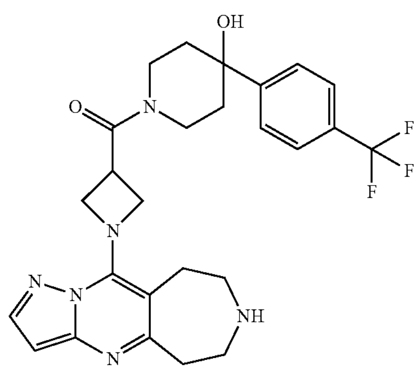 [SMILES: O=C(C1CN(c2c3c(nc4ccnn24)CCNCC3)C1)N1CCC(O)(c2ccc(C(F)(F)F)cc2)CC1] | 36 | TF | 515.5 [M + H]⁺ | 1.57 (G) |
| 31.228 | 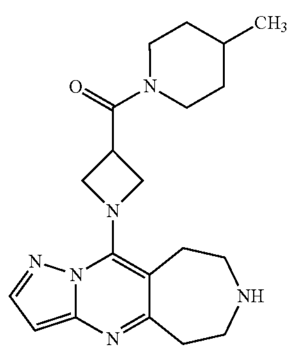 [SMILES: CC1CCN(C(=O)C2CN(c3c4c(nc5ccnn35)CCNCC4)C2)CC1] | 36 | TF | 369.3 [M + H]⁺ | 1.42 (G) |
| 31.229 | 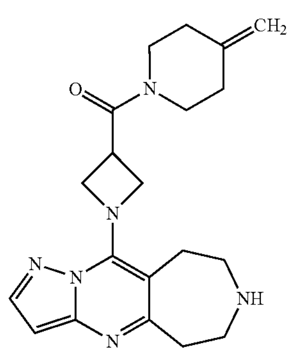 [SMILES: C=C1CCN(C(=O)C2CN(c3c4c(nc5ccnn35)CCNCC4)C2)CC1] | 45 | TF | 367.3 [M + H]⁺ | 1.4 (G) |

TABLE 14-continued

| Example | Structure | Yield of final step (%) | Salt type | Mass spec result | HPLC retention time (method) |
|---|---|---|---|---|---|
| 31.230 | 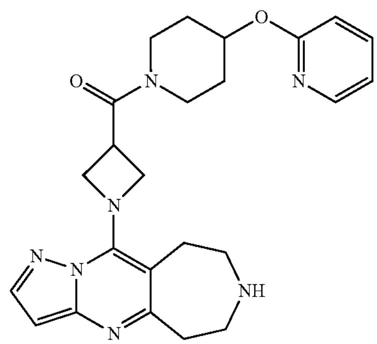 [SMILES: O=C(C1CN(c2c3c(nc4ccnn24)CCNCC3)C1)N1CCC(Oc2ccccn2)CC1] | 51 | TF | 448.6 [M + H]⁺ | 1.32 (G) |
| 31.231 | 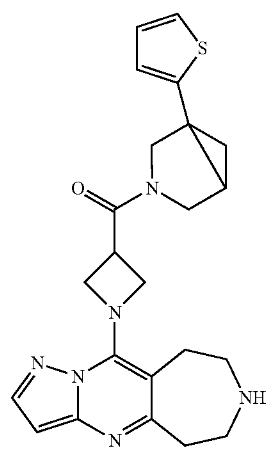 [SMILES: O=C(C1CN(c2c3c(nc4ccnn24)CCNCC3)C1)N1CC2CC2(c2cccs2)C1] | 15 | TF | 435.4 [M + H]⁺ | 1.5 (G) |
| 31.232 | 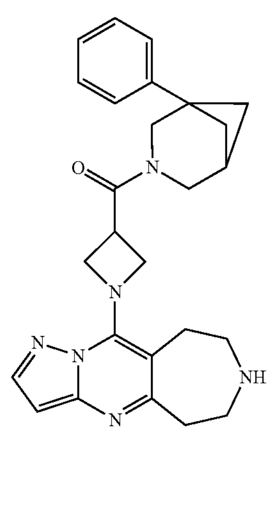 [SMILES: O=C(C1CN(c2c3c(nc4ccnn24)CCNCC3)C1)N1CC2CC(c3ccccc3)(C2)C1] | 43 | TF | 443.5 [M + H]⁺ | 1.56 (G) |

TABLE 14-continued

| Example | Structure | Yield of final step (%) | Salt type | Mass spec result | HPLC retention time (method) |
| --- | --- | --- | --- | --- | --- |
| 31.233 | 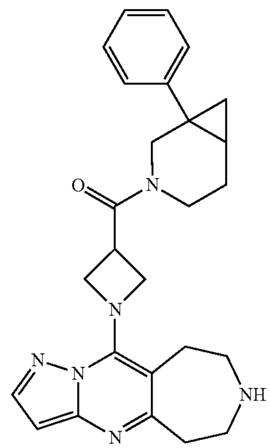 [SMILES: O=C(C1CN(c2c3c(nc4ccnn24)CCNCC3)C1)N1CCC2CC2(c2ccccc2)C1] | 22 | TF | 443.4 [M + H]+ | 1.56 (G) |
| 31.234 | 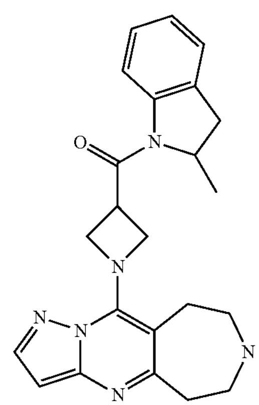 [SMILES: CC1Cc2ccccc2N1C(=O)C1CN(c2c3c(nc4ccnn24)CCNCC3)C1] | 60 | BS | 403 [M + H]+ | 1.17 (M) |
| 31.235 | 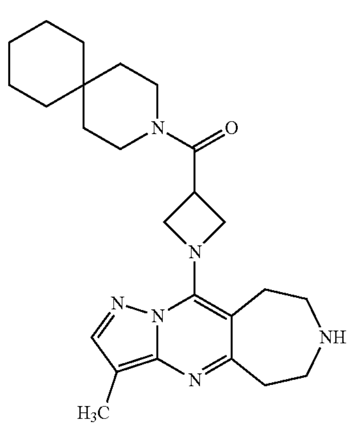 [SMILES: Cc1cnn2c(N3CC(C(=O)N4CCC5(CCCCC5)CC4)C3)c3c(nc12)CCNCC3] | 58 | TF | 437.5 [M + H]+ | 1.64 (F) |

TABLE 14-continued

| Example | Structure | Yield of final step (%) | Salt type | Mass spec result | HPLC retention time (method) |
|---|---|---|---|---|---|
| 31.236 | 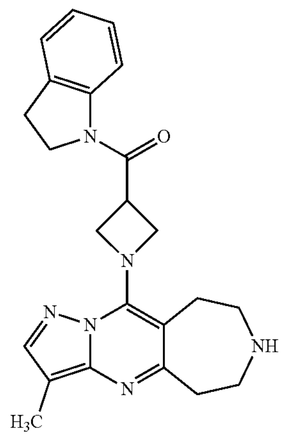 [SMILES: Cc1cnn2c(N3CC(C(=O)N4CCc5ccccc54)C3)c3c(nc12)CCNCC3] | 47 | TF | 403.2 [M + H]⁺ | 1.51 (F) |
| 31.237 | 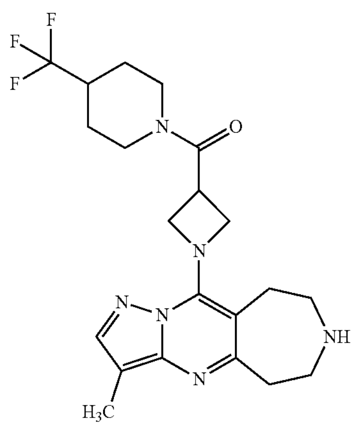 [SMILES: Cc1cnn2c(N3CC(C(=O)N4CCC(C(F)(F)F)CC4)C3)c3c(nc12)CCNCC3] | 43 | TF | 437.2 [M + H]⁺ | 1.5 (F) |
| 31.238 | 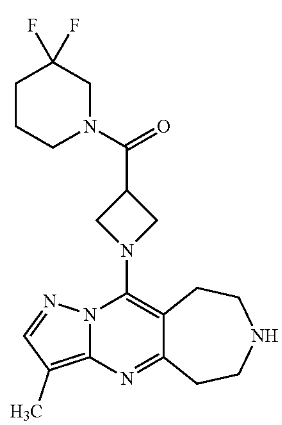 [SMILES: Cc1cnn2c(N3CC(C(=O)N4CCCC(F)(F)C4)C3)c3c(nc12)CCNCC3] | 31 | TF | 405.2 [M + H]⁺ | 1.41 (F) |

TABLE 14-continued

| Example | Structure | Yield of final step (%) | Salt type | Mass spec result | HPLC retention time (method) |
| --- | --- | --- | --- | --- | --- |
| 31.239 | 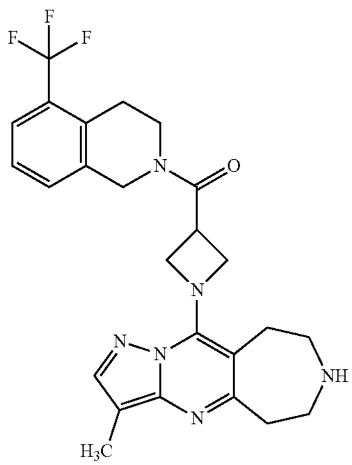 [SMILES: Cc1cnn2c(N3CC(C(=O)N4CCc5c(cccc5C(F)(F)F)C4)C3)c3c(nc12)CCNCC3] | 32 | TF | 485.2 [M + H]⁺ | 1.62 (F) |
| 31.240 | 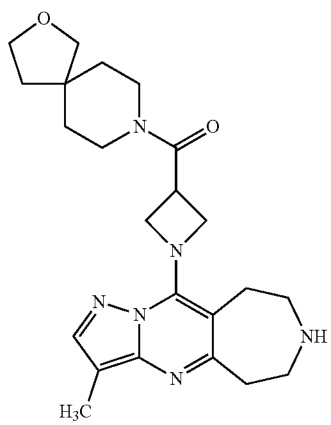 [SMILES: Cc1cnn2c(N3CC(C(=O)N4CCC5(CCOC5)CC4)C3)c3c(nc12)CCNCC3] | 31 | TF | 425.2 [M + H]⁺ | 1.34 (F) |
| 31.241 | 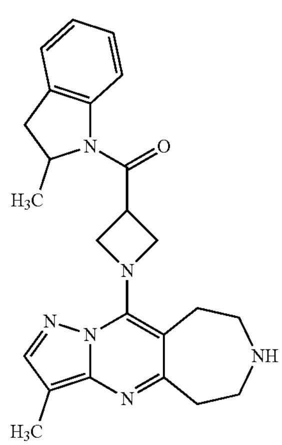 [SMILES: Cc1cnn2c(N3CC(C(=O)N4c5ccccc5CC4C)C3)c3c(nc12)CCNCC3] | 35 | TF | 417.2 [M + H]⁺ | 1.55 (F) |

TABLE 14-continued

| Example | Structure | Yield of final step (%) | Salt type | Mass spec result | HPLC retention time (method) |
|---|---|---|---|---|---|
| 31.242 | 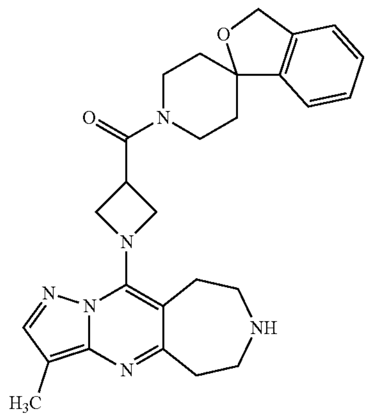 [SMILES: Cc1cnn2c(N3CC(C(=O)N4CCC5(CC4)OCc4ccccc45)C3)c3c(nc12)CCNCC3] | 19 | TF | 473.2 [M + H]⁺ | 1.54 (F) |
| 31.243 | 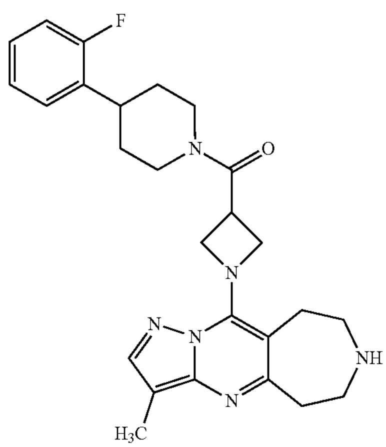 [SMILES: Cc1cnn2c(N3CC(C(=O)N4CCC(c5ccccc5F)CC4)C3)c3c(nc12)CCNCC3] | 42 | TF | 463.2 [M + H]⁺ | 1.6 (F) |
| 31.244 | 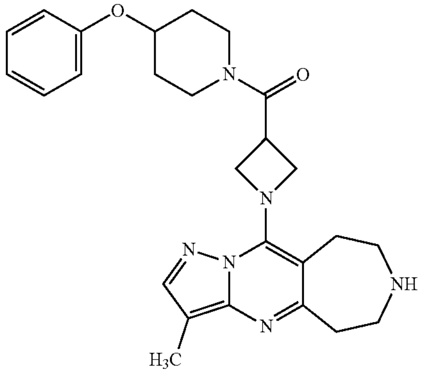 [SMILES: Cc1cnn2c(N3CC(C(=O)N4CCC(Oc5ccccc5)CC4)C3)c3c(nc12)CCNCC3] | 43 | TF | 461.2 [M + H]⁺ | 1.58 (F) |

TABLE 14-continued

| Example | Structure | Yield of final step (%) | Salt type | Mass spec result | HPLC retention time (method) |
|---|---|---|---|---|---|
| 31.245 | 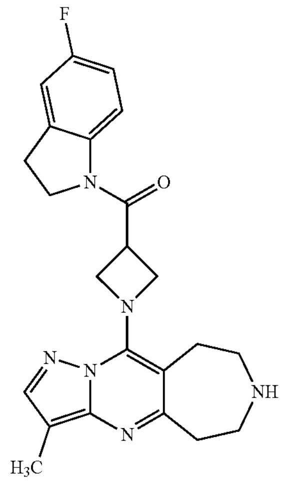 [SMILES: Cc1cnn2c(N3CC(C(=O)N4CCc5cc(F)ccc54)C3)c3c(nc12)CCNCC3] | 56 | TF | 421.2 [M + H]+ | 1.53 (F) |
| 31.246 | 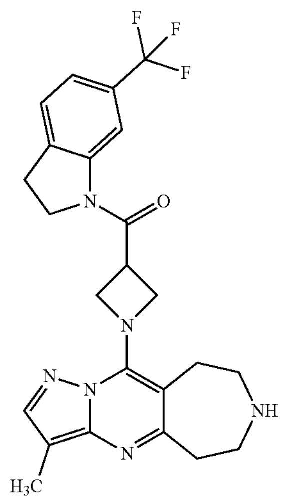 [SMILES: Cc1cnn2c(N3CC(C(=O)N4CCc5ccc(C(F)(F)F)cc54)C3)c3c(nc12)CCNCC3] | 46 | TF | 471.4 [M + H]+ | 1.63 (F) |
| 31.247 | 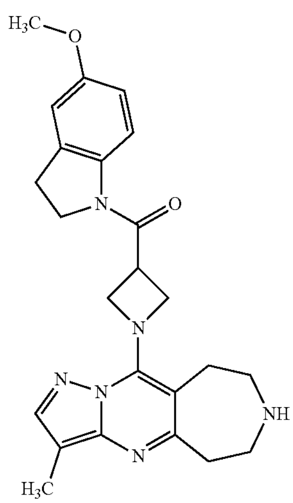 [SMILES: COc1ccc2c(c1)CCN2C(=O)C1CN(c2c3c(nc4c(C)cnn24)CCNCC3)C1] | 54 | TF | 433.2 [M + H]+ | 1.5 (F) |

TABLE 14-continued

| Example | Structure | Yield of final step (%) | Salt type | Mass spec result | HPLC retention time (method) |
|---|---|---|---|---|---|
| 31.248 | 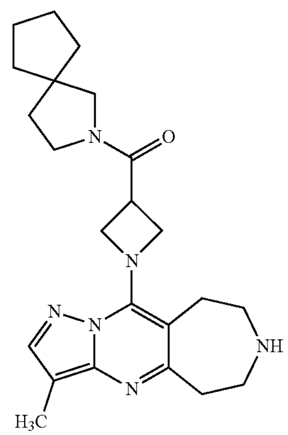 [SMILES: Cc1cnn2c(N3CC(C(=O)N4CCC5(CCCC5)C4)C3)c3c(nc12)CCNCC3] | 64 | TF | 409.2 [M + H]+ | 1.52 (F) |
| 31.249 | 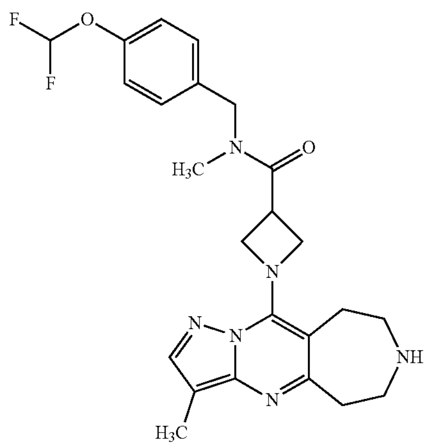 [SMILES: Cc1cnn2c(N3CC(C(=O)N(C)Cc4ccc(OC(F)F)cc4)C3)c3c(nc12)CCNCC3] | 17 | TF | 471.2 [M + H]+ | 1.56 (F) |
| 31.250 | 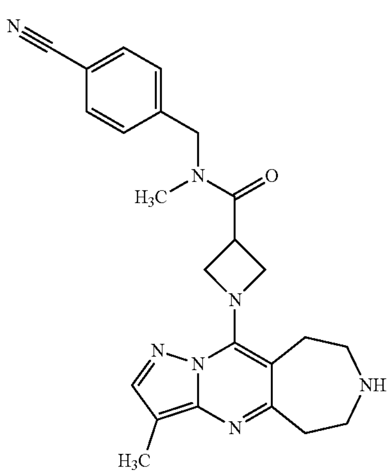 [SMILES: Cc1cnn2c(N3CC(C(=O)N(C)Cc4ccc(C#N)cc4)C3)c3c(nc12)CCNCC3] | 38 | TF | 430.2 [M + H]+ | 1.46 (F) |

Route 32

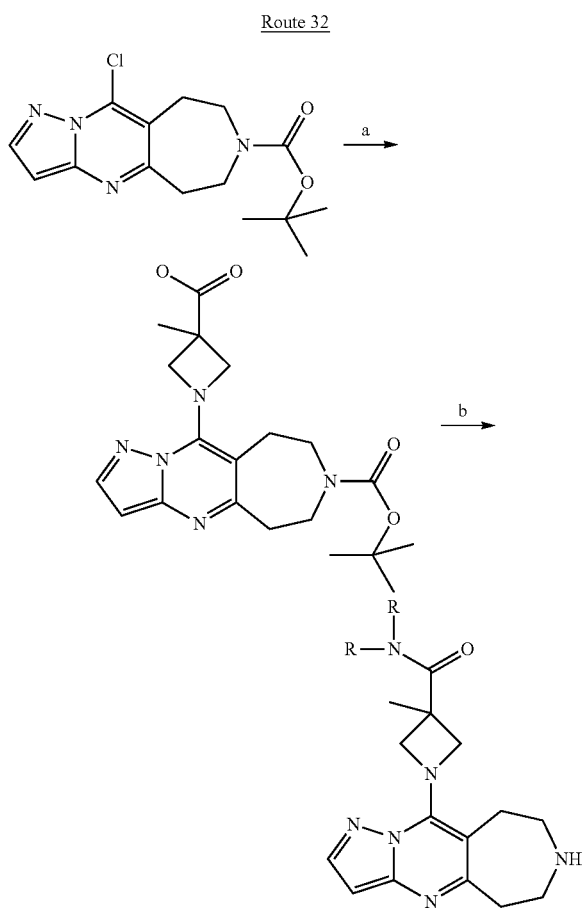

Example 32

32a 10-(3-Carboxy-3-methyl-azetidin-1-yl)-5,6,8,9-tetrahydro-1,4,7,10a-tetraaza-cyclohepta[f]indene-7-carboxylic acid tert-butyl ester 3.5 g (10.8 mmol) 10-Chloro-5,6,8,9-tetrahydro-1,4,7,10a-tetraaza-cyclohepta[f]indene-7-carboxylic acid tert-butyl ester, 2 g (12 mmol) 3-methyl-azetidine-3-carboxylic acid methyl ester hydrochloride and 6 mL (3.9 eq) triethyl amine were suspended in 100 mL NMP. The reaction mixture was stirred at 120° C. over night. After cooling down, the solvent was evaporated and the residue was purified by prep. HPLC to yield the corresponding ester as an intermediate (18% of theory).

0.82 g (1.96 mmol) of the ester intermediate were subsequently dissolved in 10 mL THF and 15 mL water and were treated with 82 mg (1.96 mmol) LiOH. The reaction mixture was stirred at room temperature for 2 h. The solvents were removed by distillation and lyophylisation to yield the lithium salt quantitative yield (0.83 g)

$C_{20}H_{26}N_5O_4$*Li: 407.4
predicted: Molecular ion (M+H)$^+$: 402 (protonated acid)
observed: Molecular ion (M+H)$^+$: 402

32b (General Route)

10-(3-Carboxy-3-methyl-azetidin-1-yl)-5,6,8,9-tetrahydro-1,4,7,10a-tetraaza-cyclohepta[f]indene-7-carboxylic acid tert-butyl ester (1 eq) was suspended in 1 mL DMF. DIPEA (1.5 eq) and TBTU (1.1 eq) were added and the reaction mixture was stirred for 30 min. The amine (1 eq) was added and the reaction was stirred at room temperature till no further conversion was observed. The intermediate was purified by prep. HPLC and the fractions were freeze-dried. The residue was suspended in 1 mL DCM/TFA 1/1 and stirred for 2 h. The solvent was evaporated to yield the final product. Products with a purity lower than 90%, were purified again by prep. HPLC.

TABLE 15

| Example | Structure | Yield of final step (%) | Salt type | Mass spec result | HPLC retention time (method) |
|---|---|---|---|---|---|
| 32.1 | 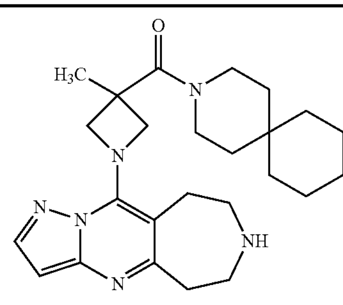 | 2 | TF | 460.2 [M + H]$^+$ | 1.63 (F) |
| 32.2 | 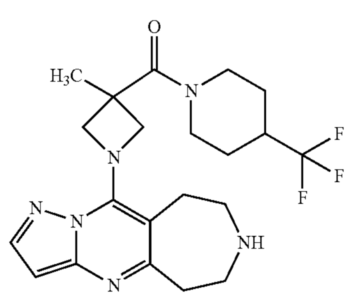 [SMILES: CC1(C(=O)N2CCC(C(F)(F)F)CC2)CN(c2c3c(nc4ccnn24)CCNCC3)C1] | 10 | TF | 437.2 [M + H]$^+$ | 1.49 (F) |

TABLE 15-continued

| Example | Structure | Yield of final step (%) | Salt type | Mass spec result | HPLC retention time (method) |
|---|---|---|---|---|---|
| 32.3 | 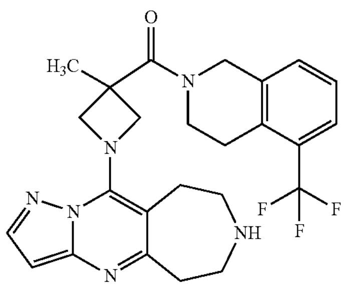 [SMILES: CC1(C(=O)N2CCc3c(cccc3C(F)(F)F)C2)CN(c2c3c(nc4ccnn24)CCNCC3)C1] | 10 | TF | 485.2 [M + H]+ | 1.62 (F) |
| 32.4 | 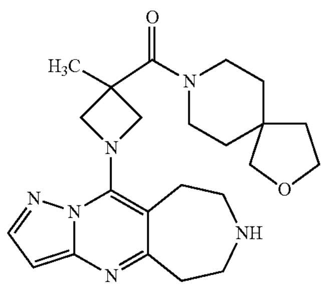 [SMILES: CC1(C(=O)N2CCC3(CCOC3)CC2)CN(c2c3c(nc4ccnn24)CCNCC3)C1] | 2 | TF | 425.2 [M + H]+ | 1.32 (F) |
| 32.5 | 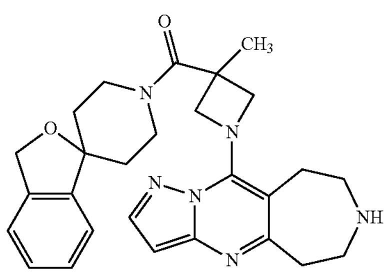 [SMILES: CC1(C(=O)N2CCC3(CC2)OCc2ccccc23)CN(c2c3c(nc4ccnn24)CCNCC3)C1] | 10 | TF | 473.2 [M + H]+ | 1.54 (F) |
| 32.6 | 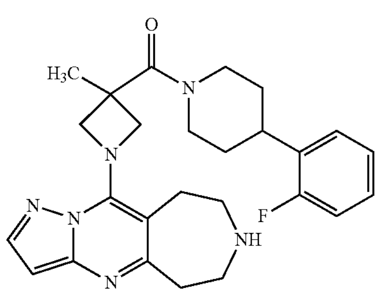 [SMILES: CC1(C(=O)N2CCC(c3ccccc3F)CC2)CN(c2c3c(nc4ccnn24)CCNCC3)C1] | 10 | TF | 463.2 [M + H]+ | 1.59 (F) |
| 32.7 | 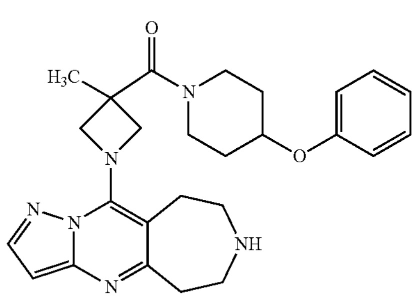 [SMILES: CC1(C(=O)N2CCC(Oc3ccccc3)CC2)CN(c2c3c(nc4ccnn24)CCNCC3)C1] | 4 | TF | 460.2 [M + H]+ | 1.57 (F) |

TABLE 15-continued

| Example | Structure | Yield of final step (%) | Salt type | Mass spec result | HPLC retention time (method) |
|---|---|---|---|---|---|
| 32.8 | 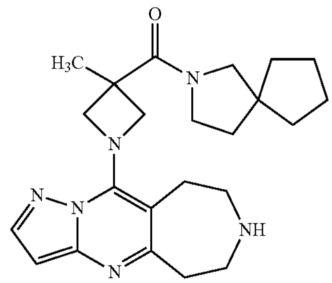 [SMILES: CC1(C(=O)N2CCC3(CCCC3)C2)CN(c2c3c(nc4ccnn24)CCNCC3)C1] | 11 | TF | 409.2 [M + H]+ | 1.53 (F) |

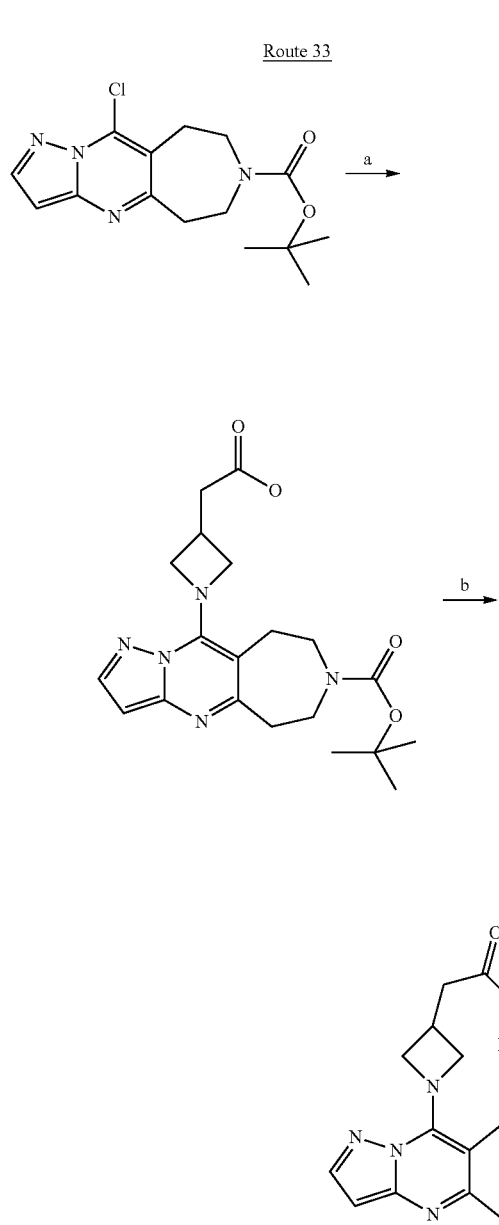

Route 33

Example 33

33a 10-(3-Carboxymethyl-azetidin-1-yl)-5,6,8,9-tetrahydro-1,4,7,10a-tetraaza-cyclohepta[f]indene-7-carboxylic acid tert-butyl ester

2.5 g (7.75 mmol) 10-Chloro-5,6,8,9-tetrahydro-1,4,7,10a-tetraaza-cyclohepta[f]indene-7-carboxylic acid tert-butyl ester, 1.1 g (9.1 mmol) azetidin-3-yl-acetic acid and 3 mL (17.4 mmol) DIPEA were suspended in 18 mL ethanol. The reaction mixture was stirred at 75° C. over night. The solvent was evaporated and the residue was taken up in EtOAc and water and was acidified using a $KHSO_4$ solution. The organic layer was dried ($Na_2SO_4$) and concentrated. The residue was purified by prep. HPLC to yield the corresponding acid (72% of theory).

$C_{20}H_{26}N_5O_4$: 401.5
predicted: Molecular ion (M+H)+: 402 observed: Molecular ion (M+H)+: 402

33b (General Route)
10-(3-Carboxymethyl-azetidin-1-yl)-5,6,8,9-tetrahydro-1,4,7,10a-tetraaza-cyclohepta[f]indene-7-carboxylic acid tert-butyl ester (1 eq) was suspended in 1 mL DMF. DIPEA (1.5 eq) and TBTU (1.1 eq) were added and the reaction mixture was stirred for 30 min. The amine (1 eq) was added and the reaction was stirred at room temperature till no further conversion was observed. The intermediate was purified by prep. HPLC and the fractions were freeze-dried. The residue was suspended in 1 mL DCM/TFA 1/1 and stirred for 2 h. The solvent was evaporated to yield the final product. Products with a purity lower than 90%, were purified again by prep. HPLC.

TABLE 16
| Example | Structure | Yield of final step % | Salt type | Mass spec result | HPLC retention time (method) |
|---------|-----------|----------------------|-----------|------------------|------------------------------|
| 33.1 | 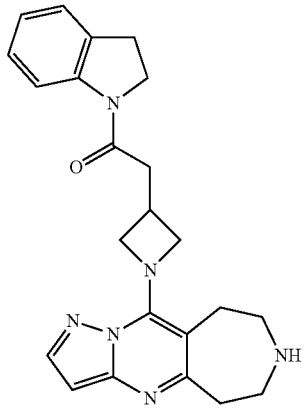 [SMILES: O=C(CC1CN(c2c3c(nc4ccnn24)CCNCC3)C1)N1CCc2ccccc21] | 21 | TF | 403.2 [M + H]⁺ | 1.5 (F) |
| 33.2 | 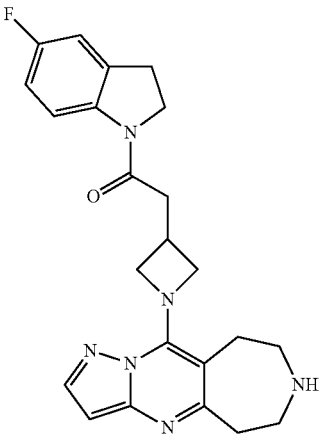 [SMILES: O=C(CC1CN(c2c3c(nc4ccnn24)CCNCC3)C1)N1CCc2cc(F)ccc21] | 21 | TF | 421.2 [M + H]⁺ | 1.52 (F) |
| 33.3 | 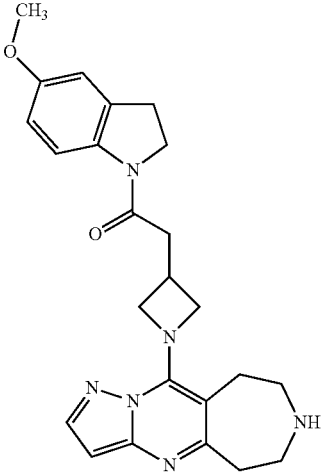 [SMILES: COc1ccc2c(c1)CCN2C(=O)CC1CN(c2c3c(nc4ccnn24)CCNCC3)C1] | 1 | TF | 433.2 [M + H]⁺ | 1.48 (F) |

Route 34

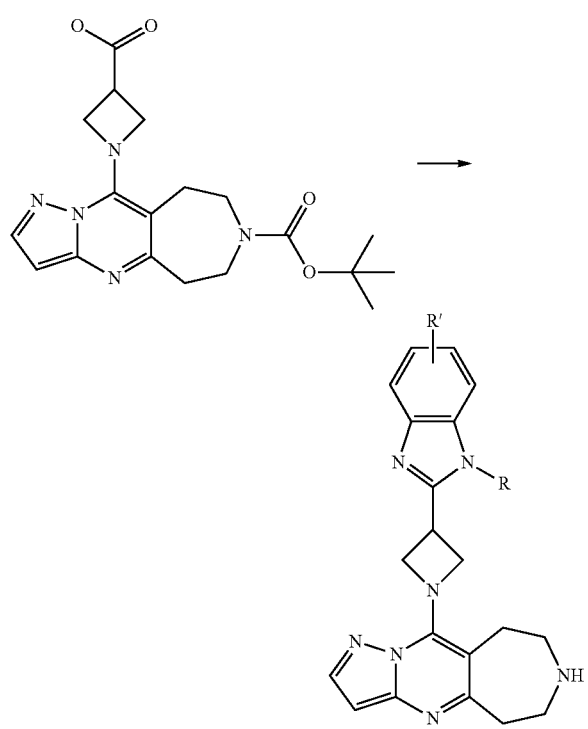

Example 34

General Route 10-(3-Carboxy-azetidin-1-yl)-5,6,8,9-tetrahydro-1,4,7,10a-tetraaza-cyclohepta[f]indene-7-carboxylic acid tert-butyl ester (1 eq), TBTU (1.1 eq) and DIPEA (1.5 eq) were suspended in DMF. This mixture was added to the corresponding diamine at room temperature.

In case the phenylen diamine was not available, the corresponding 2-nitro-aminoaryl derivative was used and its nitro group was reduced to the free amine prior to reacting it with the acid in order to form the amide. The reduction of the nitro group was conducted in MeOH/THF (1/1) together with 10 mol % Pd/C and hydrochloric acid under a hydrogen atmosphere at 3 bar for 5 h.

Subsequently the reaction mixture (diamine and acid) was stirred until no further conversion could be observed. Purification using prep. HPLC yielded the corresponding amide as an intermediate. The intermediate was then taken up in glacial acetic acid and was stirred at elevated temperature 80-120° C. until no further conversion was observed. After removal of the solvent the residue was treated with DCM/TFA 1/1 (containing 5% $H_2O$) and stirred for 1 h at room temperature. After purification using prep. HPLC one could obtain the desired product.

TABLE 17

| Example | Structure | overall yield (%) | Salt type | Mass spec result | HPLC retention time (method) |
|---|---|---|---|---|---|
| 34 | 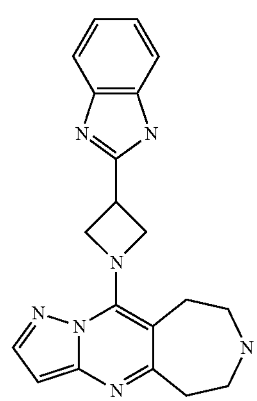 [SMILES: c1ccc2[nH]c(C3CN(c4c5c(nc6ccnn46)CCNCC5)C3)nc2c1] | 65 | TF | 360 $[M + H]^+$ | 1.48 (J) |

TABLE 17-continued
| Example | Structure | overall yield (%) | Salt type | Mass spec result | HPLC retention time (method) |
|---|---|---|---|---|---|
| 34.1 | 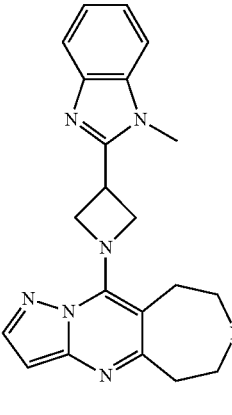 | 65 | TF | 374 [M + H]⁺ | 1.46 (J) |
| 34.2 | 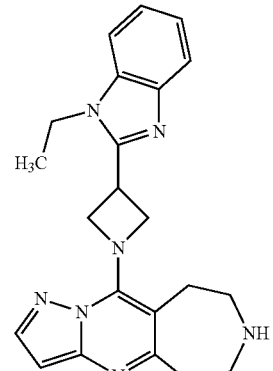 | 21 | TF | 388.1 [M + H]⁺ | 1.22 (H) |
| 34.3 | 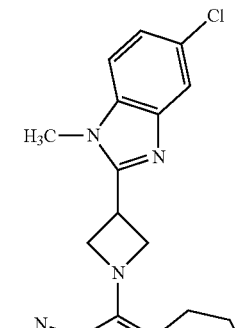 | 17 | TF | 409 [M + H]⁺ | 1.32 (H) |

TABLE 17-continued

| Example | Structure | overall yield (%) | Salt type | Mass spec result | HPLC retention time (method) |
|---|---|---|---|---|---|
| 34.4 | 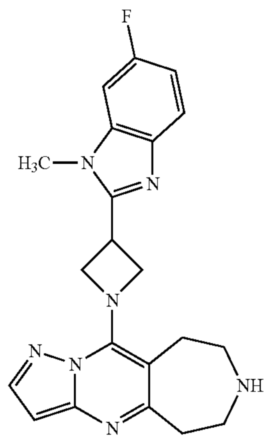 [SMILES: Cn1c(C2CN(c3c4c(nc5ccnn35)CCNCC4)C2)nc2ccc(F)cc21] | 15 | TF | 392.1 [M + H]⁺ | 1.24 (H) |
| 34.5 | 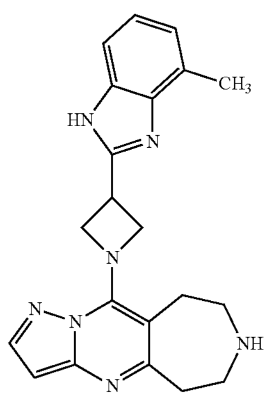 [SMILES: Cc1cccc2[nH]c(C3CN(c4c5c(nc6ccnn46)CCNCC5)C3)nc12] | 6 | BS | 374.1 [M + H]⁺ | 1.23 (H) |
| 34.6 | 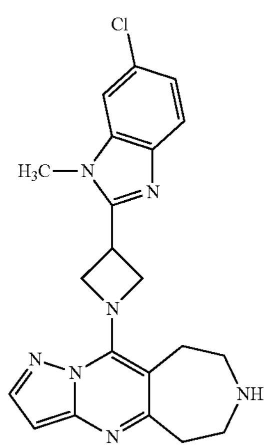 [SMILES: Cn1c(C2CN(c3c4c(nc5ccnn35)CCNCC4)C2)nc2ccc(Cl)cc21] | 19 | TF | 409 [M + H]⁺ | 1.33 (H) |

TABLE 17-continued
| Example | Structure | overall yield (%) | Salt type | Mass spec result | HPLC retention time (method) |
|---|---|---|---|---|---|
| 34.7 | 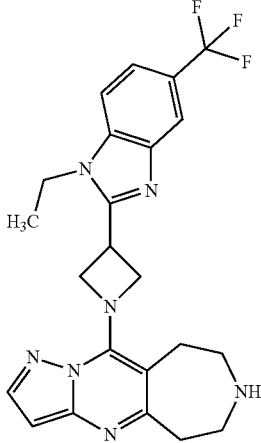 [SMILES: CCn1c(C2CN(c3c4c(nc5ccnn35)CCNCC4)C2)nc2cc(C(F)(F)F)ccc21] | 31 | TF | 456.1 [M + H]⁺ | 1.47 (H) |
| 34.8 | 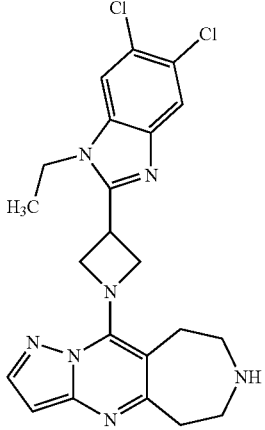 [SMILES: CCn1c(C2CN(c3c4c(nc5ccnn35)CCNCC4)C2)nc2cc(Cl)c(Cl)cc21] | 11 | TF | 457.1 [M + H]⁺ | 1.5 (H) |
| 34.9 | 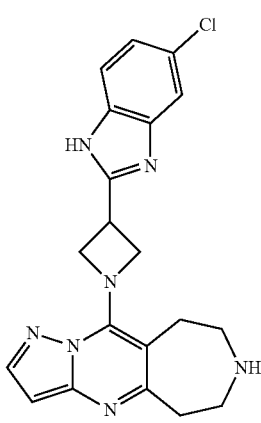 | 20 | TF | 395 [M + H]⁺ | 1.29 (H) |

TABLE 17-continued

| Example | Structure | overall yield (%) | Salt type | Mass spec result | HPLC retention time (method) |
| --- | --- | --- | --- | --- | --- |
| 34.10 | 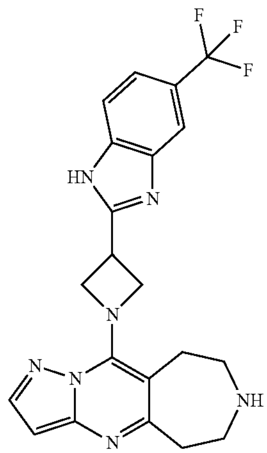 [SMILES: FC(F)(F)c1ccc2[nH]c(C3CN(c4c5c(nc6ccnn46)CCNCC5)C3)nc2c1] | 15 | TF | 428.2 [M + H]⁺ | 1.39 (H) |
| 34.11 | 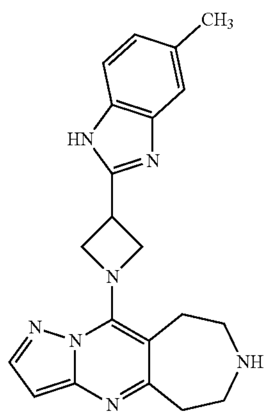 [SMILES: Cc1ccc2[nH]c(C3CN(c4c5c(nc6ccnn46)CCNCC5)C3)nc2c1] | 20 | TF | 374.1 [M + H]⁺ | 1.25 (H) |
| 34.12 | 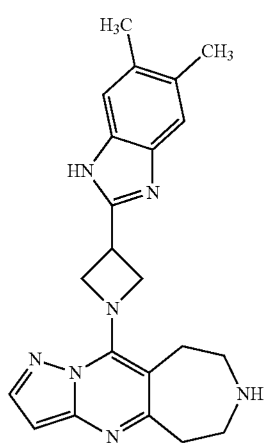 [SMILES: Cc1cc2nc(C3CN(c4c5c(nc6ccnn46)CCNCC5)C3)[nH]c2cc1C] | 15 | TF | 388.1 [M + H]⁺ | 1.3 (H) |

TABLE 17-continued

| Example | Structure | overall yield (%) | Salt type | Mass spec result | HPLC retention time (method) |
|---|---|---|---|---|---|
| 34.13 | 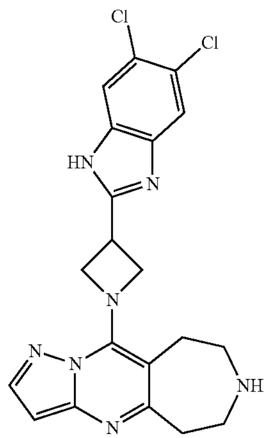 [SMILES: Clc1cc2nc(C3CN(c4c5c(nc6ccnn46)CCNCC5)C3)[nH]c2cc1Cl] | 8 | TF | 429.2 [M + H]⁺ | 1.42 (H) |
| 34.14 | 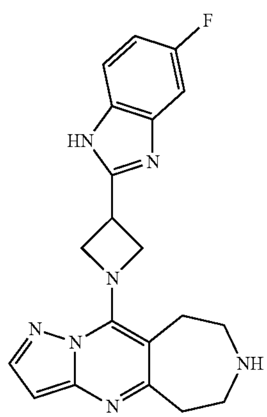 [SMILES: Fc1ccc2[nH]c(C3CN(c4c5c(nc6ccnn46)CCNCC5)C3)nc2c1] | 23 | TF | 378.2 [M + H]⁺ | 1.22 (H) |
| 34.15 | 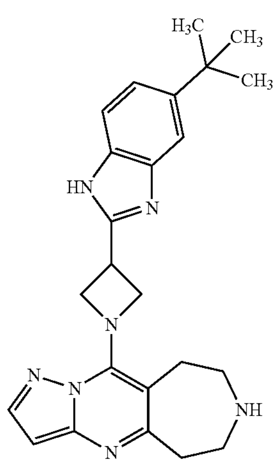 [SMILES: CC(C)(C)c1ccc2[nH]c(C3CN(c4c5c(nc6ccnn46)CCNCC5)C3)nc2c1] | 14 | TF | 416.2 [M + H]⁺ | 1.39 (H) |

TABLE 17-continued
| Example | Structure | overall yield (%) | Salt type | Mass spec result | HPLC retention time (method) |
|---|---|---|---|---|---|
| 34.16 | 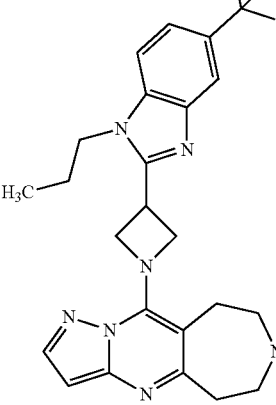 | 19 | TF | 470.6 [M + H]⁺ | 1.52 (H) |
| 34.17 | 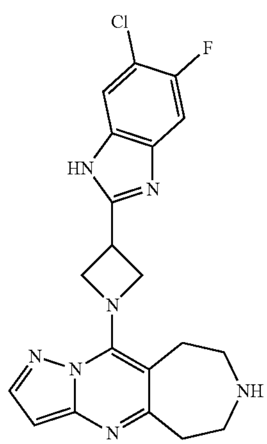 [SMILES: Fc1cc2nc(C3CN(c4c5c(nc6ccnn46)CCNCC5)C3)[nH]c2cc1Cl] | 30 | TF | 413 [M + H]⁺ | 1.36 (H) |
| 34.18 | 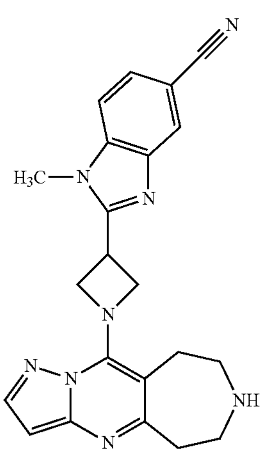 [SMILES: Cn1c(C2CN(c3c4c(nc5ccnn35)CCNCC4)C2)nc2cc(C#N)ccc21] | 13 | TF | 399.1 [M + H]⁺ | 1.3 (H) |

TABLE 17-continued

| Example | Structure | overall yield (%) | Salt type | Mass spec result | HPLC retention time (method) |
|---|---|---|---|---|---|
| 34.19 | 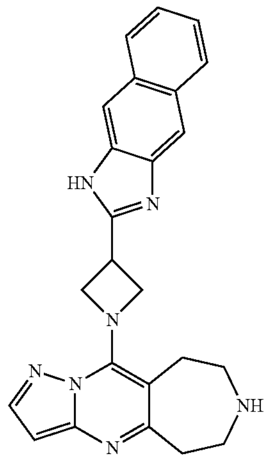 [SMILES: c1ccc2cc3[nH]c(C4CN(c5c6c(nc7ccnn57)CCNCC6)C4)nc3cc2c1] | 9 | TF | 410.1 [M + H]⁺ | 1.33 (H) |
| 34.20 | 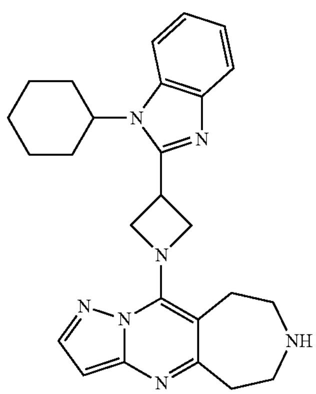 [SMILES: c1ccc2c(c1)nc(C1CN(c3c4c(nc5ccnn35)CCNCC4)C1)n2C1CCCCC1] | 14 | TF | 442.2 [M + H]⁺ | 1.39 (H) |
| 34.21 | 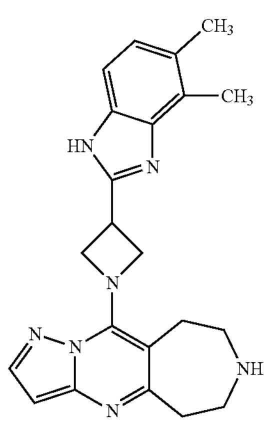 [SMILES: Cc1ccc2[nH]c(C3CN(c4c5c(nc6ccnn46)CCNCC5)C3)nc2c1C] | 24 | TF | 388.1 [M + H]⁺ | 1.29 (H) |

TABLE 17-continued
| Example | Structure | overall yield (%) | Salt type | Mass spec result | HPLC retention time (method) |
|---|---|---|---|---|---|
| 34.22 | 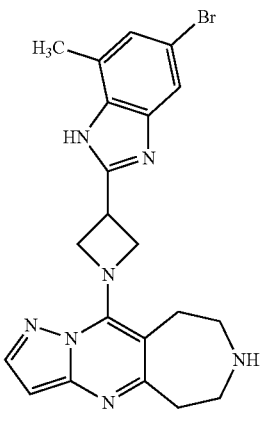 [SMILES: Cc1cc(Br)cc2nc(C3CN(c4c5c(nc6ccnn46)CCNCC5)C3)[nH]c12] | 17 | TF | 454.1 [M + H]⁺ | 1.35 (H) |
| 34.23 | 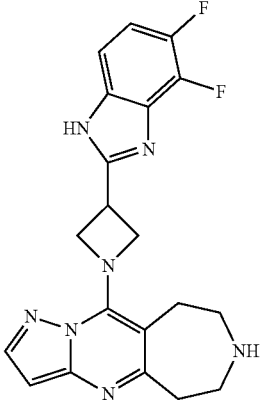 [SMILES: Fc1ccc2[nH]c(C3CN(c4c5c(nc6ccnn46)CCNCC5)C3)nc2c1F] | 40 | TF | 396.1 [M + H]⁺ | 1.34 (H) |
| 34.24 | 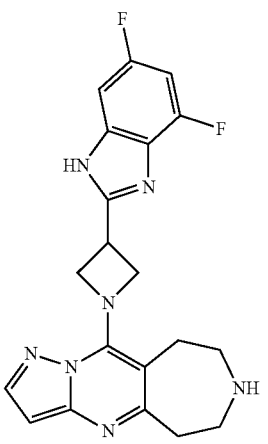 [SMILES: Fc1cc(F)c2nc(C3CN(c4c5c(nc6ccnn46)CCNCC5)C3)[nH]c2c1] | 26 | TF | 396.1 [M + H]⁺ | 1.34 (H) |

TABLE 17-continued

| Example | Structure | overall yield (%) | Salt type | Mass spec result | HPLC retention time (method) |
|---|---|---|---|---|---|
| 34.25 | 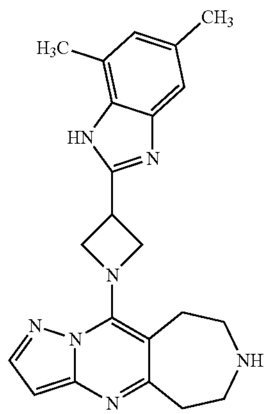 [SMILES: Cc1cc(C)c2[nH]c(C3CN(c4c5c(nc6ccnn46)CCNCC5)C3)nc2c1] | 11 | TF | 388.1 [M + H]⁺ | 1.29 (H) |
| 34.26 | 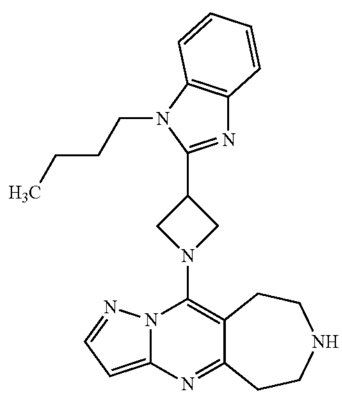 [SMILES: CCCCn1c(C2CN(c3c4c(nc5ccnn35)CCNCC4)C2)nc2ccccc21] | 24 | TF | 416.2 [M + H]⁺ | 1.34 (H) |
| 34.27 | 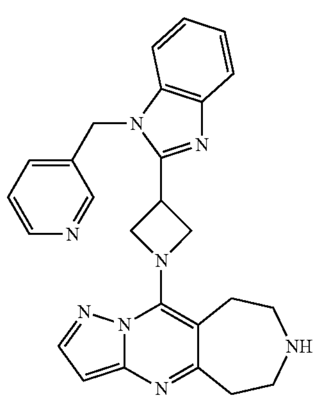 [SMILES: c1cncc(Cn2c(C3CN(c4c5c(nc6ccnn46)CCNCC5)C3)nc3ccccc32)c1] | 32 | TF | 451.2 [M + H]⁺ | 1.17 (H) |

TABLE 17-continued

| Example | Structure | overall yield (%) | Salt type | Mass spec result | HPLC retention time (method) |
|---|---|---|---|---|---|
| 34.28 | 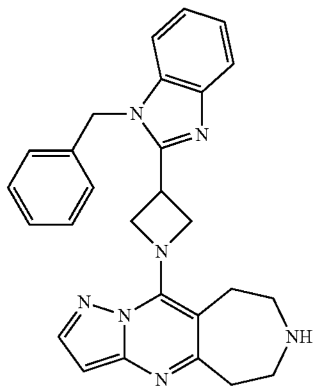 [SMILES: c1ccc(Cn2c(C3CN(c4c5c(nc6ccnn46)CCNCC5)C3)nc3ccccc32)cc1] | 18 | TF | 450.2 [M + H]+ | 1.38 (H) |
| 34.29 | 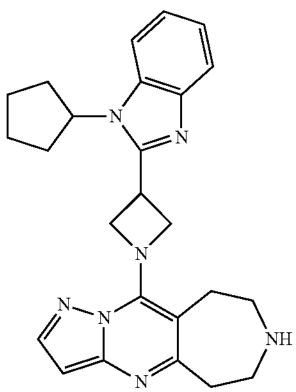 [SMILES: c1ccc2c(c1)nc(C1CN(c3c4c(nc5ccnn35)CCNCC4)C1)n2C1CCCC1] | 20 | TF | 428.2 [M + H]+ | 1.34 (H) |
| 34.30 | 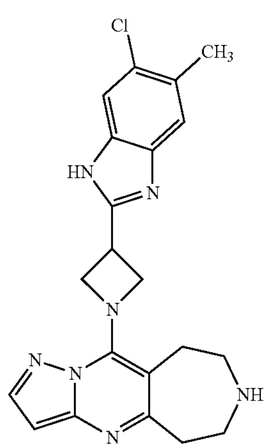 [SMILES: Cc1cc2nc(C3CN(c4c5c(nc6ccnn46)CCNCC5)C3)[nH]c2cc1Cl] | 20 | TF | 408.1 [M + H]+ | 1.34 (H) |

TABLE 17-continued

| Example | Structure | overall yield (%) | Salt type | Mass spec result | HPLC retention time (method) |
|---|---|---|---|---|---|
| 34.31 | 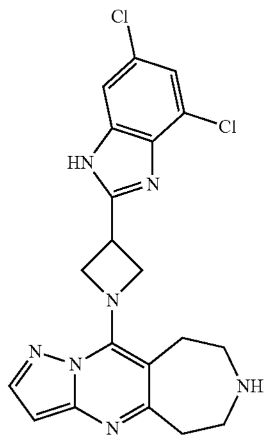 [SMILES: Clc1cc(Cl)c2nc(C3CN(c4c5c(nc6ccnn46)CCNCC5)C3)[nH]c2c1] | 9 | TF | 428.1 [M + H]⁺ | 1.44 (H) |
| 34.32 | 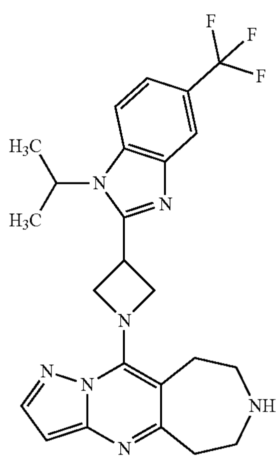 [SMILES: CC(C)n1c(C2CN(c3c4c(nc5ccnn35)CCNCC4)C2)nc2cc(C(F)(F)F)ccc21] | 38 | TF | 471 [M + H]⁺ | 1.51 (H) |
| 34.33 | 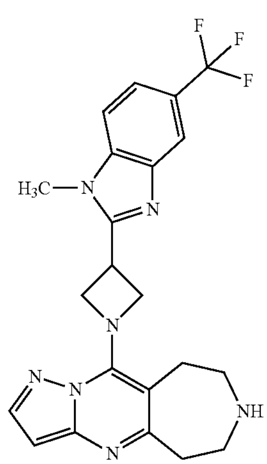 [SMILES: Cn1c(C2CN(c3c4c(nc5ccnn35)CCNCC4)C2)nc2cc(C(F)(F)F)ccc21] | 27 | TF | 443 [M + H]⁺ | 1.43 (H) |

TABLE 17-continued
| Example | Structure | overall yield (%) | Salt type | Mass spec result | HPLC retention time (method) |
|---|---|---|---|---|---|
| 34.34 | 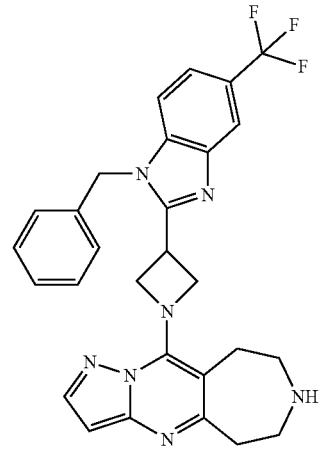 [SMILES: FC(F)(F)c1ccc2c(c1)nc(C1CN(c3c4c(nc5ccnn35)CCNCC4)C1)n2Cc1ccccc1] | 10 | TF | 518.2 [M + H]⁺ | 1.59 (H) |
| 34.35 | 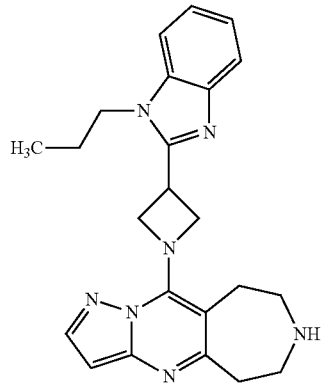 [SMILES: CCCn1c(C2CN(c3c4c(nc5ccnn35)CCNCC4)C2)nc2ccccc21] | 53 | TF | 402.2 [M + H]⁺ | 1.28 (H) |
| 34.36 | 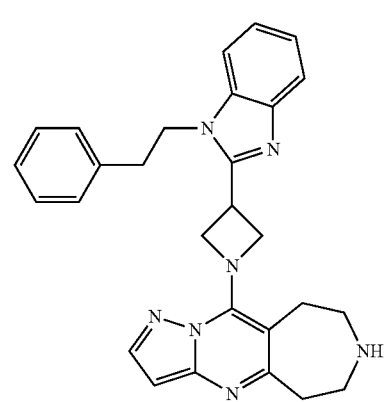 [SMILES: c1ccc(CCn2c(C3CN(c4c5c(nc6ccnn46)CCNCC5)C3)nc3ccccc32)cc1] | 17 | TF | 464.2 [M + H]⁺ | 1.38 (H) |

TABLE 17-continued

| Example | Structure | overall yield (%) | Salt type | Mass spec result | HPLC retention time (method) |
|---------|-----------|-------------------|-----------|------------------|------------------------------|
| 34.37 | 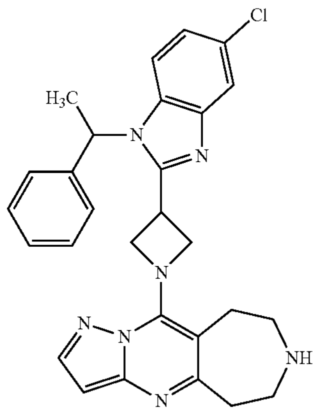 [SMILES: CC(c1ccccc1)n1c(C2CN(c3c4c(nc5ccnn35)CCNCC4)C2)nc2cc(Cl)ccc21] | 6 | TF | 499.1 [M + H]⁺ | 1.56 (H) |
| 34.38 | 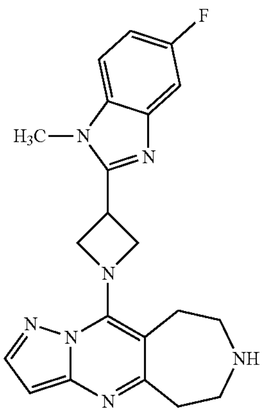 [SMILES: Cn1c(C2CN(c3c4c(nc5ccnn35)CCNCC4)C2)nc2cc(F)ccc21] | 51 | TF | 392.5 [M + H]⁺ | 1.41 (H) |
| 34.39 | 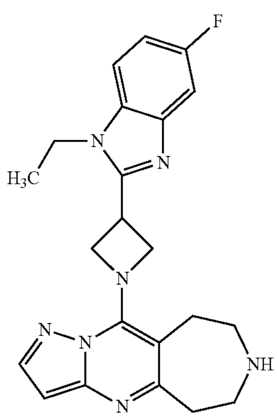 [SMILES: CCn1c(C2CN(c3c4c(nc5ccnn35)CCNCC4)C2)nc2cc(F)ccc21] | 51 | TF | 406.4 [M + H]⁺ | 1.45 (H) |

Example 35

10-[3-(4-Chloro-phenoxy)-azetidin-1-yl]-6,7,8,9-tetrahydro-5H-1,4,7,10a-tetraaza-cyclohepta[f]indene

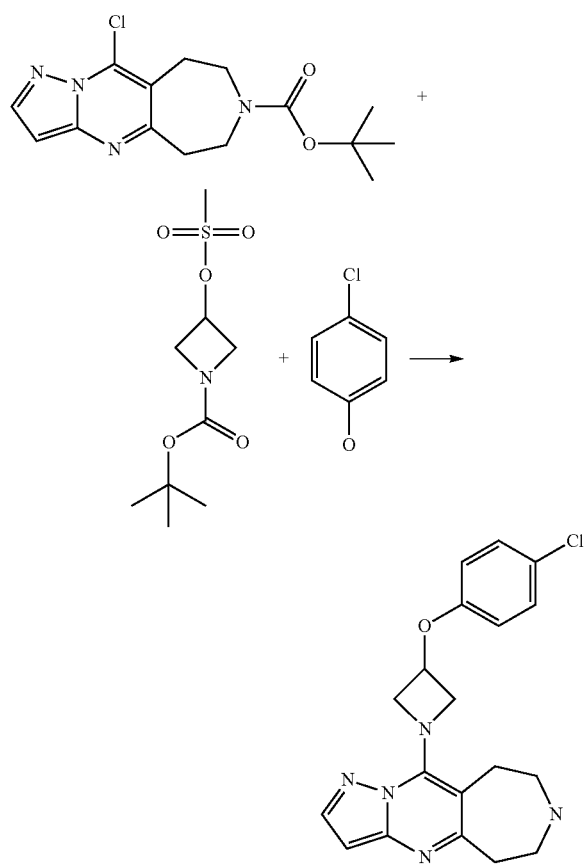

Route 35

27 mg (0.21 mmol) 4-Chlorophenole and 75 mg (0.23 mmol) $Cs_2(CO)_3$ were suspended in 1 mL DMA and the mixture was stirred for 30 min at room temperature. 50 mg (0.2 mmol) 3-Methanesulfonyloxy-azetidine-1-carboxylic acid tert-butyl ester in 1 mL DMA was added and stirring was continued over night at 80° C. The reaction mixture was filtered over basic aluminium oxide followed by washing with DMF/MeOH 9/1. The solvents were removed under reduced pressure and the residue dissolved in dichloromethane (1 mL) and was treated with 1.5 mL DCM/TFA 1/1. After 4 h the solvents were again removed. A mixture of 32 mg (0.1 mmol) 10-chloro-5,6,8,9-tetrahydro-1,4,7,10a-tetraaza-cyclohepta[f]indene-7-carboxylic acid tert-butyl ester in 1 mL EtOH and 0.053 mL (0.3 mmol) DIPEA was added and the reaction mixture was stirred at 80° C. over night. The solvent was removed and the residue was treated with 1 mL DCM/TFA 1/1 for 4 h followed by solvent removal. Finally the residue was purified by prep. HPLC to yield 10-[3-(4-chloro-phenoxy)-azetidin-1-yl]-6,7,8,9-tetrahydro-5H-1,4,7,10a-tetra-aza-cyclohepta[f]indene as its TFA salt after lyophilisation (14 mg, 29% of theory)

Yield: 14 mg (29% of theory)

$C_{19}H_{20}ClN_5O$ (M=369.86)

predicted: Molecular ion $(M+H)^+$: 370 observed: Molecular ion $(M+H)^+$: 370

HPLC-MS: 1.5 minutes (Method H)

TABLE 18

| Example | Structure | Overall yield (%) | Salt type | Mass spec result | HPLC retention time (method) |
|---|---|---|---|---|---|
| 35.1 | 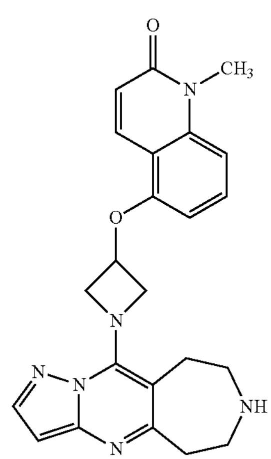 [SMILES: Cn1c(=O)ccc2c(OC3CN(c4c5c(nc6ccnn46)CCNCC5)C3)cccc21] | 16 | TF | 417.1 [M + H]⁺ | 1.33 (H) |

TABLE 18-continued

| Example | Structure | Overall yield (%) | Salt type | Mass spec result | HPLC retention time (method) |
|---|---|---|---|---|---|
| 35.2 | 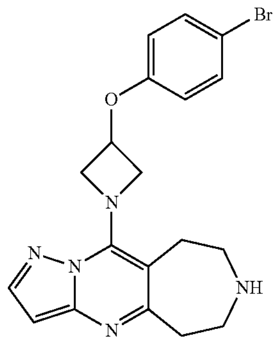 [SMILES: Brc1ccc(OC2CN(c3c4c(nc5ccnn35)CCNCC4)C2)cc1] | 24 | TF | 416 [M + H]+ | 1.51 (H) |
| 35.3 | 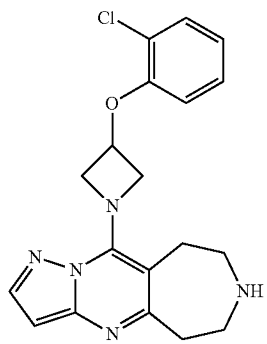 [SMILES: Clc1ccccc1OC1CN(c2c3c(nc4ccnn24)CCNCC3)C1] | 25 | TF | 370.1 [M + H]+ | 1.46 (H) |
| 35.4 | 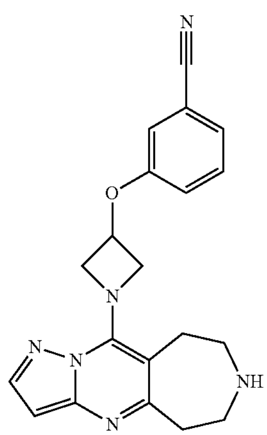 [SMILES: N#Cc1cccc(OC2CN(c3c4c(nc5ccnn35)CCNCC4)C2)c1] | 16 | TF | 361.1 [M + H]+ | 1.4 (H) |
| 35.5 | 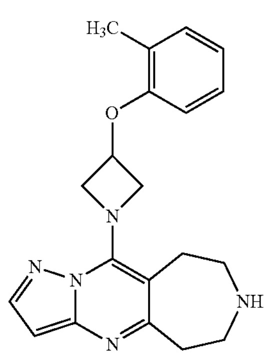 [SMILES: Cc1ccccc1OC1CN(c2c3c(nc4ccnn24)CCNCC3)C1] | 23 | TF | 350.2 [M + H]+ | 1.48 (H) |

TABLE 18-continued

| Example | Structure | Overall yield (%) | Salt type | Mass spec result | HPLC retention time (method) |
|---|---|---|---|---|---|
| 35.6 | 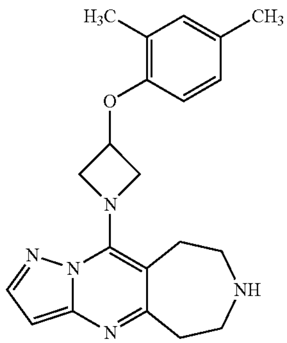 [SMILES: Cc1ccc(OC2CN(c3c4c(nc5ccnn35)CCNCC4)C2)c(C)c1] | 5 | TF | 364.2 [M + H]+ | 1.53 (H) |
| 35.7 | 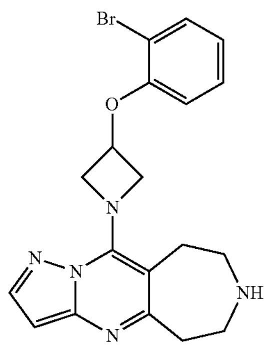 [SMILES: Brc1ccccc1OC1CN(c2c3c(nc4ccnn24)CCNCC3)C1] | 5 | TF | 416 [M + H]+ | 1.48 (H) |
| 35.8 | 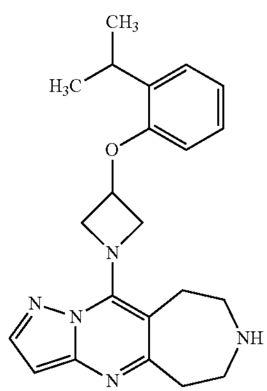 [SMILES: CC(C)c1ccccc1OC1CN(c2c3c(nc4ccnn24)CCNCC3)C1] | 1 | TF | 378.2 [M + H]+ | 1.57 (H) |
| 35.9 | 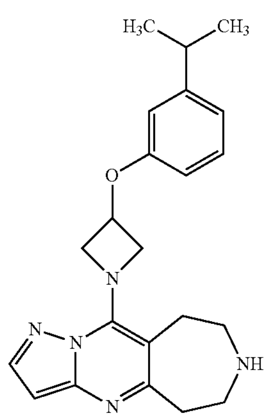 [SMILES: CC(C)c1cccc(OC2CN(c3c4c(nc5ccnn35)CCNCC4)C2)c1] | 5 | TF | 378.2 [M + H]+ | 1.57 (H) |

TABLE 18-continued

| Example | Structure | Overall yield (%) | Salt type | Mass spec result | HPLC retention time (method) |
|---|---|---|---|---|---|
| 35.10 | 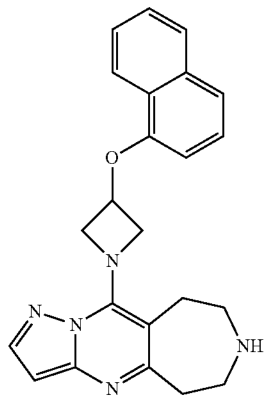 [SMILES: c1ccc2c(OC3CN(c4c5c(nc6ccnn46)CCNCC5)C3)cccc2c1] | 6 | TF | 386.2 [M + H]⁺ | 1.53 (H) |
| 35.11 | 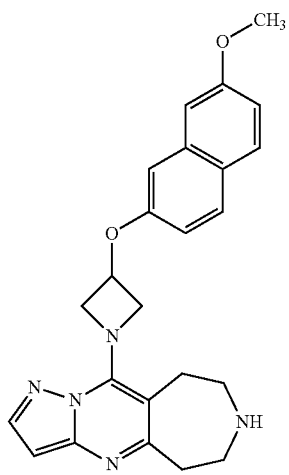 [SMILES: COc1ccc2ccc(OC3CN(c4c5c(nc6ccnn46)CCNCC5)C3)cc2c1] | 7 | TF | 416.2 [M + H]⁺ | 1.57 (H) |
| 35.12 | 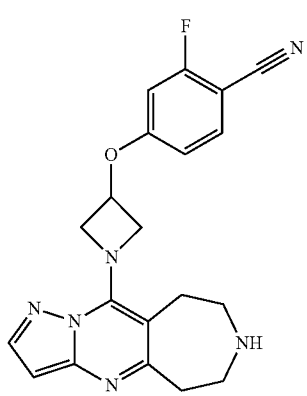 [SMILES: N#Cc1ccc(OC2CN(c3c4c(nc5ccnn35)CCNCC4)C2)cc1F] | 3 | TF | 379.1 [M + H]⁺ | 1.43 (H) |

TABLE 18-continued

| Example | Structure | Overall yield (%) | Salt type | Mass spec result | HPLC retention time (method) |
|---|---|---|---|---|---|
| 35.13 | 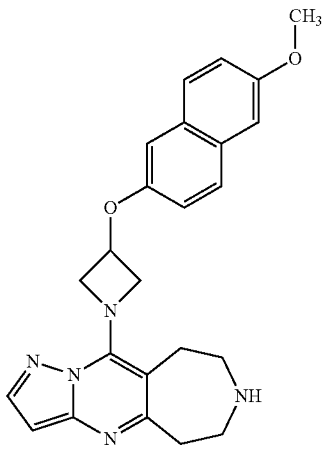 [SMILES: COc1ccc2cc(OC3CN(c4c5c(nc6ccnn46)CCNCC5)C3)ccc2c1] | 13 | TF | 416.2 [M + H]+ | 1.54 (H) |
| 35.14 | 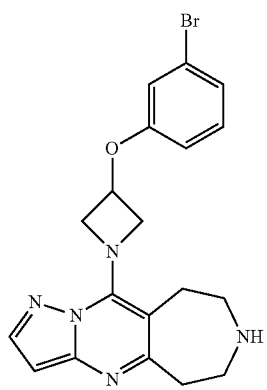 [SMILES: Brc1cccc(OC2CN(c3c4c(nc5ccnn35)CCNCC4)C2)c1] | 27 | TF | 416 [M + H]+ | 1.51 (H) |
| 35.15 | 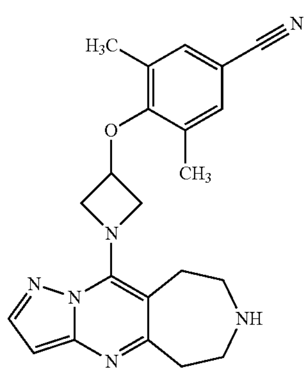 [SMILES: Cc1cc(C#N)cc(C)c1OC1CN(c2c3c(nc4ccnn24)CCNCC3)C1] | 11 | TF | 389.1 [M + H]+ | 1.47 (H) |

TABLE 18-continued

| Example | Structure | Overall yield (%) | Salt type | Mass spec result | HPLC retention time (method) |
| --- | --- | --- | --- | --- | --- |
| 35.16 | 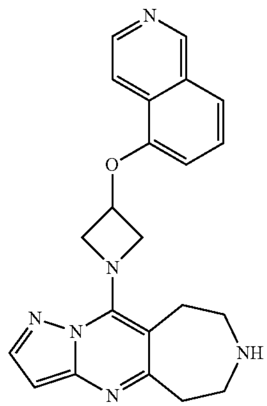 [SMILES: c1cc(OC2CN(c3c4c(nc5ccnn35)CCNCC4)C2)c2ccncc2c1] | 6 | TF | 387.5 [M + H]⁺ | 0.56 (H) |
| 35.17 | 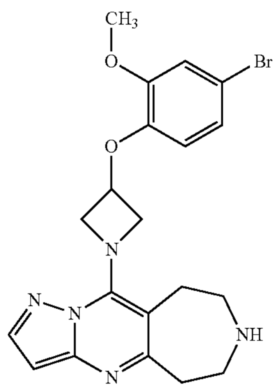 [SMILES: COc1cc(Br)ccc1OC1CN(c2c3c(nc4ccnn24)CCNCC3)C1] | 8 | TF | 446.1 [M + H]⁺ | 1.49 (H) |
| 35.18 | 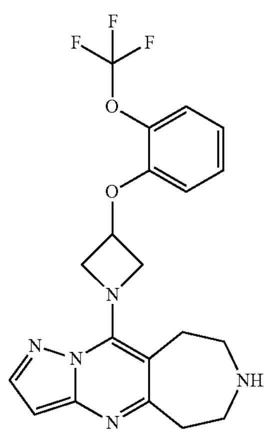 [SMILES: FC(F)(F)Oc1ccccc1OC1CN(c2c3c(nc4ccnn24)CCNCC3)C1] | 7 | TF | 420.1 [M + H]⁺ | 1.53 (H) |
| 35.19 | 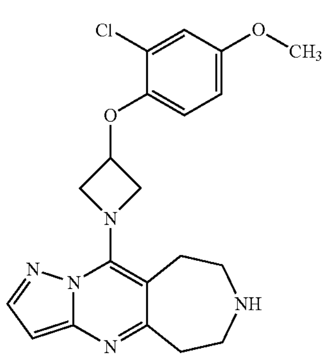 [SMILES: COc1ccc(OC2CN(c3c4c(nc5ccnn35)CCNCC4)C2)c(Cl)c1] | 7 | TF | 400.1 [M + H]⁺ | 1.48 (H) |

TABLE 18-continued

| Example | Structure | Overall yield (%) | Salt type | Mass spec result | HPLC retention time (method) |
|---------|-----------|-------------------|-----------|------------------|------------------------------|
| 35.20 | 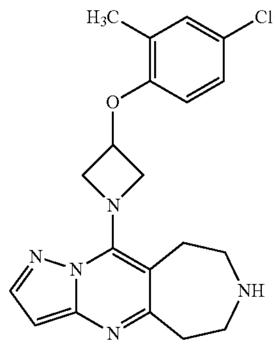 [SMILES: Cc1cc(Cl)ccc1OC1CN(c2c3c(nc4ccnn24)CCNCC3)C1] | 11 | TF | 384.1 [M + H]+ | 1.55 (H) |
| 35.21 | 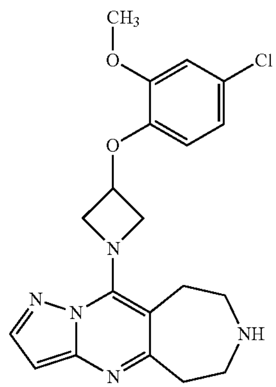 [SMILES: COc1cc(Cl)ccc1OC1CN(c2c3c(nc4ccnn24)CCNCC3)C1] | 15 | TF | 400.1 [M + H]+ | 1.48 (H) |
| 35.22 | 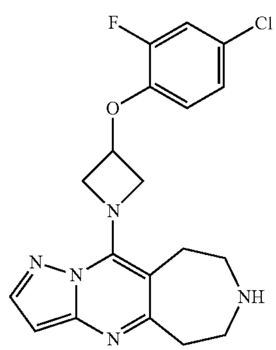 [SMILES: Fc1cc(Cl)ccc1OC1CN(c2c3c(nc4ccnn24)CCNCC3)C1] | 13 | TF | 388.1 [M + H]+ | 1.51 (H) |
| 35.23 | 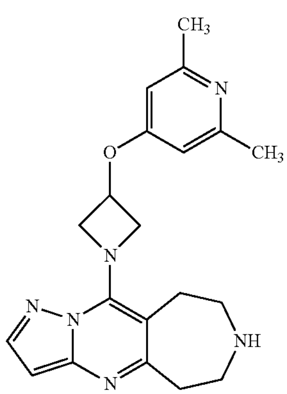 [SMILES: Cc1cc(OC2CN(c3c4c(nc5ccnn35)CCNCC4)C2)cc(C)n1] | 8 | TF | 365.5 [M + H]+ | 0.56 (H) |

TABLE 18-continued

| Example | Structure | Overall yield (%) | Salt type | Mass spec result | HPLC retention time (method) |
|---|---|---|---|---|---|
| 35.24 | 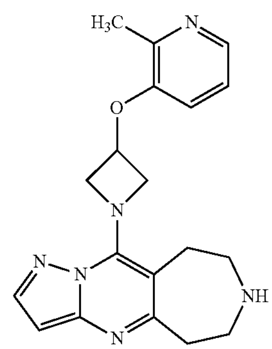 | 14 | TF | 351.5 [M + H]⁺ | 0.57 (H) |
| 35.25 | 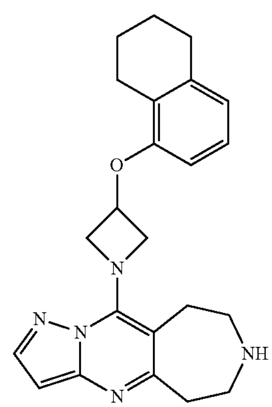 [SMILES: c1cc2c(c(OC3CN(c4c5c(nc6ccnn46)CCNCC5)C3)c1)CCCC2] | 7 | TF | 390.2 [M + H]⁺ | 1.58 (H) |
| 35.26 | 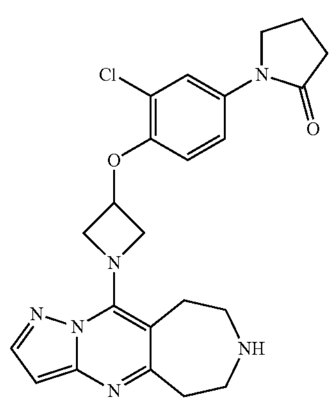 [SMILES: O=C1CCCN1c1ccc(OC2CN(c3c4c(nc5ccnn35)CCNCC4)C2)c(Cl)c1] | 5 | TF | 453.1 [M + H]⁺ | 1.41 (H) |

TABLE 18-continued

| Example | Structure | Overall yield (%) | Salt type | Mass spec result | HPLC retention time (method) |
|---------|-----------|-------------------|-----------|------------------|------------------------------|
| 35.27 | 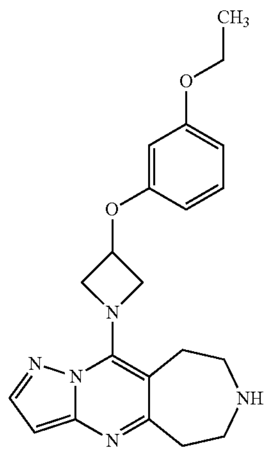 [SMILES: CCOc1cccc(OC2CN(c3c4c(nc5ccnn35)CCNCC4)C2)c1] | 14 | TF | 380.2 [M + H]+ | 1.48 (H) |
| 35.28 | 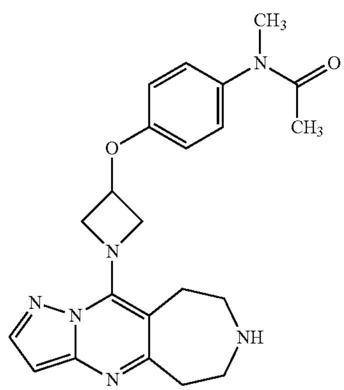 [SMILES: CC(=O)N(C)c1ccc(OC2CN(c3c4c(nc5ccnn35)CCNCC4)C2)cc1] | 27 | TF | 407.1 [M + H]+ | 1.31 (H) |
| 35.29 | 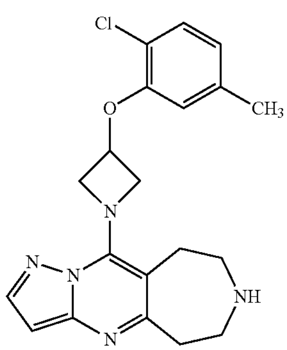 [SMILES: Cc1ccc(Cl)c(OC2CN(c3c4c(nc5ccnn35)CCNCC4)C2)c1] | 33 | TF | 384.1 [M + H]+ | 1.52 (H) |
| 35.30 | 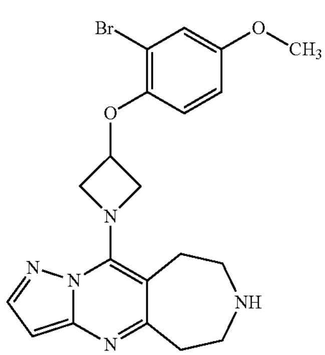 [SMILES: COc1ccc(OC2CN(c3c4c(nc5ccnn35)CCNCC4)C2)c(Br)c1] | 25 | TF | 446.1 [M + H]+ | 1.49 (H) |

TABLE 18-continued

| Example | Structure | Overall yield (%) | Salt type | Mass spec result | HPLC retention time (method) |
|---|---|---|---|---|---|
| 35.31 | 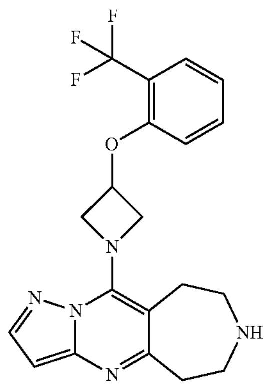 [SMILES: FC(F)(F)c1ccccc1OC1CN(c2c3c(nc4ccnn24)CCNCC3)C1] | 8 | TF | 404.1 [M + H]+ | 1.51 (H) |
| 35.32 | 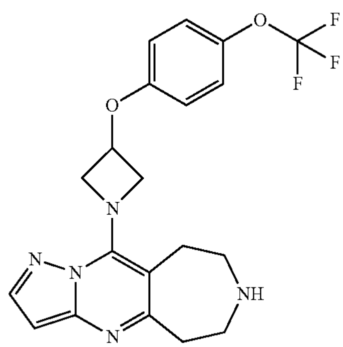 [SMILES: FC(F)(F)Oc1ccc(OC2CN(c3c4c(nc5ccnn35)CCNCC4)C2)cc1] | 16 | TF | 420.1 [M + H]+ | 1.56 (H) |
| 35.33 | 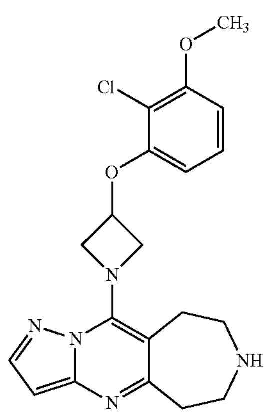 [SMILES: COc1cccc(OC2CN(c3c4c(nc5ccnn35)CCNCC4)C2)c1Cl] | 31 | TF | 400.1 [M + H]+ | 1.45 (H) |
| 35.34 | 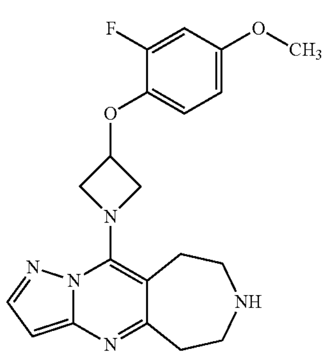 | 25 | TF | 384.1 [M + H]+ | 1.44 (H) |

TABLE 18-continued

| Example | Structure | Overall yield (%) | Salt type | Mass spec result | HPLC retention time (method) |
|---|---|---|---|---|---|
| 35.35 | 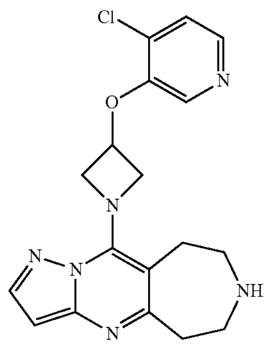 | 8 | TF | 371.1 [M + H]⁺ | 1.24 (H) |
| 35.36 | 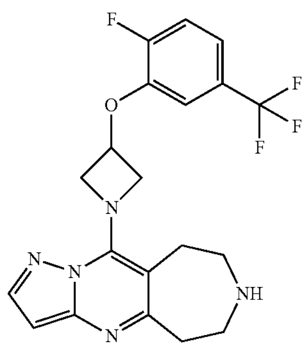 [SMILES: Fc1ccc(C(F)(F)F)cc1OC1CN(c2c3c(nc4ccnn24)CCNCC3)C1] | 7 | TF | 422.1 [M + H]⁺ | 1.53 (H) |
| 35.37 | 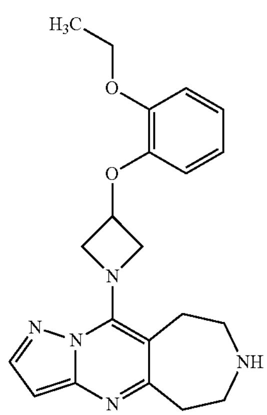 [SMILES: CCOc1ccccc1OC1CN(c2c3c(nc4ccnn24)CCNCC3)C1] | 8 | TF | 380.1 [M + H]⁺ | 1.44 (H) |
| 35.38 | 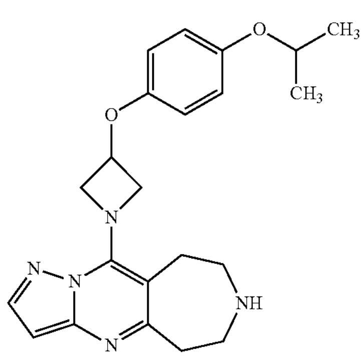 [SMILES: CC(C)Oc1ccc(OC2CN(c3c4c(nc5ccnn35)CCNCC4)C2)cc1] | 1 | TF | 394.2 [M + H]⁺ | 1.51 (H) |

TABLE 18-continued

| Example | Structure | Overall yield (%) | Salt type | Mass spec result | HPLC retention time (method) |
|---------|-----------|-------------------|-----------|------------------|------------------------------|
| 35.39 | 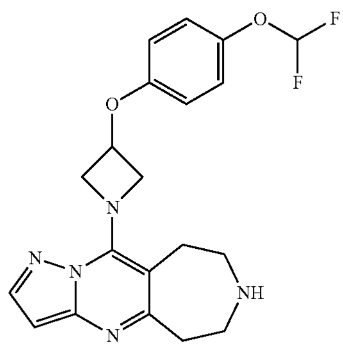 [SMILES: FC(F)Oc1ccc(OC2CN(c3c4c(nc5ccnn35)CCNCC4)C2)cc1] | 2 | TF | 402.1 [M + H]⁺ | 1.49 (H) |
| 35.40 | 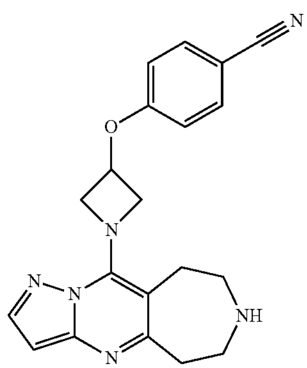 [SMILES: N#Cc1ccc(OC2CN(c3c4c(nc5ccnn35)CCNCC4)C2)cc1] | 1 | TF | 361.1 [M + H]⁺ | 1.38 (H) |
| 35.41 | 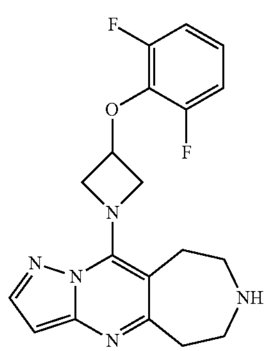 [SMILES: Fc1cccc(F)c1OC1CN(c2c3c(nc4ccnn24)CCNCC3)C1] | 27 | TF | 372.1 [M + H]⁺ | 1.42 (H) |
| 35.42 | 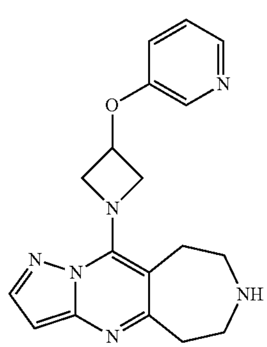 [SMILES: c1cncc(OC2CN(c3c4c(nc5ccnn35)CCNCC4)C2)c1] | 23 | TF | 337.2 [M + H]⁺ | 0.57 (H) |

TABLE 18-continued

| Example | Structure | Overall yield (%) | Salt type | Mass spec result | HPLC retention time (method) |
|---------|-----------|-------------------|-----------|------------------|------------------------------|
| 35.43 | 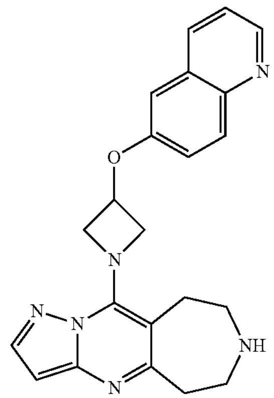 [SMILES: c1cnc2ccc(OC3CN(c4c5c(nc6ccnn46)CCNCC5)C3)cc2c1] | 16 | TF | 387.5 [M + H]⁺ | 1.17 (H) |
| 35.44 | 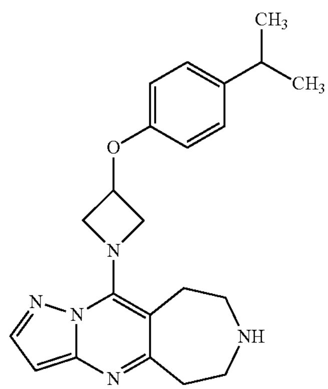 [SMILES: CC(C)c1ccc(OC2CN(c3c4c(nc5ccnn35)CCNCC4)C2)cc1] | 18 | TF | 378.2 [M + H]⁺ | 1.57 (H) |
| 35.45 | 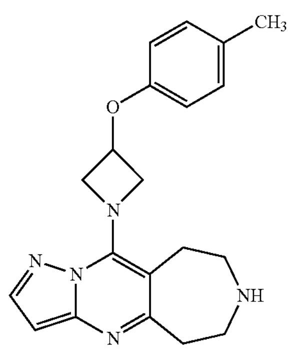 [SMILES: Cc1ccc(OC2CN(c3c4c(nc5ccnn35)CCNCC4)C2)cc1] | 13 | TF | 350.2 [M + H]⁺ | 1.47 (H) |
| 35.46 | 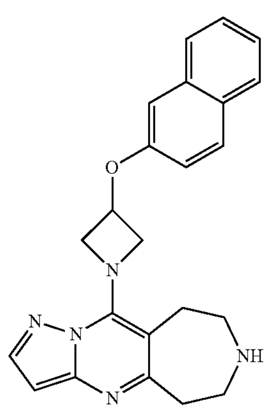 [SMILES: c1ccc2cc(OC3CN(c4c5c(nc6ccnn46)CCNCC5)C3)ccc2c1] | 5 | TF | 386.2 [M + H]⁺ | 1.53 (H) |

TABLE 18-continued

| Example | Structure | Overall yield (%) | Salt type | Mass spec result | HPLC retention time (method) |
| --- | --- | --- | --- | --- | --- |
| 35.47 | 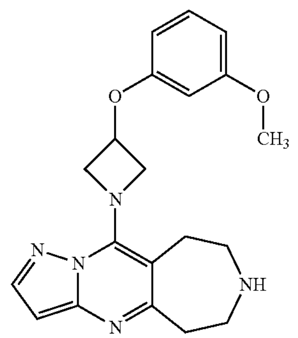 [SMILES: COc1cccc(OC2CN(c3c4c(nc5ccnn35)CCNCC4)C2)c1] | 100 | TF | 366 [M + H]⁺ | 4.37 (C) |
| 35.48 | 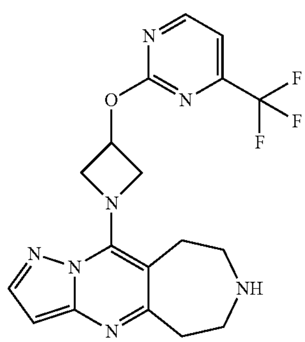 [SMILES: FC(F)(F)c1ccnc(OC2CN(c3c4c(nc5ccnn35)CCNCC4)C2)n1] | 78 | TF | 406 [M + H]⁺ | 3.96 (C) |
| 35.49 | 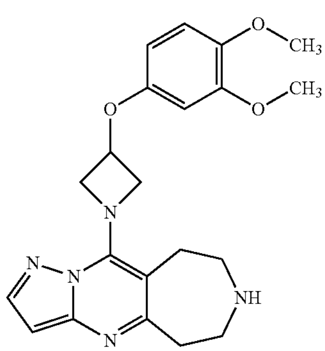 [SMILES: COc1ccc(OC2CN(c3c4c(nc5ccnn35)CCNCC4)C2)cc1OC] | 84 | TF | 396.1 [M + H]⁺ | 1.4 (F) |
| 35.50 | 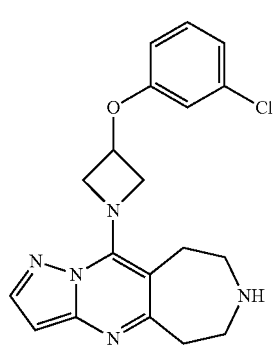 [SMILES: Clc1cccc(OC2CN(c3c4c(nc5ccnn35)CCNCC4)C2)c1] | 95 | TF | 370.1 [M + H]⁺ | 1.51 (F) |

TABLE 18-continued

| Example | Structure | Overall yield (%) | Salt type | Mass spec result | HPLC retention time (method) |
|---|---|---|---|---|---|
| 35.51 | 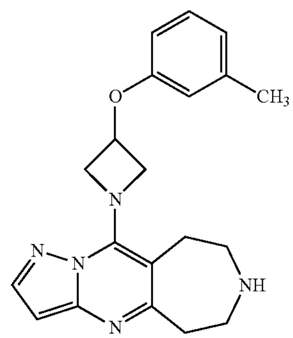 [SMILES: Cc1cccc(OC2CN(c3c4c(nc5ccnn35)CCNCC4)C2)c1] | 88 | TF | 350.1 [M + H]⁺ | 1.49 (F) |
| 35.52 | 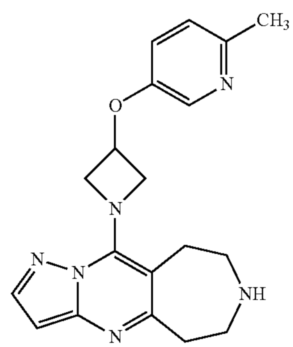 [SMILES: Cc1ccc(OC2CN(c3c4c(nc5ccnn35)CCNCC4)C2)cn1] | 58 | TF | 351.1 [M + H]⁺ | 1.07 (F) |
| 35.53 | 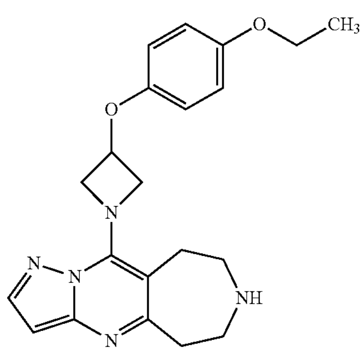 [SMILES: CCOc1ccc(OC2CN(c3c4c(nc5ccnn35)CCNCC4)C2)cc1] | 85 | TF | 380.1 [M + H]⁺ | 1.48 (F) |
| 35.54 | 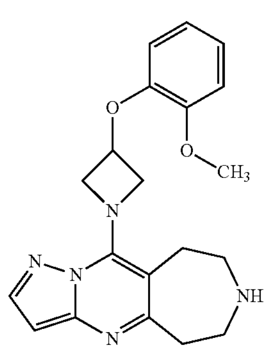 [SMILES: COc1ccccc1OC1CN(c2c3c(nc4ccnn24)CCNCC3)C1] | 95 | TF | 366.1 [M + H]⁺ | 1.39 (F) |

TABLE 18-continued

| Example | Structure | Overall yield (%) | Salt type | Mass spec result | HPLC retention time (method) |
|---|---|---|---|---|---|
| 35.55 | 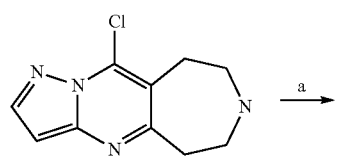 | 84 | TF | 372.1 [M + H]+ | 1.48 (F) |

Route 36

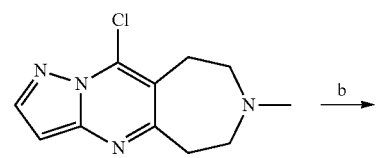

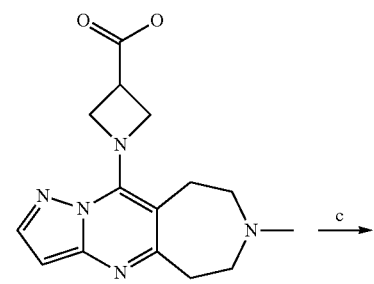

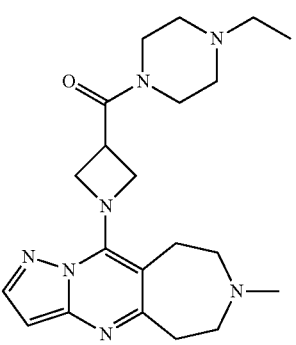 [SMILES: CCN1CCN(C(=O)C2CN(c3c4c(nc5ccnn35)CCN(C)CC4)C2)CC1]

Example 36

General Route (4-Ethyl-piperazin-1-yl)-[1-(7-methyl-6,7,8,9-tetrahydro-5H-1,4,7,10a-tetraaza-cyclohepta[f]inden-10-yl)-azetidin-3-yl]-methanone

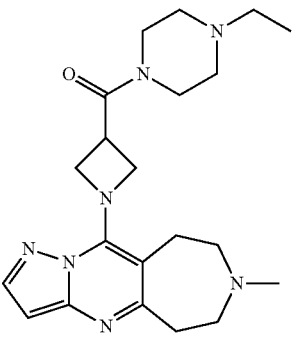

36a 10-Chloro-7-methyl-6,7,8,9-tetrahydro-5H-1,4,7,10a-tetraaza-cyclohepta[f]indene To 20.0 g (77.2 mmol) 10-Chloro-6,7,8,9-tetrahydro-5H-1,4,7,10a-tetraaza-cyclohepta[f]indene in 200 mL buffer (pH=5) 6.4 mL formaldehyde (37% in water, 84.9 mmol) and 19.7 g sodium triacetoxyborohydride (93.0 mmol) were added under cooling with ice and stirring was continued overnight. The mixture was then diluted at 0° C. with $K_2CO_3$-solution (15% in water) and extracted with ethyl acetate. The organic layers were combined, dried ($Na_2SO_4$) and concentrated. The residue was then purified by column chromatography (silica, EtOAc/MeOH/$NH_4OH$=9:1:0.1) to give the desired product.

Yield: 11.4 g (62% of theory)

$C_{11}H_{13}ClN_4$ (M=236.7)

predicted: Molecular ion (M+H)+: 237 observed: Molecular ion (M+H)+: 237

HPLC-MS: 1.4 minutes (Method K)

36b 1-(7-Methyl-6,7,8,9-tetrahydro-5H-1,4,7,10a-tetraaza-cyclohepta[f]inden-10-yl)-azetidine-3-carboxylic acid To 1.77 g (7.48 mmol) 10-Chloro-7-methyl-6,7,8,9-tetrahydro-5H-1,4,7,10a-tetraaza-cyclohepta[f]indene in 50 mL ethanol was added 0.83 g (8.22 mmol) 3-azetidinecarboxylic acid and 2.75 mL (15.7 mmol) DIPEA and the reaction mixture was heated at 75° C. for 4 hours. The mixture was concentrated and treated with diethyl ether and methanol. After ultrasound irradiation, a precipitate formed which was collected by filtration. The remaining solution was concentrated and the above mentioned procedure was repeated. The precipitates were combined and dried to yield the desired product as the DIPEA-salt.

Yield: 3.29 g (100% of theory)
$C_{15}H_{19}N_5O_2 * C_8H_{19}N$ (M=430.59)
predicted: Molecular ion (M+H)$^+$: 302 observed: Molecular ion (M+H)$^+$: 302
HPLC-MS: 0.4 minutes (Method K)

36c 10(4-Ethyl-piperazin-1-yl)-[1-(7-methyl-6,7,8,9-tetrahydro-5H-1,4,7,10a-tetraaza-cyclohepta[f]inden-10-yl)-azetidin-3-yl]-methanone To 11.4 mg (0.10 mmol) N-ethylpiperazine was added a solution of 43 mg (0.10 mmol) 1-(7-Methyl-6,7,8,9-tetrahydro-5H-1,4,7,10a-tetraaza-cyclohepta[f]inden-10-yl)-azetidine-3-carboxylic acid and 0.026 mL (0.15 mmol) DIPEA in 0.5 mL DMF at room temperature. 35.3 mg (0.11 mmol) TBTU was dissolved in 0.5 mL DMF and the solution was added to the reaction mixture. Stirring was continued for 2 h and the reaction mixture was allowed to stand for overnight. The mixture was filtered over basic alumina followed by two washing cycles with 1.5 mL DMF. The solvent was removed and the residue was purified by column chromatography to yield the desired compound.

Yield: 3.7 mg (9.3% of theory)
$C_{21}H_{31}N_7O$ (M=397.52)
predicted: Molecular ion (M+H)$^+$: 398 observed: Molecular ion (M+H)$^+$: 398
HPLC-MS: 0.7 minutes (Method Q)

In case that TF salts are listed a mixture of dichloromethane and TFA (1/1) was used to remove the boc-protection group

TABLE 19

| Example | Structure | Yield of final step (%) | Salt type | Mass spec result | HPLC retention time (method) |
|---|---|---|---|---|---|
| 36.1 | 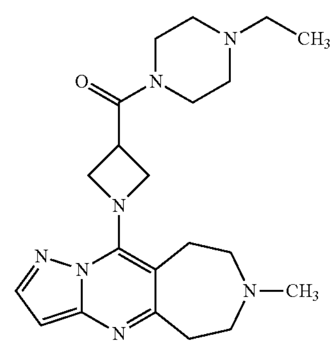 [SMILES: CCN1CCN(C(=O)C2CN(c3c4c(nc5ccnn35)CCN(C)CC4)C2)CC1] | 9.3 | none | 398.5 [M + H]$^+$ | 0.7 (R) |
| 36.2 | 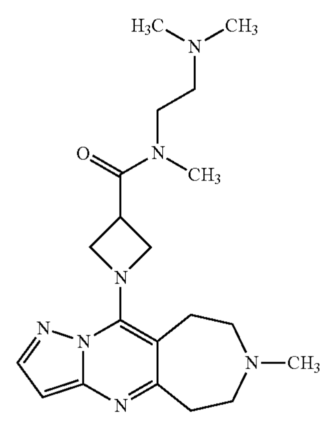 [SMILES: CN(C)CCN(C)C(=O)C1CN(c2c3c(nc4ccnn24)CCN(C)CC3)C1] | 7.0 | none | 386.5 [M + H]$^+$ | 0.69 (R) |

TABLE 19-continued

| Example | Structure | Yield of final step (%) | Salt type | Mass spec result | HPLC retention time (method) |
|---|---|---|---|---|---|
| 36.3 | 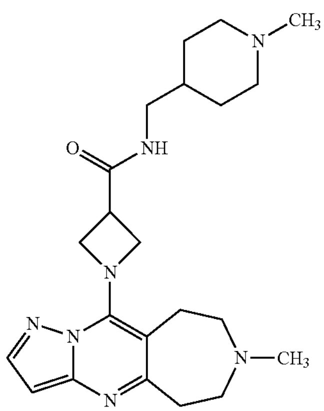 [SMILES: CN1CCc2nc3ccnn3c(N3CC(C(=O)NCC4CCN(C)CC4)C3)c2CC1] | 8.7 | none | 412.6 [M + H]+ | 0.75 (R) |
| 36.4 | 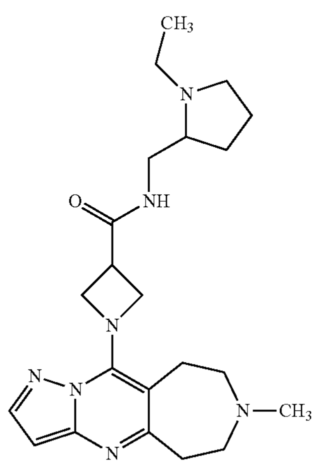 [SMILES: CCN1CCCC1CNC(=O)C1CN(c2c3c(nc4ccnn24)CCN(C)CC3)C1] | 13.1 | none | 412.6 [M + H]+ | 0.8 (R) |
| 36.5 | 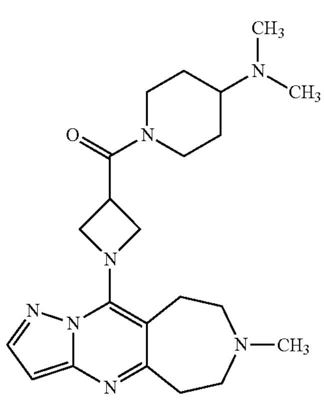 [SMILES: CN1CCc2nc3ccnn3c(N3CC(C(=O)N4CCC(N(C)C)CC4)C3)c2CC1] | 10.2 | none | 412.6 [M + H]+ | 0.72 (R) |

TABLE 19-continued

| Example | Structure | Yield of final step (%) | Salt type | Mass spec result | HPLC retention time (method) |
|---|---|---|---|---|---|
| 36.6 | 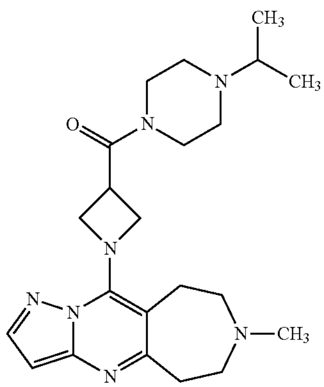 [SMILES: CC(C)N1CCN(C(=O)C2CN(c3c4c(nc5ccnn35)CCN(C)CC4)C2)CC1] | 19.7 | none | 412.6 [M + H]+ | 0.79 (R) |
| 36.7 | 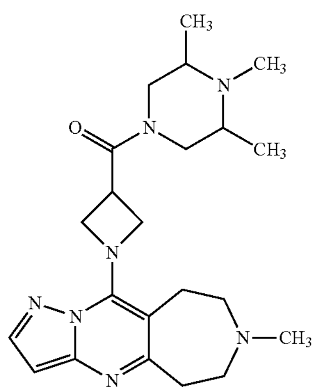 [SMILES: CC1CN(C(=O)C2CN(c3c4c(nc5ccnn35)CCN(C)CC4)C2)CC(C)N1C] | 14.1 | none | 412.6 [M + H]+ | 0.73 (R) |
| 36.8 | 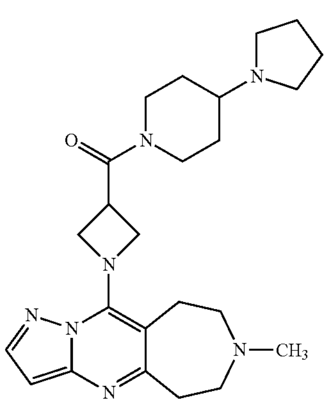 [SMILES: CN1CCc2nc3ccnn3c(N3CC(C(=O)N4CCC(N5CCCC5)CC4)C3)c2CC1] | 16.7 | none | 438.6 [M + H]+ | 0.86 (R) |

TABLE 19-continued
| Example | Structure | Yield of final step (%) | Salt type | Mass spec result | HPLC retention time (method) |
|---|---|---|---|---|---|
| 36.9 | 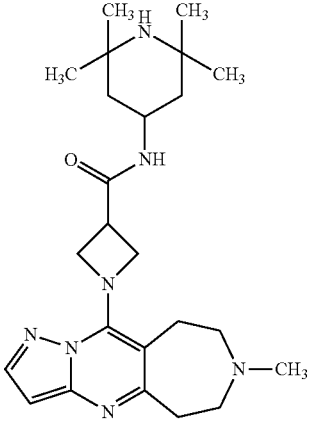 [SMILES: CN1CCc2nc3ccnn3c(N3CC(C(=O)NC4CC(C)(C)NC(C)(C)C4)C3)c2CC1] | 21.2 | none | 440.6 [M + H]⁺ | 0.79 (R) |
| 36.10 | 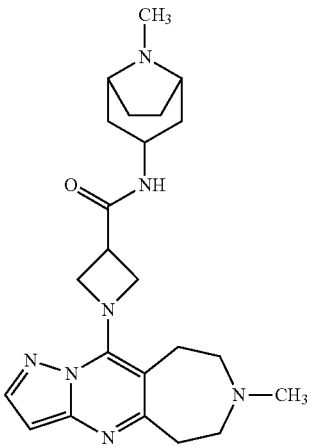 [SMILES: CN1CCc2nc3ccnn3c(N3CC(C(=O)NC4CC5CCC(C4)N5C)C3)c2CC1] | 7.1 | none | 424.6 [M + H]⁺ | 0.81 (R) |
| 36.11 | 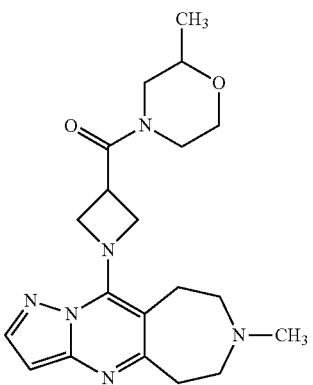 [SMILES: CC1CN(C(=O)C2CN(c3c4c(nc5ccnn35)CCN(C)CC4)C2)CCO1] | 8.6 | none | 385.5 [M + H]⁺ | 0.69 (R) |

TABLE 19-continued

| Example | Structure | Yield of final step (%) | Salt type | Mass spec result | HPLC retention time (method) |
|---|---|---|---|---|---|
| 36.12 | 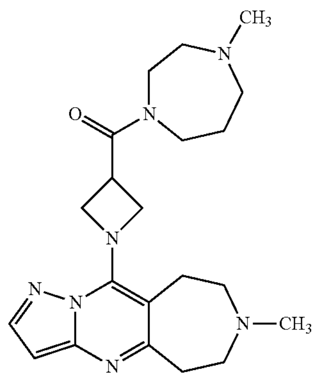 [SMILES: CN1CCc2nc3ccnn3c(N3CC(C(=O)N4CCCN(C)CC4)C3)c2CC1] | 9.8 | none | 398.5 [M + H]⁺ | 0.66 (R) |
| 36.13 | 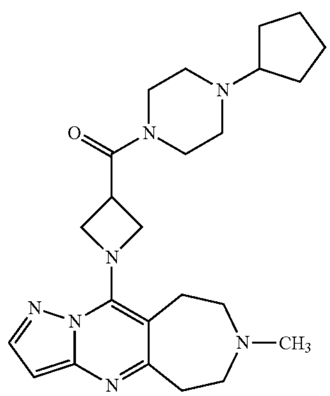 [SMILES: CN1CCc2nc3ccnn3c(N3CC(C(=O)N4CCN(C5CCCC5)CC4)C3)c2CC1] | 31.1 | none | 438.6 [M + H]⁺ | 0.91 (R) |
| 36.14 | 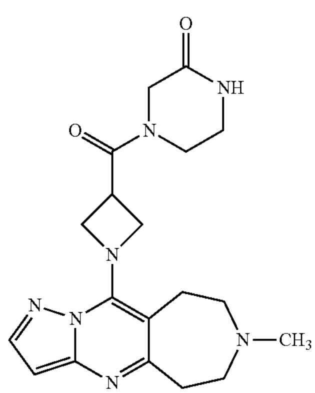 [SMILES: CN1CCc2nc3ccnn3c(N3CC(C(=O)N4CCNC(=O)C4)C3)c2CC1] | 13.6 | none | 384.5 [M + H]⁺ | 0.51 (R) |
| 36.15 | 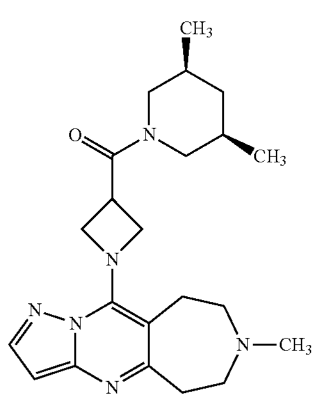 [SMILES: C[C@@H]1C[C@H](C)CN(C(=O)C2CN(c3c4c(nc5ccnn35)CCN(C)CC4)C2)C1] | 31.0 | none | 397.5 [M + H]⁺ | 1.05 (R) |

TABLE 19-continued

| Example | Structure | Yield of final step (%) | Salt type | Mass spec result | HPLC retention time (method) |
|---|---|---|---|---|---|
| 36.16 | 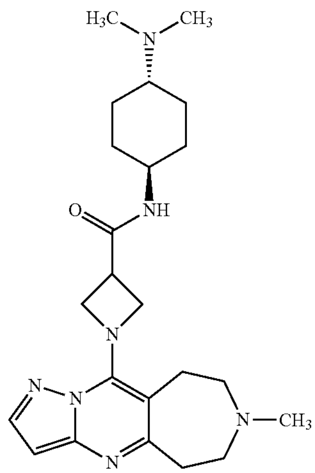 [SMILES: CN1CCc2nc3ccnn3c(N3CC(C(=O)N[C@H]4CC[C@H](N(C)C)CC4)C3)c2CC1] | 8.9 | none | 426.6 [M + H]+ | 0.85 (R) |
| 36.17 | 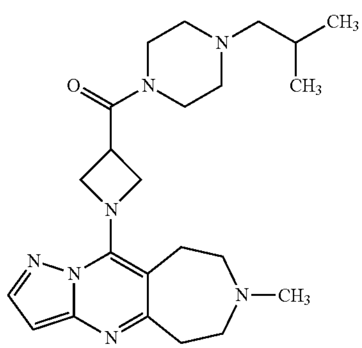 [SMILES: CC(C)CN1CCN(C(=O)C2CN(c3c4c(nc5ccnn35)CCN(C)CC4)C2)CC1] | 33.8 | none | 426.6 [M + H]+ | 1.01 (R) |
| 36.18 | 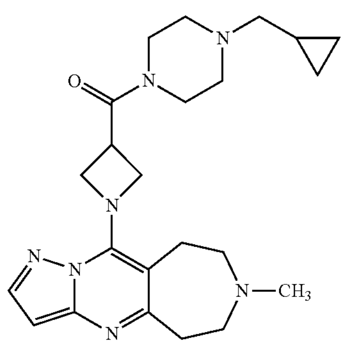 [SMILES: CN1CCc2nc3ccnn3c(N3CC(C(=O)N4CCN(CC5CC5)CC4)C3)c2CC1] | 30.0 | none | 424.6 [M + H]+ | 0.82 (R) |
| 36.19 | 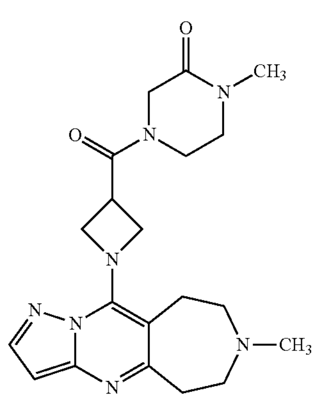 [SMILES: CN1CCc2nc3ccnn3c(N3CC(C(=O)N4CCN(C)C(=O)C4)C3)c2CC1] | 19.1 | none | 398.5 [M + H]+ | 0.55 (R) |

TABLE 19-continued

| Example | Structure | Yield of final step (%) | Salt type | Mass spec result | HPLC retention time (method) |
|---|---|---|---|---|---|
| 36.20 | 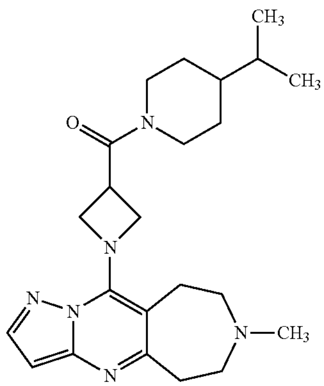 [SMILES: CC(C)C1CCN(C(=O)C2CN(c3c4c(nc5ccnn35)CCN(C)CC4)C2)CC1] | 24.8 | none | 411.6 [M + H]+ | 1.14 (R) |
| 36.21 | 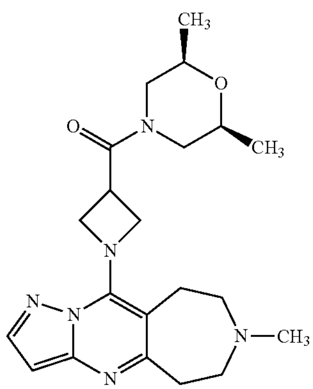 | 19.6 | none | 399.5 [M + H]+ | 0.77 (R) |
| 36.22 | 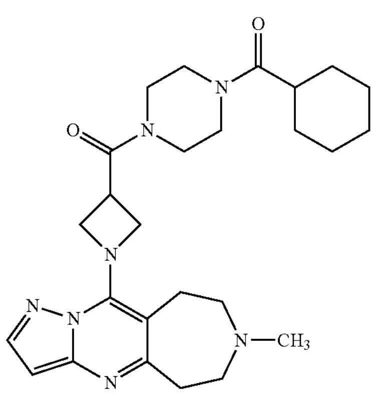 [SMILES: CN1CCc2nc3ccnn3c(N3CC(C(=O)N4CCN(C(=O)C5CCCCC5)CC4)C3)c2CC1] | 26.7 | none | 480.6 [M + H]+ | 0.9 (R) |
| 36.23 | 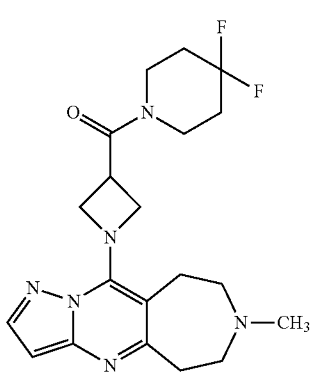 [SMILES: CN1CCc2nc3ccnn3c(N3CC(C(=O)N4CCC(F)(F)CC4)C3)c2CC1] | 20.5 | none | 405.5 [M + H]+ | 0.82 (R) |

TABLE 19-continued

| Example | Structure | Yield of final step (%) | Salt type | Mass spec result | HPLC retention time (method) |
|---|---|---|---|---|---|
| 36.24 | 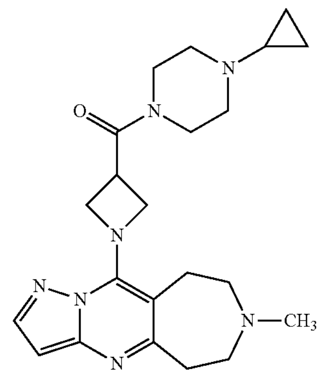 [SMILES: CN1CCc2nc3ccnn3c(N3CC(C(=O)N4CCN(C5CC5)CC4)C3)c2CC1] | 25.6 | none | 410.5 [M + H]+ | 0.79 (R) |
| 36.25 | 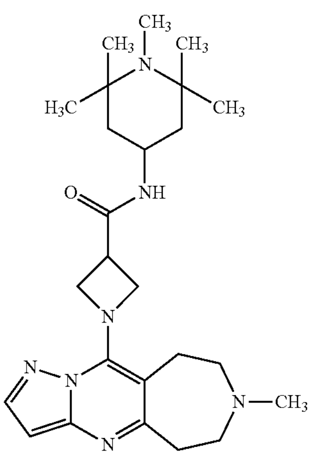 [SMILES: CN1CCc2nc3ccnn3c(N3CC(C(=O)NC4CC(C)(C)N(C)C(C)(C)C4)C3)c2CC1] | 25.4 | none | 454.6 [M + H]+ | 0.95 (R) |
| 36.26 | 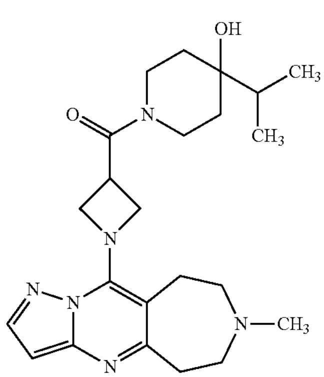 [SMILES: CC(C)C1(O)CCN(C(=O)C2CN(c3c4c(nc5ccnn35)CCN(C)CC4)C2)CC1] | 17.1 | none | 427.6 [M + H]+ | 0.8 (R) |

TABLE 19-continued

| Example | Structure | Yield of final step (%) | Salt type | Mass spec result | HPLC retention time (method) |
|---|---|---|---|---|---|
| 36.27 | 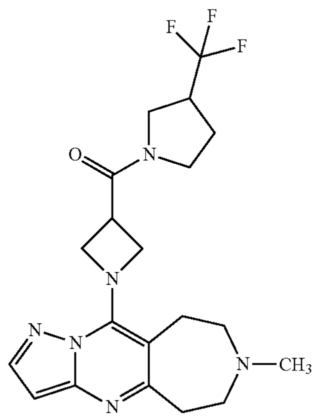 [SMILES: CN1CCc2nc3ccnn3c(N3CC(C(=O)N4CCC(C(F)(F)F)C4)C3)c2CC1] | 25.8 | none | 423.5 [M + H]+ | 0.85 (R) |
| 36.28 | 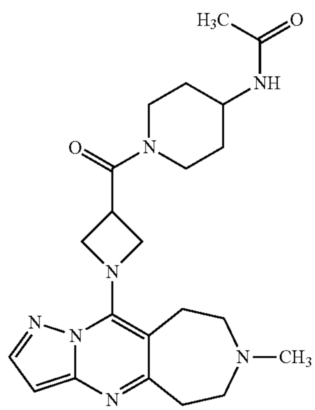 [SMILES: CC(=O)NC1CCN(C(=O)C2CN(c3c4c(nc5ccnn35)CCN(C)CC4)C2)CC1] | 10.6 | none | 426.5 [M + H]+ | 0.57 (R) |
| 36.29 | 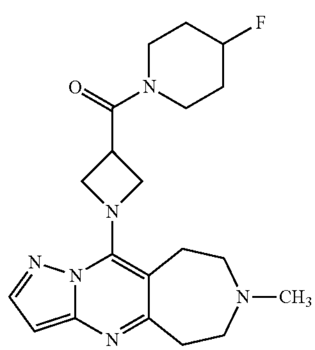 [SMILES: CN1CCc2nc3ccnn3c(N3CC(C(=O)N4CCC(F)CC4)C3)c2CC1] | 28.2 | none | 387.5 [M + H]+ | 0.75 (R) |
| 36.30 | 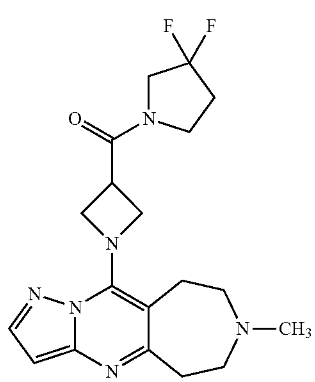 [SMILES: CN1CCc2nc3ccnn3c(N3CC(C(=O)N4CCC(F)(F)C4)C3)c2CC1] | 27.4 | none | 391.4 [M + H]+ | 0.75 (R) |

TABLE 19-continued

| Example | Structure | Yield of final step (%) | Salt type | Mass spec result | HPLC retention time (method) |
|---|---|---|---|---|---|
| 36.31 | 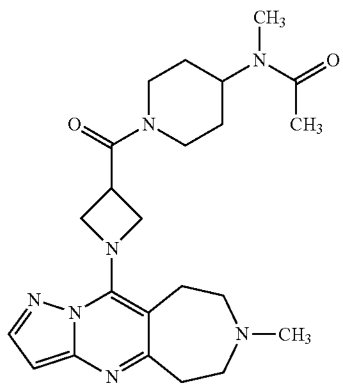 [SMILES: CC(=O)N(C)C1CCN(C(=O)C2CN(c3c4c(nc5ccnn35)CCN(C)CC4)C2)CC1] | 4.5 | none | 440.6 [M + H]+ | 0.63 (R) |
| 36.32 | 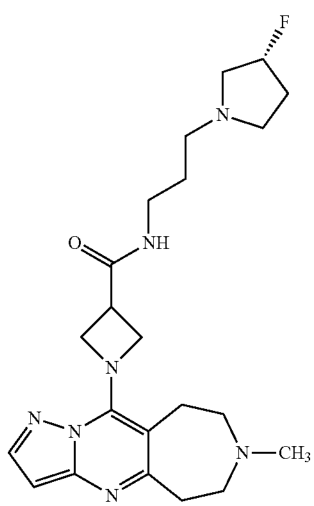 | 9.1 | Chiral none | 430.5 [M + H]+ | 0.7 (R) |
| 36.33 | 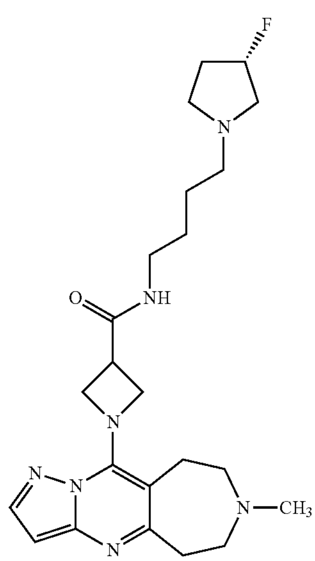 | 11.9 | Chiral none | 444.6 [M + H]+ | 0.74 (R) |

TABLE 19-continued

| Example | Structure | Yield of final step (%) | Salt type | Mass spec result | HPLC retention time (method) |
|---|---|---|---|---|---|
| 36.34 | 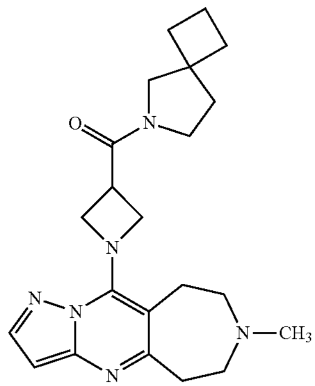 [SMILES: CN1CCc2nc3ccnn3c(N3CC(C(=O)N4CCC5(CCC5)C4)C3)c2CC1] | 22.6 | none | 395.5 [M + H]+ | 0.95 (R) |
| 36.35 | 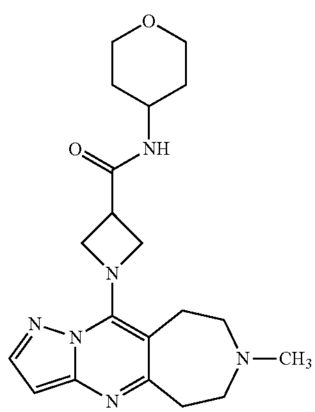 [SMILES: CN1CCc2nc3ccnn3c(N3CC(C(=O)NC4CCOCC4)C3)c2CC1] | 1.8 | none | 385.5 [M + H]+ | 0.6 (R) |
| 36.36 | 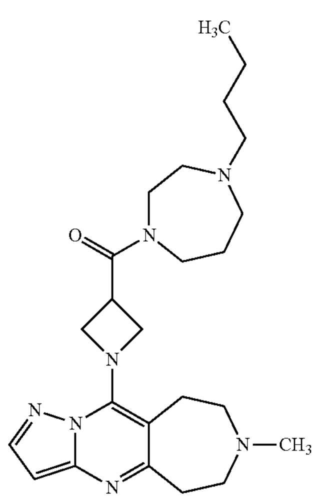 [SMILES: CCCCN1CCCN(C(=O)C2CN(c3c4c(nc5ccnn35)CCN(C)CC4)C2)CC1] | 11.8 | none | 440.6 [M + H]+ | 0.98 (R) |

TABLE 19-continued
| Example | Structure | Yield of final step (%) | Salt type | Mass spec result | HPLC retention time (method) |
|---|---|---|---|---|---|
| 36.37 | 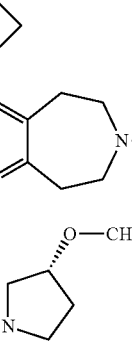 | 10.8 | none | 381.5 [M + H]⁺ | 0.85 (R) |
| 36.38 | 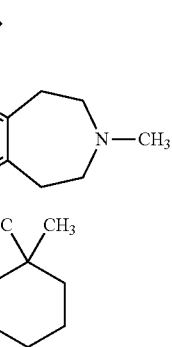 Chiral | 7.0 | none | 385.5 [M + H]⁺ | 0.66 (R) |
| 36.39 | 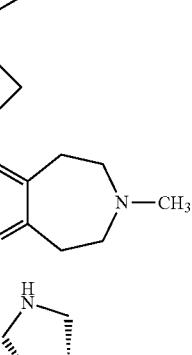 | 15.6 | none | 411.6 [M + H]⁺ | 1.08 (R) |
| 36.40 | 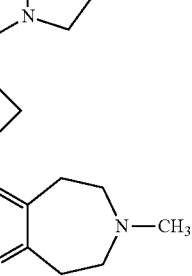 | 21.2 | none | 396.5 [M + H]⁺ | 0.65 (R) |

TABLE 19-continued
| Example | Structure | Yield of final step (%) | Salt type | Mass spec result | HPLC retention time (method) |
|---|---|---|---|---|---|
| 36.41 | 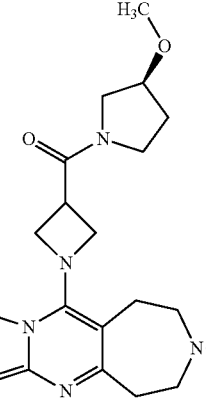 | 10.9 | Chiral none | 385.5 [M + H]+ | 0.66 (R) |
| 36.42 | 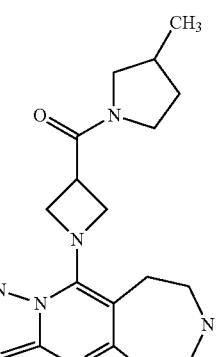 | 19.0 | none | 369.5 [M + H]+ | 0.82 (R) |
| 36.43 | 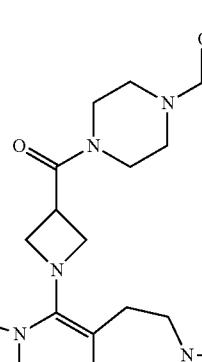 | 7.5 | none | 438.5 [M + H]+ | 0.67 (R) |
| 36.44 | 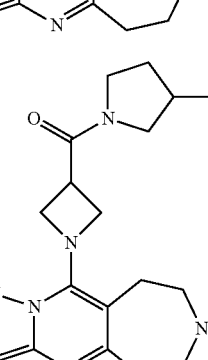 | 3.4 | none | 380.5 [M + H]+ | 0.62 (R) |

TABLE 19-continued

| Example | Structure | Yield of final step (%) | Salt type | Mass spec result | HPLC retention time (method) |
| --- | --- | --- | --- | --- | --- |
| 36.45 | 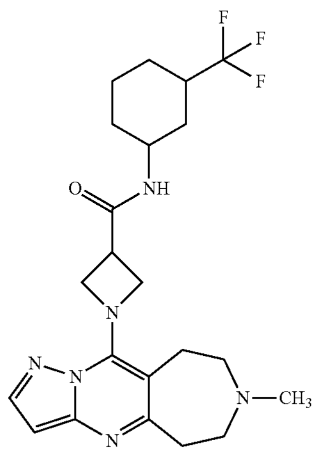 [SMILES: CN1CCc2nc3ccnn3c(N3CC(C(=O)NC4CCCC(C(F)(F)F)C4)C3)c2CC1] | 21.3 | none | 451.5 [M + H]+ | 1 (R) |
| 36.46 | 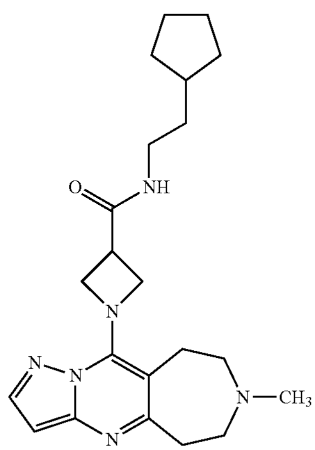 [SMILES: CN1CCc2nc3ccnn3c(N3CC(C(=O)NCCC4CCCC4)C3)c2CC1] | 20.7 | none | 397.5 [M + H]+ | 1.02 (R) |
| 36.47 | 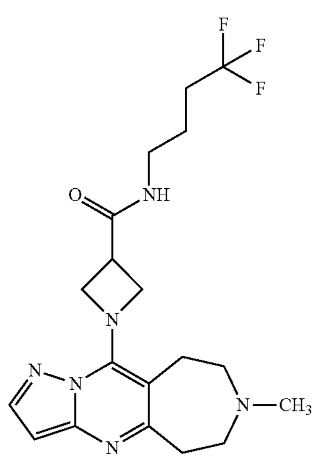 [SMILES: CN1CCc2nc3ccnn3c(N3CC(C(=O)NCCCC(F)(F)F)C3)c2CC1] | 21.0 | none | 411.4 [M + H]+ | 0.83 (R) |

TABLE 19-continued
| Example | Structure | Yield of final step (%) | Salt type | Mass spec result | HPLC retention time (method) |
|---|---|---|---|---|---|
| 36.48 | 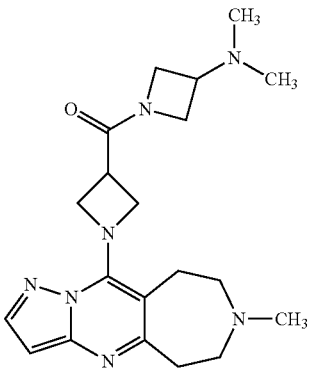 [SMILES: CN1CCc2nc3ccnn3c(N3CC(C(=O)N4CC(N(C)C)C4)C3)c2CC1] | 1.8 | none | 384.5 [M + H]⁺ | 0.62 (R) |
| 36.49 | 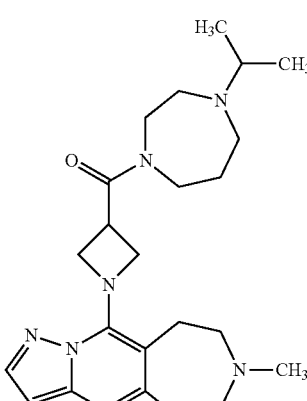 | 26.1 | none | 426.6 [M + H]⁺ | 0.85 (R) |
| 36.50 | 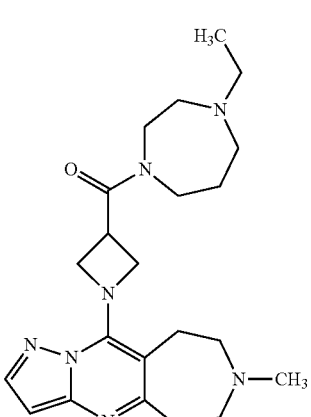 | 15.8 | none | 412.6 [M + H]⁺ | 0.74 (R) |
| 36.51 | 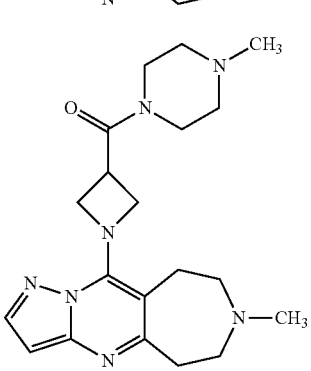 | 4.4 | none | 384.5 [M + H]⁺ | 0.63 (R) |

TABLE 19-continued

| Example | Structure | Yield of final step (%) | Salt type | Mass spec result | HPLC retention time (method) |
|---------|-----------|------------------------|-----------|------------------|------------------------------|
| 36.52 | 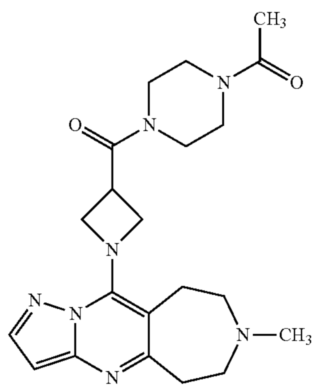 [SMILES: CC(=O)N1CCN(C(=O)C2CN(c3c4c(nc5ccnn35)CCN(C)CC4)C2)CC1] | 4.6 | none | 412.5 [M + H]⁺ | 0.57 (R) |
| 36.53 | 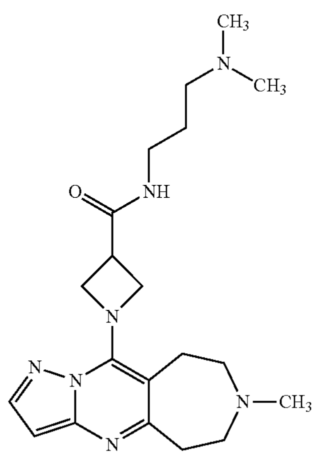 [SMILES: CN(C)CCCNC(=O)C1CN(c2c3c(nc4ccnn24)CCN(C)CC3)C1] | 2.1 | none | 386.5 [M + H]⁺ | 0.71 (R) |
| 36.54 | 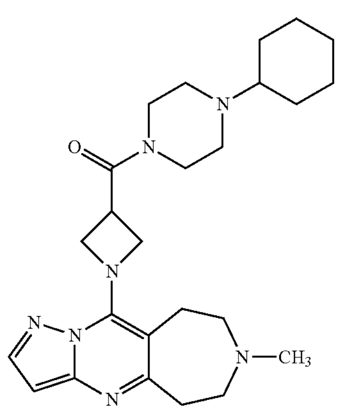 [SMILES: CN1CCc2nc3ccnn3c(N3CC(C(=O)N4CCN(C5CCCCC5)CC4)C3)c2CC1] | 25.0 | none | 452.6 [M + H]⁺ | 1.02 (R) |

TABLE 19-continued
| Example | Structure | Yield of final step (%) | Salt type | Mass spec result | HPLC retention time (method) |
|---|---|---|---|---|---|
| 36.55 | 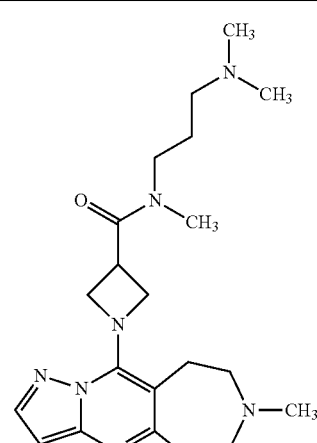 | 7.8 | none | 400.5 [M + H]+ | 0.77 (R) |
| 36.56 | 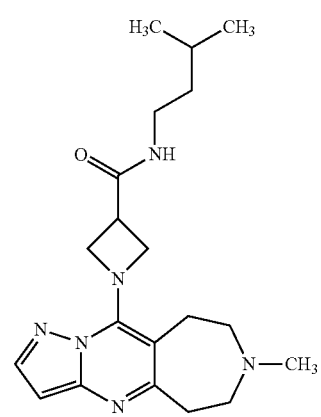 [SMILES: CC(C)CCNC(=O)C1CN(c2c3c(nc4ccnn24)CCN(C)CC3)C1] | 5.9 | none | 371.5 [M + H]+ | 0.89 (R) |
| 36.57 | 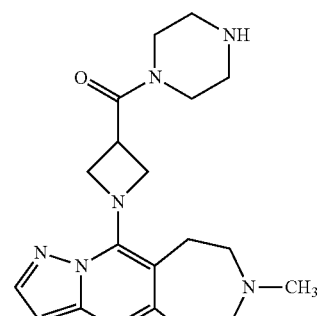 | 36.8 | none | 370.5 [M + H]+ | 0.54 (R) |

TABLE 19-continued
| Example | Structure | Yield of final step (%) | Salt type | Mass spec result | HPLC retention time (method) |
|---|---|---|---|---|---|
| 36.58 | 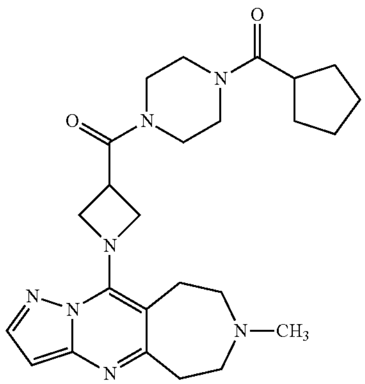 [SMILES: CN1CCc2nc3ccnn3c(N3CC(C(=O)N4CCN(C(=O)C5CCCC5)CC4)C3)c2CC1] | 27.1 | none | 466.6 [M + H]+ | 0.83 (R) |
| 36.59 | 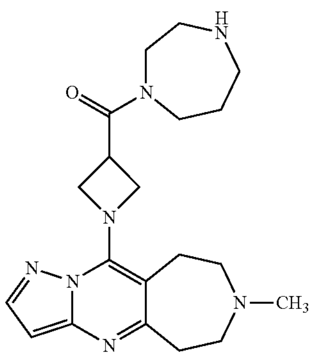 [SMILES: CN1CCc2nc3ccnn3c(N3CC(C(=O)N4CCCNCC4)C3)c2CC1] | 18.5 | none | 384.5 [M + H]+ | 0.61 (R) |
Example 37
The compounds described in Table 20 were synthesized according to General Route 31b.
TABLE 20
| Example | Structure | Yield of final step (%) | Salt type | Mass spec result | HPLC retention time (method) |
|---|---|---|---|---|---|
| 37.1 | 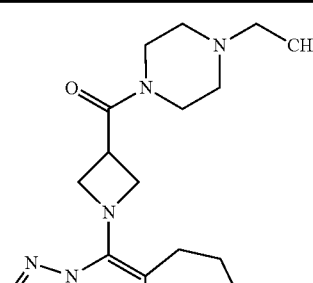 | 64.3 | TF | 384.5 [M + H]+ | 0.66 (R) |

TABLE 20-continued

| Example | Structure | Yield of final step (%) | Salt type | Mass spec result | HPLC retention time (method) |
|---|---|---|---|---|---|
| 37.2 | 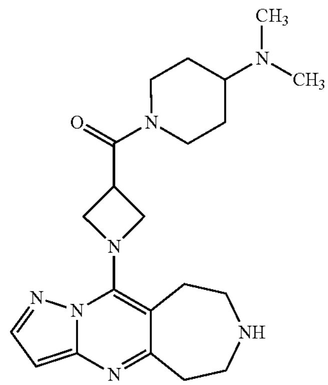 [SMILES: CN(C)C1CCN(C(=O)C2CN(c3c4c(nc5ccnn35)CCNCC4)C2)CC1] | 58.6 | TF | 398.5 [M + H]+ | 0.7 (R) |
| 37.3 | 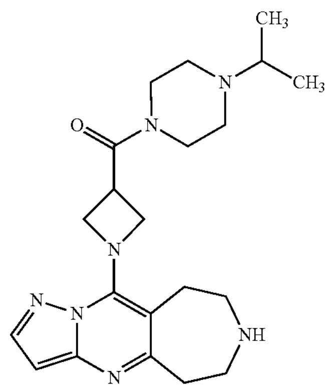 | 46.9 | TF | 398.5 [M + H]+ | 0.74 (R) |
| 37.4 | 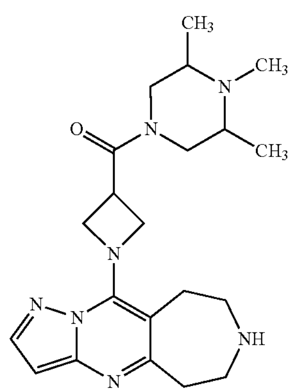 [SMILES: CC1CN(C(=O)C2CN(c3c4c(nc5ccnn35)CCNCC4)C2)CC(C)N1C] | 78.2 | TF | 398.5 [M + H]+ | 0.69 (R) |
| 37.5 | 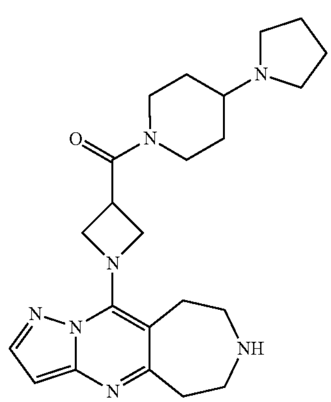 [SMILES: O=C(C1CN(c2c3c(nc4ccnn24)CCNCC3)C1)N1CCC(N2CCCC2)CC1] | 94.9 | TF | 424.6 [M + H]+ | 0.85 (R) |

TABLE 20-continued

| Example | Structure | Yield of final step (%) | Salt type | Mass spec result | HPLC retention time (method) |
|---|---|---|---|---|---|
| 37.6 | 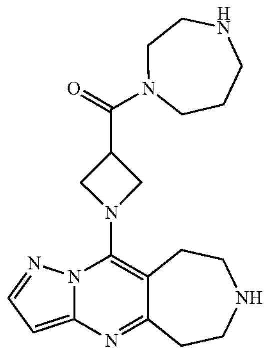 [SMILES: O=C(C1CN(c2c3c(nc4ccnn24)CCNCC3)C1)N1CCCNCC1] | 66.2 | TF | 370.5 [M + H]+ | 0.56 (R) |
| 37.7 | 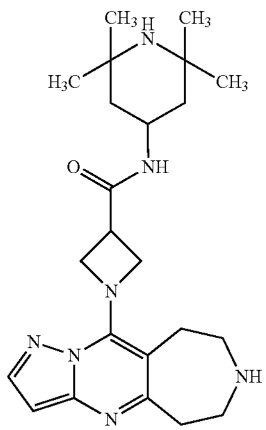 [SMILES: CC1(C)CC(NC(=O)C2CN(c3c4c(nc5ccnn35)CCNCC4)C2)CC(C)(C)N1] | 83.4 | TF | 426.6 [M + H]+ | 0.78 (R) |
| 37.8 | 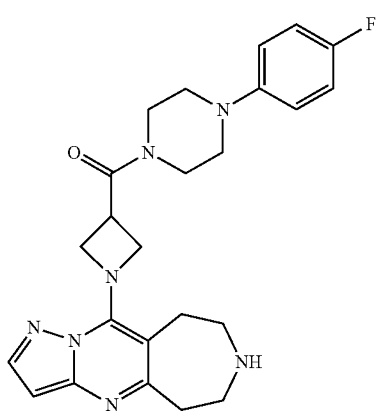 [SMILES: O=C(C1CN(c2c3c(nc4ccnn24)CCNCC3)C1)N1CCN(c2ccc(F)cc2)CC1] | 79.9 | TF | 450.5 [M + H]+ | 0.98 (R) |
| 37.9 | 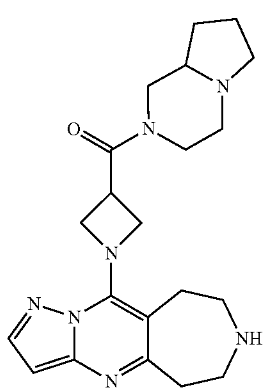 [SMILES: O=C(C1CN(c2c3c(nc4ccnn24)CCNCC3)C1)N1CCN2CCCC2C1] | 70.7 | TF | 396.5 [M + H]+ | 0.68 (R) |

TABLE 20-continued

| Example | Structure | Yield of final step (%) | Salt type | Mass spec result | HPLC retention time (method) |
|---------|-----------|-------------------------|-----------|------------------|-------------------------------|
| 37.10 | 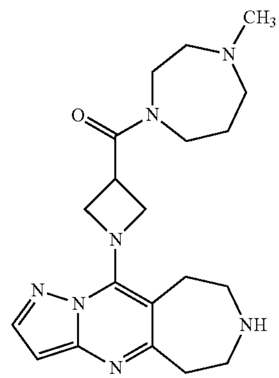 [SMILES: CN1CCCN(C(=O)C2CN(c3c4c(nc5ccnn35)CCNCC4)C2)CC1] | 62.3 | TF | 384.5 [M + H]+ | 0.62 (R) |
| 37.11 | 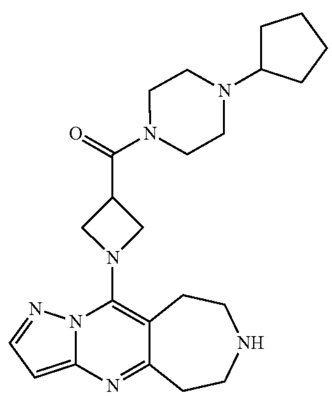 [SMILES: O=C(C1CN(c2c3c(nc4ccnn24)CCNCC3)C1)N1CCN(C2CCCC2)CC1] | 72.5 | TF | 424.6 [M + H]+ | 0.88 (R) |
| 37.12 | 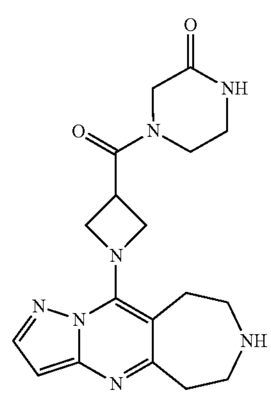 [SMILES: O=C1CN(C(=O)C2CN(c3c4c(nc5ccnn35)CCNCC4)C2)CCN1] | 74.5 | TF | 370.5 [M + H]+ | 0.44 (R) |
| 37.13 | 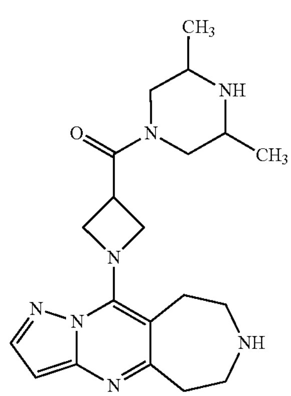 [SMILES: CC1CN(C(=O)C2CN(c3c4c(nc5ccnn35)CCNCC4)C2)CC(C)N1] | 90.4 | TF | 384.5 [M + H]+ | 0.59 (R) |

TABLE 20-continued

| Example | Structure | Yield of final step (%) | Salt type | Mass spec result | HPLC retention time (method) |
|---|---|---|---|---|---|
| 37.14 | 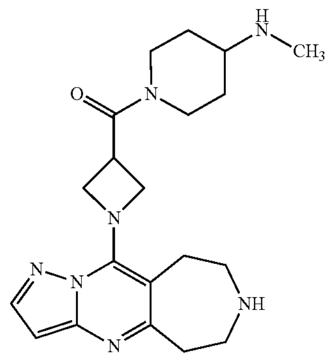 [SMILES: CNC1CCN(C(=O)C2CN(c3c4c(nc5ccnn35)CCNCC4)C2)CC1] | 20.9 | NONE | 384.5 [M + H]+ | 0.7 (R) |
| 37.15 | 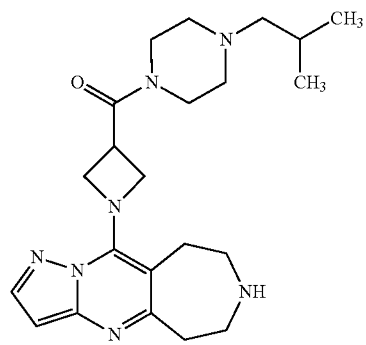 [SMILES: CC(C)CN1CCN(C(=O)C2CN(c3c4c(nc5ccnn35)CCNCC4)C2)CC1] | 49.5 | TF | 412.6 [M + H]+ | 0.98 (R) |
| 37.16 | 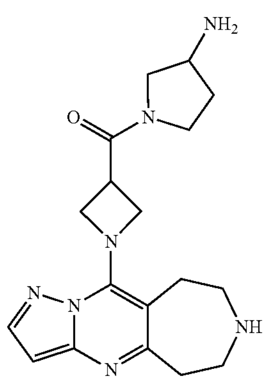 [SMILES: NC1CCN(C(=O)C2CN(c3c4c(nc5ccnn35)CCNCC4)C2)C1] | 55.4 | TF | 356.5 [M + H]+ | 0.49 (R) |
| 37.17 | 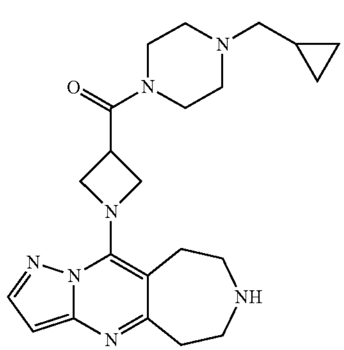 [SMILES: O=C(C1CN(c2c3c(nc4ccnn24)CCNCC3)C1)N1CCN(CC2CC2)CC1] | 53.5 | TF | 410.5 [M + H]+ | 0.79 (R) |

TABLE 20-continued

| Example | Structure | Yield of final step (%) | Salt type | Mass spec result | HPLC retention time (method) |
|---|---|---|---|---|---|
| 37.18 | 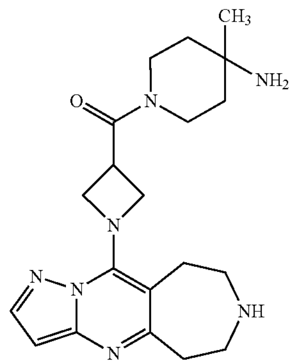 [SMILES: CC1(N)CCN(C(=O)C2CN(c3c4c(nc5ccnn35)CCNCC4)C2)CC1] | 72.4 | TF | 384.5 [M + H]+ | 0.6 (R) |
| 37.19 | 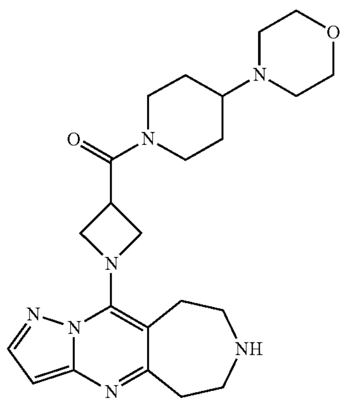 [SMILES: O=C(C1CN(c2c3c(nc4ccnn24)CCNCC3)C1)N1CCC(N2CCOCC2)CC1] | 97.5 | TF | 440.6 [M + H]+ | 0.62 (R) |
| 37.20 | 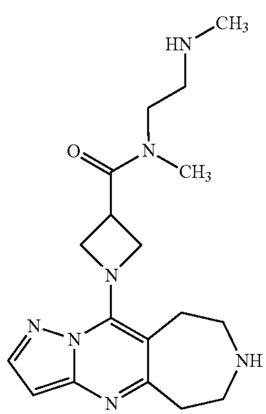 [SMILES: CNCCN(C)C(=O)C1CN(c2c3c(nc4ccnn24)CCNCC3)C1] | 70.0 | TF | 358.5 [M + H]+ | 0.63 (R) |
| 37.21 | 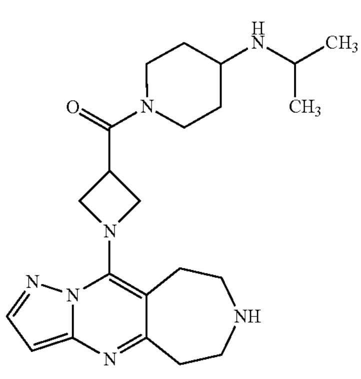 [SMILES: CC(C)NC1CCN(C(=O)C2CN(c3c4c(nc5ccnn35)CCNCC4)C2)CC1] | 22.8 | TF | 412.5 [M + H]+ | 0.83 (R) |

TABLE 20-continued

| Example | Structure | Yield of final step (%) | Salt type | Mass spec result | HPLC retention time (method) |
|---|---|---|---|---|---|
| 37.22 | 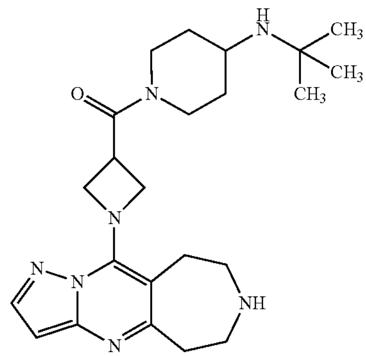 [SMILES: CC(C)(C)NC1CCN(C(=O)C2CN(c3c4c(nc5ccnn35)CCNCC4)C2)CC1] | 42.6 | TF | 426.6 [M + H]+ | 0.91 (R) |
| 37.23 | 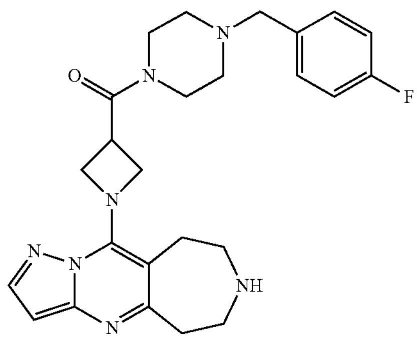 [SMILES: O=C(C1CN(c2c3c(nc4ccnn24)CCNCC3)C1)N1CCN(Cc2ccc(F)cc2)CC1] | 83.1 | TF | 464.6 [M + H]+ | 0.98 (R) |
| 37.25 | 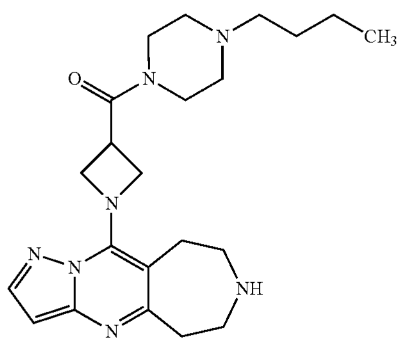 [SMILES: CCCCN1CCN(C(=O)C2CN(c3c4c(nc5ccnn35)CCNCC4)C2)CC1] | 45.7 | TF | 412.6 [M + H]+ | 0.9 (R) |
| 37.26 | 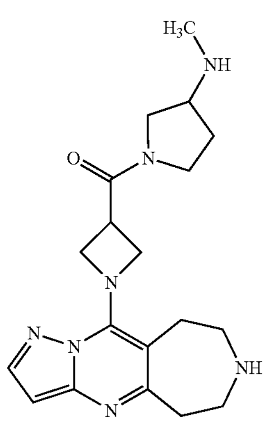 [SMILES: CNC1CCN(C(=O)C2CN(c3c4c(nc5ccnn35)CCNCC4)C2)C1] | 40.6 | | 370.5 [M + H]+ | 0.56 (R) |

TABLE 20-continued

| Example | Structure | Yield of final step (%) | Salt type | Mass spec result | HPLC retention time (method) |
|---|---|---|---|---|---|
| 37.27 | 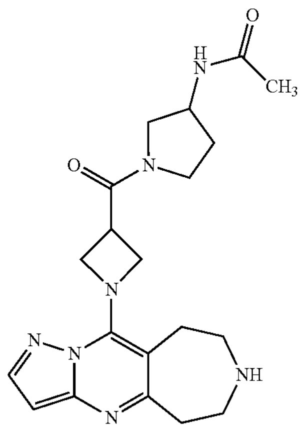 [SMILES: CC(=O)NC1CCN(C(=O)C2CN(c3c4c(nc5ccnn35)CCNCC4)C2)C1] | 60.6 | TF | 398.5 [M + H]+ | 0.5 (R) |
| 37.28 | Chiral | 93.5 | TF | 368.5 [M + H]+ | 0.49 (R) |
| 37.29 | 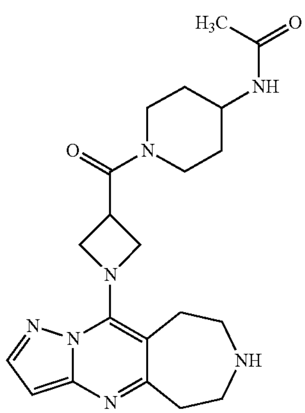 [SMILES: CC(=O)NC1CCN(C(=O)C2CN(c3c4c(nc5ccnn35)CCNCC4)C2)CC1] | 59.0 | TF | 412.5 [M + H]+ | 0.52 (R) |
| 37.30 | 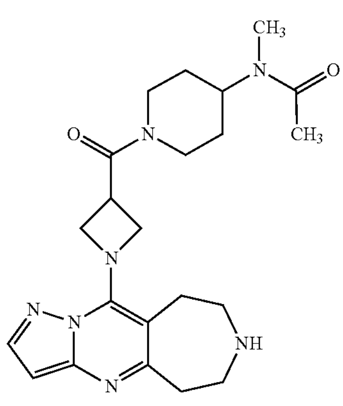 [SMILES: CC(=O)N(C)C1CCN(C(=O)C2CN(c3c4c(nc5ccnn35)CCNCC4)C2)CC1] | 55.6 | TF | 426.5 [M + H]+ | 0.59 (R) |

TABLE 20-continued

| Example | Structure | Yield of final step (%) | Salt type | Mass spec result | HPLC retention time (method) |
|---|---|---|---|---|---|
| 37.31 | 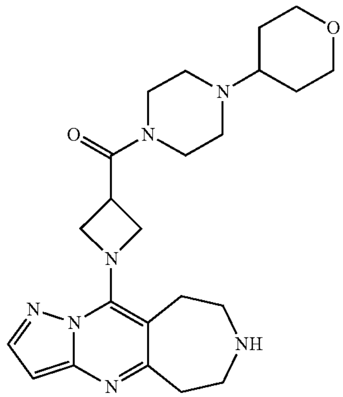 [SMILES: O=C(C1CN(c2c3c(nc4ccnn24)CCNCC3)C1)N1CCN(C2CCOCC2)CC1] | 48.8 | TF | 440.6 [M + H]+ | 0.63 (R) |
| 37.32 | 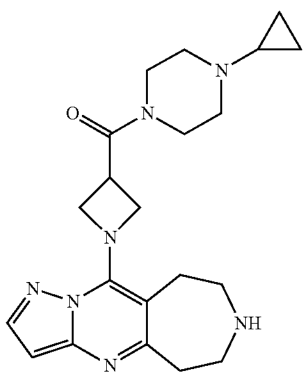 [SMILES: O=C(C1CN(c2c3c(nc4ccnn24)CCNCC3)C1)N1CCN(C2CC2)CC1] | 49.1 | TF | 396.5 [M + H]+ | 0.75 (R) |
| 37.33 | 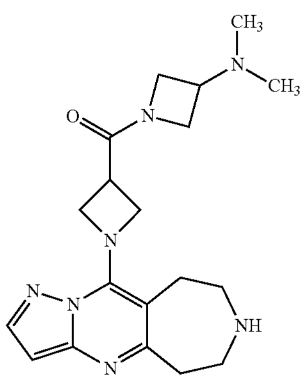 [SMILES: CN(C)C1CN(C(=O)C2CN(c3c4c(nc5ccnn35)CCNCC4)C2)C1] | 33.1 | TF | 370.5 [M + H]+ | 0.58 (R) |
| 37.34 | 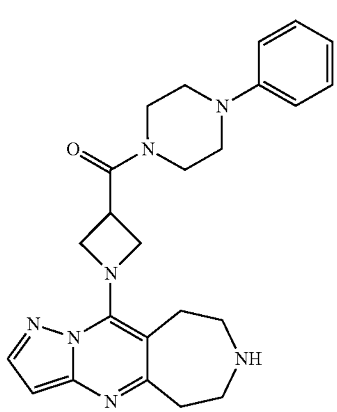 [SMILES: O=C(C1CN(c2c3c(nc4ccnn24)CCNCC3)C1)N1CCN(c2ccccc2)CC1] | 67.8 | TF | 432.5 [M + H]+ | 0.96 (R) |

TABLE 20-continued

| Example | Structure | Yield of final step (%) | Salt type | Mass spec result | HPLC retention time (method) |
|---|---|---|---|---|---|
| 37.35 | 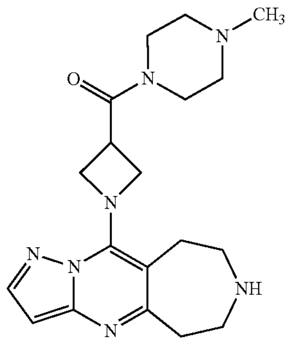 | 60.0 | TF | 370.5 [M + H]+ | 0.58 (R) |
| 37.36 | 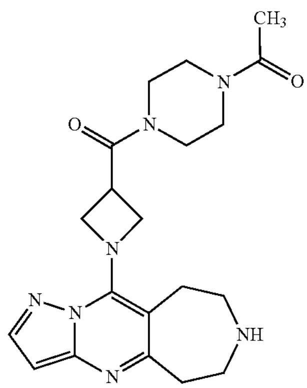 [SMILES: CC(=O)N1CCN(C(=O)C2CN(c3c4c(nc5ccnn35)CCNCC4)C2)CC1] | 70.4 | TF | 398.5 [M + H]+ | 0.52 (R) |
| 37.37 | 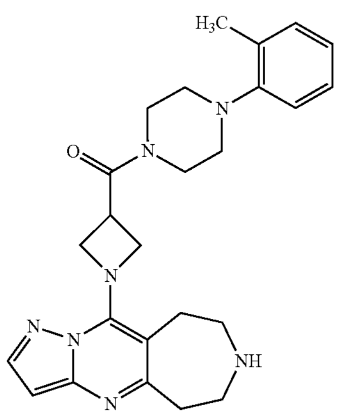 [SMILES: Cc1ccccc1N1CCN(C(=O)C2CN(c3c4c(nc5ccnn35)CCNCC4)C2)CC1] | 73.3 | TF | 446.6 [M + H]+ | 1.14 (R) |
| 37.38 | 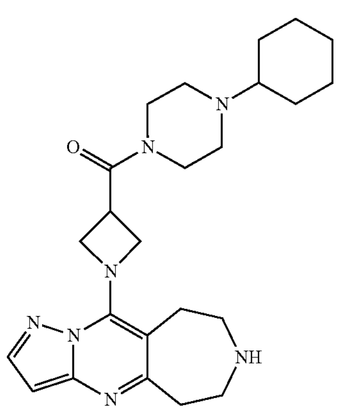 [SMILES: O=C(C1CN(c2c3c(nc4ccnn24)CCNCC3)C1)N1CCN(C2CCCCC2)CC1] | 54.4 | TF | 438.6 [M + H]+ | 1 (R) |

TABLE 20-continued

| Example | Structure | Yield of final step (%) | Salt type | Mass spec result | HPLC retention time (method) |
| --- | --- | --- | --- | --- | --- |
| 37.39 | 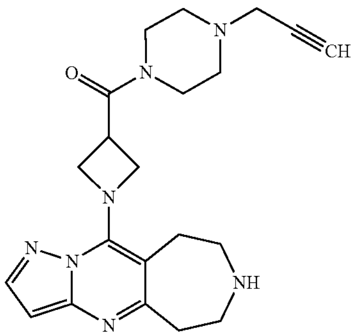 [SMILES: C#CCN1CCN(C(=O)C2CN(c3c4c(nc5ccnn35)CCNCC4)C2)CC1] | 25.4 | NONE | 394.5 [M + H]+ | 0.65 (R) |
| 37.40 | 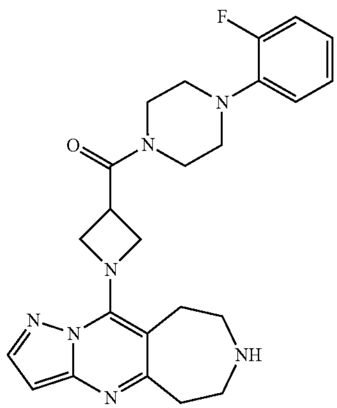 [SMILES: O=C(C1CN(c2c3c(nc4ccnn24)CCNCC3)C1)N1CCN(c2ccccc2F)CC1] | 69.2 | TF | 450.5 [M + H]+ | 1.01 (R) |
| 37.41 | 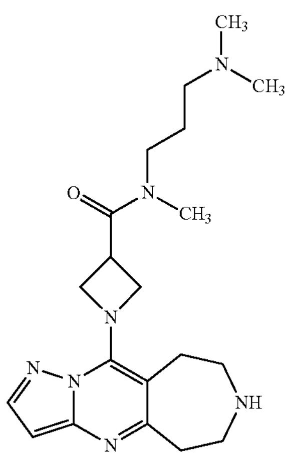 [SMILES: CN(C)CCCN(C)C(=O)C1CN(c2c3c(nc4ccnn24)CCNCC3)C1] | 64.1 | TF | 386.5 [M + H]+ | 0.78 (R) |
| 37.42 | 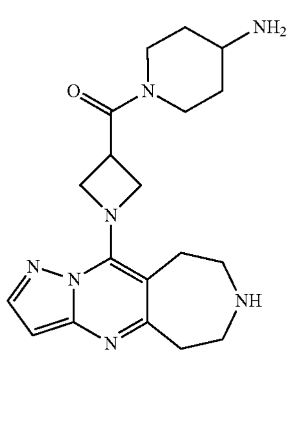 [SMILES: NC1CCN(C(=O)C2CN(c3c4c(nc5ccnn35)CCNCC4)C2)CC1] | 91.0 | TF | 370.5 [M + H]+ | 0.55 (R) |

TABLE 20-continued

| Example | Structure | Yield of final step (%) | Salt type | Mass spec result | HPLC retention time (method) |
|---------|-----------|------------------------|-----------|------------------|------------------------------|
| 37.43 | 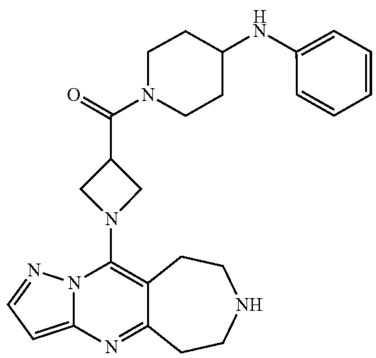 [SMILES: O=C(C1CN(c2c3c(nc4ccnn24)CCNCC3)C1)N1CCC(Nc2ccccc2)CC1] | 73.3 | TF | 446.6 [M + H]+ | 0.98 (R) |
| 37.44 | 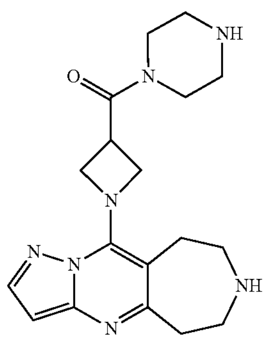 [SMILES: O=C(C1CN(c2c3c(nc4ccnn24)CCNCC3)C1)N1CCNCC1] | 83.1 | TF | 356.5 [M + H]+ | 0.48 (R) |
| 37.45 | 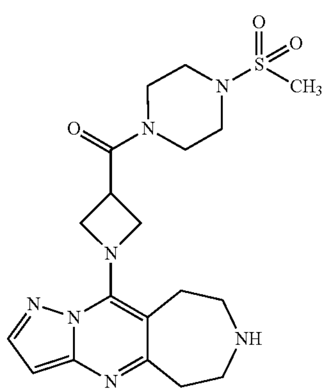 [SMILES: CS(=O)(=O)N1CCN(C(=O)C2CN(c3c4c(nc5ccnn35)CCNCC4)C2)CC1] | 49.3 | TF | 434.5 [M + H]+ | 0.58 (R) |
| 37.46 | 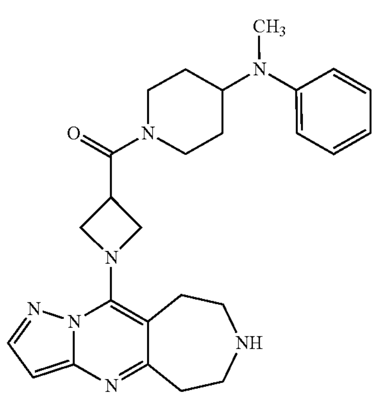 [SMILES: CN(c1ccccc1)C1CCN(C(=O)C2CN(c3c4c(nc5ccnn35)CCNCC4)C2)CC1] | 50.0 | NONE | 460.6 [M + H]+ | 1.1 (R) |

TABLE 20-continued

| Example | Structure | Yield of final step (%) | Salt type | Mass spec result | HPLC retention time (method) |
|---|---|---|---|---|---|
| 37.47 | 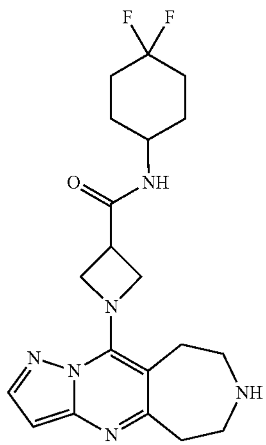 [SMILES: O=C(NC1CCC(F)(F)CC1)C1CN(c2c3c(nc4ccnn24)CCNCC3)C1] | 26.8 | TF | 405.5 [M + H]+ | 0.77 (R) |
| 37.48 | 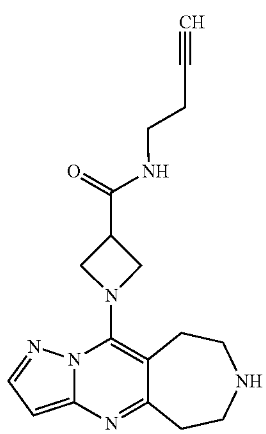 [SMILES: C#CCCNC(=O)C1CN(c2c3c(nc4ccnn24)CCNCC3)C1] | 25.6 | TF | 339.4 [M + H]+ | 0.57 (R) |
| 37.49 | 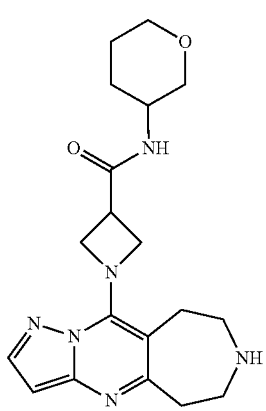 [SMILES: O=C(NC1CCCOC1)C1CN(c2c3c(nc4ccnn24)CCNCC3)C1] | 32.8 | TF | 371.5 [M + H]+ | 0.57 (R) |

TABLE 20-continued

| Example | Structure | Yield of final step (%) | Salt type | Mass spec result | HPLC retention time (method) |
|---|---|---|---|---|---|
| 37.50 | 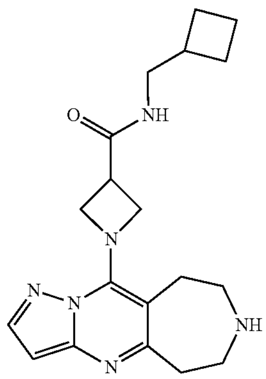 [SMILES: O=C(NCC1CCC1)C1CN(c2c3c(nc4ccnn24)CCNCC3)C1] | 35.2 | TF | 355.5 [M + H]+ | 0.77 (R) |
| 37.51 | 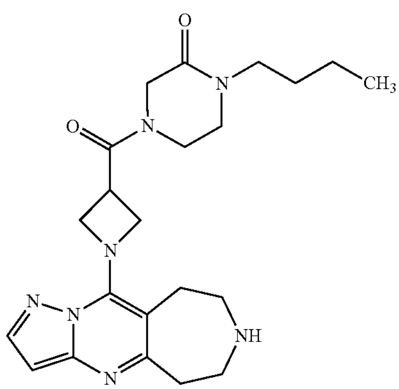 [SMILES: CCCCN1CCN(C(=O)C2CN(c3c4c(nc5ccnn35)CCNCC4)C2)CC1=O] | 37.3 | TF | 426.5 [M + H]+ | 0.72 (R) |
| 37.52 | 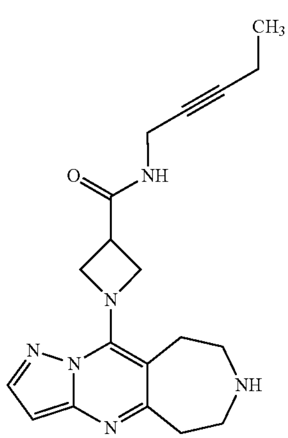 [SMILES: CCC#CCNC(=O)C1CN(c2c3c(nc4ccnn24)CCNCC3)C1] | 27.2 | TF | 353.4 [M + H]+ | 0.72 (R) |

TABLE 20-continued
| Example | Structure | Yield of final step (%) | Salt type | Mass spec result | HPLC retention time (method) |
|---|---|---|---|---|---|
| 37.53 | 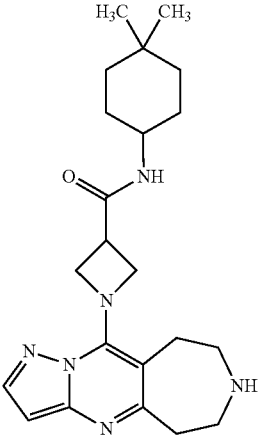 [SMILES: CC1(C)CCC(NC(=O)C2CN(c3c4c(nc5ccnn35)CCNCC4)C2)CC1] | 36.4 | TF | 397.5 [M + H]+ | 1.03 (R) |
| 37.54 | 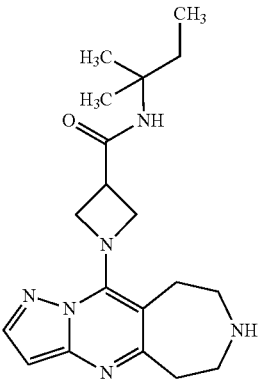 [SMILES: CCC(C)(C)NC(=O)C1CN(c2c3c(nc4ccnn24)CCNCC3)C1] | 16.6 | TF | 357.5 [M + H]+ | 0.84 (R) |
| 37.55 | 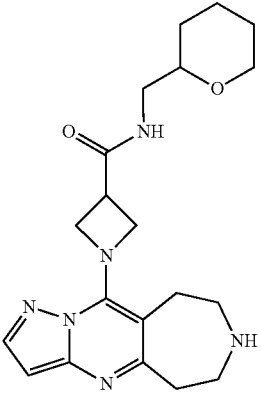 [SMILES: O=C(NCC1CCCCO1)C1CN(c2c3c(nc4ccnn24)CCNCC3)C1] | 37.3 | TF | 385.5 [M + H]+ | 0.57 (R) |

TABLE 20-continued

| Example | Structure | Yield of final step (%) | Salt type | Mass spec result | HPLC retention time (method) |
|---|---|---|---|---|---|
| 37.56 | 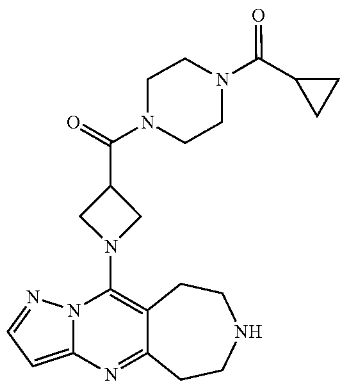 [SMILES: O=C(C1CC1)N1CCN(C(=O)C2CN(c3c4c(nc5ccnn35)CCNCC4)C2)CC1] | 16.9 | TF | 424.5 [M + H]+ | 0.61 (R) |
| 37.57 | 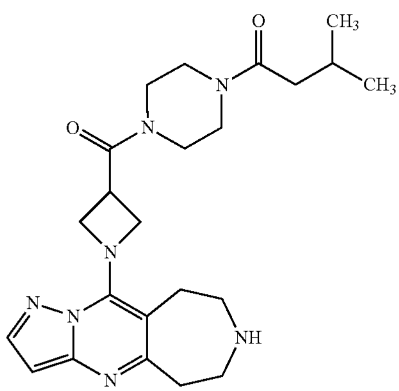 [SMILES: CC(C)CC(=O)N1CCN(C(=O)C2CN(c3c4c(nc5ccnn35)CCNCC4)C2)CC1] | 41.0 | TF | 440.6 [M + H]+ | 0.73 (R) |
| 37.58 | 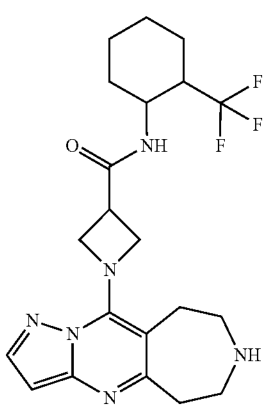 [SMILES: O=C(NC1CCCCC1C(F)(F)F)C1CN(c2c3c(nc4ccnn24)CCNCC3)C1] | 31.8 | TF | 437.5 [M + H]+ | 0.91 (R) |

TABLE 20-continued
| Example | Structure | Yield of final step (%) | Salt type | Mass spec result | HPLC retention time (method) |
|---|---|---|---|---|---|
| 37.59 | 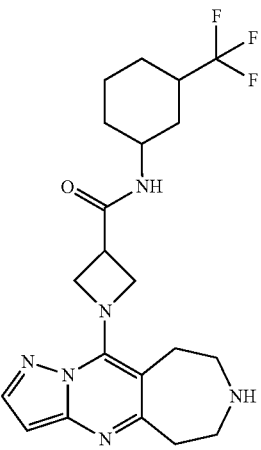 [SMILES: O=C(NC1CCCC(C(F)(F)F)C1)C1CN(c2c3c(nc4ccnn24)CCNCC3)C1] | 42.5 | TF | 437.5 [M + H]+ | 0.95 (R) |
| 37.60 | 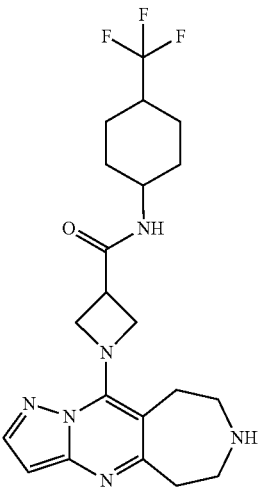 [SMILES: O=C(NC1CCC(C(F)(F)F)CC1)C1CN(c2c3c(nc4ccnn24)CCNCC3)C1] | 43.2 | TF | 437.5 [M + H]+ | 0.94 (R) |
| 37.61 | 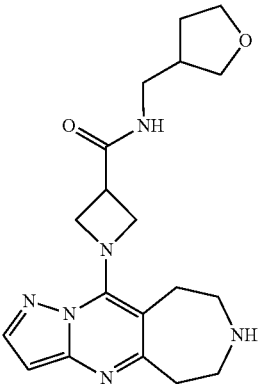 [SMILES: O=C(NCC1CCOC1)C1CN(c2c3c(nc4ccnn24)CCNCC3)C1] | 43.3 | TF | 371.5 [M + H]+ | 0.53 (R) |

TABLE 20-continued
| Example | Structure | Yield of final step (%) | Salt type | Mass spec result | HPLC retention time (method) |
|---|---|---|---|---|---|
| 37.62 | 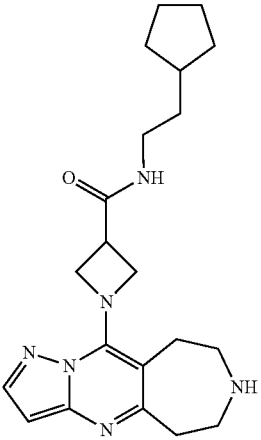 [SMILES: O=C(NCCC1CCCC1)C1CN(c2c3c(nc4ccnn24)CCNCC3)C1] | 33.4 | TF | 383.5 [M + H]+ | 0.97 (R) |
| 37.63 | 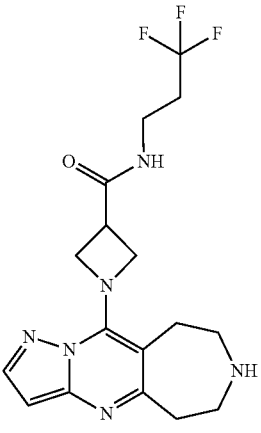 [SMILES: O=C(NCCC(F)(F)F)C1CN(c2c3c(nc4ccnn24)CCNCC3)C1] | 24.8 | TF | 383.4 [M + H]+ | 0.67 (R) |
| 37.64 | 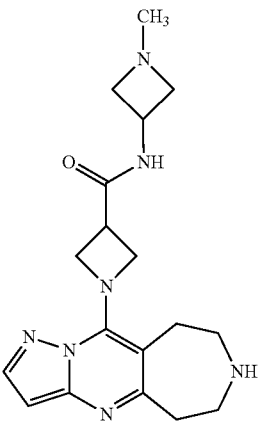 [SMILES: CN1CC(NC(=O)C2CN(c3c4c(nc5ccnn35)CCNCC4)C2)C1] | 15.3 | TF | 356.4 [M + H]+ | 0.83 (R) |

TABLE 20-continued
| Example | Structure | Yield of final step (%) | Salt type | Mass spec result | HPLC retention time (method) |
|---|---|---|---|---|---|
| 37.65 | 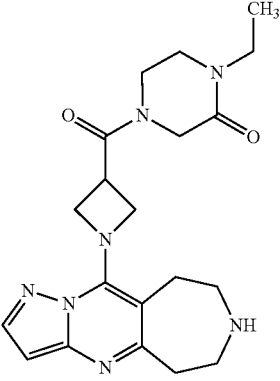 [SMILES: CCN1CCN(C(=O)C2CN(c3c4c(nc5ccnn35)CCNCC4)C2)CC1=O] | 20.5 | TF | 398.5 [M + H]+ | 0.55 (R) |
| 37.66 | 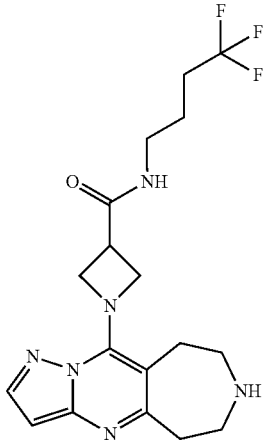 [SMILES: O=C(NCCCC(F)(F)F)C1CN(c2c3c(nc4ccnn24)CCNCC3)C1] | 36.0 | TF | 397.4 [M + H]+ | 0.75 (R) |
| 37.67 | 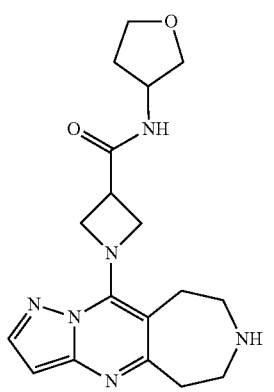 [SMILES: O=C(NC1CCOC1)C1CN(c2c3c(nc4ccnn24)CCNCC3)C1] | 4.0 | TF | 357.4 [M + H]+ | 0.51 (R) |

TABLE 20-continued

| Example | Structure | Yield of final step (%) | Salt type | Mass spec result | HPLC retention time (method) |
|---|---|---|---|---|---|
| 37.68 | 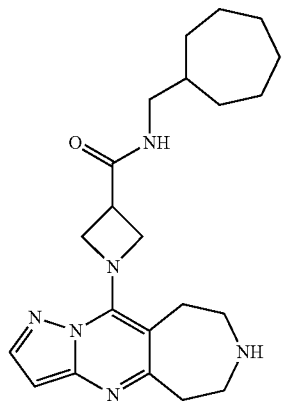 [SMILES: O=C(NCC1CCCCCC1)C1CN(c2c3c(nc4ccnn24)CCNCC3)C1] | 38.0 | TF | 397.5 [M + H]+ | 1.04 (R) |
| 37.69 | 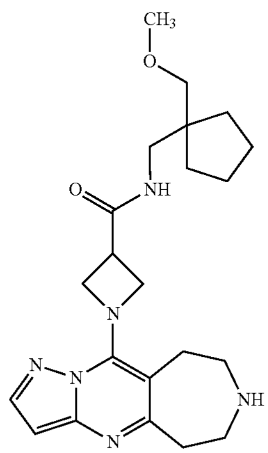 [SMILES: COCC1(CNC(=O)C2CN(c3c4c(nc5ccnn35)CCNCC4)C2)CCCC1] | 18.8 | TF | 413.5 [M + H]+ | 0.90 (R) |
| 37.70 | 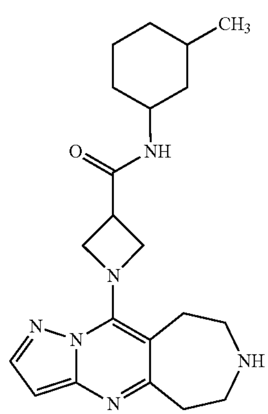 [SMILES: CC1CCCC(NC(=O)C2CN(c3c4c(nc5ccnn35)CCNCC4)C2)C1] | 37.1 | TF | 383.5 [M + H]+ | 0.95 (R) |

TABLE 20-continued
| Example | Structure | Yield of final step (%) | Salt type | Mass spec result | HPLC retention time (method) |
|---|---|---|---|---|---|
| 37.71 | 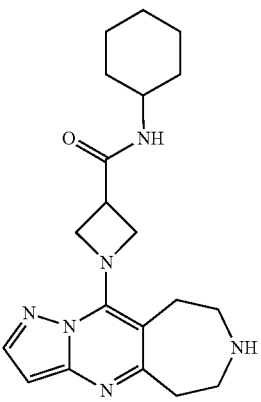 [SMILES: O=C(NC1CCCCC1)C1CN(c2c3c(nc4ccnn24)CCNCC3)C1] | 38.5 | TF | 369.5 [M + H]+ | 0.83 (R) |
| 37.72 | 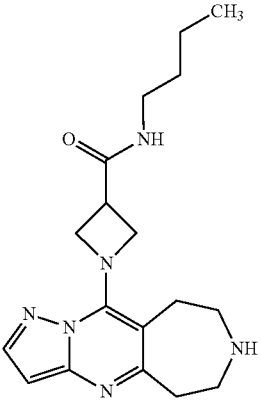 | 15.8 | TF | 343.4 [M + H]+ | 0.73 (R) |
| 37.73 | 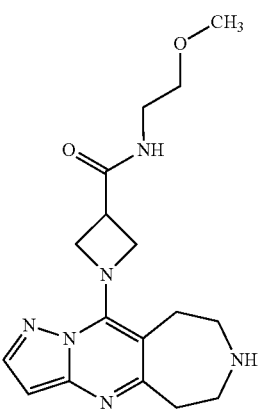 [SMILES: COCCNC(=O)C1CN(c2c3c(nc4ccnn24)CCNCC3)C1] | 36.4 | TF | 345.4 [M + H]+ | 0.51 (R) |

TABLE 20-continued

| Example | Structure | Yield of final step (%) | Salt type | Mass spec result | HPLC retention time (method) |
|---|---|---|---|---|---|
| 37.74 | 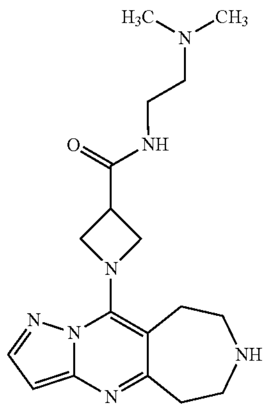 [SMILES: CN(C)CCNC(=O)C1CN(c2c3c(nc4ccnn24)CCNCC3)C1] | 56.6 | TF | 358.5 [M + H]+ | 0.59 (R) |
| 37.75 | 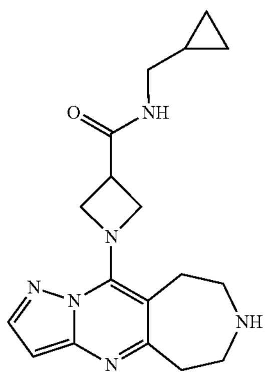 [SMILES: O=C(NCC1CC1)C1CN(c2c3c(nc4ccnn24)CCNCC3)C1] | 25.3 | TF | 341.4 [M + H]+ | 0.64 (R) |
| 37.76 | 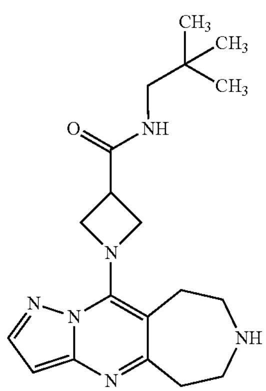 [SMILES: CC(C)(C)CNC(=O)C1CN(c2c3c(nc4ccnn24)CCNCC3)C1] | 22.5 | TF | 357.5 [M + H]+ | 0.80 (R) |
| 37.77 | 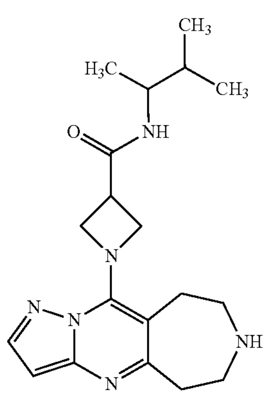 [SMILES: CC(C)C(C)NC(=O)C1CN(c2c3c(nc4ccnn24)CCNCC3)C1] | 36.3 | TF | 357.5 [M + H]+ | 0.79 (R) |

TABLE 20-continued

| Example | Structure | Yield of final step (%) | Salt type | Mass spec result | HPLC retention time (method) |
| --- | --- | --- | --- | --- | --- |
| 37.78 | 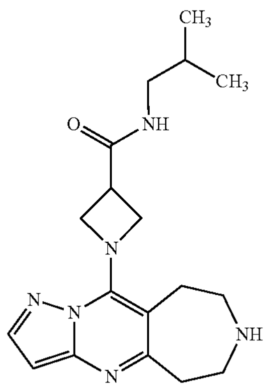 [SMILES: CC(C)CNC(=O)C1CN(c2c3c(nc4ccnn24)CCNCC3)C1] | 5.5 | TF | 343.4 [M + H]+ | 1.05 (R) |
| 37.79 | 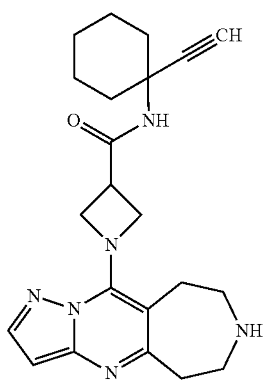 [SMILES: C#CC1(NC(=O)C2CN(c3c4c(nc5ccnn35)CCNCC4)C2)CCCCC1] | 37.9 | TF | 393.5 [M + H]+ | 0.89 (R) |
| 37.80 | 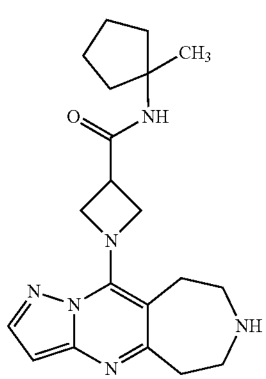 [SMILES: CC1(NC(=O)C2CN(c3c4c(nc5ccnn35)CCNCC4)C2)CCCC1] | 23.2 | TF | 369.5 [M + H]+ | 0.86 (R) |

TABLE 20-continued

| Example | Structure | Yield of final step (%) | Salt type | Mass spec result | HPLC retention time (method) |
|---|---|---|---|---|---|
| 37.81 | 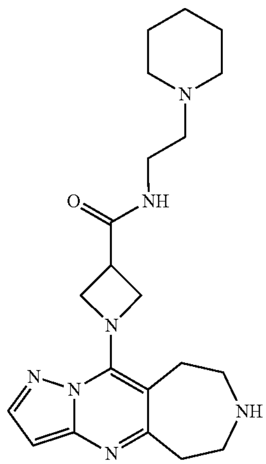 [SMILES: O=C(NCCN1CCCCC1)C1CN(c2c3c(nc4ccnn24)CCNCC3)C1] | 51.2 | TF | 398.5 [M + H]+ | 0.81 (R) |
| 37.82 | 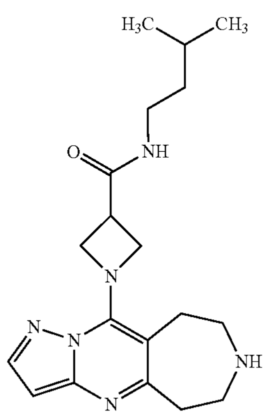 [SMILES: CC(C)CCNC(=O)C1CN(c2c3c(nc4ccnn24)CCNCC3)C1] | 25.9 | TF | 357.5 [M + H]+ | 0.83 (R) |
| 37.83 | 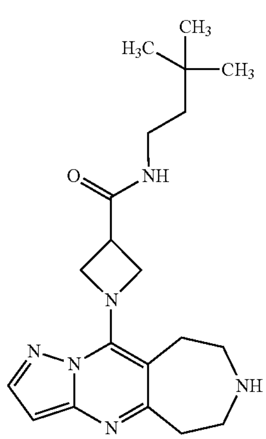 [SMILES: CC(C)(C)CCNC(=O)C1CN(c2c3c(nc4ccnn24)CCNCC3)C1] | 35.1 | TF | 371.5 [M + H]+ | 0.91 (R) |

TABLE 20-continued
| Example | Structure | Yield of final step (%) | Salt type | Mass spec result | HPLC retention time (method) |
|---|---|---|---|---|---|
| 37.84 | 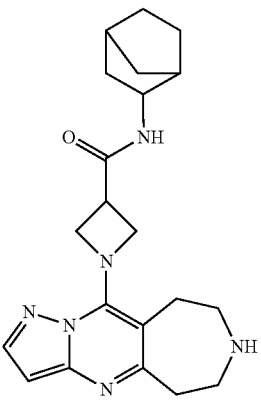 [SMILES: O=C(NC1CC2CCC1C2)C1CN(c2c3c(nc4ccnn24)CCNCC3)C1] | 36.8 | TF | 381.5 [M + H]+ | 0.87 (R) |
| 37.85 | 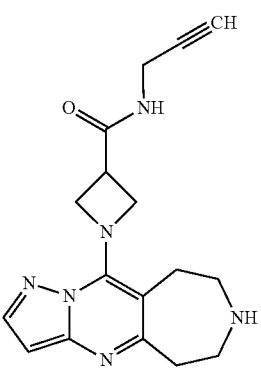 [SMILES: C#CCNC(=O)C1CN(c2c3c(nc4ccnn24)CCNCC3)C1] | 26.0 | TF | 325.4 [M + H]+ | 0.52 (R) |
| 37.86 | 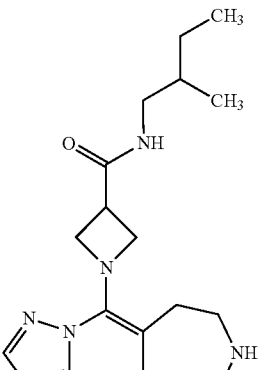 | 19.1 | TF | 357.5 [M + H]+ | 0.82 (R) |
| 37.87 | 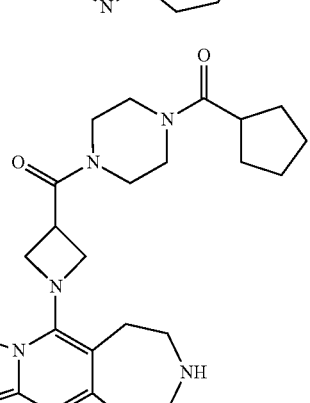 | 44.4 | TF | 452.6 [M + H]+ | 0.78 (R) |

TABLE 20-continued
| Example | Structure | Yield of final step (%) | Salt type | Mass spec result | HPLC retention time (method) |
|---|---|---|---|---|---|
| 37.88 | 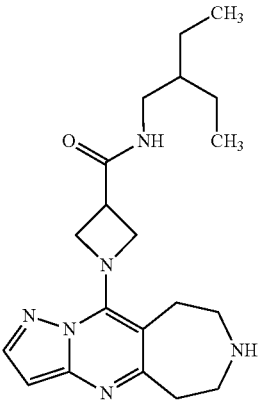 [SMILES: CCC(CC)CNC(=O)C1CN(c2c3c(nc4ccnn24)CCNCC3)C1] | 12.4 | TF | 371.5 [M + H]+ | 0.92 (R) |
| 37.89 | 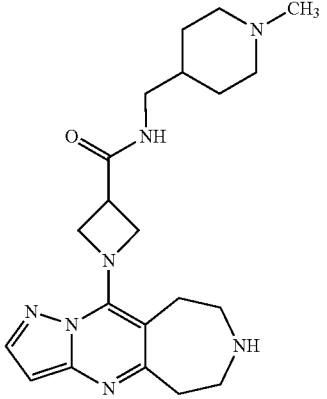 [SMILES: CN1CCC(CNC(=O)C2CN(c3c4c(nc5ccnn35)CCNCC4)C2)CC1] | 53.0 | TF | 398.5 [M + H]+ | 0.97 (R) |
| 37.90 | 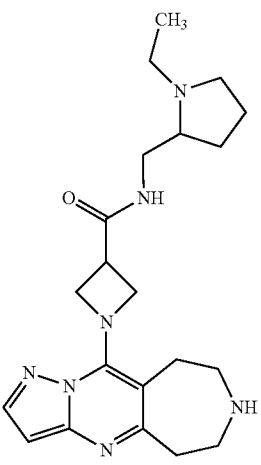 [SMILES: CCN1CCCC1CNC(=O)C1CN(c2c3c(nc4ccnn24)CCNCC3)C1] | 57.9 | TF | 398.5 [M + H]+ | 0.81 (R) |

TABLE 20-continued

| Example | Structure | Yield of final step (%) | Salt type | Mass spec result | HPLC retention time (method) |
|---|---|---|---|---|---|
| 37.91 | 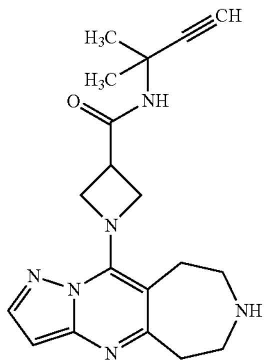 [SMILES: C#CC(C)(C)NC(=O)C1CN(c2c3c(nc4ccnn24)CCNCC3)C1] | 23.2 | TF | 353.4 [M + H]+ | 0.67 (R) |
| 37.92 | 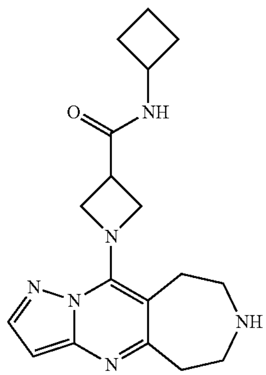 [SMILES: O=C(NC1CCC1)C1CN(c2c3c(nc4ccnn24)CCNCC3)C1] | 24.9 | TF | 341.4 [M + H]+ | 0.66 (R) |
| 37.93 | 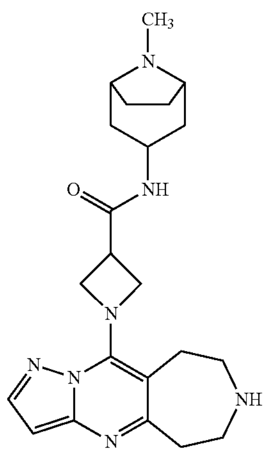 [SMILES: CN1C2CCC1CC(NC(=O)C1CN(c3c4c(nc5ccnn35)CCNCC4)C1)C2] | 22.7 | TF | 410.5 [M + H]+ | 1.00 (R) |
| 37.94 | 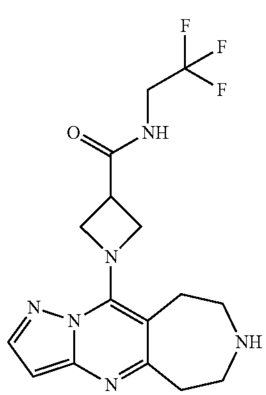 [SMILES: O=C(NCC(F)(F)F)C1CN(c2c3c(nc4ccnn24)CCNCC3)C1] | 48.1 | TF | 369.4 [M + H]+ | 0.64 (R) |

TABLE 20-continued
| Example | Structure | Yield of final step (%) | Salt type | Mass spec result | HPLC retention time (method) |
|---|---|---|---|---|---|
| 37.95 | 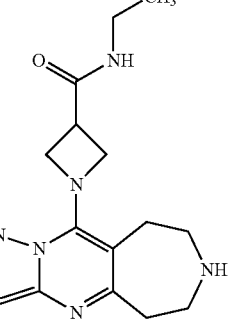 | 39.2 | TF | 315.4 [M + H]+ | 0.52 (R) |
| 37.96 | 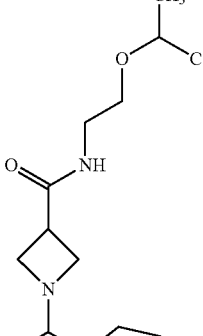 | 35.1 | TF | 373.5 [M + H]+ | 0.66 (R) |
| 37.97 | 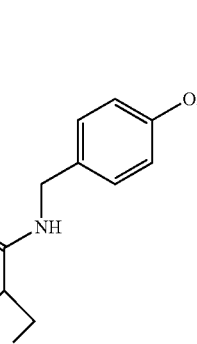 | 46.9 | TF | 443.5 [M + H]+ | 0.87 (R) |

TABLE 20-continued
| Example | Structure | Yield of final step (%) | Salt type | Mass spec result | HPLC retention time (method) |
|---|---|---|---|---|---|
| 37.98 | 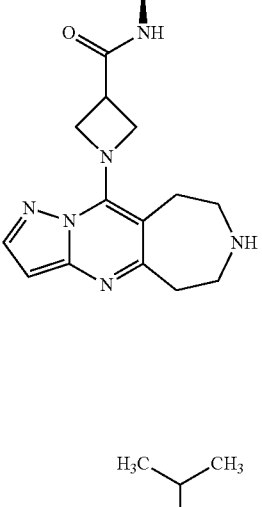 | 24.2 | TF | 412.6 [M + H]+ | 1.04 (R) |
| 37.99 | 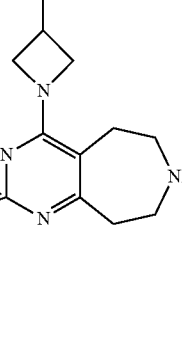 | 47.1 | TF | 371.5 [M + H]+ | 0.90 (R) |
| 37.100 | 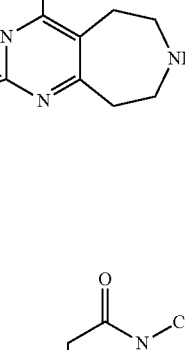 | 24.3 | TF | 384.5 [M + H]+ | 0.49 (R) |

TABLE 20-continued

| Example | Structure | Yield of final step (%) | Salt type | Mass spec result | HPLC retention time (method) |
|---------|-----------|------------------------|-----------|------------------|------------------------------|
| 37.101 | 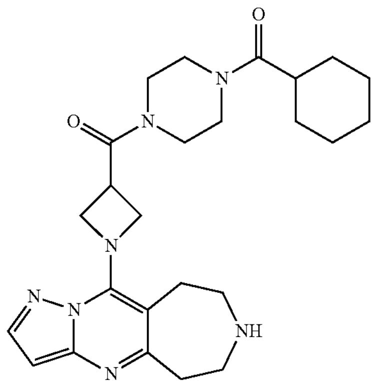 [SMILES: O=C(C1CCCCC1)N1CCN(C(=O)C2CN(c3c4c(nc5ccnn35)CCNCC4)C2)CC1] | 40.2 | TF | 466.6 [M + H]+ | 0.85 (R) |
| 37.102 | 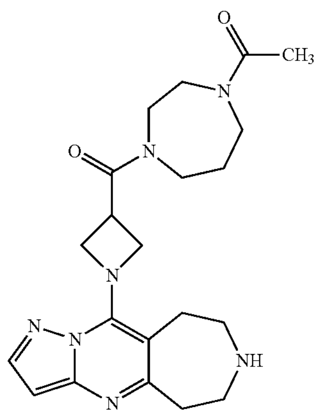 [SMILES: CC(=O)N1CCCN(C(=O)C2CN(c3c4c(nc5ccnn35)CCNCC4)C2)CC1] | 39.2 | TF | 412.5 [M + H]+ | 0.53 (R) |
| 37.103 | 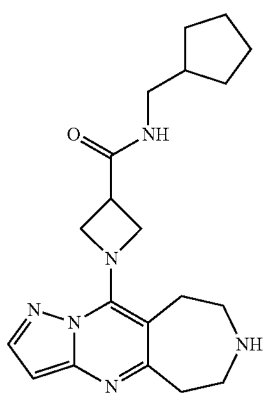 [SMILES: O=C(NCC1CCCC1)C1CN(c2c3c(nc4ccnn24)CCNCC3)C1] | 44.1 | TF | 369.5 [M + H]+ | 0.85 (R) |
| 37.104 | 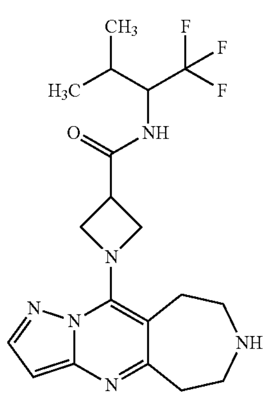 [SMILES: CC(C)C(NC(=O)C1CN(c2c3c(nc4ccnn24)CCNCC3)C1)C(F)(F)F] | 12.6 | TF | 411.4 [M + H]+ | 0.92 (R) |

TABLE 20-continued
| Example | Structure | Yield of final step (%) | Salt type | Mass spec result | HPLC retention time (method) |
|---|---|---|---|---|---|
| 37.105 | 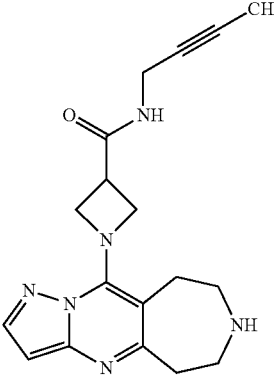 | 23.2 | TF | 339.4 [M + H]+ | 0.61 (R) |
| 37.106 | 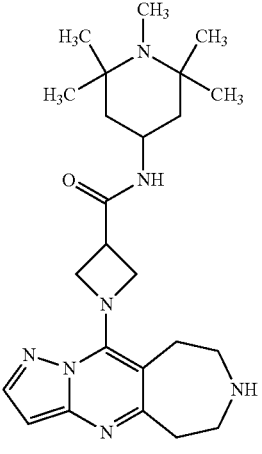 [SMILES: CN1C(C)(C)CC(NC(=O)C2CN(c3c4c(nc5ccnn35)CCNCC4)C2)CC1(C)C] | 49.7 | TF | 440.6 [M + H]+ | 1.19 (R) |
| 37.107 | 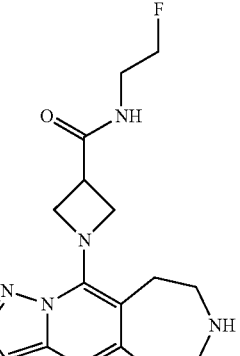 | 18.1 | TF | 333.4 [M + H]+ | 0.50 (R) |

TABLE 20-continued

| Example | Structure | Yield of final step (%) | Salt type | Mass spec result | HPLC retention time (method) |
|---|---|---|---|---|---|
| 37.108 | 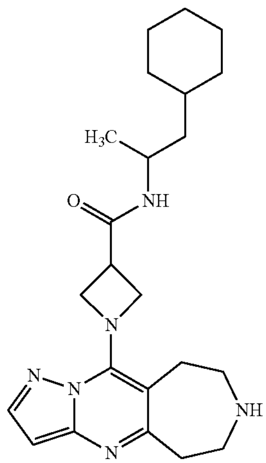 [SMILES: CC(CC1CCCCC1)NC(=O)C1CN(c2c3c(nc4ccnn24)CCNCC3)C1] | 40.2 | TF | 411.6 [M + H]+ | 1.13 (R) |
| 37.109 | 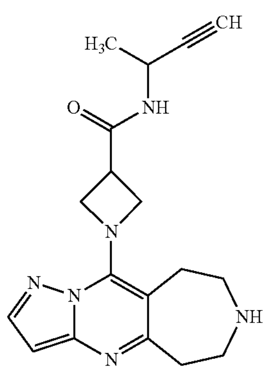 [SMILES: C#CC(C)NC(=O)C1CN(c2c3c(nc4ccnn24)CCNCC3)C1] | 27.4 | TF | 339.4 [M + H]+ | 0.61 (R) |
| 37.110 | 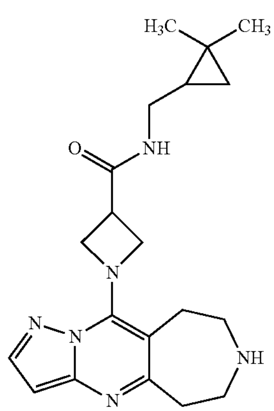 [SMILES: CC1(C)CC1CNC(=O)C1CN(c2c3c(nc4ccnn24)CCNCC3)C1] | 25.1 | TF | 369.5 [M + H]+ | 0.86 (R) |

TABLE 20-continued

| Example | Structure | Yield of final step (%) | Salt type | Mass spec result | HPLC retention time (method) |
|---|---|---|---|---|---|
| 37.111 | 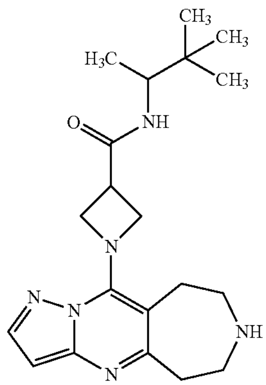 [SMILES: CC(NC(=O)C1CN(c2c3c(nc4ccnn24)CCNCC3)C1)C(C)(C)C] | 43.5 | TF | 371.5 [M + H]+ | 0.87 (R) |

Example 38

(3-Ethynyl-pyrrolidin-1-yl)-[1-(6,7,8,9-tetrahydro-5H-1,4,7,10a-tetraaza-cyclohepta[f]inden-10-yl)-azetidin-3-yl]-methanone

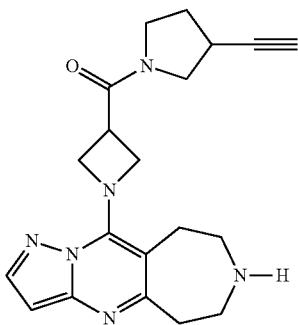 [SMILES: C#CC1CCN(C(=O)C2CN(c3c4c(nc5ccnn35)CCNCC4)C2)C1]

38a 3-Ethynyl-pyrrolidine-1-carboxylic acid tert-butyl ester

To 1.23 g (6.17 mmol) 3-Formyl-pyrrolidine-1-carboxylic acid tert-butyl ester in 30 mL dry MeOH was added at room temperature 1.42 g (7.41 mmol) (1-Diazo-2-oxo-propyl)-phosphonic acid diethyl ester and 1.71 g (12.4 mmol) $K_2CO_3$ and stirring was continued for 2 h. 10 g of silica gel was added to the reaction mixture, stirring continued for 20 min and then filtered. After evaporation of the solvent the residue was purified by column chromatography (silica, cyclohexane/EtOAc 1:1).

Yield: 0.85 g (71% of theory)
$C_{11}H_{17}NO_2$ (M=195.26)
Predicted (EI): Molecular ion $(M)^+$: 195 observed: Molecular ion $(M)^+$: 195
$R_f$-value: 0.64 (silica, cyclohexane/EtOAc 2:1).

38b 3-Ethynyl-pyrrolidinium trifluoro-acetate

To 0.85 g (4.35 mmol) 3-Ethynyl-pyrrolidine-1-carboxylic acid tert-butyl ester in 30 mL DCM was added 2 mL (26.0 mmol) TFA and stirring was continued at room temperature for 3 h. The solvents were evaporated and the residue was used for the next step without further purification.

Yield: 0.91 g (100% of theory)
$C_6H_9NO$ (M=95.15)
Predicted (EI): Molecular ion $(M)^+$: 95 observed: Molecular ion $(M)^+$: 95

38c 10-[3-(3-Ethynyl-pyrrolidine-1-carbonyl)-azetidin-1-yl]-5,6,8,9-tetrahydro-1,4,7,10a-tetraaza-cyclohept[f]indene-7-carboxylic acid tert-butyl ester To 150 mg (0.29 mmol) of 10-(3-Carboxy-azetidin-1-yl)-5,6,8,9-tetrahydro-1,4,7,10a-tetraaza-cyclohept[f]indene-7-carboxylic acid tert-butyl ester (as DIPEA salt) in 1.0 mL NMP was added 105 mg (0.33 mmol) TBTU and 120 µL (0.70 mmol) DIPEA and stirring was continued at room temperature for 1 h. Then 60.7 mg (0.29 mmol) of 3-Ethynyl-pyrrolidinium trifluoro-acetate was added and the reaction mixture was stirred overnight. The reaction mixture was filtered and the purified by HPLC.

Yield: 36 mg (27% of theory)
$C_{25}H_{32}N_6O_3$ (M=464.56)
predicted: Molecular ion $(M+H)^+$: 465 observed: Molecular ion $(M+H)^+$: 465
HPLC-MS: 2.1 minutes (Method R)

38d (3-Ethynyl-pyrrolidin-1-yl)-[1-(6,7,8,9-tetrahydro-5H-1,4,7,10a-tetraaza-cyclohepta[f]inden-10-yl)-azetidin-3-yl]methanone To 36 mg (0.08 mmol) 10-[3-(3-Ethynyl-pyrrolidine-1-carbonyl)-azetidin-1-yl]-5,6,8,9-tetrahydro-1,4,7,10a-tetraaza-cyclohept[f]indene-7-carboxylic acid tert-butyl ester in 10 mL DCM was added 0.4 mL TFA and stirring was continued for 3 h at room temperature. After addition of 2 mL of MeOH 2M NaOH added drop wise to neutralize the reaction mixture. The solvents were evaporated and the residue was purified by HPLC.

Yield: 12 mg (44% of theory)
$C_{20}H_{24}N_6O$ (M=364.44)
predicted: Molecular ion $(M+H)^+$: 365 observed: Molecular ion $(M+H)^+$: 365
HPLC-MS: 1.3 minutes (Method K)

Example 39

(3-Ethynyl-pyrrolidin-1-yl)-[1-(7-methyl-6,7,8,9-tetrahydro-5H-1,4,7,10a-tetraaza-cyclohept[f]inden-10-yl)-azetidin-3-yl]-methanone

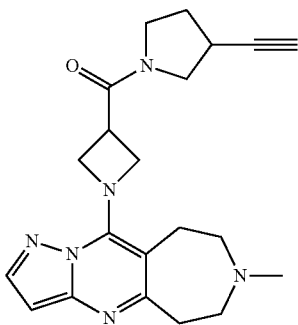 [SMILES: C#CC1CCN(C(=O)C2CN(c3c4c(nc5ccnn35)CCN(C)CC4)C2)C1]

To 50 mg (0.14 mmol) of (3-Ethynyl-pyrrolidin-1-yl)-[1-(6,7,8,9-tetrahydro-5H-1,4,7,10a-tetraaza-cyclohepta[f]inden-10-yl)-azetidin-3-yl]-methanone in 2 mL of THF and 1 mL of puffer solution (pH 5) was added 11.3 µL (0.15 mmol) of formaldehyde (37% in water) and 35 mg (0.17 mmol) of sodium triacetoxyborohydride. Stirring was continued overnight, the reaction mixture diluted with 1 mL of water, filtered and purified by HPLC.

Yield: 39 mg (76% of theory)

$C_{21}H_{26}N_6O$ (M=378.47)

predicted: Molecular ion (M+H)$^+$: 379 observed: Molecular ion (M+H)$^+$: 379

HPLC-MS: 1.3 minutes (Method K)

Example 40

(4,4-Difluoro-perhydro-azepin-1-yl)-[1-(6,7,8,9-tetrahydro-5H-1,4,7,10a-tetraaza-cyclohept[f]inden-10-yl)-azetidin-3-yl]-methanone

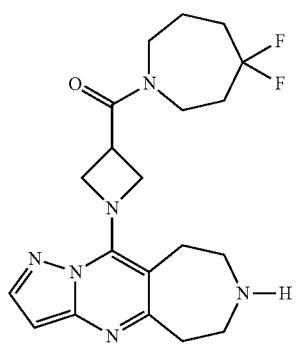 [SMILES: O=C(C1CN(c2c3c(nc4ccnn24)CCNCC3)C1)N1CCCC(F)(F)CC1]

40a 4,4-Difluoro-perhydro-azepine-1-carboxylic acid tert-butyl ester

Under an argon atmosphere was added to 2.50 g (11.7 mmol) 4-oxo-perhydro-azepine-1-carboxylic acid tert-butyl ester in 15 mL DCM at 0° C. slowly 8.7 mL (24.0 mmol) Bis-(2-methoxyethyl)-aminosulfurtrifluoride (50% in THF). After addition of 0.14 mL (2.34 mmol) of ethanole the cooling bath was removed and stirring was continued for 4 h at room temperature. The reaction mixture was neutralized by addition of saturated NaHCO$_3$-solution, the organic layer was separated, dried and evaporated. The residue was purified by column chromatography (silica, cyclohexane/EtOAc 4:1)

Yield: 0.83 g (30% of theory)

$C_{11}H_{19}F_2NO_2$ (M=235.27)

Predicted (El): Molecular ion (M)$^+$: 235 observed: Molecular ion (M)$^+$: 235

HPLC-MS: 1.9 minutes (Method K)

40b 4,4-Difluoro-perhydro-azepinium chloride

To 830 mg (3.53 mmol) of 4,4-Difluoro-perhydro-azepine-1-carboxylic acid tert-butyl ester was added 5 mL of 2 M aq. HCl and stirring was continued overnight at room temperature. The reaction mixture was freeze dried and used for the next step without further purification Yield: 0.38 g (62% of theory)

$C_6H_{16}F_2N^*HCl$ (M=171.62)

Predicted (El): Molecular ion (M+H)$^+$: 136 observed: Molecular ion (M+H)$^+$: 136

HPLC-MS: 1.1 minutes (Method K)

40c 10-[3-(4,4-Difluoro-perhydro-azepine-1-carbonyl)-azetidin-1-yl]-5,6,8,9-tetrahydro-1,4,7,10a-tetraaza-cyclohept[f]indene-7-carboxylic acid tert-butyl ester Prepared according to example 38c starting from 300 mg (0.58 mmol) of 10-(3-Carboxy-azetidin-1-yl)-5,6,8,9-tetrahydro-1,4,7,10a-tetraaza-cyclohept[f]indene-7-carboxylic acid tert-butyl ester (as DIPEA salt) and 120 mg (0.70 mmol) of 4,4-Difluoro-perhydro-azepinium chloride.

Yield: 190 mg (65% of theory)

$C_{25}H_{34}F_2N_6O_3$ (M=504.57)

Predicted (El): Molecular ion (M+H)$^+$: 505 observed: Molecular ion (M+H)$^+$: 505

HPLC-MS: 1.7 minutes (Method K)

39d (4,4-Difluoro-perhydro-azepin-1-yl)-[1-(6,7,8,9-tetrahydro-5H-1,4,7,10a-tetraaza-cyclohept[f]inden-10-yl)-azetidin-3-yl]-methanone To 190 mg (0.38 mmol) 10-[3-(4,4-Difluoro-perhydro-azepine-1-carbonyl)-azetidin-1-yl]-5,6,8,9-tetrahydro-1,4,7,10a-tetraaza-cyclohept[f]indene-7-carboxylic acid tert-butyl ester in 5 mL DCM was added 0.38 mL TFA and stirring was continued overnight at room temperature. To neutralize TFA sat. NaHCO$_3$-solution was added, the organic layer separated and dried over Na$_2$SO$_4$. After filtration and evaporation of the solvent was the residue purified by HPLC.

Yield: 118 mg (78% of theory)

$C_{20}H_{26}F_2N_6O$ (M=404.46)

predicted: Molecular ion (M+H)$^+$: 405 observed: Molecular ion (M+H)$^+$: 405

HPLC-MS: 1.4 minutes (Method K)

Example 41

(3,3-Difluoro-perhydro-azepin-1-yl)-[1-(6,7,8,9-tetrahydro-5H-1,4,7,10a-tetraaza-cyclohept[f]inden-10-yl)-azetidin-3-yl]-methanone

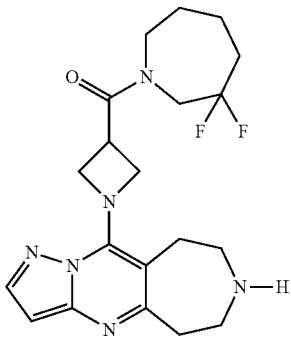 [SMILES: O=C(C1CN(c2c3c(nc4ccnn24)CCNCC3)C1)N1CCCCC(F)(F)C1]

41a 3,3-Difluoro-perhydro-azepine-1-carboxylic acid tert-butyl ester

Prepared according to example 40a starting from 5.0 g (23.4 mmol) of 3-oxo-perhydro-azepine-1-carboxylic acid tert-butyl ester.

Yield: 0.66 g (12% of theory)

$C_{11}H_{19}F_2NO_2$ (M=235.27)

Predicted (EI): Molecular ion (M+H)⁺: 236 observed: Molecular ion (M+H)⁺: 236

HPLC-MS: 1.9 minutes (Method K)

41b 3,3-Difluoro-perhydro-azepinium chloride

Prepared according to example 40b starting from 655 mg (2.78 mmol) of 3,3-Difluoro-perhydro-azepine-1-carboxylic acid tert-butyl ester Yield: 478 mg (100% of theory)

$C_6H_{16}F_2N*HCl$ (M=171.62)

Predicted (EI): Molecular ion (M+H)⁺: 136 observed: Molecular ion (M+H)⁺: 136

HPLC-MS: 1.1 minutes (Method K)

41c 10-[3-(3,3-Difluoro-perhydro-azepine-1-carbonyl)-azetidin-1-yl]-5,6,8,9-tetrahydro-1,4,7,10a-tetraaza-cyclohept[f]indene-7-carboxylic acid tert-butyl ester Prepared according to example 38c starting from 300 mg (0.58 mmol) of 10-(3-Carboxy-azetidin-1-yl)-5,6,8,9-tetrahydro-1,4,7,10a-tetraaza-cyclohept[f]indene-7-carboxylic acid tert-butyl ester (as DIPEA salt) and 120 mg (0.70 mmol) of 3,3-Difluoro-perhydro-azepinium chloride.

Yield: 160 mg (55% of theory)

$C_{25}H_{34}F_2N_6O_3$ (M=504.57)

Predicted (EI): Molecular ion (M+H)⁺: 505 observed: Molecular ion (M+H)⁺: 505

HPLC-MS: 1.7 minutes (Method K)

41d (3,3-Difluoro-perhydro-azepin-1-yl)-[1-(6,7,8,9-tetrahydro-5H-1,4,7,10a-tetraaza-cyclohept[f]inden-10-yl)-azetidin-3-yl]methanone Prepared according to example 40d starting from 160 mg (0.32 mmol) of 10-[3-(3,3-Difluoro-perhydro-azepine-1-carbonyl)-azetidin-1-yl]-5,6,8,9-tetrahydro-1,4,7,10a-tetraaza-cyclohept[f]indene-7-carboxylic acid tert-butyl ester.

Yield: 106 mg (83% of theory)

$C_{20}H_{26}F_2N_6O$ (M=404.46)

predicted: Molecular ion (M+H)⁺: 405 observed: Molecular ion (M+H)⁺: 405

HPLC-MS: 1.4 minutes (Method K)

Example 42

(3,3-Dimethyl-pyrrolidin-1-yl)-[1-(5-methyl-6,7,8,9-tetrahydro-5H-1,4,7,10a-tetraaza-cyclohept[f]inden-10-yl)-azetidin-3-yl]-methanone

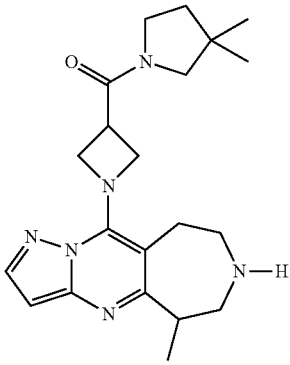 [SMILES: CC1CNCCc2c1nc1ccnn1c2N1CC(C(=O)N2CCC(C)(C)C2)C1]

42a 10-(3-Carboxy-azetidin-1-yl)-5-methyl-5,6,8,9-tetrahydro-1,4,7,10a-tetraaza-cyclohept[f]indene-7-carboxylic acid tert-butyl ester To 2.24 g (6.65 mmol) 5-methyl-10-chloro-6,7,8,9-tetrahydro-5H-1,4,7,10a-tetraaza-cyclohepta[f]indene-7-carboxylic acid tert-butyl ester (example 3d) in 100 mL ethanol was added 2.2 mL (13.3 mmol) of diisopropylethylamine followed by 0.74 g (7.32 mmol) 3-azetidine carboxylic acid and the reaction was stirred at 90° C. overnight. Addition of a further 1.7 g (1.66 mmol) of 3-azetidine carboxylic acid and 2.2 mL (13.3 mmol) of diisopropylethylamine followed by heating at 90° C. for an additional 24 hrs was required for complete conversion. Evaporation of the solvent yielded the crude product which was determined to be the diisopropylethylamine salt by NMR analysis.

Yield: 4.39 g (127% of theory, residual diisopropylethylamine present)

$C_{18}H_{28}N_8O_4$ (M=401.47)

predicted: Molecular ion (M+H)⁺: 402 observed: Molecular ion (M+H)⁺: 402

HPLC-MS: 1.4 minutes (Method B)

42b 10-[3-(3,3-Dimethyl-pyrrolidine-1-carbonyl)-azetidin-1-yl]-5-methyl-5,6,8,9-tetrahydro-1,4,7,10a-tetraaza-cyclohept[f]indene-7-carboxylic acid tert-butyl ester To 300 mg (0.57 mmol) of 10-(3-Carboxy-azetidin-1-yl)-5-methyl-5,6,8,9-tetrahydro-1,4,7,10a-tetraaza-cyclohept[f]indene-7-carboxylic acid tert-butyl ester (as DIPEA salt) in 6.0 mL DMF was added 484 mg (1.51 mmol) TBTU and 243 µL (1.41 mmol) DIPEA and stirring was continued at room temperature for 30 min. Then 84.3 mg (0.62 mmol) of 3,3-Dimethyl-pyrrolidinium chloride was added and the reaction mixture was stirred additional 4 h. The reaction mixture was filtered and the purified by HPLC.
Yield: 162 mg (59% of theory)
$C_{26}H_{38}N_6O_3$ (M=482.62)
predicted: Molecular ion (M+H)$^+$: 483 observed: Molecular ion (M+H)$^+$: 483
HPLC-MS: 3.0 minutes (Method R)

42c (3,3-Dimethyl-pyrrolidin-1-yl)-[1-(5-methyl-6,7,8,9-tetrahydro-5H-1,4,7,10a-tetraaza-cyclohept[f]inden-10-yl)-azetidin-3-yl]-methanone Prepared according to example 38d starting from 162 mg (0.34 mmol) of 10-[3-(3,3-Dimethyl-pyrrolidine-1-carbonyl)-azetidin-1-yl]-5-methyl-5,6,8,9-tetrahydro-1,4,7,10a-tetraaza-cyclohept[f]indene-7-carboxylic acid tert-butyl ester.
Yield: 65 mg (51% of theory)
$C_{21}H_{30}N_6O$ (M=382.50)
Predicted (ESI): Molecular ion (M+H)$^+$: 383 observed: Molecular ion (M+H)$^+$: 383
HPLC-MS: 1.0 minutes (Method K)

Example 43

1-(6,7,8,9-Tetrahydro-5H-1,4,7,10a-tetraaza-cyclohept[f]inden-10-yl)-azetidine-3-carboxylic acid [1-(3-methyl-but-2-enyl)-piperidin-4-yl]amide

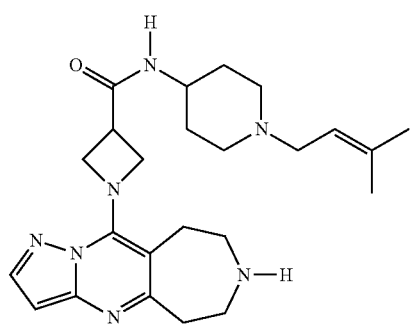 [SMILES: CC(C)=CCN1CCC(NC(=O)C2CN(c3c4c(nc5ccnn35)CCNCC4)C2)CC1]

43a [1-(3-Methyl-but-2-enyl)-piperidin-4-yl]carbamic acid tert-butyl ester

To 0.75 g (3.75 mmol) Piperidin-4-yl-carbamic acid tert-butyl ester and 0.78 g (5.62 mmol) K2CO3 in 5 mL THF was added drop wise 0.65 mL (5.62 mmol) of 1-Bromo-3-methyl-but-2-ene and stirring was continued for 2 h at room temperature. The reaction mixture was filtered, the filtrate was concentrated and the residue purified by column chromatography (silica, EtOAc).

Yield: 0.59 g (58% of theory)
$C_{15}H_{28}N_2O_2$ (M=268.40)
predicted: Molecular ion (M+H)$^+$: 269 observed: Molecular ion (M+H)$^+$: 269
HPLC-MS: 2.0 minutes (Method K)

43b 1-(3-Methyl-but-2-enyl)-piperidin-4-yl-ammonium bis trifluoroacetate

To 0.59 g (2.18 mmol) [1-(3-Methyl-but-2-enyl)-piperidin-4-yl]-carbamic acid tert-butyl ester in 10 mL of DCM was added 2.19 mL TFA and stirring was continued for 2.5 h at room temperature. The reaction mixture was concentrated and the residue used without further purification.
Yield: 0.90 g (100% of theory)
$C_{15}H_{28}N_2O_2*2C_2HF_3O_2$ (M=396.33)
predicted: Molecular ion (M+H)$^+$: 169 observed: Molecular ion (M+H)$^+$: 169
HPLC-MS: 2.5 minutes (Method L)

43c 10-{3-[1-(3-Methyl-but-2-enyl)-piperidin-4-ylcarbamoyl]-azetidin-1-yl}-5,6,8,9-tetrahydro-1,4,7,10a-tetraaza-cyclohept[f]indene-7-carboxylic acid tert-butyl ester Prepared according to example 38c starting from 150 mg (0.29 mmol) of 10-(3-Carboxy-azetidin-1-yl)-5,6,8,9-tetrahydro-1,4,7,10a-tetraaza-cyclohept[f]indene-7-carboxylic acid tert-butyl ester (as DIPEA salt) and 126 mg (0.32 mmol) of 1-(3-Methyl-but-2-enyl)-piperidin-4-yl-ammonium bis trifluoroacetate.
Yield: 70 mg (45% of theory)
$C_{29}H_{43}N_7O_3$ (M=537.70)
Predicted: Molecular ion (M+H)$^+$: 538 observed: Molecular ion (M+H)$^+$: 538
HPLC-MS: 1.2 minutes (Method K)

43d 1-(6,7,8,9-Tetrahydro-5H-1,4,7,10a-tetraaza-cyclohept[f]inden-10-yl)-azetidine-3-carboxylic acid [1-(3-methyl-but-2-enyl)-piperidin-4-yl]amide To 70 mg (0.13 mmol) 10-{3-[1-(3-Methyl-but-2-enyl)-piperidin-4-ylcarbamoyl]-azetidin-1-yl}-5,6,8,9-tetrahydro-1,4,7,10a-tetraaza-cyclohept[f]indene-7-carboxylic acid tert-butyl ester in 2 mL of DCM was added 0.13 mL TFA and stirring was continued for 2.5 h at room temperature. The reaction mixture was concentrated and the residue, after addition of small amounts of 1N NaOH and MeOH, purified by HPLC.
Yield: 48 mg (85% of theory)
$C_{24}H_{35}N_7O$ (M=437.58)
Predicted (EI): Molecular ion (M)$^+$: 437 observed: Molecular ion (M)$^+$: 437
HPLC-MS: 1.0 minutes (Method K)

Example A

Tablets Containing 100 mg of Active Substance

Composition:
1 tablet contains:

| | |
|---|---|
| active substance | 100.0 mg |
| lactose | 80.0 mg |
| corn starch | 34.0 mg |

-continued

|                      |         |
|----------------------|---------|
| polyvinylpyrrolidone | 4.0 mg  |
| magnesium stearate   | 2.0 mg  |
|                      | 220.0 mg |

Method of Preparation:

The active substance, lactose and starch are mixed together and uniformly moistened with an aqueous solution of the polyvinylpyrrolidone. After the moist composition has been screened (2.0 mm mesh size) and dried in a rack-type drier at 50° C. it is screened again (1.5 mm mesh size) and the lubricant is added. The finished mixture is compressed to form tablets.

Weight of tablet: 220 mg

Diameter: 10 mm, biplanar, facetted on both sides and notched on one side.

Example B

Tablets Containing 150 mg of Active Substance

Composition:

1 tablet contains:

|                      |         |
|----------------------|---------|
| active substance     | 150.0 mg |
| powdered lactose     | 89.0 mg  |
| corn starch          | 40.0 mg  |
| colloidal silica     | 10.0 mg  |
| polyvinylpyrrolidone | 10.0 mg  |
| magnesium stearate   | 1.0 mg   |
|                      | 300.0 mg |

Preparation:

The active substance mixed with lactose, corn starch and silica is moistened with a 20% aqueous polyvinylpyrrolidone solution and passed through a screen with a mesh size of 1.5 mm. The granules, dried at 45° C., are passed through the same screen again and mixed with the specified amount of magnesium stearate. Tablets are pressed from the mixture.

Weight of tablet: 300 mg die: 10 mm, flat

Example C

Hard Gelatine Capsules Containing 150 mg of Active Substance

Composition:

1 capsule contains:

|                    |                |
|--------------------|----------------|
| active substance   | 150.0 mg       |
| corn starch (dried)| approx. 180.0 mg |
| lactose (powdered) | approx. 87.0 mg  |
| magnesium stearate | 3.0 mg         |
|                    | approx. 420.0 mg |

Preparation:

The active substance is mixed with the excipients, passed through a screen with a mesh size of 0.75 mm and homogeneously mixed using a suitable apparatus. The finished mixture is packed into size 1 hard gelatine capsules.

Capsule filling: approx. 320 mg

Capsule shell: size 1 hard gelatine capsule.

Example D

Suppositories Containing 150 mg of Active Substance

Composition:

1 suppository contains:

|                                    |          |
|------------------------------------|----------|
| active substance                   | 150.0 mg |
| polyethyleneglycol 1500            | 550.0 mg |
| polyethyleneglycol 6000            | 460.0 mg |
| polyoxyethylene sorbitan monostearate | 840.0 mg |
|                                    | 2,000.0 mg |

Preparation:

After the suppository mass has been melted the active substance is homogeneously distributed therein and the melt is poured into chilled moulds.

Example E

Ampoules Containing 10 mg Active Substance

Composition:

|                         |           |
|-------------------------|-----------|
| active substance        | 10.0 mg   |
| 0.01N hydrochloric acid | q.s.      |
| double-distilled water  | ad 2.0 mL |

Preparation:

The active substance is dissolved in the necessary amount of 0.01 N HCl, made isotonic with common salt, filtered sterile and transferred into 2 mL ampoules.

Example F

Ampoules Containing 50 mg of Active Substance

Composition:

|                         |            |
|-------------------------|------------|
| active substance        | 50.0 mg    |
| 0.01N hydrochloric acid | q.s.       |
| double-distilled water  | ad 10.0 mL |

Preparation:

The active substance is dissolved in the necessary amount of 0.01 N HCl, made isotonic with common salt, filtered sterile and transferred into 10 mL ampoules.

The invention claimed is:
1. A compound of formula (I)

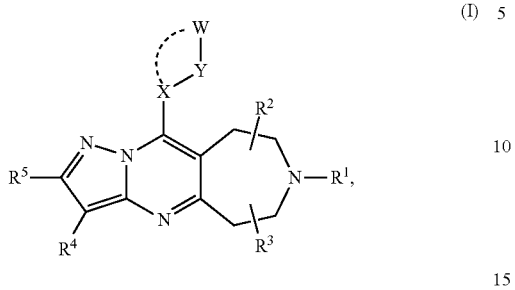

wherein:
X denotes a divalent 4- to 10-membered monocylic, 7- to 12-membered spirocyclic or 6- to 12-membered bicyclic saturated, partially or fully unsaturated group selected from a carbocycle, a monoaza-heterocycle and a diaza-heterocycle, which is linked to the adjacent groups via carbon atoms or, if present, via nitrogen atoms, via one carbon and one nitrogen atom or via two nitrogen atoms,
wherein 1 or 2 —CH$_2$— groups optionally are replaced independently of each other by O, S, carbonyl, or sulfonyl, with the proviso that two heteroatoms are not directly linked together, and/or
1 —CH$_2$— group optionally is replaced by the divalent group >C=C(R$^x$)$_2$, wherein R$^x$ independently denotes H or C$_{1-3}$-alkyl, and/or
wherein in an unsaturated group 1 double bond optionally is condensed with an aryl or a 5- or 6-membered hetaryl group, and/or
wherein in any of the resulting groups one or two carbon atoms optionally and independently are substituted by halogen atoms, C$_{1-6}$-alkyl, C$_{2-6}$-alkenyl, C$_{2-6}$-alkynyl, cyclo C$_{3-7}$-alkyl, cyclo-C$_{3-7}$-alkenyl, phenyl, cyano, hydroxy, hydroxy-C$_{1-6}$-alkyl, hydroxy-C$_{3-6}$-alkenyl, hydroxy-C$_{3-6}$-alkynyl, C$_{1-6}$-alkoxy, C$_{1-6}$-alkoxy-C$_{1-6}$-alkyl, C$_{1-6}$-alkoxy-C$_{3-6}$-alkenyl, C$_{1-6}$-alkoxy-C$_{3-6}$-alkynyl, C$_{3-6}$-alkenoxy-C$_{1-6}$-alkyl, thiohydroxy, C$_{1-6}$-alkylthio, C$_{3-6}$-alkenylthio, C$_{3-6}$-alkynylthio, amino, C$_{1-6}$-alkyl-amino, C$_{3-6}$-alkenyl-amino, C$_{3-6}$-alkynyl-amino, di-(C$_{1-6}$-alkyl)-amino, di-(C$_{3-6}$-alkenyl)-amino, di-(C$_{3-6}$-alkynyl)-amino, amino-C$_{1-6}$-alkyl, C$_{1-3}$-alkyl-amino-C$_{1-6}$-alkyl, di-(C$_{1-3}$-alkyl)-amino-C$_{1-6}$-alkyl, amino-C$_{3-6}$-alkenyl, C$_{1-3}$-alkyl-amino-C$_{3-6}$-alkenyl, di-(C$_{1-3}$-alkyl)-amino-C$_{3-6}$-alkenyl, amino-C$_{3-6}$-alkynyl, C$_{1-3}$-alkyl-amino-C$_{3-6}$-alkynyl, di-(C$_{1-3}$-alkyl)-amino-C$_{3-6}$-alkynyl, hydroxycarbonyl, C$_{1-6}$-alkyl-carbonyl, C$_{2-6}$-alkenyl-carbonyl, C$_{2-6}$-alkynyl-carbonyl, formyl, C$_{1-6}$-alkoxy-carbonyl, C$_{3-6}$-alkenoxy-carbonyl, C$_{3-6}$-alkynoxy-carbonyl, aminocarbonyl, C$_{1-6}$-alkyl-aminocarbonyl, C$_{3-6}$-alkenyl-amino-carbonyl, C$_{3-6}$-alkynyl-aminocarbonyl, di-(C$_{1-6}$-alkyl)-aminocarbonyl, di-(C$_{3-6}$-alkenyl)-aminocarbonyl, di-(C$_{3-6}$-alkynyl)-aminocarbonyl, formylamino, C$_{1-6}$-alkyl-carbonylamino, C$_{1-6}$-alkyl-carbonyl-(C$_{1-3}$-alkyl)-amino, C$_{2-6}$-alkenyl-carbonylamino, C$_{2-6}$-alkynyl-carbonylamino, C$_{1-6}$-alkyl-sulphonyl, C$_{2-6}$-alkenyl-sulphonyl, C$_{2-6}$-alkynyl-sulphonyl, C$_{1-6}$-alkyl-sulphinyl, C$_{2-6}$-alkenyl-sulphinyl, C$_{2-6}$-alkynyl-sulphinyl, C$_{1-6}$-alkyl-sulphonylamino, C$_{2-6}$-alkenyl-sulphonylamino, C$_{2-6}$-alkynyl-sulphonylamino, aminosulphonyl, C$_{1-6}$-alkylaminosulphonyl, di-(C$_{1-6}$-alkyl)-aminosulphonyl, C$_{3-6}$-alkenylamino-sulphonyl, di-(C$_{3-6}$-alkenyl)-aminosulphonyl, C$_{3-6}$-alkynylaminosulphonyl, or di-(C$_{3-6}$-alkynyl)-aminosulphonyl groups, while the substituents may be identical or different, and/or
wherein one ring member nitrogen atom optionally is substituted by a C$_{1-6}$-alkyl, C$_{3-6}$-alkenyl, C$_{3-6}$-alkynyl, cyclo-C$_{3-7}$-alkenyl, hydroxy, hydroxy-C$_{1-6}$-alkyl, hydroxy-C$_{3-6}$-alkenyl, hydroxy-C$_{3-6}$-alkynyl, C$_{1-6}$-alkoxy, C$_{1-6}$-alkoxy-C$_{1-6}$-alkyl, C$_{1-6}$-alkoxy-C$_{3-6}$-alkenyl, C$_{1-6}$-alkoxy-C$_{3-6}$-alkynyl, C$_{3-6}$-alkenoxy-C$_{1-6}$-alkyl, C$_{1-6}$-alkyl-carbonyl, C$_{2-6}$-alkenyl-carbonyl, C$_{2-6}$-alkynyl-carbonyl, formyl, C$_{1-6}$-alkoxy-carbonyl, C$_{3-6}$-alkenoxy-carbonyl, C$_{3-6}$-alkynoxy-carbonyl, C$_{1-6}$-alkyl-sulphonyl, C$_{2-6}$-alkenyl-sulphonyl, C$_{2-6}$-alkynyl-sulphonyl, C$_{1-6}$-alkyl-sulphinyl, C$_{2-6}$-alkenyl-sulphinyl, C$_{2-6}$-alkynyl-sulphinyl, aminosulphonyl, phenyl or phenyl-C$_{1-3}$-alkyl group,
Y is absent or denotes a —(CH$_2$)$_n$— group, wherein n is 1, 2, 3, 4, 5 or 6 and wherein 1 or 2 —CH$_2$— groups optionally are replaced independently by O, S, carbonyl, sulfonyl, or —NH—, with the proviso that two heteroatoms are not directly linked together, or
wherein 1 —CH$_2$— group is replaced by O, S, carbonyl, sulfonyl, or —NH—, and additionally a —CH$_2$—CH$_2$— subgroup is replaced by —C(O)—O—, —O—C(O)—, —C(O)—NH—, or —NH—C(O)—, with the proviso that two heteroatoms are not directly linked together, and
wherein any hydrogen atom of the —NH— groups mentioned hereinbefore optionally and independently is replaced by a C$_{3-6}$-cycloalkyl or phenyl group, or by a straight-chained or branched C$_{1-6}$-alkyl, C$_{3-6}$-alkenyl, C$_{3-6}$-alkynyl, phenyl-C$_{1-6}$-alkyl, C$_{1-6}$-alkyl-carbonyl, or C$_{1-6}$-alkyl-sulphonyl group, and/or
wherein 1 or 2 hydrogen atoms attached to carbon atoms optionally are replaced by halogen atoms, trifluoromethyl, C$_{1-6}$-alkyl, C$_{2-6}$-alkenyl, C$_{2-6}$-alkynyl, C$_{3-6}$-cycloalkyl, phenyl, phenyl-C$_{1-6}$-alkyl, cyano, hydroxy, hydroxy-C$_{1-6}$-alkyl, C$_{1-6}$-alkoxy, C$_{1-6}$-alkoxy-C$_{1-6}$-alkyl, C$_{1-6}$-alkyl-carbonyl, C$_{1-6}$-alkoxy-carbonyl, C$_{1-6}$-alkyl-carbonylamino, C$_{1-6}$-alkyl-carbonyl-(C$_{1-3}$-alkyl)-amino, C$_{1-3}$-alkyl-aminocarbonyl, di-(C$_{1-3}$-alkyl)-aminocarbonyl or C$_{1-6}$-alkyl-sulphonyl groups, while the substituents may be identical or different, or 2 geminal hydrogen atoms are replaced by a —(CH$_2$)$_m$— bridge, wherein m is 2, 3, 4, or 5,
W denotes H or an optionally substituted straight-chained or branched C$_{1-6}$-alkyl, C$_{2-6}$-alkenyl or C$_{2-6}$-alkynyl group, wherein 1 or 2 methyl groups optionally are replaced by optionally substituted phenyl groups or
an optionally substituted cyclo-C$_{3-9}$-alkyl group, wherein independently
in a cyclo-C$_{4-9}$-alkyl group 2 hydrogen atoms attached to adjacent carbon atoms optionally are replaced to form a double bond within the ring, which optionally is condensed with an optionally substituted aryl or an optionally substituted 5- or 6-membered hetaryl group, and the resulting group is bound via a saturated or unsaturated carbon atom, or
in a cyclo-C$_{4-9}$-alkyl group 2 hydrogen atoms attached to the same carbon atom (relative 1,1-position) optionally are replaced by a C$_{2-5}$-alkylenyl bridge or 2 hydrogen atoms attached to carbon atoms in relative 1,2-, 1,3- or 1,4-position optionally are replaced by a $C_{1-5}$-alkylenyl bridge, wherein any of the resulting polycyclic groups one or two —$CH_2$— groups optionally are replaced by —NH— (or N-atoms for replacement of —CH< members), >N—($C_{1-6}$-alkyl), O, S, carbonyl, or sulfonyl, and/or two —$CH_2$— groups in relative 1,3-position within a $C_{4-5}$-alkylenyl bridge optionally are replaced by O atoms, and/or 2 hydrogen atoms attached to adjacent carbon atoms within a $C_{4-5}$-alkylenyl bridge optionally are replaced to form a double bond, which optionally is condensed with an optionally substituted aryl or an optionally substituted 5- or 6-membered hetaryl group, and/or in a cyclo-$C_{4-8}$-alkyl group one, two or three ring members optionally are replaced independently of each other by —NH—, >N—($C_{1-6}$-alkyl) (or N-atoms for replacement of —CH< members), O, S, carbonyl, or sulfonyl, with the proviso that two heteroatoms are not directly linked together, and additionally but optionally 2 or 4 hydrogen atoms attached to adjacent ring carbon atoms are replaced to form a double bond or two conjugated double bonds within the ring, either of the double bonds optionally being condensed with an optionally substituted aryl or an optionally substituted 5- or 6-membered hetaryl group, and any of the resulting groups is bound via a saturated or unsaturated carbon atom or a nitrogen atom, and wherein any of the resulting open-chained or cyclic groups independently 1 to 4 hydrogen atoms optionally are replaced by $C_{1-6}$-alkyl or $C_{1-6}$-alkoxy groups, and/or any 1 to 6 hydrogen atoms attached to carbon atoms optionally are replaced by fluorine atoms, or W denotes an optionally substituted aryl or hetaryl group, an optionally substituted cyclo-$C_{3-8}$-alkyl-aryl or cyclo-$C_{3-8}$-alkyl-hetaryl group, wherein the cyclo-$C_{5-8}$-alkyl-submoieties one or two ring members optionally are replaced independently of each other by —NH— (or N-atoms for replacement of —CH< members), >N($C_{1-3}$-alkyl), O, S, carbonyl, or sulfonyl, with the proviso that two heteroatoms are not directly linked together, or if Y is absent W additionally denotes
a divalent —$(CH_2)_p$— group, wherein p is 2, 3, 4, 5, 6 or 7, attached via the dotted line in formula I, and via the bond connecting W to X, when Y is absent, in relative 1,1-position (geminal) to a carbon atom of group X, including the options:
 if p is 3, 4, 5, 6 or 7 it follows that 1 —$CH_2$— group optionally is replaced by O, S, carbonyl, sulfonyl, —NH— or —N($C_{1-6}$-alkyl)-, or
 if p is 4, 5, 6 or 7 it follows that a —$CH_2$—$CH_2$— group optionally is replaced by —C(O)—O—, —O—C(O)—, —C(O)—NH—, —NH—C(O)—, —C(O)—N($C_{1-6}$-alkyl)-, —N($C_{1-6}$-alkyl)-C(O)—, or —CH=CH—, wherein the double bond optionally is condensed with an aryl or a 5- or 6-membered hetaryl group,
a divalent —$(CH_2)_q$— group, wherein q is 3, 4, or 5, attached via the dotted line in formula I, and via the bond connecting W to X, when Y is absent, in relative 1,2-position (vicinal) to carbon atoms of group X, including the options:
 that 1 —$CH_2$— group optionally is replaced by O, S, carbonyl, sulfonyl, —NH— or —N($C_{1-6}$-alkyl)-, or
 a —$CH_2$—$CH_2$— group optionally is replaced by —C(O)—O—, —O—C(O)—, —C(O)—NH—, —NH—C(O)—, —C(O)—N($C_{1-6}$-alkyl)-, —N($C_{1-6}$-alkyl)-C(O)—, or
 that in the resulting 5-, 6- and 7-membered carbocyclic ring 2, 4 or 6 hydrogen atoms optionally are replaced by 1, 2 or 3 bonds to form a partially or fully unsaturated ring with isolated or conjugated double bonds, wherein 1 —$CH_2$— group optionally is replaced by O, S, carbonyl, sulfonyl, —NH— or —N($C_{1-6}$-alkyl)-, and/or one —CH= unit is replaced by —N=, a divalent —$(CH_2)_r$— group, wherein r is 5, 6 or 7, attached via the dotted line in formula I, and via the bond connecting W to X, when Y is absent, in relative 1,3-position to carbon atoms as binding sites of group X, including the options:
 that in the resulting 8-, 9- or 10-membered carbocyclic ring 2, 4, 6, 8 or 10 hydrogen atoms optionally are replaced by 1, 2, 3, 4 or 5 bonds to form a partially or fully unsaturated ring with isolated or conjugated double bonds, and/or
 that in the resulting 8-, 9- or 10-membered carbocyclic ring 1 hydrogen atom attached to the carbon atom in position 2 relative to the binding sites of group X and 1 hydrogen atom attached to a carbon atom of the —$(CH_2)_r$— group in position 6 or 7 relative to the binding sites of group X optionally are replaced by a bond ($C_0$-bridge) to form a bicyclic ring system condensed with the group X,
or
a divalent —$(CH_2)_r$— group, wherein r is 7, attached via the dotted line in formula I and the bond connecting W to X, when Y is absent, in relative 1,3-position to carbon atoms as binding sites of group X, including the option:
 that in the resulting 10-membered carbocyclic ring 8 hydrogen atoms are replaced by 4 bonds to form fully unsaturated ring conjugated double bonds, and
 that in the resulting 10-membered carbocyclic ring 1 hydrogen atom attached to the carbon atom in position 2 relative to the binding sites of group X and 1 hydrogen atom attached to a carbon atom of the —$(CH_2)_r$— group in position 7 relative to the binding sites of group X are replaced by a bond ($C_0$-bridge) to form a bicyclic ring system condensed with the group X, resulting in the trivalent group

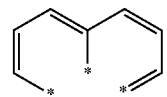 [SMILES: *\C=C/C=C(*)/C=C\C=*]

attached in relative 1,2,3-position to carbon atoms * as binding sites of group X, $R^1$ denotes H, $C_{3-6}$-alkenyl or $C_{3-6}$-alkynyl, any of those groups being optionally substituted by 1 to 3 fluorine, chlorine or bromine atoms, or by a cyano, hydroxy, $C_{1-3}$-alkoxy or cyclo-$C_{3-7}$-alkyl-group, $R^2$ and $R^3$ independently denote H, halogen, $C_{1-6}$-alkyl, $C_{2-6}$-alkenyl, $C_{2-6}$-alkynyl, hydroxy or $C_{1-6}$-alkoxy, any of those $C_{1-6}$-alkyl, $C_{2-6}$-alkenyl or $C_{3-6}$-alkynyl groups being optionally substituted by 1 to 3 fluorine, chlorine or bromine atoms, or by a cyano or cyclo-$C_{3-7}$-alkyl-group, $R^4$ and $R^5$ independently denote H, halogen, $C_{1-6}$-alkyl, $C_{2-6}$-alkenyl, $C_{2-6}$-alkynyl, cyclo-$C_{3-7}$-alkyl, hydroxy or $C_{1-3}$-alkoxy, any of those $C_{1-6}$-alkyl, $C_{2-6}$-alkenyl or $C_{3-6}$-alkynyl groups being optionally substituted by 1 to 3 fluorine, chlorine or bromine atoms, by a cyano, hydroxy, $C_{1-3}$-alkoxy, or cyclo-$C_{3-5}$-alkyl-group, or by a phenyl or pyridyl group both optionally substituted independently by 1, 2 or 3 substituents selected from halogen atoms, $C_{1-6}$-alkyl, cyano, hydroxy, $C_{1-6}$-alkoxy, amino, $C_{1-6}$-alkyl-amino, or di-($C_{1-6}$-alkyl)-amino groups, wherein, if not specified otherwise, any alkyl groups or subgroups mentioned hereinbefore are straight-chained or branched, the term "aryl" as used hereinbefore, either alone or as a sub-moiety within another substituent, if not otherwise specified means either an optionally substituted aromatic monocyclic or multicyclic system, the term "hetaryl" as used hereinbefore, either alone or as a sub-moiety within another substituent, if not otherwise specified denotes five- or six-membered heterocyclic aromatic groups or 5-10 membered, bicyclic heteroaromatic groups comprising one, two or three heteroatoms selected from oxygen, sulphur and nitrogen, linked through a carbon atom or, if present, through a nitrogen atom, and optionally substituted at carbon atoms and/or a nitrogen atoms, and wherein the expression "substituted" or "optionally substituted" as used hereinbefore if not otherwise specified means substitution with one, two, three, four or more substituents attached to carbon atoms selected from the group consisting of halogen atoms (fluorine, chlorine, bromine or iodine atoms), $C_{1-6}$-alkyl, $C_{2-6}$-alkenyl, $C_{2-6}$-alkynyl, cyclo-$C_{3-8}$-alkyl, cyclo-$C_{3-7}$-alkenyl, cyano, hydroxy, hydroxy-$C_{1-6}$-alkyl, hydroxy-$C_{3-6}$-alkenyl, hydroxy-$C_{3-6}$-alkynyl, $C_{1-6}$-alkoxy, $C_{1-6}$-alkoxy-$C_{1-6}$-alkyl, $C_{1-6}$-alkoxy-$C_{3-6}$-alkenyl, $C_{1-6}$-alkoxy-$C_{3-6}$-alkynyl, $C_{3-6}$-alkenoxy-$C_{1-6}$-alkyl, $C_{3-6}$-alkenoxy-$C_{3-6}$-alkenyl, $C_{3-6}$-alkenoxy-$C_{3-6}$-alkynyl, $C_{3-6}$-alkynoxy-$C_{1-6}$-alkyl, $C_{3-6}$-alkynoxy-$C_{3-6}$-alkenyl, $C_{3-6}$-alkynoxy-$C_{3-6}$-alkynyl, oxetanyl, tetrahydrofuranyl, tetrahydropyranyl, pyrrolidino, piperidino, thiohydroxy, $C_{1-6}$-alkylthio, $C_{3-6}$-alkenylthio, $C_{3-6}$-alkynylthio, amino, $C_{1-6}$-alkyl-amino, $C_{3-6}$-alkenyl-amino, $C_{3-6}$-alkynyl-amino, di-($C_{1-6}$-alkyl)-amino, di-($C_{3-6}$-alkenyl)-amino, di-($C_{3-6}$-alkynyl)-amino, amino-$C_{1-6}$-alkyl, $C_{1-3}$-alkyl-amino-$C_{1-6}$-alkyl, di-($C_{1-3}$-alkyl)-amino-$C_{1-6}$-alkyl, amino-$C_{3-6}$-alkenyl, $C_{1-3}$-alkyl-amino-$C_{3-6}$-alkenyl, di-($C_{1-3}$-alkyl)-amino-$C_{3-6}$-alkenyl, amino-$C_{3-6}$-alkynyl, $C_{1-3}$-alkyl-amino-$C_{3-6}$-alkynyl, di-($C_{1-3}$-alkyl)-amino-$C_{3-6}$-alkynyl, hydroxycarbonyl, phenyl, phenyl-$C_{1-3}$-alkyl, phenyloxy, phenyl-$C_{1-3}$-alkoxy, phenyloxy-$C_{1-3}$-alkyl, phenylcarbonyl, pyridyl, thiazolyl; pyridylcarbonyl, $C_{1-6}$-alkyl-carbonyl, $C_{2-6}$-alkenyl-carbonyl, $C_{2-6}$-alkynyl-carbonyl, formyl, $C_{1-6}$-alkoxy-carbonyl, $C_{3-6}$-alkenoxy-carbonyl, $C_{3-6}$-alkynoxy-carbonyl, aminocarbonyl, $C_{1-6}$-alkyl-aminocarbonyl, $C_{3-6}$-alkenyl-aminocarbonyl, $C_{3-6}$-alkynyl-aminocarbonyl, di-($C_{1-6}$-alkyl)-aminocarbonyl, di-($C_{3-6}$-alkenyl)-aminocarbonyl, di-($C_{3-6}$-alkynyl)-aminocarbonyl, formylamino, $C_{1-6}$-alkyl-carbonylamino, $C_{2-6}$-alkenyl-carbonylamino, $C_{2-6}$-alkynyl-carbonylamino, formyl-$C_{1-6}$-alkyl-amino, formyl-$C_{3-6}$-alkenyl-amino, formyl-$C_{3-6}$-alkynyl-amino, $C_{1-6}$-alkyl-carbonyl-$C_{1-6}$-alkyl-amino, $C_{2-6}$-alkenyl-carbonyl-$C_{1-6}$-alkyl-amino, $C_{2-6}$-alkynyl-carbonyl-$C_{1-6}$-alkyl-amino, $C_{1-6}$-alkyl-carbonyl-$C_{3-6}$-alkenyl-amino, $C_{2-6}$-alkenyl-carbonyl-$C_{3-6}$-alkenyl-amino, $C_{2-6}$-alkynyl-carbonyl-$C_{3-6}$-alkenyl-amino, $C_{1-6}$-alkyl-carbonyl-$C_{3-6}$-alkynyl-amino, $C_{2-6}$-alkenyl-carbonyl-$C_{3-6}$-alkynyl-amino, $C_{2-6}$-alkynyl-carbonyl-$C_{3-6}$-alkynyl-amino, $C_{1-6}$-alkyl-sulphonyl, $C_{2-6}$-alkenyl-sulphonyl, $C_{2-6}$-alkynyl-sulphonyl, $C_{1-6}$-alkyl-sulphinyl, $C_{2-6}$-alkenyl-sulphinyl, $C_{2-6}$-alkynyl-sulphinyl, $C_{1-6}$-alkyl-sulphonylamino, $C_{2-6}$-alkenyl-sulphonylamino, $C_{2-6}$-alkynyl-sulphonylamino, $C_{1-6}$-alkyl-sulphonyl-$C_{1-6}$-alkylamino, $C_{1-6}$-alkyl-sulphonyl-$C_{3-6}$-alkenylamino, $C_{1-6}$-alkyl-sulphonyl-$C_{3-6}$-alkynylamino, $C_{2-6}$-alkenyl-sulphonyl-$C_{1-6}$-alkylamino, $C_{2-6}$-alkenyl-sulphonyl-$C_{3-6}$-alkenylamino, $C_{2-6}$-alkenyl-sulphonyl-$C_{3-6}$-alkynylamino, $C_{2-6}$-alkynyl-sulphonyl-$C_{1-6}$-alkylamino, $C_{2-6}$-alkynyl-sulphonyl-$C_{3-6}$-alkenylamino, $C_{2-6}$-alkynyl-sulphonyl-$C_{3-6}$-alkynylamino, aminosulphonyl, $C_{1-6}$-alkylaminosulphonyl, di-($C_{1-6}$-alkyl)-aminosulphonyl, $C_{3-6}$-alkenylaminosulphonyl, di-($C_{3-6}$-alkenyl)-aminosulphonyl, $C_{3-6}$-alkynylaminosulphonyl and di-($C_{3-6}$-alkynyl)-aminosulphonyl groups, while the substituents may be identical or different and wherein any alkyl groups or alkyl sub-moieties optionally are partially or fully fluorinated, and wherein any phenyl, pyridyl and thiazolyl groups or phenyl-, pyridyl and thiazolyl-submoieties optionally are substituted with 1 or 2 substituents independently of each other selected from fluorine, chlorine, bromine, iodine, $C_{1-3}$-alkyl, $C_{1-3}$-alkoxy, amino, $C_{1-3}$-alkyl-amino, di-($C_{1-3}$-alkyl)-amino, $C_{1-3}$-alkylcarbonyl-amino, $C_{1-3}$-alkylcarbonyl-$C_{1-3}$-alkyl-amino, cyano or hydroxy, or with substituents attached to a nitrogen atom selected from the group consisting of $C_{1-6}$-alkyl, $C_{3-6}$-alkenyl, $C_{3-6}$-alkynyl, cyclo-$C_{3-7}$-alkyl, cyclo-$C_{3-7}$-alkenyl, cyclo-$C_{3-7}$-alkyl-$C_{1-6}$-alkyl, pyrrolidino, piperidino, morpholino, oxetanyl, tetrahydrofuranyl, tetrahydropyranyl, cyano, hydroxy, hydroxy-$C_{1-6}$-alkyl, hydroxy-$C_{3-6}$-alkenyl, hydroxy-$C_{3-6}$-alkynyl, $C_{1-6}$-alkoxy $C_{1-6}$-alkoxy-$C_{1-6}$-alkyl, $C_{1-6}$-alkoxy-$C_{3-6}$-alkenyl, $C_{1-6}$-alkoxy-$C_{3-6}$-alkynyl, $C_{3-6}$-alkenoxy-$C_{1-6}$-alkyl, $C_{3-6}$-alkenoxy-$C_{3-6}$-alkenyl, $C_{3-6}$-alkenoxy-$C_{3-6}$-alkynyl, $C_{3-6}$-alkynoxy-$C_{1-6}$-alkyl, $C_{3-6}$-alkynoxy-$C_{3-6}$-alkenyl, $C_{3-6}$-alkynoxy-$C_{3-6}$-alkynyl, amino-$C_{1-6}$-alkyl, $C_{1-3}$-alkyl-amino-$C_{1-6}$-alkyl, di-($C_{1-3}$-alkyl)-amino-$C_{1-6}$-alkyl, amino-$C_{3-6}$-alkenyl, $C_{1-3}$-alkyl-amino-$C_{3-6}$-alkenyl, di-($C_{1-3}$-alkyl)-amino-$C_{3-6}$-alkenyl, amino-$C_{3-6}$-alkynyl, $C_{1-3}$ alkyl-amino-$C_{3-6}$-alkynyl, di-($C_{1-3}$-alkyl)-amino $C_{3-6}$-alkynyl, hydroxycarbonyl, phenyl, phenyl-$C_{1-6}$-alkyl, phenyl-carbonyl, pyridyl, pyridylcarbonyl, $C_{1-6}$-alkyl-carbonyl, $C_{2-6}$-alkenyl-carbonyl, $C_{2-6}$-alkynyl-carbonyl, $C_{1-6}$-alkoxy-carbonyl, $C_{3-6}$-alkenoxy-carbonyl, $C_{3-6}$-alkynoxy-carbonyl, aminocarbonyl, $C_{1-6}$-alkyl-aminocarbonyl, $C_{3-6}$-alkenyl-aminocarbonyl, $C_{3-6}$-alkynyl-aminocarbonyl, di-($C_{1-6}$-alkyl)-aminocarbonyl, di-($C_{3-6}$-alkenyl)-aminocarbonyl, di-($C_{3-6}$-alkynyl)-aminocarbonyl, $C_{1-6}$-alkyl-sulphonyl, $C_{2-6}$-alkenyl-sulphonyl, $C_{2-6}$-alkynyl-sulphonyl, $C_{1-6}$-alkyl-sulphinyl, $C_{2-6}$-alkenyl-sulphinyl, $C_{2-6}$-alkynyl-sulphinyl, aminosulphonyl, $C_{1-6}$-alkylaminosulphonyl, di-($C_{1-6}$-alkyl)-aminosulphonyl, $C_{3-6}$-alkenylaminosulphonyl, di-($C_{3-6}$-alkenyl)-aminosulphonyl, $C_{3-6}$-alkynylaminosulphonyl and di-($C_{3-6}$-alkynyl)-aminosulphonyl groups, while the substituents may be identical or different and wherein any alkyl groups or alkyl sub-moieties optionally are partially or fully fluorinated, and wherein any of the di-($C_{1-3}$-alkyl)-amino or di-($C_{1-6}$-alkyl)-amino moieties may form optionally with the nitrogen atom a 4 to 8 membered ring system, and wherein any phenyl and pyridyl groups or phenyl- and pyridyl-submoieties optionally are substituted with 1 or 2 substituents independently of each other selected from fluorine, chlorine, bromine, iodine, $C_{1-3}$-alkyl, $C_{1-3}$-alkoxy, amino, $C_{1-3}$-alkyl-amino, $C_{1-3}$-alkylcarbonyl-amino, cyano or hydroxy, or a salt thereof.

2. The compound according to claim 1, wherein

X denotes a divalent 4- to 8-membered monocylic, 7- to 10-membered spirocyclic or 6- to 12-membered bicyclic saturated, partially or fully unsaturated group selected from a carbocycle, a monoaza-heterocycle and a diaza-heterocycle, which is linked to the adjacent groups via carbon atoms or, if present, via nitrogen atoms, via one carbon and one nitrogen atom or via both nitrogen atoms, wherein 1 to 2 —$CH_2$— groups optionally are replaced independently of each other by O, S, carbonyl, or sulfonyl, with the proviso that two heteroatoms are not directly linked together, and/or wherein 1 double bond optionally is condensed with an aryl or a 5- or 6-membered hetaryl group, and/or wherein in all groups falling under the above definition of X one or two carbon atoms optionally and independently are substituted by halogen atoms, $C_{1-6}$-alkyl, $C_{2-6}$-alkenyl, $C_{2-6}$-alkynyl, cyclo-$C_{3-7}$-alkyl, cyclo-$C_{3-7}$-alkenyl, phenyl, cyano, hydroxy, hydroxy-$C_{1-6}$-alkyl, $C_{1-6}$-alkoxy, $C_{1-6}$-alkoxy-$C_{1-6}$-alkyl, formyl, aminocarbonyl, $C_{1-6}$-alkyl-aminocarbonyl, $C_{3-6}$-alkenyl-aminocarbonyl, $C_{3-6}$-alkynyl-aminocarbonyl, di-($C_{1-6}$-alkyl)-aminocarbonyl, di-($C_{3-6}$-alkenyl)-aminocarbonyl, di-($C_{3-6}$-alkynyl)-aminocarbonyl, formylamino, $C_{1-6}$-alkyl-carbonylamino, $C_{1-6}$-alkyl-carbonyl-($C_{1-3}$-alkyl)-amino $C_{2-6}$-alkenyl-carbonylamino or $C_{2-6}$-alkynyl-carbonylamino groups, while the substituents may be identical or different, and/or, wherein one ring member nitrogen atom optionally is substituted by a $C_{1-3}$-alkyl, cyclo-$C_{3-6}$-alkyl, $C_{1-3}$-alkoxy, $C_{1-3}$-alkoxy-$C_{1-3}$-alkyl, $C_{1-3}$-alkyl-carbonyl, $C_{1-3}$-alkoxy-carbonyl or $C_{1-3}$-alkyl-sulphonyl group;

Y and W are defined as in claim 1, $R^1$ denotes H, $C_{1-4}$-alkyl, $C_{3-4}$-alkenyl or $C_{3-4}$-alkynyl, any of those groups being optionally substituted by 1 to 3 fluorine, chlorine or bromine atoms, or by a cyano, hydroxy, $C_{1-3}$-alkoxy or cyclo-$C_{3-6}$-alkyl-group, $R^2$ and $R^3$ independently denote H, halogen, $C_{1-3}$-alkyl, hydroxy or $C_{1-3}$-alkoxy, any of those $C_{1-3}$-alkyl groups being optionally substituted by 1 to 3 fluorine atoms, $R^4$ and $R^5$ independently denote H, halogen, $C_{1-3}$-alkyl, $C_{2-4}$-alkenyl, $C_{2-3}$-alkynyl, cyclo-$C_{3-6}$-alkyl, hydroxy or $C_{1-3}$-alkoxy, any of those $C_{1-3}$-alkyl, $C_{2-4}$-alkenyl or $C_{2-3}$-alkynyl groups being optionally substituted by 1 to 3 fluorine atoms, by a methyl, hydroxy, $C_{1-3}$-alkoxy, or cyclo-$C_{3-5}$-alkyl-group, or by a phenyl or pyridyl group both optionally substituted independently by 1, 2 or 3 substituents selected from halogen atoms, $C_{1-3}$-alkyl, cyclo-$C_{3-6}$-alkyl, cyano, hydroxy, $C_{1-3}$-alkoxy, amino, $C_{1-3}$-alkyl-amino, and di-($C_{1-3}$-alkyl)-amino groups, or a salt thereof.

3. The compound according to claim 1, wherein

X denotes a divalent 4- to 8-membered monocylic, 7- to 10-membered spirocyclic or 6- to 12-membered bicyclic saturated, partially or fully unsaturated group selected from a carbocycle, a monoaza-heterocycle and a diaza-heterocycle, which is linked to the adjacent groups via carbon atoms or, if present, via nitrogen atoms, via one carbon and one nitrogen atom or via both nitrogen atoms, wherein 1 to 2 —$CH_2$— groups optionally are replaced independently of each other by O, S, carbonyl, or sulfonyl, with the proviso that two heteroatoms are not directly linked together, and/or wherein 1 double bond optionally is condensed with an aryl or a 5- or 6-membered hetaryl group, and/or wherein in all groups falling under the above definition of X one or two carbon atoms optionally and independently are substituted by halogen atoms, $C_{1-6}$-alkyl, $C_{2-6}$-alkenyl, $C_{2-6}$-alkynyl, cyclo-$C_{3-7}$-alkyl, cyclo-$C_{3-7}$-alkenyl, phenyl, cyano, hydroxy, hydroxy-$C_{1-6}$-alkyl, $C_{1-6}$-alkoxy, $C_{1-6}$-alkoxy-$C_{1-6}$-alkyl, formyl, aminocarbonyl, $C_{1-6}$-alkyl-aminocarbonyl, $C_{3-6}$-alkenyl-aminocarbonyl, $C_{3-6}$-alkynyl-aminocarbonyl, di-($C_{1-6}$-alkyl)-aminocarbonyl, di-($C_{3-6}$-alkenyl)-aminocarbonyl, di-($C_{3-6}$-alkynyl)-aminocarbonyl, formylamino, $C_{1-6}$-alkyl-carbonylamino, $C_{1-6}$-alkyl-carbonyl-($C_{1-3}$-alkyl)-amino $C_{2-6}$-alkenyl-carbonylamino or $C_{2-6}$-alkynyl-carbonylamino groups, while the substituents may be identical or different, and/or, wherein one ring member nitrogen atom optionally is substituted by a $C_{1-3}$-alkyl, cyclo-$C_{3-6}$-alkyl, $C_{1-3}$-alkoxy, $C_{1-3}$-alkoxy-$C_{1-3}$-alkyl, $C_{1-3}$-alkyl-carbonyl, $C_{1-3}$-alkoxy-carbonyl or $C_{1-3}$-alkyl-sulphonyl group;

Y is absent or denotes a —$(CH_2)_n$— group, wherein n is 1, 2, 3, 4, 5 or 6 and wherein 1 —$CH_2$— group optionally is replaced by O, carbonyl or —NH—, or wherein 1 —$CH_2$— group is replaced by O or —NH—, and additionally a second —$CH_2$— group is replaced by carbonyl, or wherein 1 —$CH_2$— group is replaced by O and additionally a —$CH_2$—$CH_2$— subgroup is replaced by —C(O)—NH—, or —NH—C(O)—, and wherein any hydrogen atom of the —NH— groups mentioned hereinbefore optionally and independently is replaced by a $C_{3-6}$-cycloalkyl or phenyl group, or by a straight-chained or branched $C_{1-4}$-alkyl, phenyl-$C_{1-3}$-alkyl, $C_{1-4}$-alkyl-carbonyl, or $C_{1-4}$-alkyl-sulphonyl group, and/or wherein 1 or 2 hydrogen atoms attached to carbon atoms optionally are replaced by halogen atoms, trifluoromethyl, $C_{1-4}$-alkyl, $C_{2-4}$-alkenyl, $C_{3-6}$-cycloalkyl, phenyl, phenyl-$C_{1-3}$-alkyl, hydroxy, hydroxy-$C_{1-3}$-alkyl, $C_{1-3}$-alkoxy, $C_{1-3}$-alkoxy-$C_{1-3}$-alkyl, $C_{1-4}$-alkyl-carbonyl, $C_{1-4}$-alkoxy-carbonyl, $C_{1-4}$-alkyl-carbonylamino, $C_{1-4}$-alkyl-carbonyl-($C_{1-3}$-alkyl)-amino, $C_{1-3}$-alkyl-aminocarbonyl, or di-($C_{1-3}$-alkyl)-aminocarbonyl groups, while the substituents may be identical or different, or 2 geminal hydrogen atoms are replaced by a —$(CH_2)_m$— bridge, wherein m is 2, 3, 4, or 5;

W is defined as in claim 1, and $R^1$ denotes H, $C_{1-4}$-alkyl, $C_{3-4}$-alkenyl or $C_{3-4}$-alkynyl, any of those groups being optionally substituted by 1 to 3 fluorine, chlorine or bromine atoms, or by a cyano, hydroxy, $C_{1-3}$-alkoxy or cyclo-$C_{3-6}$-alkyl-group, $R^2$ and $R^3$ independently denote H, halogen, $C_{1-3}$-alkyl, hydroxy or $C_{1-3}$-alkoxy, any of those $C_{1-3}$-alkyl groups being optionally substituted by 1 to 3 fluorine atoms, $R^4$ and $R^5$ independently denote H, halogen, $C_{1-3}$-alkyl, $C_{2-4}$-alkenyl, $C_{2-3}$-alkynyl, cyclo-$C_{3-6}$-alkyl, hydroxy or $C_{1-3}$-alkoxy, any of those $C_{1-3}$-alkyl, $C_{2-4}$-alkenyl or $C_{2-3}$-alkynyl groups being optionally substituted by 1 to 3 fluorine atoms, by a methyl, hydroxy, $C_{1-3}$-alkoxy, or cyclo-$C_{3-5}$-alkyl-group, or by a phenyl or pyridyl group both optionally substituted independently by 1, 2 or 3 substituents selected from halogen atoms, $C_{1-3}$-alkyl, cyclo-$C_{3-6}$-alkyl, cyano, hydroxy, $C_{1-3}$-alkoxy, amino, $C_{1-3}$-alkyl-amino, and di-($C_{1-3}$-alkyl)-amino groups, or a salt thereof.

4. The compound according to claim 1, wherein

X denotes a divalent phenyl group or a group selected from formulas (II) to (XIII),

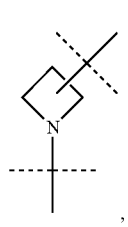
(II)

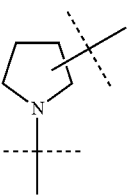
(III)

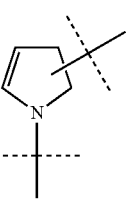
(IV)

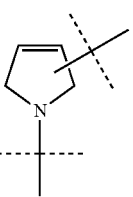
(V)

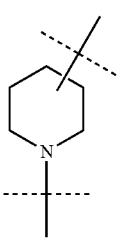
(VI)

-continued

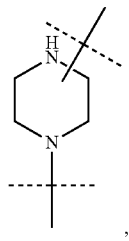
(VII)

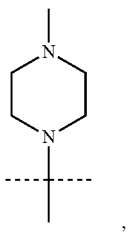
(VIII)

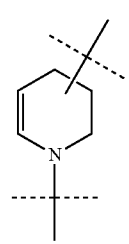
(IX)

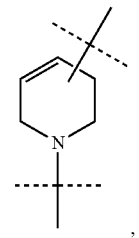
(X)

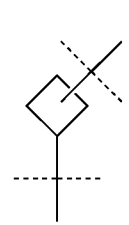
(XI)

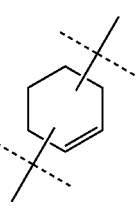
(XII)

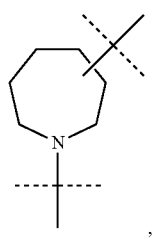

(XIII)

wherein 1 —CH$_2$— group optionally is replaced by O, S, carbonyl, or sulfonyl, with the proviso that two heteroatoms are not directly linked together, and/or wherein a double bond, if present, optionally is condensed with an aryl or a 5- or 6-membered hetaryl group, and/or wherein in all groups falling under the above definition of X one or two carbon atoms optionally and independently are substituted by halogen atoms, C$_{1-6}$-alkyl, C$_{2-6}$-alkenyl, C$_{2-6}$-alkynyl, cyclo-C$_{3-7}$-alkyl, cyclo-C$_{3-7}$-alkenyl, phenyl, cyano, hydroxy, hydroxy-C$_{1-6}$-alkyl, C$_{1-6}$-alkoxy, C$_{1-6}$-alkoxy-C$_{1-6}$-alkyl, formyl, aminocarbonyl, C$_{1-6}$-alkyl-aminocarbonyl, C$_{3-6}$-alkenyl-aminocarbonyl, C$_{3-6}$-alkynyl-aminocarbonyl, di-(C$_{1-6}$-alkyl)-aminocarbonyl, di-(C$_{3-6}$-alkenyl)-aminocarbonyl, di-(C$_{3-6}$-alkynyl)-aminocarbonyl, formylamino, C$_{1-6}$-alkyl-carbonylamino, C$_{1-6}$-alkyl-carbonyl-(C$_{1-3}$-alkyl)-amino C$_{2-6}$-alkenyl-carbonylamino or C$_{2-6}$-alkynyl-carbonylamino groups, while the substituents may be identical or different, and/or, wherein one ring member nitrogen atom, if present, optionally is substituted by a C$_{1-3}$-alkyl, cyclo-C$_{3-6}$-alkyl, C$_{1-3}$-alkoxy, C$_{1-3}$-alkoxy-C$_{1-3}$-alkyl, C$_{1-3}$-alkyl-carbonyl, C$_{1-3}$-alkoxy-carbonyl or C$_{1-3}$-alkyl-sulphonyl group;

Y is absent;

W denotes H or an optionally substituted straight-chained or branched C$_{1-6}$-alkyl, C$_{2-6}$-alkenyl or C$_{2-6}$-alkynyl group, wherein 1 or 2 methyl groups optionally are replaced by optionally substituted phenyl groups or an optionally substituted cyclo-C$_{3-9}$-alkyl group, wherein independently in a cyclo-C$_{4-7}$-alkyl group 2 hydrogen atoms attached to adjacent carbon atoms optionally are replaced to form a double bond within the ring, which optionally is condensed with an optionally substituted aryl or an optionally substituted 5- or 6-membered hetaryl group, and the resulting group is bound via a saturated or unsaturated carbon atom, or in a cyclo-C$_{4-9}$-alkyl group 2 hydrogen atoms attached to the same carbon atom (relative 1,1-position) optionally are replaced by a C$_{2-5}$-alkylenyl bridge, or 2 hydrogen atoms attached to carbon atoms in relative 1,2-, 1,3- or 1,4-position optionally are replaced by a C$_{1-5}$-alkylenyl bridge, wherein any of the resulting polycyclic groups one or two —CH$_2$— groups optionally are replaced by —NH—, >N—(C$_{1-6}$-alkyl), (or N-atoms for replacement of —CH< members), O, or carbonyl, and/or two —CH$_2$— groups in relative 1,3-position of a C$_{4-5}$-alkylenyl bridge optionally are replaced by O atoms, and/or 2 hydrogen atoms attached to adjacent carbon atoms within a C$_{4-5}$-alkylenyl bridge optionally are replaced to form a double bond, which optionally is condensed with an optionally substituted aryl or an optionally substituted 5- or 6-membered hetaryl group, and/or in a cyclo-C$_{4-8}$-alkyl group one, two or three ring members optionally are replaced independently of each other by —NH—, >N—(C$_{1-6}$-alkyl), (or N-atoms for replacement of CH< members), O, or carbonyl, with the proviso that two heteroatoms are not directly linked together, and additionally but optionally 2 or 4 hydrogen atoms attached to adjacent ring carbon atoms are replaced to form a double bond or two conjugated double bonds within the ring, either of the double bonds optionally being condensed with an optionally substituted aryl or an optionally substituted 5- or 6-membered hetaryl group, and any of the resulting groups is bound via a saturated or unsaturated carbon atom or a nitrogen atom, and wherein any of the resulting open-chained or cyclic groups independently 1 to 3 hydrogen atoms optionally are replaced by C$_{1-4}$-alkyl or C$_{1-4}$-alkoxy groups, and/or any 1 to 6 hydrogen atoms attached to carbon atoms optionally are replaced by fluorine atoms, or W denotes an optionally substituted aryl or hetaryl group, an optionally substituted cyclo-C$_{3-8}$-alkyl-aryl or cyclo-C$_{3-8}$-alkyl-hetaryl group, wherein the cyclo-C$_{5-8}$-alkyl-submoieties one or two ring members optionally are replaced independently of each other by —NH— (or N-atoms for replacement of —CH< members), O, or carbonyl, with the proviso that two heteroatoms are not directly linked together, or a divalent —(CH$_2$)$_p$— group, wherein p is 2, 3, 4, or 5, attached in relative 1,1-position (geminal) to a carbon atom of group X, including the options:

if p is 3, 4, or 5 it follows that 1 —CH$_2$— group optionally is replaced by O, carbonyl, —NH— or —N(C$_{1-6}$-alkyl)-, or if p is 4 or 5 it follows that a —CH$_2$—CH$_2$— group optionally is replaced by —C(O)—NH—, —NH—C(O)—, —C(O)—N(C$_{1-6}$-alkyl)-, —N(C$_{1-6}$-alkyl)-C(O)—, or —CH=CH—, wherein the double bond optionally is condensed with an aryl or a 5- or 6-membered hetaryl group, a divalent —(CH$_2$)$_q$— group, wherein q is 3, or 4 attached in relative 1,2-position (vicinal) to carbon atoms of group X, including the options:

that 1 —CH$_2$— group optionally is replaced by O, carbonyl, —NH— or —N(C$_{1-6}$-alkyl)-, or a —CH$_2$—CH$_2$— group optionally is replaced by —C(O)—NH—, —NH—C(O)—, —C(O)—N(C$_{1-6}$-alkyl)-, —N(C$_{1-6}$-alkyl)-C(O)—, or that in the resulting 5- or 6-membered carbocyclic ring 2, 4 or, in case of the 6-membered ring, also 6 hydrogen atoms optionally are replaced by 1, 2 or 3 bonds to form a partially or fully unsaturated ring with isolated or conjugated double bonds, wherein 1 —CH$_2$— group optionally is replaced by O, S, carbonyl, —NH— or —N(C$_{1-6}$-alkyl)-, and/or one —CH= unit is replaced by —N=, a divalent —(CH$_2$)$_r$— group, wherein r is 7, attached in relative 1,3-position to carbon atoms as binding sites of group X, including the options:

that in the resulting 10-membered carbocyclic ring 2, 4, 6, 8 or 10 hydrogen atoms optionally are replaced by 1, 2, 3, 4 or 5 bonds to form a partially or fully unsaturated ring with isolated or conjugated double bonds, and/or that in the resulting 10-membered carbocyclic ring 1 hydrogen atom attached to the carbon atom in position 2 relative to the binding sites of group X and 1 hydrogen atom attached to a carbon atom of the —(CH$_2$)$_r$— group in position 7 relative to the binding sites of group X optionally are replaced by a bond (C$_0$-bridge) to form a bicyclic ring system condensed with the group X, wherein any aryl groups or subgroups mentioned above in the definition of W are selected from optionally substituted phenyl, and naphthyl groups, and wherein any hetaryl groups or subgroups mentioned above in the definition of W are selected from optionally substituted pyridyl, pyrimidinyl, pyrazinyl, pyridazinyl, pyrazolyl, imidazolyl, triazolyl, furyl, thienyl, oxazolyl, benzoxazolyl, thiazolyl, benzthiazolyl, indolyl, indolinyl, benzimidazolyl, indazolyl, benztriazolyl, quinolyl, isoquinolyl, cinnolyl, and quinoxazolyl groups, wherein the expression "substituted" or "optionally substituted" as used herein has the same meaning as in claim 1; and R$^1$ denotes H, C$_{1-4}$-alkyl, C$_{3-4}$-alkenyl or C$_{3-4}$-alkynyl, any of those groups being optionally substituted by 1 to 3 fluorine, chlorine or bromine atoms, or by a cyano, hydroxy, C$_{1-3}$-alkoxy or cyclo-C$_{3-6}$-alkyl-group, R$^2$ and R$^3$ independently denote H, halogen, C$_{1-3}$-alkyl, hydroxy or C$_{1-3}$-alkoxy, any of those C$_{1-3}$-alkyl groups being optionally substituted by 1 to 3 fluorine atoms, R$^4$ and R$^5$ independently denote H, halogen, C$_{1-3}$-alkyl, C$_{2-4}$-alkenyl, C$_{2-3}$-alkynyl, cyclo-C$_{3-6}$-alkyl, hydroxy or C$_{1-3}$-alkoxy, any of those C$_{1-3}$-alkyl, C$_{2-4}$-alkenyl or C$_{2-3}$-alkynyl groups being optionally substituted by 1 to 3 fluorine atoms, by a methyl, hydroxy, C$_{1-3}$-alkoxy, or cyclo-C$_{3-5}$-alkyl-group, or by a phenyl or pyridyl group both optionally substituted independently by 1, 2 or 3 substituents selected from halogen atoms, C$_{1-3}$-alkyl, cyclo-C$_{3-6}$-alkyl, cyano, hydroxy, C$_{1-3}$-alkoxy, amino, C$_{1-3}$-alkyl-amino, and di-(C$_{1-3}$-alkyl)-amino groups, or a salt thereof.

5. The compound according to claim 1, wherein

X denotes a group selected from formulas (II), (III), (VI) or (XIII),

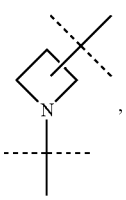
(II)

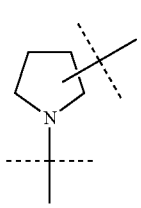
(III)

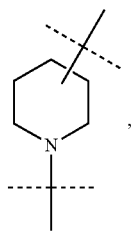
(VI)

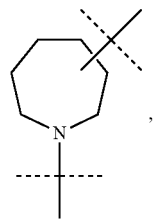
(XIII)

wherein 1 —CH$_2$— group optionally is replaced independently of each other by O or carbonyl, wherein one or two carbon atoms optionally and independently are substituted by halogen atoms, C$_{1-6}$-alkyl, C$_{2-6}$-alkenyl, C$_{2-6}$-alkynyl, cyclo-C$_{3-7}$-alkenyl, phenyl, cyano, hydroxy, hydroxy-C$_{1-6}$-alkyl, C$_{1-6}$-alkoxy, C$_{1-6}$-alkoxy-C$_{1-6}$-alkyl, formyl, aminocarbonyl, C$_{1-6}$-alkyl-aminocarbonyl, C$_{3-6}$-alkenyl-aminocarbonyl, C$_{3-6}$-alkynyl-aminocarbonyl, di-(C$_{1-6}$-alkyl)-aminocarbonyl, di-(C$_{3-6}$-alkenyl)-aminocarbonyl, di-(C$_{3-6}$-alkynyl)-aminocarbonyl, formylamino, C$_{1-6}$-alkyl-carbonylamino, C$_{1-6}$-alkyl-carbonyl-(C$_{1-3}$-alkyl)-amino C$_{2-6}$-alkenyl-carbonylamino or C$_{2-6}$-alkynyl-carbonylamino groups, while the substituents may be identical or different;

Y denotes a —(CH$_2$)$_n$— group, wherein n is 1, 2, 3, 4, 5 or 6 and wherein 1 —CH$_2$— group optionally is replaced by O, carbonyl or —NH—, or wherein 1 —CH$_2$— group is replaced by O or —NH—, and additionally a second —CH$_2$— group is replaced by carbonyl, or wherein 1 —CH$_2$— group is replaced by O and additionally a —CH$_2$—CH$_2$— subgroup is replaced by —C(O)—NH—, or —NH—C(O)—, and wherein any hydrogen atom of the —NH— groups mentioned hereinbefore optionally and independently is replaced by a C$_{3-6}$-cycloalkyl or phenyl group, or by a straight-chained or branched C$_{1-4}$-alkyl, phenyl-C$_{1-3}$-alkyl, or C$_{1-3}$-alkyl-carbonyl, and/or wherein 1 or 2 hydrogen atoms attached to carbon atoms optionally are independently replaced by F, Cl, C$_{1-4}$-alkyl or trifluoromethyl, or 1 hydrogen atom attached to a carbon atom optionally is replaced by C$_{3-6}$-cycloalkyl, phenyl, phenyl-C$_{1-3}$-alkyl, hydroxy, or C$_{1-3}$-alkoxy groups, while the substituents may be identical or different, or 2 geminal hydrogen atoms are replaced by a —(CH$_2$)$_m$— bridge, wherein m is 2, 3, or 4;

W denotes H or an optionally substituted straight-chained or branched C$_{1-6}$-alkyl, C$_{2-6}$-alkenyl or C$_{2-6}$-alkynyl group, wherein 1 or 2 methyl groups optionally are replaced by optionally substituted phenyl groups or an optionally substituted cyclo-C$_{3-9}$-alkyl group, wherein independently in a cyclo-C$_{4-7}$-alkyl group 2 hydrogen atoms attached to adjacent carbon atoms optionally are replaced to form a double bond within the ring, which optionally is condensed with an optionally substituted aryl or an optionally substituted 5- or 6-membered hetaryl group, and the resulting group is bound via a saturated or unsaturated carbon atom, or in a cyclo-$C_{4-9}$-alkyl group 2 hydrogen atoms attached to the same carbon atom (relative 1,1-position) optionally are replaced by a $C_{2-5}$-alkylenyl bridge, or 2 hydrogen atoms attached to carbon atoms in relative 1,2-, 1,3- or 1,4-position optionally are replaced by a $C_{1-5}$-alkylenyl bridge, wherein any of the resulting polycyclic groups one or two —$CH_2$— groups optionally are replaced by —NH—, >N—($C_{1-6}$-alkyl), (or N-atoms for replacement of —CH< members), O, or carbonyl, and/or two —$CH_2$— groups in relative 1,3-position of a $C_{4-5}$-alkylenyl bridge optionally are replaced by O atoms, and/or 2 hydrogen atoms attached to adjacent carbon atoms within a $C_{4-5}$-alkylenyl bridge optionally are replaced to form a double bond, which optionally is condensed with an optionally substituted aryl or an optionally substituted 5- or 6-membered hetaryl group, and/or in a cyclo-$C_{4-8}$-alkyl group, two or three ring members optionally are replaced independently of each other by —NH—, >N—($C_{1-6}$-alkyl), (or N-atoms for replacement of a —CH< members), O, or carbonyl, with the proviso that two heteroatoms are not directly linked together, and additionally but optionally 2 or 4 hydrogen atoms attached to adjacent ring carbon atoms are replaced to form a double bond or two conjugated double bonds within the ring, either of the double bonds optionally being condensed with an optionally substituted aryl or an optionally substituted 5- or 6-membered hetaryl group, and any of the resulting groups is bound via a saturated or unsaturated carbon atom or a nitrogen atom, and wherein any of the resulting open-chained or cyclic groups independently 1 to 3 hydrogen atoms optionally are replaced by $C_{1-4}$-alkyl or $C_{1-4}$-alkoxy groups, and/or any 1 to 6 hydrogen atoms attached to carbon atoms optionally are replaced by fluorine atoms, or W denotes an optionally substituted aryl or hetaryl group, an optionally substituted cyclo-$C_{3-6}$-alkyl-aryl or cyclo-$C_{3-6}$-alkyl-hetaryl group, wherein the cyclo-$O_{5-6}$-alkyl-submoieties one or two ring members optionally are replaced independently of each other by —NH— (or a N-atom for replacement of a —CH< member), O, or carbonyl, with the proviso that two heteroatoms are not directly linked together, $R^1$ denotes H, $C_{1-4}$-alkyl, $C_{3-4}$-alkenyl or $C_{3-4}$-alkynyl, any of those groups being optionally substituted by 1 to 3 fluorine, chlorine or bromine atoms, or by a cyano, hydroxy, $C_{1-3}$-alkoxy or cyclo-$C_{3-6}$-alkyl-group, $R^2$ and $R^3$ independently denote H, halogen, $C_{1-3}$-alkyl, hydroxy or $C_{1-3}$-alkoxy, any of those $C_{1-3}$-alkyl groups being optionally substituted by 1 to 3 fluorine atoms, $R^4$ and $R^5$ independently denote H, halogen, $C_{1-3}$-alkyl, $C_{2-4}$-alkenyl, $C_{2-3}$-alkynyl, cyclo-$C_{3-6}$-alkyl, hydroxy or $C_{1-3}$-alkoxy, any of those $C_{1-3}$-alkyl, $C_{2-4}$-alkenyl or $C_{2-3}$-alkynyl groups being optionally substituted by 1 to 3 fluorine atoms, by a methyl, hydroxy, $C_{1-3}$-alkoxy, or cyclo-$C_{3-5}$-alkyl-group, or by a phenyl or pyridyl group both optionally substituted independently by 1, 2 or 3 substituents selected from halogen atoms, $C_{1-3}$-alkyl, cyclo-$C_{3-6}$-alkyl, cyano, hydroxy, $C_{1-3}$-alkoxy, amino, $C_{1-3}$-alkyl-amino, and di-($C_{1-3}$-alkyl)-amino groups, or a salt thereof.

6. The compound according to claim 1, wherein

X denotes a group selected from formulas (II), (III), (VII) or (XIII),

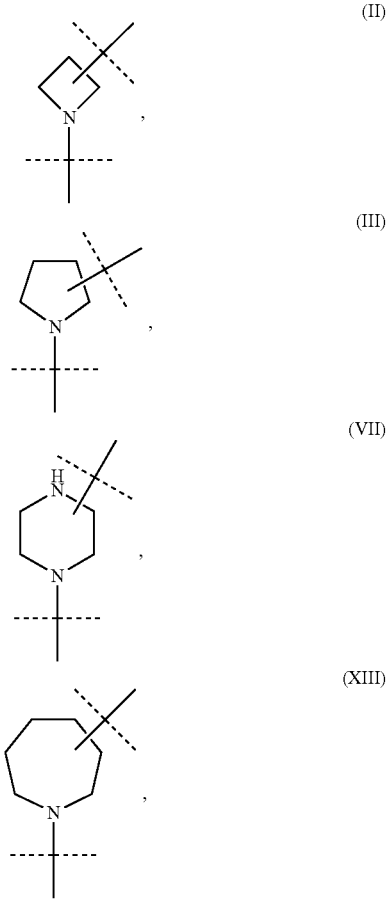

wherein 1 —$CH_2$— group optionally is replaced independently of each other by O, S, carbonyl, or sulfonyl, with the proviso that two heteroatoms are not directly linked together, wherein one or two carbon atoms optionally and independently are substituted by halogen atoms, $C_{1-6}$-alkyl, $C_{2-6}$-alkenyl, $C_{2-6}$-alkynyl, cyclo-$C_{3-7}$-alkyl, cyclo-$C_{3-7}$-alkenyl, phenyl, cyano, hydroxy, hydroxy-$C_{1-6}$-alkyl, $C_{1-6}$-alkoxy, $C_{1-6}$-alkoxy-$C_{1-6}$-alkyl, formyl, aminocarbonyl, $C_{1-6}$-alkyl-aminocarbonyl, $C_{3-6}$-alkenyl-aminocarbonyl, $C_{3-6}$-alkynyl-aminocarbonyl, di-($C_{1-6}$-alkyl)-aminocarbonyl, di-($C_{3-6}$-alkenyl)-aminocarbonyl, di-($C_{3-6}$-alkynyl)-aminocarbonyl, formylamino, $C_{1-6}$-alkyl-carbonylamino, $C_{1-6}$-alkyl-carbonyl-($C_{1-3}$-alkyl)-amino $C_{2-6}$-alkenyl-carbonylamino or $C_{2-6}$-alkynyl-carbonylamino groups, while the substituents may be identical or different, and/or one ring member nitrogen atom is substituted by $C_{1-6}$-alkyl, $C_{3-6}$-alkenyl, $C_{3-6}$-alkynyl, cyclo-$C_{3-7}$-alkyl or cyclo-$C_{3-7}$-alkenyl;

Y denotes a carbonyl group;

W denotes H or an optionally substituted straight-chained or branched $C_{1-6}$-alkyl, $C_{2-6}$-alkenyl or $C_{2-6}$-alkynyl group, wherein 1 or 2 methyl groups optionally are replaced by optionally substituted phenyl groups or an optionally substituted cyclo-$C_{3-8}$-alkyl group, wherein independently in a cyclo-$C_{4-8}$-alkyl group one or two ring members optionally are replaced independently of each other by —NH—, >N—($C_{1-6}$-alkyl) (or N-atoms for replacement of —CH< members), O, or carbonyl, with the proviso that two heteroatoms are not directly linked together, and additionally but optionally 2 or 4 hydrogen atoms attached to adjacent ring carbon atoms are replaced to form a double bond or two conjugated double bonds within the ring, either of the double bonds optionally being condensed with an optionally substituted aryl or an optionally substituted 5- or 6-membered hetaryl group, and/or in a cyclo-$C_{4-5}$-alkyl group 2 hydrogen atoms attached to the same carbon atom (relative 1,1-position) optionally are replaced by a $C_{2-5}$-alkylenyl bridge, wherein one —$CH_2$— group optionally is replaced by —NH—, >N—($C_{1-6}$-alkyl), O, or carbonyl or wherein two —$CH_2$— groups in relative 1,3-position of a $C_{4-5}$-alkylenyl bridge optionally are replaced O atoms, or wherein a —$CH_2$—$CH_2$— group optionally is replaced by —C(O)—NH—, —NH—C(O)—, —C(O)—N($C_{1-6}$-alkyl)- or —N($C_{1-6}$-alkyl)-C(O)— and/or 2 hydrogen atoms attached to adjacent carbon atoms within a $C_{4-5}$-alkylenyl bridge optionally are replaced to form a double bond, which optionally is condensed with an optionally substituted aryl or an optionally substituted 5- or 6-membered hetaryl group, or an optionally substituted cyclo-$C_{5-9}$-alkyl group, wherein independently 2 hydrogen atoms attached to carbon atoms in relative 1,2-, 1,3-, or 1,4 position optionally are replaced by a $C_{1-3}$-alkylenyl bridge, wherein any of the resulting polycyclic groups one —$CH_2$— group optionally is replaced by —NH—, >N—($C_{1-6}$-alkyl), O, or carbonyl, wherein any of the resulting groups is bound via a saturated or unsaturated carbon atom or a nitrogen atom, and wherein any of the resulting open-chained or cyclic groups independently 1 to 3 hydrogen atoms optionally are replaced by $C_{1-4}$-alkyl or $C_{1-4}$-alkoxy groups, and/or any 1 to 6 hydrogen atoms attached to carbon atoms optionally are replaced by fluorine atoms, or W denotes an optionally substituted aryl or hetaryl group, an optionally substituted cyclo-$C_{3-6}$-alkyl-aryl or cyclo-$C_{3-6}$-alkyl-hetaryl group, wherein the cyclo-$O_{5-6}$-alkyl-submoieties one or two ring members optionally are replaced independently of each other by —NH— (or a N-atom for replacement of a —CH< member), O, or carbonyl, with the proviso that two heteroatoms are not directly linked together, or if Y is absent W additionally denotes a divalent —$(CH_2)_p$— group, wherein p is 2, 3, 4, or 5, attached in relative 1,1-position (geminal) to a carbon atom of group X, including the options:

if p is 4 or 5 it follows that 1 —$CH_2$— group optionally is replaced by O, —NH— or —N($C_{1-4}$-alkyl)-, or that a —$CH_2$—$CH_2$— group optionally is replaced by —C(O)—NH—, —NH—C(O)—, —C(O)—N($C_{1-4}$-alkyl)-, —N($C_{1-4}$-alkyl)-C(O)—, or —CH=CH—, wherein the double bond optionally is condensed with an aryl or a 5- or 6-membered hetaryl group, a divalent —$(CH_2)_q$— group, wherein q is 3 or 4 attached in relative 1,2-position (vicinal) to carbon atoms of group X, including the options:

a —$CH_2$—$CH_2$— group optionally is replaced by —C(O)—NH—, —NH—C(O)—, —C(O)—N($C_{1-6}$-alkyl)-, —N($C_{1-6}$-alkyl)-C(O)—, or that in the resulting 5- or 6-membered carbocyclic ring 2, 4 or, in case of the 6-membered ring, also 6 hydrogen atoms optionally are replaced by 1, 2 or 3 bonds to form a partially or fully unsaturated ring with isolated or conjugated double bonds, wherein 1 —$CH_2$— group optionally is replaced by O, —NH— or —N($C_{1-6}$-alkyl)-, and/or one —CH= unit is replaced by —N=, the trivalent group

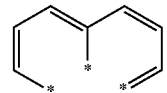 [SMILES: *\C=C/C=C(*)/C=C\C=*]

attached in relative 1,2,3-position to carbon atoms * as binding sites of group X, wherein any aryl groups or aryl-subgroups mentioned above in the definition of W are selected from optionally substituted phenyl, and naphthyl group, and wherein any hetaryl groups or hetaryl-subgroups mentioned above in the definition of W are selected from optionally substituted pyridyl, pyrimidinyl, pyrazinyl, pyridazinyl, pyrazolyl, imidazolyl, triazolyl, furyl, thienyl, oxazolyl, benzoxazolyl, thiazolyl, benzthiazolyl, indolyl, indolinyl, benzimidazolyl, indazolyl, benztriazolyl, quinolyl, isoquinolyl, cinnolyl, and quinoxazolyl groups, wherein the expression "optionally substituted" means that 1, 2 or 3 hydrogen atoms of the respective group independently are optionally replaced by substituents selected from fluorine, chlorine and bromine atoms, atoms, by $C_{1-6}$-alkyl, trifluoromethyl, $C_{2-6}$-alkenyl, $C_{2-6}$-alkynyl, cyclo-$C_{3-7}$-alkyl, cyclo-$C_{3-7}$-alkenyl, cyano, hydroxy, hydroxy-$C_{1-6}$-alkyl, $C_{1-6}$-alkoxy, $C_{1-6}$-alkoxy-$C_{1-6}$-alkyl, formyl, amino, $C_{1-4}$-alkyl-amino, ($C_{1-4}$-alkyl)$_2$-amino, pyrrolidino, piperidino, aminocarbonyl, $C_{1-6}$-alkyl-aminocarbonyl, $C_{3-6}$-alkenyl-amino-carbonyl, $C_{3-6}$-alkynyl-aminocarbonyl, di-($C_{1-6}$-alkyl)-aminocarbonyl, di-($C_{3-6}$-alkenyl)-aminocarbonyl, di-($C_{3-6}$-alkynyl)-aminocarbonyl, formylamino, $C_{1-6}$-alkyl-carbonylamino, $C_{1-6}$-alkyl-carbonyl-($C_{1-3}$-alkyl)-amino $C_{2-6}$-alkenyl-carbonylamino or $C_{2-6}$-alkynyl-carbonylamino groups, or the expression "optionally substituted" means that 4 hydrogen atoms of the respective group independently are optionally replaced by substituents selected from fluorine atoms and $C_{1-6}$-alkyl groups, and/or wherein a hydrogen atom attached to a nitrogen atom, if present in the respective group, optionally is replaced by a $C_{1-4}$-alkyl, cyclo-$C_{3-6}$-alkyl, cyclo-$C_{3-7}$-alkyl-$C_{1-3}$-alkyl, pyrrolidino, piperidino, morpholino, $C_{1-3}$-alkoxy, $C_{1-3}$-alkoxy-$C_{1-3}$-alkyl, phenyl, phenyl-$C_{1-3}$-alkyl, $C_{1-4}$-alkyl-carbonyl, $C_{1-3}$-alkoxy-carbonyl or $C_{1-3}$-alkyl-sulphonyl group and wherein any phenyl and pyridyl groups or phenyl- and pyridyl-submoieties optionally are substituted with 1 or 2 substituents independently of each other selected from fluorine, chlorine, bromine, $C_{1-3}$-alkyl, $C_{1-3}$-alkoxy, amino, $C_{1-3}$-alkyl-amino, $C_{1-3}$-alkylcarbonyl-amino or hydroxy;

$R^1$ denotes H, $C_{1-4}$-alkyl, $C_{3-4}$-alkenyl or $C_{3-4}$-alkynyl, any of those groups being optionally substituted by 1 to 3 fluorine or chlorine atoms, or by a cyclo-$C_{3-6}$-alkyl-group, $R^2$ and $R^3$ independently denote H, halogen, $C_{1-3}$-alkyl, any of those $C_{1-3}$-alkyl groups being optionally substituted by 1 to 3 fluorine atoms, $R^4$ and $R^5$ independently denote H, halogen, $C_{1-3}$-alkyl, cyclo-$C_{3-6}$-alkyl, any of those $C_{1-3}$-alkyl, groups being optionally substituted by 1 to 3 fluorine atoms, by a methyl, or cyclo-$C_{3-5}$-alkyl group, or by a phenyl or pyridyl group, both optionally substituted independently by 1, 2 or 3 substituents selected from halogen atoms, $C_{1-3}$-alkyl, hydroxy, $C_{1-3}$-alkoxy, amino, and $C_{1-3}$-alkyl-amino groups, or a salt thereof.

7. A physiologically acceptable salt of a compound according to claim 1 with inorganic or organic acids or bases.

8. A pharmaceutical composition containing a compound according to claim 1, or a physiologically acceptable salt with inorganic or organic acids or bases, optionally together with one or more inert carriers and/or diluents.

9. A method of treating a disease comprising administering an effective amount of a compound of claim 1 or a physiologically acceptable salt thereof to a patient in need, wherein the disease is selected from a group consisting of diabetes mellitus type 1, diabetes mellitus type II and diabetes mellitus type III.

* * * * *